(12) United States Patent
Buynak et al.

(10) Patent No.: US 8,575,144 B2
(45) Date of Patent: Nov. 5, 2013

(54) BETA-LACTAMASE INHIBITORY COMPOUNDS

(71) Applicant: Southern Methodist University, Dallas, TX (US)

(72) Inventors: John D. Buynak, Dallas, TX (US); Anjaneyulu Sheri, Woburn, MA (US); Sundar Ram Reddy Pagadala, Dallas, TX (US)

(73) Assignee: Southern Methodist University, Dallas, TX (US)

( * ) Notice: Subject to any disclaimer, the term of this patent is extended or adjusted under 35 U.S.C. 154(b) by 0 days.

(21) Appl. No.: 13/629,007

(22) Filed: Sep. 27, 2012

(65) Prior Publication Data

US 2013/0079318 A1  Mar. 28, 2013

Related U.S. Application Data

(62) Division of application No. 12/463,762, filed on May 11, 2009, now Pat. No. 8,299,051.

(60) Provisional application No. 61/052,922, filed on May 13, 2008.

(51) Int. Cl.
*A61K 31/545* (2006.01)
*A61K 31/546* (2006.01)
*C07D 501/14* (2006.01)

(52) U.S. Cl.
USPC ............ 514/202; 514/207; 540/222; 540/228

(58) Field of Classification Search
USPC ............................ 514/202, 207; 540/222, 228
See application file for complete search history.

(56) References Cited

U.S. PATENT DOCUMENTS

| | | | |
|---|---|---|---|
| 4,512,999 A | 4/1985 | Adam-Molina et al. | |
| 4,647,457 A | 3/1987 | Adam-molina | |
| 4,826,833 A | 5/1989 | Chen | |
| 6,156,745 A | 12/2000 | Buynak et al. | |
| 6,916,801 B2 * | 7/2005 | Buynak et al. | 514/200 |
| 2010/0009954 A1 | 1/2010 | Buynak et al. | |

FOREIGN PATENT DOCUMENTS

LV        12540 B    *  12/2000

OTHER PUBLICATIONS

Vorona, Chemistry of Heterocyclic Compounds (2008), 44(6), 739-749.*
Buynak, Bioorganic & Medicinal Chemistry Letters (2000), 10(9), 853-857.*
Beharry, Zanna, et al., "Evaluation of penicillin-based inhibitors of the class A and B-lactamases from *Bacillus anthracis*", Biochemical and Biophysical Research Communications 313, (2004), 541-545.
U.S. Appl. No. 12/463,762, filed May 11, 2009, Beta-Lactamase Inhibitory Compounds.

* cited by examiner

*Primary Examiner* — Andrew D Kosar
*Assistant Examiner* — John Mauro
(74) *Attorney, Agent, or Firm* — Schwegman Lundberg & Woessner, P.A.

(57) ABSTRACT

Inhibitors of the enzyme beta-lactamase are provided comprising compounds of formula (II)

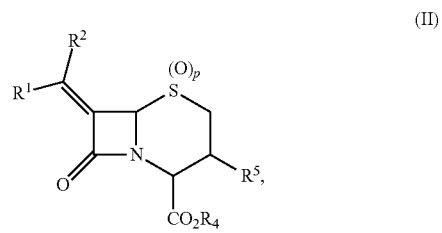

wherein $R^1$ or $R^2$ is a pyridyl group and $R^5$ is a group of formula

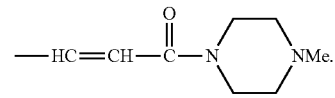

The compounds are adapted to inhibit beta-lactamase as produced by beta-lactam resistant bacterial strains. Methods of treatment of beta-lactam resistant bacterial infections in patients are provided.

10 Claims, No Drawings

BETA-LACTAMASE INHIBITORY COMPOUNDS

CROSS-REFERENCE TO RELATED APPLICATIONS

This application is a divisional of U.S. Ser. No. 12/463,762, filed May 11, 2009, which is a non-provisional utility of U.S. Ser. No. 61/052,922, filed May 13, 2008, the disclosure of which is incorporated herein by reference in its entirety.

BACKGROUND

Beta-lactam antibiotics, as are well known in the art, include the penicillin and cephalosporin classes of compounds, which have been used extensively for decades for the treatment of bacterial infections. However, certain bacterial strains have developed resistance to some or all of the beta-lactam antibiotics available to the physician. In some cases, this resistance is due to the production by the bacterial strain of an enzyme that degrades the antibiotic by hydrolytic ring opening of the beta-lactam four-membered ring. Such enzymes are termed beta-lactamases.

To counter this mechanism of resistance involving beta-lactamase production by infectious bacterial strains and allow for the continued use of beta-lactam antibiotics, various compounds that inhibit the beta-lactamase enzymes produced by resistant bacteria have been developed. For example, clavulanic acid is a beta-lactamase inhibitor well known in the art, which is used in combination with beta-lactam antibiotics for treatment of infections. An example of a composition including clavulanic acid is Augmentin®.

SUMMARY

The present invention is directed to novel inhibitors of the beta-lactamase enzyme, adapted for treatment of infections in humans and other mammals caused by populations of beta-lactam resistant bacteria, and to methods of use of the inhibitors in the treatment.

In various embodiments, the invention provides a compound of Formula (I):

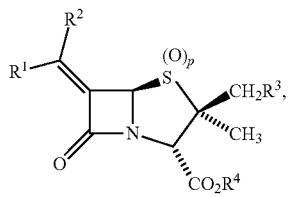

(I)

wherein p is 0, 1, or 2;

$R^1$ and $R^2$ each independently comprises H, alkyl, aryl, cycloalkyl, cycloalkylalkyl, heterocyclyl, or heteroaryl, wherein any alkyl, aryl, cycloalkyl, cycloalkylalkyl, heterocyclyl, or heteroaryl can be independently substituted with 0-3 J;

J is R' except H, haloalkyl, $(CH_2)_n$—OR', $(CH_2)_n$—OC(O)N(R)$_2$, $(CH_2)_n$—CN, $CF_3$, $OCF_3$, O, S, C(O), S(O), methylenedioxy, ethylenedioxy, $(CH_2)_n$—N(R')$_2$, $(CH_2)_n$—SR', $(CH_2)_n$—S(O)R', $(CH_2)_n$—S(O)$_2$R', $(CH_2)_n$—S(O)$_2$N(R')$_2$, $(CH_2)_n$—SO$_3$R', $(CH_2)_n$—C(O)R', $(CH_2)_n$—C(O)C(O)R', $(CH_2)_n$—C(O)CH$_2$C(O)R', $(CH_2)_n$—C(S)R', $(CH_2)_n$—C(O)OR', $(CH_2)_n$—OC(O)R', $(CH_2)_n$—C(O)N(R')$_2$, $(CH_2)_n$—OC(O)N(R')$_2$, $(CH_2)_n$—C(S)N(R')$_2$, $(CH_2)_n$—NHC(O)R', $(CH_2)_n$—N(R')N(R')C(O)R', $(CH_2)_n$—N(R')N(R')C(O)OR', $(CH_2)_n$—N(R')N(R')CON(R')$_2$, $(CH_2)_n$—N(R')SO$_2$R', $(CH_2)_n$—N(R')SO$_2$N(R')$_2$, $(CH_2)_n$—N(R')C(O)OR', $(CH_2)_n$—N(R')C(O)R', $(CH_2)_n$—N(R')C(S)R', $(CH_2)_n$—N(R')C(O)N(R')$_2$, $(CH_2)_n$—N(R')C(S)N(R')$_2$, $(CH_2)_n$—N(R')C(=NR)N(R')$_2$, $(CH_2)_n$—C(=NR)N(R')$_2$, $(CH_2)_n$—N(COR')COR', $(CH_2)_n$—N(OR')R', $(CH_2)_n$—C(=NH)N(R')$_2$, $(CH_2)_n$—C(O)N(OR')R', $(CH_2)_n$N(R')C(=NR')N(R')$_2$ or $(CH_2)_n$—C(=NOR')R', wherein n is 0 to about 4, and wherein;

each R' is independently at each occurrence hydrogen, $(C_1$-$C_{12})$-alkyl, $(C_3$-$C_{10})$-cycloalkyl or $(C_3$-$C_{10})$-cycloalkenyl, [$(C_3$-$C_{10})$cycloalkyl or $(C_3$-$C_{10})$-cycloalkenyl]-$(C_1$-$C_{12})$-alkyl, $(C_6$-$C_{10})$-aryl, $(C_6$-$C_{10})$-aryl-$(C_1$-$C_{12})$-alkyl, $(C_3$-$C_{10})$-heterocyclyl, $(C_3$-$C_{10})$-heterocyclyl-$(C_1$-$C_{12})$-alkyl, $(C_5$-$C_{10})$-heteroaryl, or $(C_5$-$C_{10})$-heteroaryl-$(C_1$-$C_{12})$-alkyl, wherein any alkyl, cycloalkyl, cycloalkenyl, cycloalkylalkyl, cycloalkenylalkyl, aryl, arylalkyl, heterocyclyl, heterocyclylalkyl, heteroaryl, or heteroarylalkyl is substituted with 0-3 substituents selected independently from J; or, two R' groups together with a nitrogen atom to which both R' groups are attached or with two adjacent nitrogen atoms to which each R' group is respectively attached form a mono- or bicyclic ring system;

$R^3$ comprises hydrogen, OH, OC(O)R'', OC(O)OR'', OC(O)NHR'', NHC(O)R'', NHC(O)NHR'', or NHC(=NH)NHR'', where R'' is H, $(C_1$-$C_{12})$alkyl, aryl, heteroaryl, or $(CH_2)_n$NHR''', wherein n=2, 3, or 4 and R'''=H, C(=NH)NH$_2$, C(=NH)H, or $R^3$ comprises $(C_1$-$C_{12})$-alkyl, $(C_3$-$C_{10})$-cycloalkyl or $(C_3$-$C_{10})$-cycloalkenyl, [$(C_3$-$C_{10})$cycloalkyl or $(C_3$-$C_{10})$-cycloalkenyl]-$(C_1$-$C_{12})$-alkyl, $(C_6$-$C_{10})$-aryl, $(C_6$-$C_{10})$-aryl-$(C_1$-$C_{12})$-alkyl, $(C_3$-$C_{10})$-heterocyclyl, $(C_3$-$C_{10})$-heterocyclyl-$(C_1$-$C_{12})$-alkyl, $(C_5$-$C_{10})$-heteroaryl, or $(C_5$-$C_{10})$-heteroaryl-$(C_1$-$C_{12})$-alkyl, wherein R'' is substituted with 0-3 substituents selected independently from J; and, $R^4$ is H, a $(C_1$-$C_6$)alkyl or aryl group, or a pharmaceutically acceptable cation; or, a compound of Formula (II):

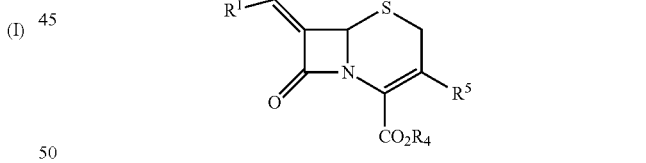

(II)

wherein p, $R^1$, $R^2$, $R^4$, R', and J are as defined above, and $R^5$ comprises H, alkyl, aryl, cycloalkyl, cycloalkylalkyl, heterocyclyl, or heteroaryl, wherein any alkyl, aryl, cycloalkyl, cycloalkylalkyl, heterocyclyl, or heteroaryl can be independently substituted with 0-3 J;

or a salt, zwitterion, pharmaceutically acceptable salt, hydrate, solvent, tautomer, stereoisomer, or prodrug thereof.

In various embodiments, a pharmaceutical composition comprising a compound of the invention and a suitable excipient is provided.

In various embodiments, a pharmaceutical combination comprising a compound of the invention and a second medicament is provided. The second medicament can be a beta-lactam antibiotic.

In various embodiments, a method of inhibition of a beta-lactamase enzyme comprising contacting the enzyme with an effective amount of any of the compounds, compositions, or combinations, is provided. The beta-lactamase enzyme can be produced by a beta-lactam resistant bacterial population within the body of a patient.

In various embodiments, the use of any of the compounds, compositions, or combinations for preparation of a medicament for treatment of a beta-lactam resistant bacterial infection in a patient in need thereof is provided.

In various embodiments, a method of treatment of a beta-lactam resistant bacterial infection in a patient in need thereof comprising administering a combination of an inventive compound in combination with a beta-lactam antibiotic in a dose, at a frequency, and for a duration effective to provide a beneficial effect to the patient.

In various embodiments, a method of treatment of a beta-lactam resistant bacterial infection in a patient in need thereof comprising administering an inventive compound to the patient in a dose, at a frequency, and for a duration effective to provide a beneficial effect to the patient wherein the patient is further administered a beta-lactam antibiotic in an effective dose.

DETAILED DESCRIPTION

The term "treatment" is defined as the management and care of a patient for the purpose of combating the disease, condition, or disorder and includes administering a compound of the present invention to prevent the onset of the symptoms or complications, or alleviating the symptoms or complications, or eliminating the disease, condition, or disorder.

"Treating" within the context of the instant invention means an alleviation of symptoms associated with a disorder or disease, or inhibition of further progression or worsening of those symptoms, or prevention or prophylaxis of the disease or disorder. Thus, treating a bacterial infection includes slowing, halting or reversing the growth of the bacterial population and/or the control, alleviation or prevention of symptoms of the infection. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects. For example, in the context of using a beta-lactamase inhibitor in combination with a beta-lactam antibiotic for treatment of a beta-lactam resistant bacterial infection, a therapeutically effective amount of a beta-lactamase inhibitor of the invention is an amount sufficient to allow control of the bacterial infection by the beta-lactam antibiotic without causing undue side effects or toxicity to the patient.

All chiral, diastereomeric, racemic forms of a structure are intended, unless the specific stereochemistry or isomeric form is specifically indicated. Compounds used in the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

By "chemically feasible" is meant a bonding arrangement or a compound where the generally understood rules of organic structure are not violated; for example a structure within a definition of a claim that would contain in certain situations a pentavalent carbon atom that would not be believed to exist in nature would be understood to not be within the claim.

When a substituent is specified to be an atom or atoms of specified identity, "or a bond", a configuration is referred to when the substituent is "a bond" that the groups that are immediately adjacent to the specified substituent are directly connected to each other by a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboyxlate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O) CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R') C(O)R', N(R')N(R')C(O)OR', N(R')N(R')CON(R')$_2$, N(R') SO$_2$R', N(R')SO$_2$N(R')$_2$, N(R')C(O)OR', N(R')C(O)R', N(R') C(S)R', N(R')C(O)N(R')$_2$, N(R')C(S)N(R')$_2$, N(COR')COR', N(OR')R', N(R')C(=NR)N(R')$_2$, C(=NH)N(R')$_2$, C(O)N (OR')R', or C(=NOR')R' wherein R' can be hydrogen or a carbon-based moiety, and wherein the carbon-based moiety can itself be further substituted. When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a

[2.2.1]-oxabicyclo system. Further, any substituent can be bonded to a carbon or other atom by a linker, such as $(CH_2)_n$ or $(CR'_2)_n$ wherein n is 1, 2, 3, or more, and each R' is independently selected.

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic" and "carbocycle" denote a ring structure wherein the atoms of the ring are carbon. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C (CH$_2$CH$_3$), —CH$_2$C≡CH, —CH$_2$C≡C(CH$_3$), and —CH$_2$C≡C(CH$_2$CH$_3$) among others.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups include aromatic and non-aromatic ring compounds containing 3 or more ring members, of which, one or more is a heteroatom such as, but not limited to, N, O, and S. In some embodiments, heterocyclyl groups include 3 to 20 ring members, whereas other such groups have 3 to 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a b-ring with two heteroatoms, and so forth. The number of carbon atoms plus the number of heteroatoms sums up to equal the total number of ring atoms. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above. Heteroaryl groups are aromatic ring compounds containing 5 or more ring members, of which, one or more is a heteroatom such as, but not limited to, N, O, and S. A heteroaryl group designated as a $C_2$-heteroaryl can be a 5-ring with two carbon atoms and three heteroatoms, a b-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl-1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

More specifically, aryl and heteroaryl groups can include phenyl, isoindolidinyl, imidazolyl, oxazolyl, benzimidazolyl, and benzoxazolyl; wherein any aryl or heteroaryl can be unsubstituted, mono-substituted, or independently pluri-substituted, for example with J groups as defined herein.

Heterocyclylalkyl groups are alkyl groups as defined above in which a hydrogen or carbon bond of an alkyl group is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

"Halo" as the term is used herein includes fluoro, chloro, bromo, and iodo. A "haloalkyl" group includes mono-halo alkyl groups, and poly-halo alkyl groups wherein all halo atoms can be the same or different. Examples of haloalkyl include trifluoromethyl, 1,1-dichloroethyl, 1,2-dichloroethyl, 1,3-dibromo-3,3-difluoropropyl and the like.

The terms "aryloxy" and "arylalkoxy" refer to, respectively, an aryl group bonded to an oxygen atom and an aralkyl group bonded to the oxygen atom at the alkyl moeity. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N (group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R3N wherein each R is independently selected, such as trialkylamines, dialkylarylamines, alkyldiarylamines, triarylamines, and the like. The term "amine" also includes ammonium ions as used herein. An "amino" group is a substituent of the form —NH$_2$, —NHR, —NR$_2$, —NR$_3^+$, wherein each R is independently selected, and protonated forms of each. Accordingly, any compound substituted with an amino group can be viewed as an amine.

An "ammonium" ion includes the unsubstituted ammonium ion NH$_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)NR$_2$, and —NRC(O)R groups, respectively. Amide groups therefore include but are not limited to carbamoyl groups (—C(O)NH$_2$) and formamide groups (—NHC(O)H). A "carboxamido" group is a group of the formula C(O)NR$_2$, wherein R can be H, alkyl, aryl, etc.

The term "urethane" (or "carbamyl") includes N- and O-urethane groups, i.e., —NRC(O)OR and —OC(O)NR$_2$ groups, respectively.

The term "sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)NR$_2$. Typically, an amidino group is —C(NH)NH$_2$.

The term "guanidine" or "guanidino" includes groups of the formula —NRC(NR)NR$_2$. Typically, a guanidino group is —NHC(NH)NH$_2$.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aralipathic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula I compounds, for example in their purification by recrystallization. All of these salts may be prepared by conventional means from the corresponding compound according to Formula I by reacting, for example, the appropriate acid or base with the compound according to Formula I. The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometic quantities, such as a monohydrate or a dihydrate, or can include water in random amounts. A "solvate" is a similar composition except that a solvent other that water replaces the water. For example, methanol or ethanol can form an "alcoholate", which can again be stoichiometic or non-stoichiometric.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals.

Isomerism and Tautomerism in Compounds of the Invention

Tautomerism

Within the present invention it is to be understood that a compound of the formula I or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein.

For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

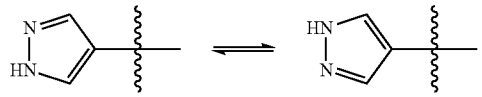 [SMILES: *c1cn[nH]c1 ; *c1cn[nH]c1]

Such tautomerism can also occur with substituted pyrazoles such as 3-methyl, 5-methyl, or 3,5-dimethylpyrazoles, and the like.

Optical Isomerism

It will be understood that when compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

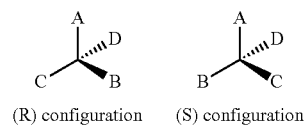

The present invention is meant to encompass diastereomers as well as their racemic and resolved, diastereomerically and enantiomerically pure forms and salts thereof.

Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of formula I which are biologically active in the treatment of cancer or other proliferative disease states.

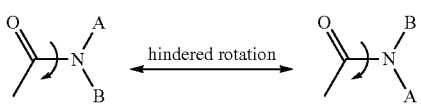

Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

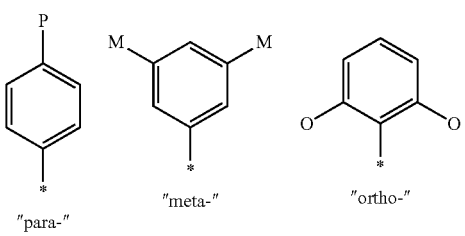

"para-" "meta-" "ortho-"

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

In various embodiments, the compound or set of compounds, such as are used in the inventive methods, can be any one of any of the combinations and/or sub-combinations of the above-listed embodiments.

In various embodiments, the invention provides a compound of Formula (I):

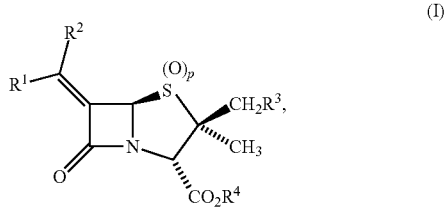

(I)

wherein p is 0, 1, or 2;

$R^1$ and $R^2$ each independently comprises H, alkyl, aryl, cycloalkyl, cycloalkylalkyl, heterocyclyl, or heteroaryl, wherein any alkyl, aryl, cycloalkyl, cycloalkylalkyl, heterocyclyl, or heteroaryl can be independently substituted with 0-3 J;

J is R' except H, haloalkyl, $(CH_2)_n$—OR', $(CH_2)_n$—OC(O)N(R')$_2$, $(CH_2)_n$—CN, $CF_3$, $OCF_3$, O, S, C(O), S(O), methylenedioxy, ethylenedioxy, $(CH_2)_n$—N(R')$_2$, $(CH_2)_n$—SR', $(CH_2)_n$—S(O)R'$, $(CH_2)_n$—S(O)$_2$R', $(CH_2)_n$—S(O)$_2$N(R')$_2$, $(CH_2)_n$—SO$_3$R', $(CH_2)_n$—C(O)R', $(CH_2)_n$—C(O)C(O)R', $(CH_2)_n$—C(O)CH$_2$C(O)R', $(CH_2)_n$—C(S)R', $(CH_2)_n$—C(O)OR', $(CH_2)_n$—OC(O)R', $(CH_2)_n$—C(O)N(R')$_2$, $(CH_2)_n$—OC(O)N(R')$_2$, $(CH_2)_n$—C(S)N(R')$_2$, $(CH_2)_n$—NHC(O)R', $(CH_2)_n$—N(R')N(R')C(O)R', $(CH_2)_n$—N(R')N(R')C(O)OR', $(CH_2)_n$—N(R')N(R')CON(R')$_2$, $(CH_2)_n$—N(R')SO$_2$R', $(CH_2)_n$—N(R')SO$_2$N(R')$_2$, $(CH_2)_n$—N(R')C(O)OR', $(CH_2)_n$—N(R')C(O)R', $(CH_2)_n$—N(R')C(S)R', $(CH_2)_n$—N(R')C(O)N(R')$_2$, $(CH_2)_n$—N(R')C(S)N(R')$_2$, $(CH_2)_n$—N(R')N(COR')COR', $(CH_2)_n$—N(OR')R', $(CH_2)_n$—C(=NH)N(R')$_2$, $(CH_2)_n$—C(O)N(OR')R', $(CH_2)_n$N(R)C(=NR')N(R')$_2$ or $(CH_2)_n$—C(=NOR')R', wherein n is 0 to about 4, and wherein;

each R' is independently at each occurrence hydrogen, $(C_1-C_{12})$-alkyl, $(C_3-C_{10})$-cycloalkyl or $(C_3-C_{10})$-cycloalkenyl, $[(C_3-C_{10})$cycloalkyl or $(C_3-C_{10})$-cycloalkenyl]-$(C_1-C_{12})$-alkyl, $(C_6-C_{10})$-aryl, $(C_6-C_{10})$-aryl-$(C_1-C_{12})$-alkyl, $(C_3-C_{10})$-heterocyclyl, $(C_3-C_{10})$-heterocyclyl-$(C_1-C_{12})$-alkyl, $(C_5-C_{10})$-heteroaryl, or $(C_5-C_{10})$-heteroaryl-$(C_1-C_{12})$-alkyl, wherein any alkyl, cycloalkyl, cycloalkenyl, cycloalkylalkyl, cycloalkenylalkyl, aryl, arylalkyl, heterocyclyl, heterocylylalkyl, heteroaryl, or heteroarylalkyl is substituted with 0-3 substituents selected independently from J; or, two R' groups together with a nitrogen atom to which both R' groups are attached or with two adjacent nitrogen atoms to which each R' group is respectively attached form a mono- or bicyclic ring system;

$R^3$ comprises hydrogen, OH, OC(O)R", OC(O)OR", OC(O)NHR", NHC(O)R", NHC(O)NHR", or NHC(=NH)NHR", where R" is H, $(C_1-C_{12})$alkyl, aryl, heteroaryl, or $(CH_2)_n$NHR''', wherein n=2, 3, or 4 and R'''=H, C(=NH)NH$_2$, C(=NH)H, or $R^3$ comprises $(C_1-C_{12})$-alkyl, $(C_3-C_{10})$-cycloalkyl or $(C_3-C_{10})$-cycloalkenyl, $[(C_3-C_{10})$cycloalkyl or $(C_3-C_{10})$-cycloalkenyl]-$(C_1-C_{12})$-alkyl, $(C_6-C_{10})$-aryl, $(C_6-C_{10})$-aryl-$(C_1-C_{12})$-alkyl, $(C_3-C_{10})$-heterocyclyl, $(C_3-C_{10})$-heterocyclyl-$(C_1-C_{12})$-alkyl, $(C_5-C_{10})$-heteroaryl, or $(C_5-C_{10})$-heteroaryl-$(C_1-C_{12})$-alkyl, wherein R" is substituted with 0-3 substituents selected independently from J; and, $R^4$ is H, a $(C_1-C_6)$alkyl or aryl group, or a pharmaceutically acceptable cation; or, a compound of Formula (II):

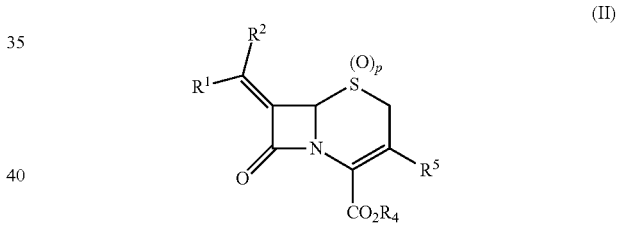

(II)

wherein p, $R^1$, $R^2$, $R^4$, R', and J, are as defined above, and $R^5$ comprises H, alkyl, aryl, cycloalkyl, cycloalkylalkyl, heterocyclyl, or heteroaryl, wherein any alkyl, aryl, cycloalkyl, cycloalkylalkyl, heterocyclyl, or heteroaryl can be independently substituted with 0-3 J;

or a salt, zwitterion, pharmaceutically acceptable salt, hydrate, solvent, tautomer, stereoisomer, or prodrug thereof.

For example, $R^1$, $R^2$, or both can comprise a substituted or unsubstituted heteroaryl. More specifically, $R^1$ or $R^2$, or both, can comprises a substituted or unsubstituted pyridyl. Alternatively, $R^1$ or $R^2$, or both, can comprise a substituted or unsubstituted alkyl, substituted or unsubstituted alkenyl, halo, $S(O)_p(C_1-C_6)$alkyl, C(O)OR', or C(O)N(R')$_2$ group.

In other embodiments, in a compound of Formula (I), $R^3$ can be hydrogen. Or, $R^3$ can be OH, OC(O)R", OC(O)OR", OC(O)NHR", NHC(O)R", NHC(O)NHR", or NHC(=NH)NHR", where R" is H, $(C_1-C_{12})$alkyl, aryl, heteroaryl, or $(CH_2)_n$NHR''', wherein n=2, 3, or 4 and R'''=H, C(=NH)NH$_2$, or C(=NH)H.

In other embodiments the inventive compound can be a compound of Formula (I), wherein n, p, $R^1$, $R^2$, $R^3$, and $R^4$ are as defined herein. For example, a compound of Formula (I) can be a compound wherein one of $R^1$ or $R^2$ is H and another is pyridyl substituted with aminomethyl, $R^3$ comprises OC(O)N(R')$_2$, and R$^4$ is H or M wherein M is a cation. Or, a compound of Formula (I) can be a compound wherein one of R$^1$ or R$^2$ is H and another is pyridyl substituted with aminomethyl, R$^3$ comprises OC(O)N(R')$_2$, and R$^4$ is H or M wherein M is a cation.

In various embodiments, n can be 0, 1 or 2.

In various embodiments, in compounds of Formula (I) and of Formula (II), p can be 2.

In various embodiments, R$^4$ can be a cation; for example R4 can be sodium, potassium, or another pharmacologically acceptable cation.

Alternatively, the inventive compound can be a compound of Formula (II), wherein n, p, R$^1$, R$^2$, R$^4$ and R$^5$ are as defined therein. For example, R$^5$ can be an alkylthio group.

The following examples are provided as illustrations of the inventive compounds and methods. Other embodiments will be apparent to a person of skill in the art based on the disclosure herein. All examples are non-limiting; the invention is defined by the claims as recited below.

EXAMPLES

The following Examples are provided by way of illustration, and do not serve to define limitations on what is claimed, which are expressed in the Claims.

Supporting spectroscopic data include nuclear magnetic resonance (NMR) spectra, observing $^1$H and $^{13}$C nuclei, with resonances expressed as ppm downfield (δ) with respect to tetramethylsilane in the solvent noted, s=singlet, d=doublet, t=triplet, q=quartet, m=multiplet, br=broad, H=relative number of resonating nuclei, J=coupling constant (Hz); and infrared (IR) spectra, obtained as indicated, expressed in wave numbers (cm$^{-1}$).

The following abbreviations are used throughout the Examples:
DAST diethylaminosulfurtrifluoride
DCM dichloromethane
DIPEA di-isopropylethylamine
DMAP 4-(N,N-dimethylamino)pyridine
Et$_3$N triethylamine
EtOAc ethyl acetate
EtOH ethanol
IR infrared spectroscopy
hr hours
MeOH methanol
IPA, i-PrOH isopropanol
min minutes
MHz megahertz
mCPBA meta-chloroperbenzoic acid
NMR nuclear magnetic resonance
THF tetrahydrofuran
TLC thin layer chromatography
TFA trifluoroacetic acid Scheme 1

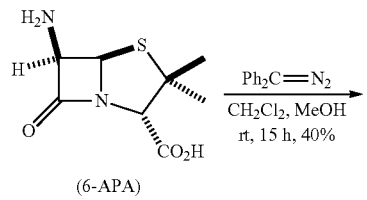

(6-APA)

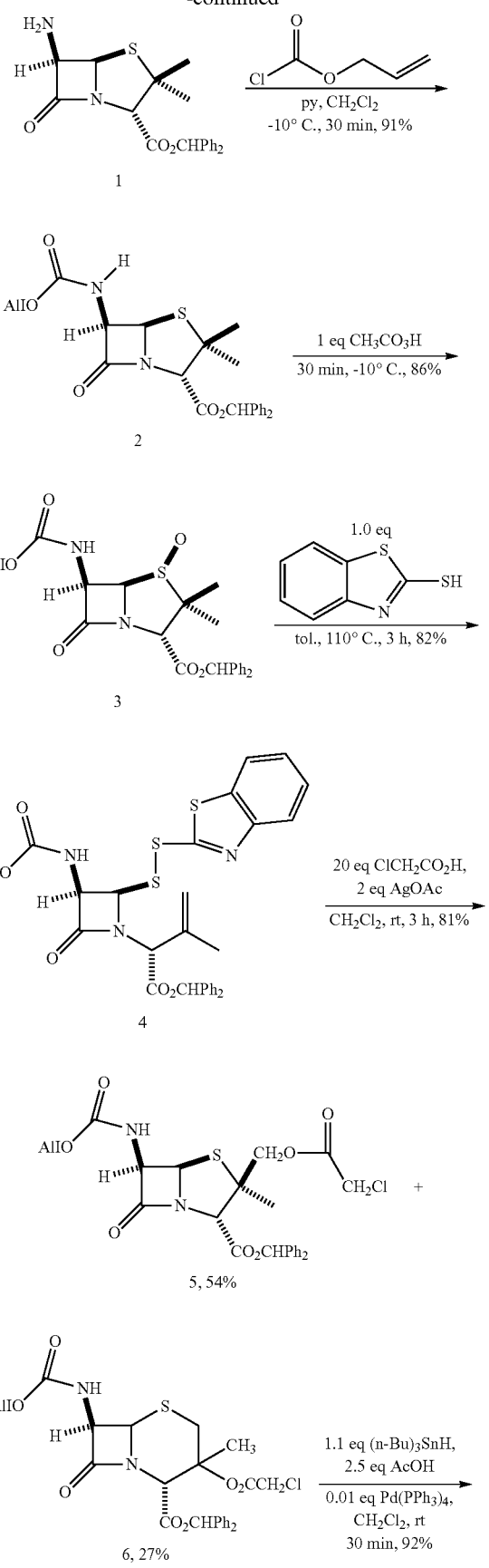

-continued

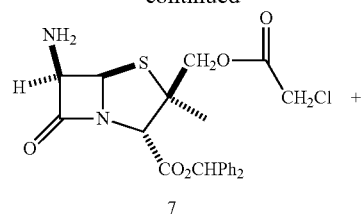
7

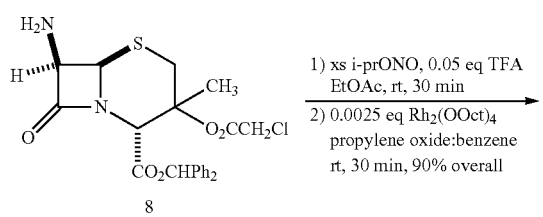
8

1) xs i-prONO, 0.05 eq TFA
   EtOAc, rt, 30 min
2) 0.0025 eq Rh₂(OOct)₄
   propylene oxide:benzene
   rt, 30 min, 90% overall

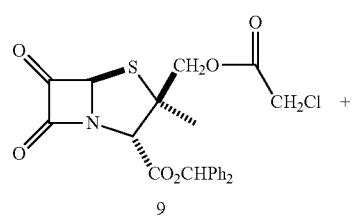
9

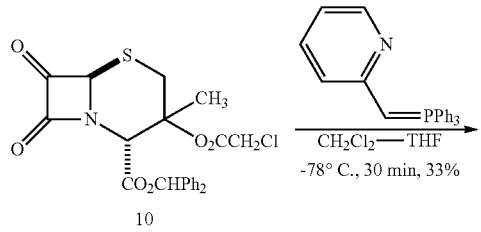 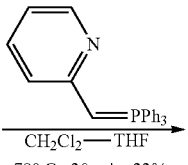
10

$\xrightarrow[\text{CH}_2\text{Cl}_2\text{—THF}]{\text{-78° C., 30 min, 33%}}$

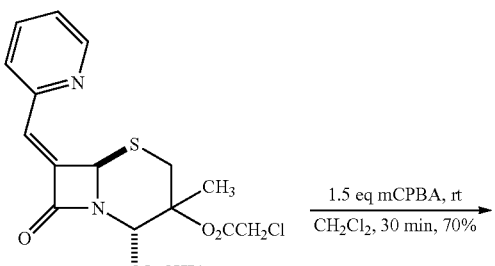
11

12

$\xrightarrow[\text{CH}_2\text{Cl}_2, \text{30 min, 70\%}]{1.5 \text{ eq mCPBA, rt}}$ -continued

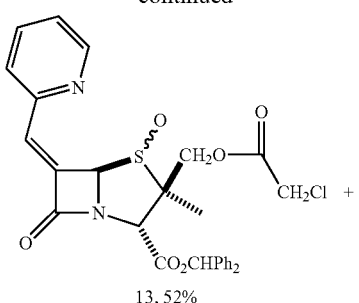
13, 52%

14, 5%
(Separable by Column Chromatography)

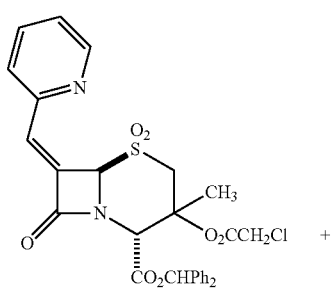
15, 13%

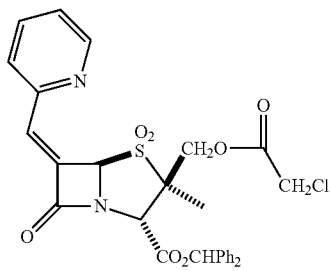
13

$\xrightarrow[\text{CH}_2\text{Cl}_2, 12 \text{ h, 85\%}]{1.2 \text{ eq mCPBA, rt}}$

15

$\xrightarrow[\text{EtOH, 60° C., 20 min, 65\%}]{5 \text{ eq } S=C(NH_2)_2}$

-continued

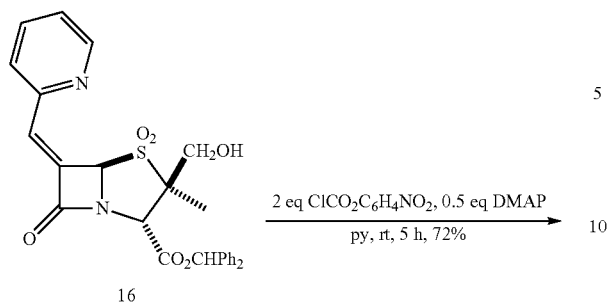

16

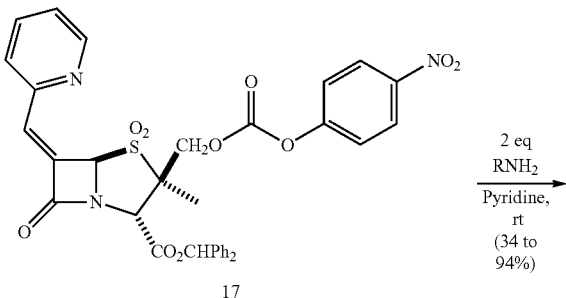

17

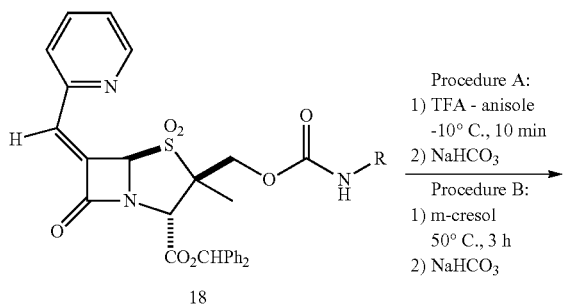

18

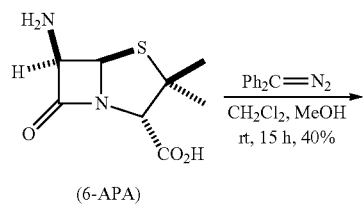

19

Example 1

Preparation of Benzhydryl 6-aminopenicillinate (1)

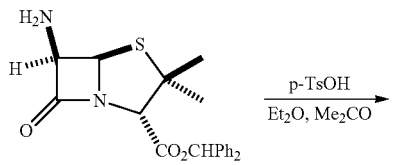

(6-APA)

-continued

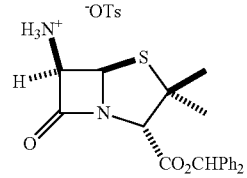

1

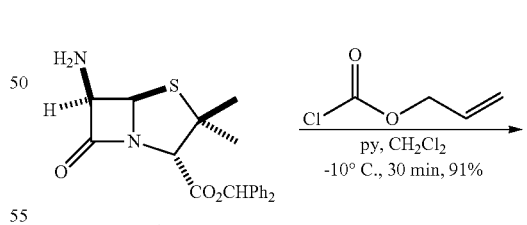

To a rapidly stirred (overhead stirrer) suspension of 6-aminopenicillanic acid (6-APA, 200 g, 0.93 mol) dissolved in 1 L of MeOH and 1 L of $CH_2Cl_2$ was added a solution of diphenyldiazomethane (180.5 g, 0.93 mol) dissolved in 1 L of $CH_2Cl_2$. The resultant solution was allowed to stir overnight, during which time the color of the reaction changed from pink to yellow. Then the reaction mixture was filtered to remove unreacted 6-APA, and concentrated in vacuo. The remaining benzhydryl 6-aminopenicillinate was then dissolved in ether (1 L) and treated, with stirring, with a solution of p-toluenesulfonic acid monohydrate (177 g, 0.93 mol) in acetone (500 mL) to produce the corresponding tosylate salt (198 g, 40% yield), which was collected by filtration and washed extensively with ether. This tosylate salt was then converted to the free base as needed for subsequent experiments by treatment with excess aq $NaHCO_3$ in the presence of EtOAc, and subsequent concentration of the EtOAc layer.

$^1$H NMR of 1: (400 MHz, $CDCl_3$): δ 1.26 (s, 3H), 1.63 (s, 3H), 1.96 (br s, 2H), 4.53 (d, 1H, J=4.5 Hz), 4.56 (s, 1H), 5.53 (d, 1H, J=4.5 Hz), 7.00 (s, 1H) 7.18-7.27 (m, 10H).

Example 2

Preparation of Benzhydryl 6-(Allyloxycarbonylamino)penicillinate (2)

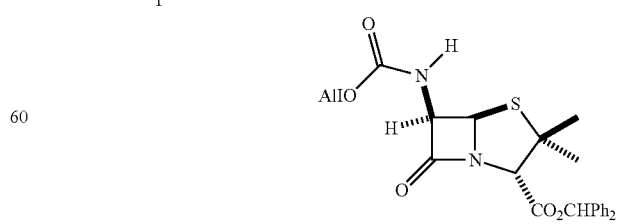

2

To a chilled (−10° C.) solution of amine 1 (150 g, 392.6 mmol) in CH₂Cl₂ (600 mL) was added pyridine (35 mL, 431.8 mmol). Then, allyl chloroformate (43.5 mL, 412.2 mmol) was added dropwise. After completion of the reaction (30 min), the reaction mixture was poured into cold 1.0 M HCl solution (500 mL). The layers were separated, and the organic layer was washed with aq NaHCO₃ (500 mL), water (500 mL) and brine (500 mL). The organic layer was separated, dried over Na₂SO₄, concentrated to give 165 g of crude product (91% yield), and used for the next reaction without further purification.

¹H NMR (400 MHz, CDCl₃): δ 1.2 (s, 3H), 1.55 (s, 3H), 4.46 (s, 1H), 4.52 (d, 2H, J=4.54 Hz), 5.15-5.27 (dd, 1H, J=10.31 Hz, J=17.12 Hz), 5.44 (s, 1H), 5.49 (s, 1H), 5.83-5.84 (m, 1H), 6.87 (s, 1H) 7.18-7.27 (m, 10H).

Example 3

Preparation of Benzhydryl 6-(Allyloxycarbonylamino)penicillinate-1-oxide (3)

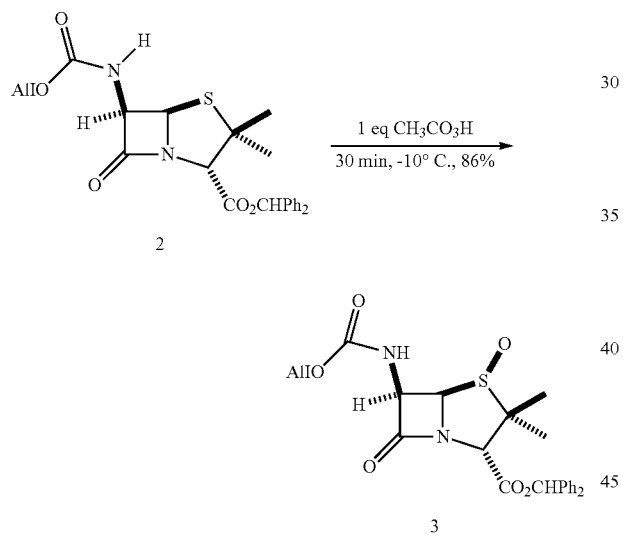

To a chilled (−10° C.) solution of sulfide 2 (165 g, 354 mmol) in CH₂Cl₂ (500 mL) was added peracetic acid (109 mL of 40-45% solution) slowly. The reaction mixture was stirred for an additional 10 min, then sodium meta-bisulfite solution (30 g, in 500 mL water) was added. The layers were separated and the organic layer was washed with aq NaHCO₃ then washed with water (500 mL) followed by brine solution (500 mL). The organic layer was dried over Na₂SO₄, concentrated and purified by column chromatography to remove sulfone (about 5-10%) to produce 147 g (86% yield) of product.

¹H NMR (400 MHz, CDCl₃): δ 0.91 (s, 3H), 1.69 (s, 3H), 4.59 (d, 2H, J=5.38 Hz), 4.75 (s, 1H), 5.00 (d, 1H, J=4.56 Hz), 5.21-5.33 (dd, 1H, J=10.42 Hz, J=16.65 Hz), 5.77 (d, 1H, J=4.41 Hz, J=6.23 Hz), 5.86-5.9 (m, 1H), 6.31 (d, 1H, J=10.48 Hz), 6.99 (s, 1H), 7.32-7.37 (m, 10H).

Example 4

Preparation of (R)-benzhydryl-2-((2R,3R)-3-(allyloxycarbonyl)amino-2-(benzo[d]thiazol-2-yldisulfanyl)-4-oxoazetidin-1-yl)-3-methylbut-3-enoate (4)

To a solution of sulfoxide 3 (100 g, 207.5 mmol) in toluene was added mercaptobenzothiazole (34.5 g, 207.5 mmol) and the resultant solution was refluxed for 3 h, with the removal of water by a Dean Stark trap. The toluene was subsequently removed under reduced pressure and the residue was purified by column chromatography using 2% EtOAc in CH₂Cl₂ to give 108 g of product (82% yield).

¹H NMR (400 MHz, CDCl₃): δ 1.9 (s, 3H), 4.53-4.59 (m, 2H), 4.94-5.32 (m, 6H), 5.54 (d, 1H, J=4.55 Hz), 5.86-5.98 (m, 1H), 6.58 (d, 1H, J=8.75 Hz), 6.9 (s, 1H), 7.2-7.4 (m, 12H), 7.70 (d, 1H, J=7.92 Hz), 7.86 (d, 1H, J=8.09 Hz).

Example 5

Preparation of Benzhydryl 6-(Allyloxycarbonylamino)-2'β-(chloroacetoxy)penicillinate (5) and Benzhydryl 7-(Allyloxycarbonylamino)-3-(chloroacetoxy)-3-methylcephalosporanate (6)

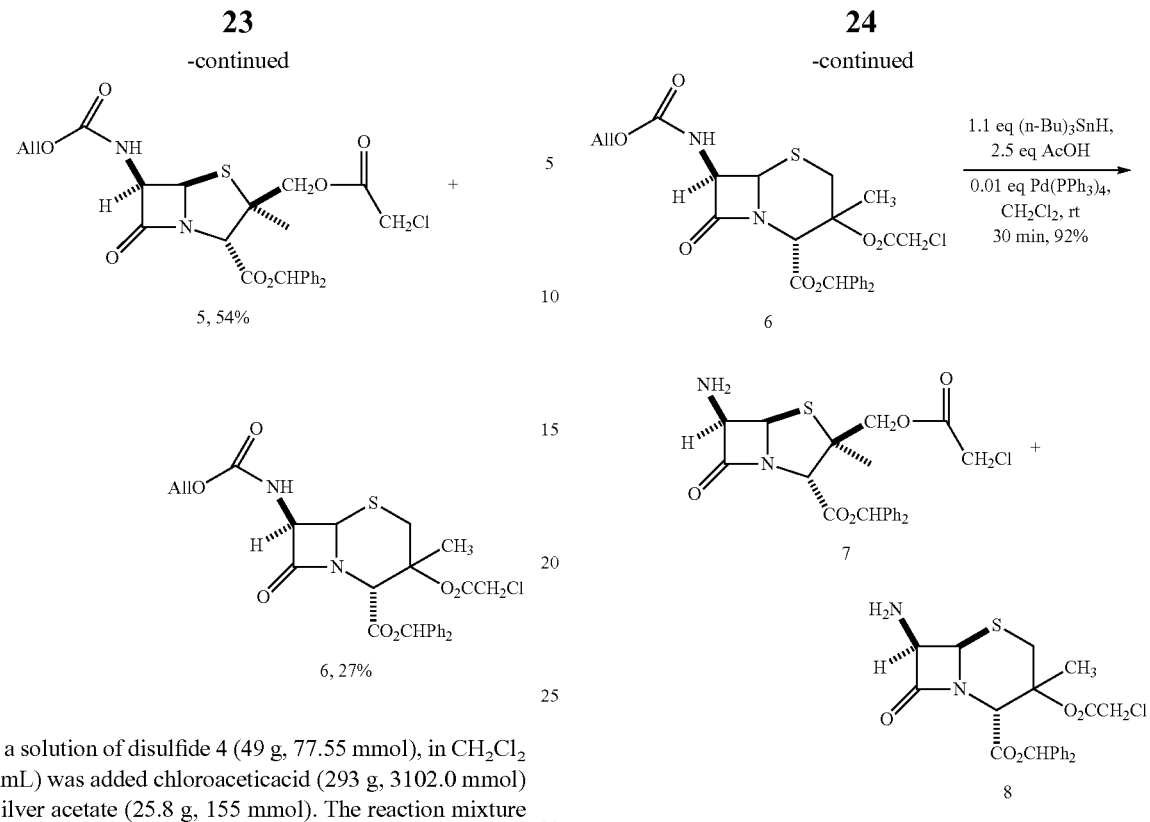

To a solution of disulfide 4 (49 g, 77.55 mmol), in CH$_2$Cl$_2$ (500 mL) was added chloroaceticacid (293 g, 3102.0 mmol) and silver acetate (25.8 g, 155 mmol). The reaction mixture was stirred for 3.0 h at room temperature and the suspended silver salts were then removed by filtration. The CH$_2$Cl$_2$ layer was slowly neutralized with aq NaHCO$_3$ solution to pH: 8.0, then the layers were separated, and the organic layer was washed with water (500 mL) followed by brine (500 mL). The organic layer was dried over Na$_2$SO$_4$, concentrated in vacuo, and the residue was purified by silica gel column chromatography using 2% EtOAc in CH$_2$Cl$_2$ an eluent to give 35.0 g (81% yield) of penam and cepham (2:1) mixture.

$^1$H NMR (400 MHz, CDCl$_3$): δ 1.28 (s, 3H), 3.92 (d, 1H, J=11.4 Hz), 4.05 (d, 1H, J=8.3 Hz), 4.12 (s, 2H), 4.40 (d, 1H, J=11.3 Hz), 4.60 (d, 1H, J=5.16 Hz), 4.77 (s, 1H), 5.23-5.35 (m, 3H), 5.65 (d, 1H, J=4 Hz), 5.88-5.92 (m, 1H), 6.94 (s, 1H), 7.34-7.36 (m, 10H).

Example 6

Preparation of Benzhydryl 6-amino-2'β-(chloroacetoxy)penicillinate (7) and Benzhydryl 7-amino-3-(chloroacetoxy)-3-methylcephalosporanate (8)

To a solution of allyl carbamates 5 and 6 (32.0 g, 57.24 mmol), in CH$_2$Cl$_2$ (400 mL) were added acetic acid (8.5 mL, 143.0 mmol), tributyltin hydride (16.9 mL, 62.9 mmol) and tetrakis triphenylphosphine palladium (660 mg, 1 mol %). The reaction was observed to evolve gas. After completion of such gas evolution the reaction mixture was stirred another 15 min. Then saturated NaHCO$_3$ solution (300 mL) was carefully added, followed by brine (300 mL). The layers were separated and the organic layer was dried over Na$_2$SO$_4$, concentrated, and purified on silica gel using 20% EtOAc in CH$_2$Cl$_2$ as an eluent to produce 25.0 g (92% yield).

$^1$H NMR (400 MHz, CDCl$_3$): δ 1.28 (s, 3H), 2.0 (brs, 2H), 3.98 (d, 1H, J=11.5 Hz), 4.14 (s, 2H), 4.35 (d, 1H, J=11.5), 4.55 (d, 1H, J=3.4 Hz) 4.79 (s, 1H) 5.61 (d, 1H, J=3.4), 6.94 (s, 1H), 7.34-7.35 (m, 10H).

Example 7

Preparation of Benzhydryl 6-oxo-2'β-(chloroacetoxy)penicillinate (9) and Benzhydryl 7-oxo-3-(chloroacetoxy)-3-methylcephalosporanate (10)

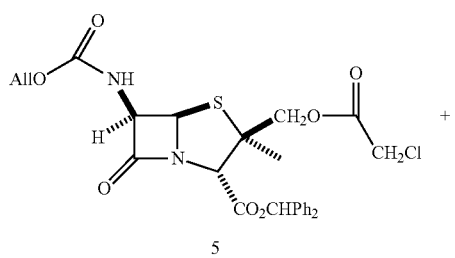

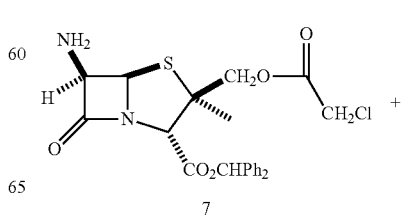

-continued

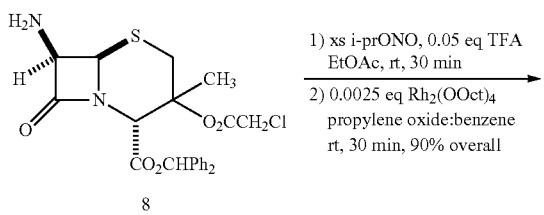
8

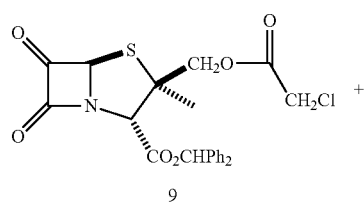
9

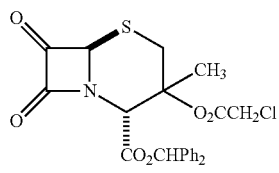
10

Preparation of the intermediate 6-diazopenicillinate and 7-diazocephalosporinate: To a solution of amines 7 and 8 (24 g, 50.6 mmol) in ethyl acetate (400 mL) were added catalytic trifluoroacetic acid (200 µL) and isopropyl nitrite (48 mL, 30-50% in $CH_2Cl_2$). The reaction was then stirred at room temperature while monitoring by TLC over the course of approximately 30 min. After completion of the reaction, ethyl acetate was removed under reduced pressure. This compound was used without further purification.

$^1$H NMR (400 MHz, $CDCl_3$): δ 1.2 (s, 3H), 3.99 (d, 1H, J=11.71 Hz), 4.1-4.12 (m, 2H), 4.32 (d, 1H, J=11.72), 4.75 (s, 1H), 6.2 (s, 1H), 6.92 (s, 1H), 7.29-7.38 (m, 10H).

Oxidation of the Diazo Functionality to the Ketones:

The resultant diazo compounds were then immediately dissolved in anhydrous benzene (150 mL) and propylene oxide (150 mL) and treated with catalytic amount of rhodium octanoate (100 mg). This reaction was observed to evolve gas. After the completion of such gas evolution, the benzene solvent was removed in vacuo. The solid ketone (24 g, ~90% pure, 90% yield) was used without further purification.

$^1$H NMR (400 MHz, $CDCl_3$): ☐ 1.29 (s, 3H), 3.87 (d, 1H, J=11.82), 4.00-4.13 (dd, 2H, J=15.26 Hz, J=20.86 Hz), 4.22 (d, 1H, J=11.83), 5.1 (s, 1H), 5.81 (s, 1H), 6.98 (s, 1H), 7.3-7.38 (m, 10H).

Example 8

Preparation of Benzhydryl 6-(α-pyridylmethylidene)-2'β-(chloroacetoxy)penicillinate (11a) and Benzhydryl 7-(α-pyridylmethylidene)-3-(chloroacetoxy)-3-methylcephalosporanate (12a)

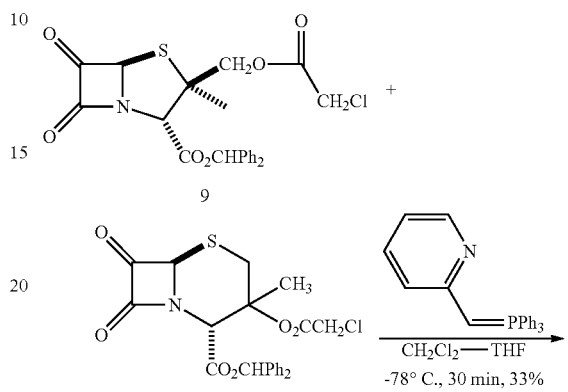
9

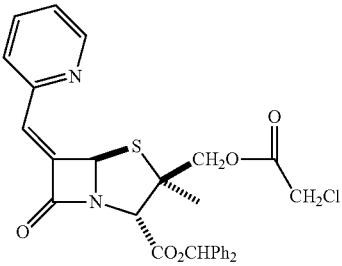
10

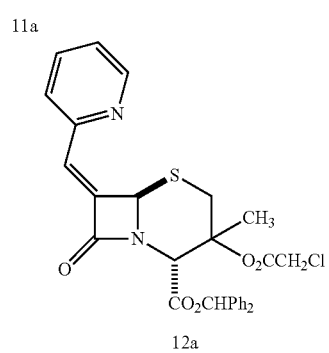
11a

12a

To a solution of triphenyl(2-pyridylmethyl)phosphonium chloride (19.5 g, 50 mmol), in dry THF (200 mL) was added potassium tert-butoxide (4.48 g, 40.0 mmol) and reaction mixture was stirred at room temperature for 2 h to generate the corresponding ylide, and then chilled to −78° C. In a separate flask, the ketone 9 (50 mmol) was dissolved in dry $CH_2Cl_2$ (400 mL) and the resultant solution also cooled to −78° C. The cold (−78° C.) solution of the above Wittig reagent was then slowly added to ketone at −78° C. by cannula and the reaction mixture stirred at this temperature for 30 min. Then a saturated aqueous solution of $NH_4Cl$ was added and the reaction mixture slowly warmed to room temperature with stirring. The layers were separated and the aqueous layers extracted with an additional portion of $CH_2Cl_2$. The combined organic layers were washed with water (400 mL) and brine (400 mL) and then dried over $Na_2SO_4$. The solution was then concentrated in vacuo and purified by column chromatography using 2% EtOAc-CH$_2$Cl$_2$ as eluent to give 9.0 g (33% yield) of product. This penam was contaminated with 25-30% of cepham.

$^1$H NMR (400 MHz, CDCl$_3$): δ 1.23 (s, 3H), 3.92 (d, 1H, J=11.6 Hz), 4.05-4.12 (m, 2H), 4.22 (d, 1H, J=11.6), 4.99 (s, 1H), 6.31 (s, 1H), 6.94 (s, 1H), 7.3-7.43 (m, 13H), 7.69-7.73 (t of d, 1H, J=1.6 Hz, J=7.6 Hz), 8.63 (d, 1H, J=3.36 Hz).

Example 9

Preparation of Benzhydryl 6-(α-pyridylmethylidene)-2'β-(chloroacetoxy)penicillinate-1-oxide (13a) and Benzhydryl 7-(α-pyridylmethylidene)-3-(chloroacetoxy)-3-methylcephalosporanate-1-oxide (14a)

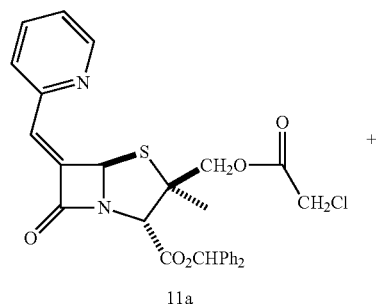

11a

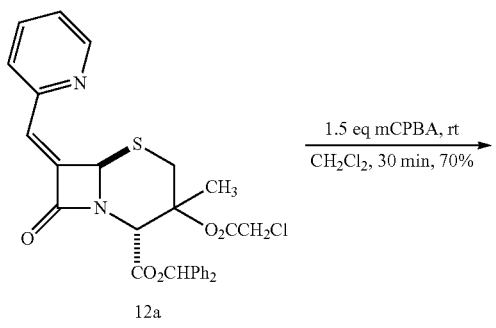

12a 1.5 eq mCPBA, rt
CH$_2$Cl$_2$, 30 min, 70%

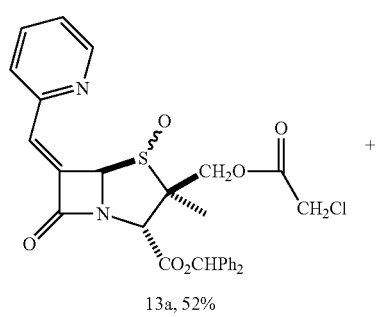

13a, 52%

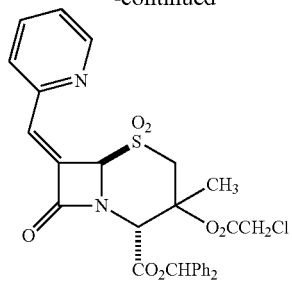

14a, 5%

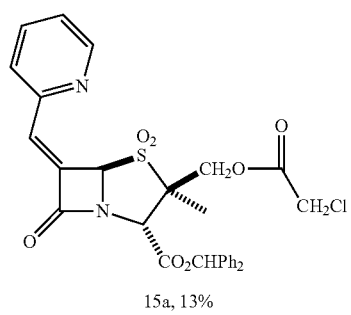

15a, 13%

To a solution of sulfides 11a and 12a (8 g, 14.5 mmol), in CH$_2$Cl$_2$ (100 mL) were added mCPBA (4.85 g of 77% mCPBA, 21.75 mmol) and the mixture was stirred at room temperature for 30 min. The reaction mixture was quenched with aqueous sodium metabisulfite solution (5 g NaHSO$_3$ in 100 mL water) and the layers were separated. The organic layer was washed with aqueous NaHCO$_3$ (100 mL) followed by water and brine (100 mL each). Then it was dried over Na$_2$SO$_4$, concentrated, and purified by column chromatography using 10% ethyl acetate-CH$_2$Cl$_2$ as eluent to give two different penam sulfoxides 13a (4.22 g), penam sulfone 15a (1.08 g) and cepham sulfone 14a (0.43 g), (at this stage cepham was separated from penam).

Sulfoxide 1:

$^1$H NMR (400 MHz, CDCl$_3$): δ 1.19 (s, 3H), 3.98-4.15 (dd, 2H, J=11.9 Hz, J=12.3 Hz), 4.25-4.43 (AB q, 2H, J=11.97 Hz, J=12.39 Hz), 4.86 (s, 1H), 5.85 (s, 1H), 6.97 (s, 1H), 7.15 (s, 1H), 7.26-7.45 (m, 12H), 7.74-7.78 (t of d, 1H, J=6.0 Hz, J=1.7 Hz), 8.78 (d, 1H, J=4.5 Hz).

$^{13}$C NMR (100 MHz, CDCl$_3$): δ 12.54, 40.42, 63.73, 69.3, 74.81, 79.17, 88.97, 124.34, 126.46, 127.23, 127.51, 128.3, 128.45, 128.6, 128.71, 137.05, 137.09, 138.78, 139.0, 150.74, 151.56, 166.4, 166.53, 166.64.

Sulfoxide 2:

$^1$H NMR (400 MHz, CDCl$_3$): δ 1.05 (s, 3H), 4.06 (s, 2H), 4.59 (d, 1H, J=11.8 Hz), 4.78 (s, 1H), 4.86 (d, 2H, J=11.8 Hz), 5.91 (s, 1H), 7.01 (s, 1H), 7.31-7.43 (m, 12H), 7.70-7.74 (t of d, 1H, J=6.0 Hz, J=1.6 Hz), 8.65 (d, 1H, J=3.9 Hz)

$^{13}$C NMR (100 MHz, CDCl$_3$): δ 13.39, 40.46, 63.09, 63.55, 75.23, 79.11, 82.62, 124.16, 126.98, 127.66, 128.13, 128.33, 128.58, 128.69, 128.81, 134.00, 137.08, 138.79, 138.98, 150.44, 152.24, 166.3, 167.18, 167.51.

Example 10

Preparation of Benzhydryl 6-(α-pyridylmethylidene)-2'β-(chloroacetoxy)penicillinate-1,1-dioxide (15a)

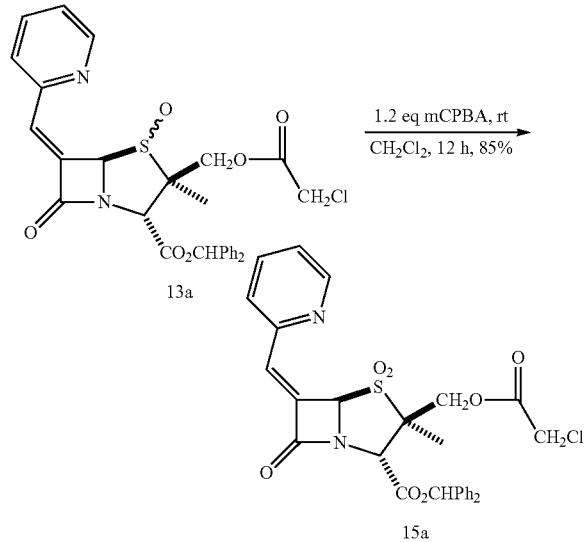

To a solution of sulfoxides 13a (4.22 g, 7.46 mmol), in CH$_2$Cl$_2$ (50 mL) was added mCPBA (1.99 g, 8.88 mmol) and reaction mixture was stirred at room temperature overnight. The reaction mixture was quenched with aqueous sodium metabisulfite solution (5 g NaHSO$_3$, in 100 mL water) the layers were separated, and the organic layer washed with aqueous NaHCO$_3$ solution (100 mL) followed by water and brine (100 mL each). Then it was dried over Na$_2$SO$_4$, concentrated and purified by column chromatography using 5% ethyl acetate-CH$_2$Cl$_2$ as eluent to give 3.67 g (85% yield) of pure product.

$^1$H NMR (400 MHz, CDCl$_3$): δ 1.24 (s, 3H), 4.07-4.08 (m, 2H) 4.49 (d, 1H, J=12.1 Hz), 4.71 (d, 1H, J=12.1 Hz), 4.77 (s, 1H), 5.77 (s, 1H), 7.0 (s, 1H), 7.25-7.37 (m, 13H), 7.70-7.75 (t of d, J=5.9 Hz, J=1.8 Hz), 8.67 (d, 1H, J=3.5 Hz).

$^{13}$C NMR (100 MHz, CDCl$_3$): δ 15.73, 40.47, 59.7, 64.88, 65.87, 73.8, 77.31, 79.41, 125.03, 126.36, 126.53, 127.02, 127.56, 128.45, 128.48, 128.71, 128.83, 129.94, 133.45, 137.03, 138.52, 138.66, 150.55, 150.74, 166.01, 166.39, 167.47.

Example 11

Preparation of Benzhydryl 6-(α-pyridylmethylidene)-2'β-hydroxypenicillinate-1,1-dioxide (16a)

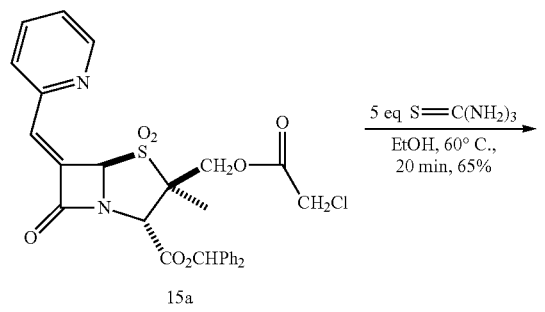

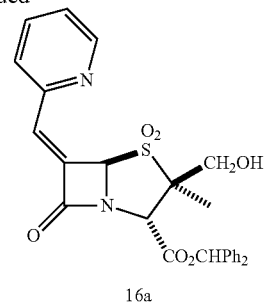

To a solution of sulfone 15a (4.52 g, 7.77 mmol), in ethanol (90 mL) was added thiourea (2.95 g, 38.8 mmol) and reaction mixture was heated to 60° C. for 20 min. After completion of the reaction ethanol was removed under reduced pressure and to the residue was added water (100 mL) and CH$_2$Cl$_2$ (150 mL). The layers were separated, and the organic layer was washed with water (100 mL) followed by brine (100 mL). Then it was dried over Na$_2$SO$_4$, concentrated and purified by column chromatography using 5% ethyl acetate-CH$_2$Cl$_2$ as eluent to give 2.56 g (65% yield) product.

$^1$H NMR (400 MHz, CDCl$_3$): δ 1.09 (s, 3H), 2.73 (bs, 1H), 3.78-4.04 (AB q, 2H), 5.22 (s, 1H), 5.72 (s, 1H), 7.0 (s, 1H), 7.29-7.36 (m, 13H), 7.68-7.71 (t of d, J=7.7 Hz, J=1.6 Hz), 8.67 (d, 1H, J=4 Hz).

$^{13}$C NMR (100 MHz, CDCl$_3$): δ 15.65, 58.23, 63.35, 68.13, 73.67, 78.88, 124.89, 126.21, 126.81, 127.57, 128.23, 128.56, 128.6, 128.72, 129.66, 133.37, 136.99, 138.68, 138.88, 150.43, 150.75, 166.71, 167.53.

Example 12

Preparation of Benzhydryl 6-(α-Pyridylmethylidene)-2'β-((4-nitrophenoxy)carbonyloxy)penicillinate-1,1-dioxide (17a)

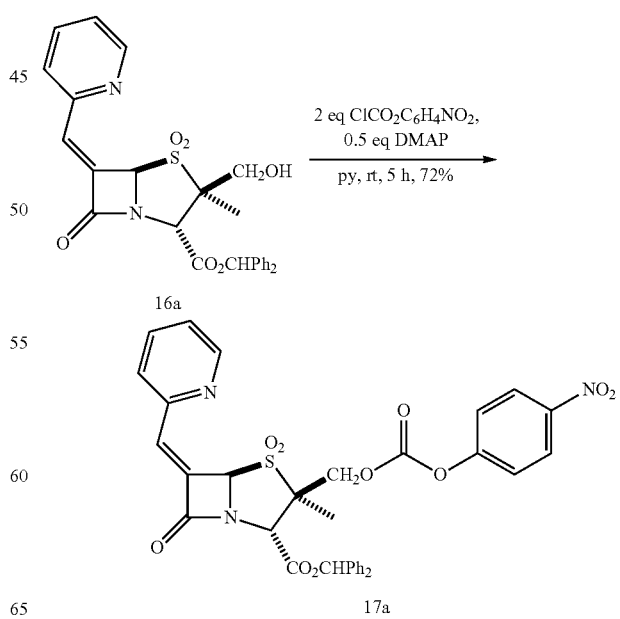

To a solution of alcohol 16a (680 mg, 1.35 mmol) in pyridine (12.0 mL) was added p-nitrophenyl chloroformate (542 mg, 2.7 mmol) and DMAP (82 mg, 0.674 mmol) at room temperature. The reaction mixture was stirred for 5 h at rt then diluted with $CH_2Cl_2$ (50 mL) and washed with water and brine (50 mL each). The organic layer was dried over $Na_2SO_4$, concentrated and purified by silica gel column chromatography using 2% EtOAc in $CH_2Cl_2$ to give 650 mg of product (72% yield).

$^1$H NMR (400 MHz, $CDCl_3$): δ 1.32 (s, 3H), 4.63 (d, 1H, J=12.0 Hz) 4.77 (d, 1H, J=12.0 Hz), 4.83 (s, 1H), 5.79 (s, 1H), 7.01 (s, 1H), 7.25-7.39 (m, 15H), 7.73 (t, 1H, J=5.92 Hz), 8.24 (d, 2H, J=7.07 Hz), 8.68 (d, 1H, J=3.86 Hz).
$^{13}$C NMR (100 MHz, $CDCl_3$): δ 15.72, 59.34, 65.91, 67.34, 73.69, 79.45, 115.58, 121.75, 125.09, 125.29, 126.13, 126.37, 127.02, 127.49, 128.48, 128.68, 128.71, 128.82, 130.24, 133.07, 137.09, 138.52, 138.65, 145.54, 150.55, 150.67, 151.58, 155.23, 166.02, 167.59.

TABLE 1

Preparation of Compounds 19(a-m)

| R—$NH_2$ | time/temp | Coupling yield | | Deprotection yield |
|---|---|---|---|---|
| 2-amino-1,3,4-thiadiazole | 2 h/rt | 53 | thiadiazole carbamate | 11 |
| 4-aminopyridine | 1 h/rt | 71 | 4-pyridyl carbamate | 39 |

TABLE 1-continued
| Amine | Conditions | Yield (%) | Product | Yield (%) |
|---|---|---|---|---|
| 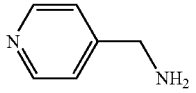 | 10 min/rt | 85 | 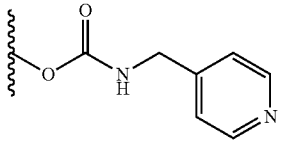 [SMILES: *OC(=O)NCc1ccncc1] | 40 |
| 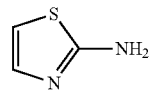 | 1 h/rt | 34 | 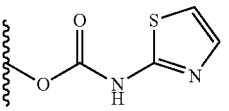 [SMILES: *OC(=O)Nc1nccs1] | 59 |
| 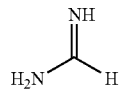 | 1 h/rt | 36 | 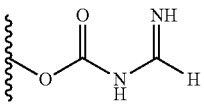 [SMILES: *OC(=O)NC=N] | 30 |
| $H_2N-NH_2$ | 1 h/0° C. | 45 | 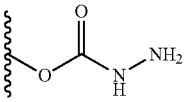 | 40 |
| 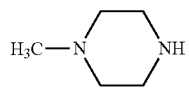 | 10 min/0° C. | 94 | 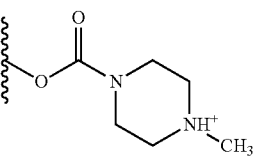 [SMILES: *OC(=O)N1CC[NH+](C)CC1] | 71 |
| 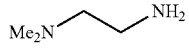 | 10 min/0° C. | 84 | 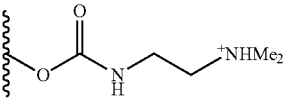 | 37 |
| 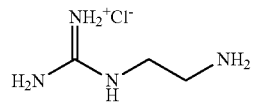 | 10 min/rt | 62 | 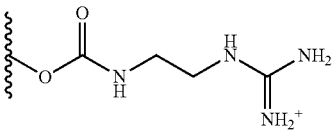 | 31 |
| 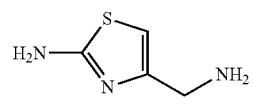 | 10 min/rt | 70 | 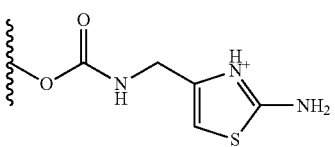 | 51 |
| 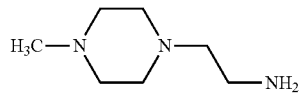 | 10 min/rt | 88 | 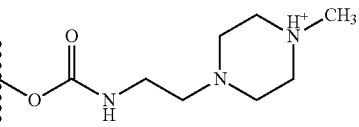 | 19 |
| 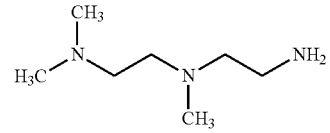 | 10 min/rt | 62 | 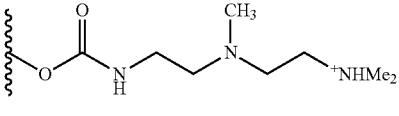 | 15 |
| 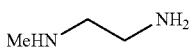 | 10 min/rt | 80 | 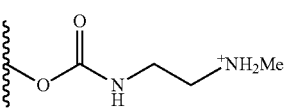 | 37 |

Example 13

Preparation of Benzhydryl 6-(α-Pyridylmethylidene)-2'β-aminocarbonyloxy)penicillinate-1,1-dioxide (18(a-m))

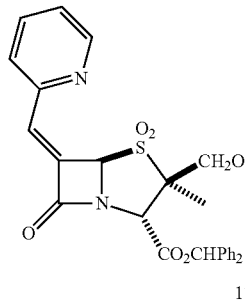

17a $\xrightarrow{\begin{array}{c}2 \text{ eq} \\ R^b NH_2 \\ \text{py,} \\ \text{rt,} \\ 10 \text{ min}\end{array}}$

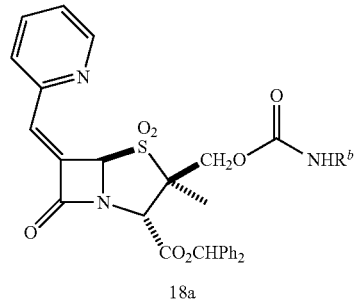

18a

General Coupling Procedure: To a solution of p-nitrophenyl carbonate 17a (1.0 eq) in pyridine (2.0 mL) was added amine (2.0 eq) and the reaction mixture was stirred for 10 min at rt. The reaction mixture was then diluted with $CH_2Cl_2$ and washed with water and brine. The organic layer was dried over $Na_2SO_4$, concentrated and purified by column chromatography using 50% EtOAc in $CH_2Cl_2$ as eluent to obtain pure product.

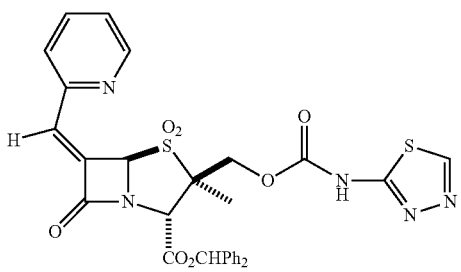

18a $^1$H NMR (400 MHz, $CDCl_3$): δ 1.25 (s, 3H), 4.48 (d, 1H, J=11.92 Hz), 4.59 (d, 1H, J=11.92 Hz), 4.79 (s, 1H), 5.78 (s, 1H), 6.97 (s, 1H), 7.26-7.36 (m, 14H), 7.67-7.71 (t, 1H, J=5.9 Hz), 8.67 (d, 1H, J=3.7 Hz).

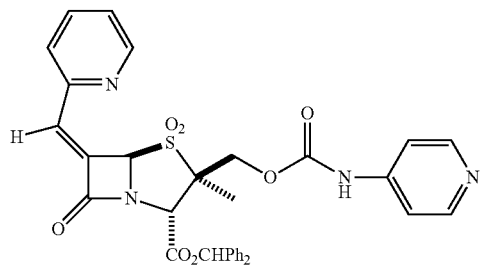

18b $^1$H NMR (400 MHz, $CDCl_3$): δ 1.13 (s, 3H), 4.28 (d, 1H, J=11.92 Hz), 4.68 (d, 1H, J=11.92 Hz), 4.85 (s, 1H), 5.75 (s, 1H), 6.93 (s, 1H), 7.16-7.34 (m, 14H), 7.61-7.65 (t, 1H, J=6.06 Hz), 7.67 (s, 1H), 8.39 (brs, 2H), 8.61-8.62 (d, 1H, J=3.92 Hz).

$^{13}$C NMR (100 MHz, $CDCl_3$): δ 15.69, 60.18, 65.38, 66.29, 74.26, 79.47, 125.04, 126.45, 127.08, 127.56, 128.46, 128.66, 128.69, 128.79, 129.66, 133.78, 136.99, 138.45, 138.62, 144.92, 150.5, 150.7, 151.25, 166.02, 168.09.

IR (thin film): 1211.06, 1332.85, 1527.28, 1596.01, 1746.78, 1784.34, 2927.15 $cm^{-1}$.

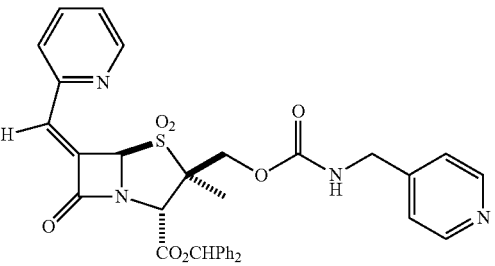

18c $^1$H NMR (400 MHz, $CDCl_3$): δ 1.19 (s, 3H), 4.29-4.38 (m, 3H), 4.68 (d, 1H, J=11.91 Hz) 4.91 (s, 1H), 5.61 (t, 1H, J=6.06 Hz), 5.80 (s, 1H), 6.99 (s, 1H), 7.15-7.4 (m, 15H), 7.71 (t, 1H, J=1.73 Hz), 8.51 (brs, 2H), 8.69 (d, 1H, J=3.97 Hz).

$^{13}$C NMR (100 MHz, $CDCl_3$): δ 15.66, 43.77, 60.39, 65.43, 66.32, 74.28, 77.32, 79.34, 121.93, 124.98, 126.36, 127.1, 127.55, 128.42, 128.59, 128.67, 128.75, 129.36, 134.08, 136.97, 138.51, 138.68, 147.3, 149.97, 150.51, 150.76, 155.11, 166.14, 167.77.

IR (thin film): 912.03, 1166.41, 1250.57, 1330.18, 1731.71, 1782.41, 3386.38 $cm^{-1}$.

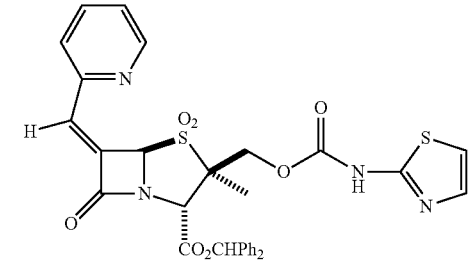

18d $^1$H NMR (400 MHz, $CDCl_3$): δ 1.19 (s, 3H), 4.55 (d, 1H, J=12.04 Hz), 4.72 (s, 1H), 4.83 (d, 1H, J=12.08 Hz), 5.72 (s,

1H), 6.8 (d, 1H), 6.94 (s, 1H), 7.18-7.37 (m, 13H), 7.51 (d, 1H, J=3.59 Hz), 7.65 (t, 1H, J=5.96 Hz), 8.61 (d, 1H, J=3.76 Hz).

$^{13}$C NMR (100 MHz, CDCl$_3$): δ 15.51, 59.75, 64.91, 66.36, 73.84, 79.48, 124.98, 126.38, 127.05, 127.65, 128.41, 128.65, 128.69, 128.82, 129.99, 133.45, 136.99, 137.97, 138.54, 138.63, 150.53, 150.8, 166.0, 167.76.

IR (thin film): 1225.94, 1331.02, 1450.98, 1784.47, 2924.68 cm$^{-1}$.

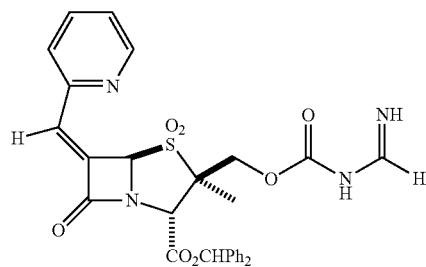

18e $^1$H NMR (400 MHz, CDCl$_3$): δ 1.21 (s, 3H), 1.67 (brs, 1H), 4.40 (d, 1H, J=11.88 Hz), 4.76 (d 1H, J=11.88 Hz), 4.85 (s, 1H), 5.81 (s, 1H), 7.0 (s, 1H), 7.26-7.4 (m, 13H), 7.73 (t, 1H, J=5.94 Hz), 8.01 (brs, 1H), 8.68 (d, 1H, J=3.0 Hz), 8.90 (d, 1H, J=10.14 Hz).

$^{13}$C NMR (100 MHz, CDCl$_3$): δ 15.6, 60.07, 65.83, 66.1, 74.24, 77.31, 79.51, 125.11, 126.52, 127.1, 127.53, 127.64, 128.51, 128.72, 128.83, 129.94, 137.05, 138.39, 138.58, 150.53, 150.68, 162.0, 165.9.

IR (thin film): 1202.55, 1330.21, 1494.95, 1712.67, 1781.02, 3297.66 cm$^{-1}$.

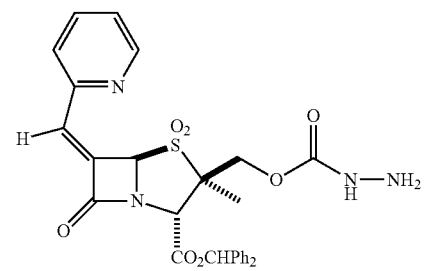

18f $^1$H NMR (400 MHz, CDCl$_3$): δ 1.17 (s, 3H), 4.33 (d, 1H, J=11.88 Hz), 4.71 (d, 1H, J=11.88 Hz), 4.93 (s, 1H), 5.82 (s, 1H), 6.98 (s, 1H), 7.26-7.41 (m, 13H), 7.72 (t, 1H, J=1.73 Hz), 7.85 (brs, 1H), 8.69-8.71 (d, 1H, J=5.2 Hz).

IR (thin film): 911.76, 1215.35, 1330.33, 1454.79, 1750.69, 1780.25, 3330.4 cm$^{-1}$.

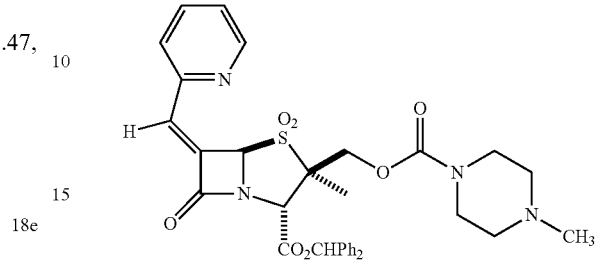

18g $^1$H NMR (400 MHz, CDCl$_3$): δ 1.26 (s, 3H), 2.27 (s, 3H), 2.32-2.36 (m, 4H), 3.49-3.5 (m, 4H), 4.5-4.53 (d, 1H, J=11.88 Hz), 4.67 (s, 1H), 4.69-4.72 (d, 1H, J=11.88 Hz), 5.74 (s, 1H), 6.99 (s, 1H), 7.26-7.42 (m, 13H), 7.68-7.73 (t, 1H, J=6.12 Hz), 8.66-8.67 (d, 1H, J=4.18 Hz).

$^{13}$C NMR (100 MHz, CDCl$_3$): δ 15.73, 43.85, 46.05, 54.49, 59.46, 64.06, 66.62, 73.15, 79.25, 124.87, 126.24, 126.93, 127.52, 128.3, 128.5, 128.61, 128.73, 130.01, 133.02, 136.94, 138.6, 138.67, 150.48, 150.74, 153.74, 166.04, 167.78.

IR (thin film): 912.24, 1237.77, 1332.16, 1436.71, 1707.88, 1785.49, 2940.53 cm$^{-1}$.

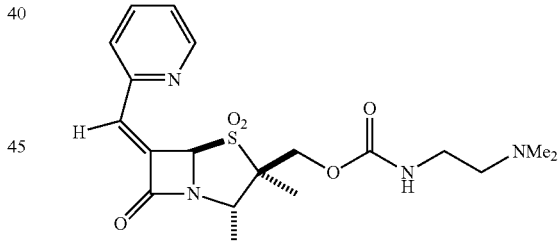

18h $^1$H NMR (400 MHz, CDCl$_3$): δ 1.13 (s, 3H), 2.13 (s, 6H), 2.28-2.31 (t, 2H, J=6.04 Hz), 3.14-3.18 (t, 2H, J=5.68 Hz), 4.28 (d, 1H, J=11.88 Hz), 4.55 (d, 1H, J=11.88 Hz), 4.73 (s, 1H), 5.33 (brs, 1H), 5.69 (s, 1H), 6.91 (s, 1H), 7.16-7.34 (m, 13H), 7.6-7.64 (t, 1H, J=7.64 Hz), 8.59-8.6 (d, 1H, J=4.04 Hz).

$^{13}$C NMR (100 MHz, CDCl$_3$): δ 15.59, 38.52, 45.13, 57.98, 60.01, 64.31, 66.41, 73.81, 79.23, 124.83, 126.22, 127.01, 127.51, 128.29, 128.48, 128.6, 128.7, 129.5, 133.79, 136.88, 138.6, 138.71, 150.42, 150.8, 154.98, 166.15, 167.63.

IR (thin film): 912.63, 1166.33, 1250.36, 1331.15, 1457.4, 1730.05, 1783.8, 2945.02 cm$^{-1}$.

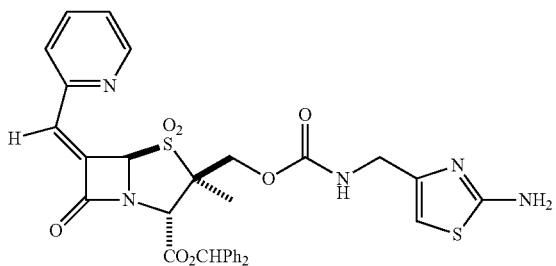

18j

¹H NMR (400 MHz, CDCl₃): δ 1.18 (s, 3H), 4.13-4.2 (m, 2H), 4.3 (d, 1H, J=11.88 Hz), 4.65 (d, 1H, J=11.88 Hz), 4.87 (s, 1H), 5.6 (t, 1H, Amide), 5.78-5.81 (d, 2H, Amine), 6.2 (s, 1H), 6.98 (s, 1H), 7.19-7.4 (m, 14H), 7.64-7.66 (t, 1H, J=7.63 Hz), 8.66-8.67 (d, 1H, J=4.17 Hz).
¹³C NMR (100 MHz, CDCl₃): δ 15.56, 41.26, 60.32, 65.11, 66.37, 74.22, 79.31, 103.87, 124.87, 126.41, 127.06, 127.52, 128.35, 128.55, 128.64, 128.74, 129.69, 133.74, 136.89, 138.54, 138.68, 148.25, 150.43, 150.76, 154.7, 166.15, 167.83, 168.97.

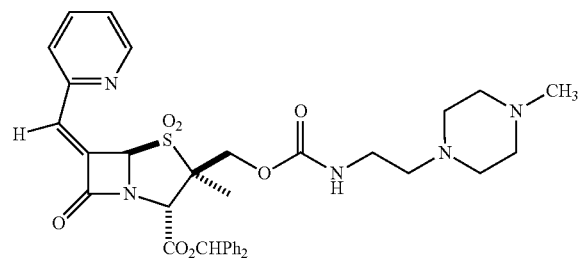

18k

¹H NMR (400 MHz, CDCl₃): δ 1.21 (s, 3H), 2.3 (s, 3H), 2.45-2.5 (m, 10H), 3.25-3.27 (t, 2H, J=5.44), 4.35 (d, 1H, J=11.96 Hz), 4.63 (d, 1H, J=11.96 Hz), 4.83 (s, 1H), 5.4-5.42 (t, 1H, Amide), 5.77 (s, 1H), 6.99 (s, 1H), 7.24-7.42 (m, 13H), 7.69-7.71 (t, 1H, J=5.96 Hz), 8.67-8.68 (d, 1H, J=3.88 Hz).
¹³C NMR (100 MHz, CDCl₃): δ 15.6, 37.7, 45.66, 52.48, 54.73, 56.71, 60.01, 64.38, 66.4, 73.87, 79.23, 124.84, 126.22, 127.0, 127.46, 128.3, 128.47, 128.58, 128.68, 129.37, 133.87, 136.91, 138.55, 138.67, 150.41, 150.75, 154.97, 166.12, 167.56.
IR (thin film): 913.19, 1165.58, 1250.49, 1330.68, 1456.41, 1729.25, 1783.55, 2804.68, 2941.36, 3397.6 cm⁻¹.

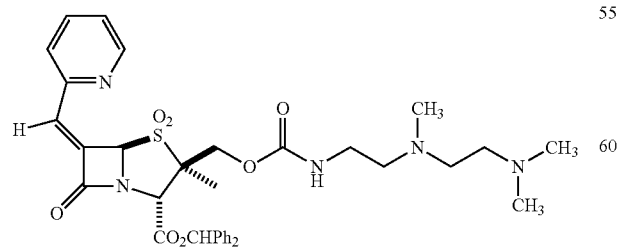

18l

¹H NMR (400 MHz, CDCl₃): δ 1.15 (s, 3H), 2.19 (s, 3H), 2.26 (s, 6H), 2.4-2.47 (m, 6H), 3.16 (s, 2H), 4.3 (d, 1H, J=11.96 Hz), 4.53 (d, 1H, J=11.96 Hz), 4.72 (s, 1H), 5.68 (s, 1H), 6.42 (brs, 1H, Amide), 6.91 (s, 1H), 7.19-7.34 (m, 13H), 7.62-7.65 (t, 1H, J=6.0 Hz), 8.6 (d, 1H, J=3.88 Hz).
¹³C NMR (100 MHz, CDCl₃): δ 15.67, 38.93, 42.24, 44.82, 54.3, 55.67, 56.53, 59.95, 64.03, 66.54, 73.76, 79.29, 124.86, 126.29, 127.05, 127.55, 128.32, 128.52, 128.64, 128.75, 129.62, 133.77, 136.95, 138.63, 138.73, 150.46, 150.86, 155.3, 166.18, 167.73.
IR (thin film): 1167.43, 1251.43, 1330.48, 1457.21, 1724.22, 1783.1, 2949.55 cm⁻¹.

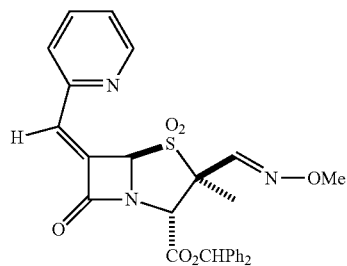

18n

¹H NMR (400 MHz, CDCl₃): δ 1.18 (s, 3H), 3.88 (s, 3H), 5.05 (s, 1H), 5.7 (s, 1H), 6.88 (s, 1H), 7.17-7.29 (m, 13H), 7.45 (s, 1H), 7.61-7.64 (t, 1H, J=7.36 Hz), 8.58-8.59 (d, 1H, J=3.88 Hz).
¹³C NMR (100 MHz, CDCl₃): δ 16.1, 29.65, 60.0, 62.69, 68.08, 73.69, 79.12, 124.95, 126.31, 126.83, 127.51, 128.24, 128.42, 128.56, 128.61, 130.07, 132.87, 137.0, 138.87, 142.14, 150.5, 150.72, 165.88, 167.68.
IR (thin film): 911.66, 1056.21, 1162.06, 1336.67, 1454.5, 1786.49, 2925.93 cm⁻¹.

Preparation of the sodium salts of 6-(substitutedmethylidene)-2'β-aminocarbonyloxy)penicillinate-1,1-dioxides (19(a-m))

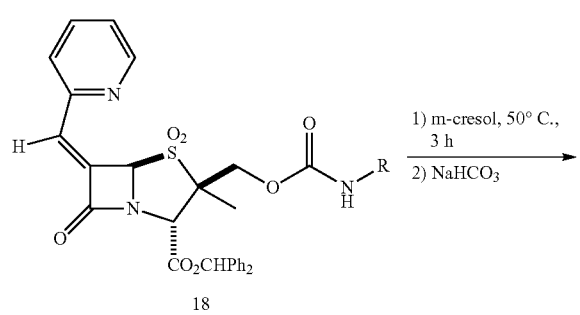

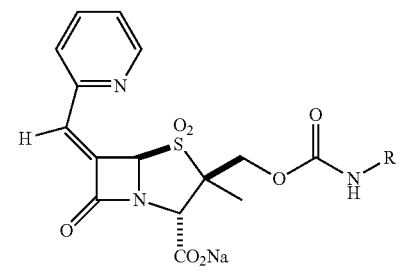

General Deprotection Procedure (Procedure A): A solution of benzhydryl ester 18 (0.32 mmol) in m-cresol (2.0 mL) was heated at 50° C. for 3 h under an argon atmosphere. The mixture was then cooled to room temperature, diluted with ether (10 mL) and treated with aqueous NaHCO₃ solution (29.5 mg, 0.35 mmol, was dissolved in 5 mL of deionized water). The separated aqueous layer was then purified on a column of CHP2OP (Mitsubishi Chemical Corporation) using increasing concentrations of ethanol in deionised water (0% to 50%) as eluent and the product collected and lyophilized to produce sodium salt, 19(a-m).

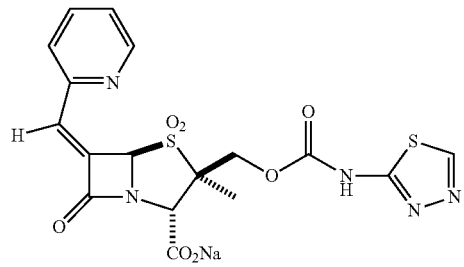

19a

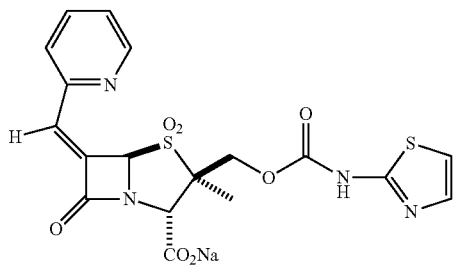

19d $^1$H NMR (400 MHz, D$_2$O): δ 1.66 (s, 3H), 4.55 (s, 1H), 6.1 (s, 1H), 7.14 (d, 1H, J=3.44 Hz) 7.38 (d, 1H, J=3.32 Hz), 7.45-7.48 (m, 1H), 7.54 (s, 1H), 7.61 (d, 1H, J=7.68 Hz), 7.90 (t, 1H, J=7.56 Hz), 8.66 (d, 1H, J=4.2 Hz).

$^1$H NMR (400 MHz, D$_2$O): δ 1.6 (s, 3H), 4.55 (s, 1H), 6.07 (s, 1H), 7.44-7.52 (m, 4H), 7.85-7.89 (t, 1H, J=6.12 Hz), 8.67-8.68 (d, 1H, J=4.52 Hz).

19b

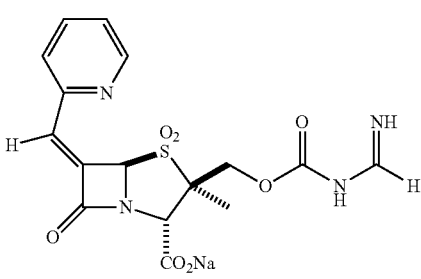

19e $^1$H NMR (400 MHz, D$_2$O): δ 1.65 (s, 3H), 4.51 (s, 1H), 6.1 (s, 1H), 7.45-7.48 (m, 1H), 7.54 (s, 1H), 7.62 (d, 1H, J=7.72 Hz), 7.90 (t, 1H, J=6.28 Hz), 8.66 (d, 1H, J=4.44 Hz), 8.89 (s, 1H).

$^1$H NMR (400 MHz, D$_2$O): δ 1.65 (s, 3H), 4.54 (s, 1H), 6.09 (s, 1H), 7.44-7.47 (m, 3H), 7.52 (s, 1H), 7.60 (d, 2H, J=7.83 Hz), 7.89 (t, 1H, J=7.52 Hz), 8.37 (brs, 2H), 8.65 (d, 1H, J=4.39 Hz).

$^{13}$C NMR (100 MHz, D$_2$O): δ 18.33, 64.54, 67.09, 70.56, 75.86, 116.33, 128.52, 129.71, 133.5, 134.31, 140.83, 151.96, 153.23, 156.27, 173.32, 175.21.

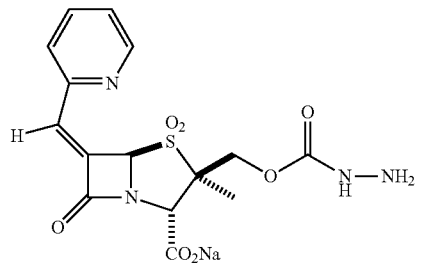

19f $^1$H NMR (400 MHz, D$_2$O): δ 1.61 (s, 3H), 4.53 (s, 1H), 4.6-4.63 (d, 1H, J=12.2 Hz), 6.08 (s, 1H), 7.45-7.48 (m, 1H), 7.52 (s, 1H), 7.61 (d, 1H, J=7.48 Hz), 7.90 (t, 1H, J=7.72 Hz), 8.66 (d, 1H, J=4.28 Hz).

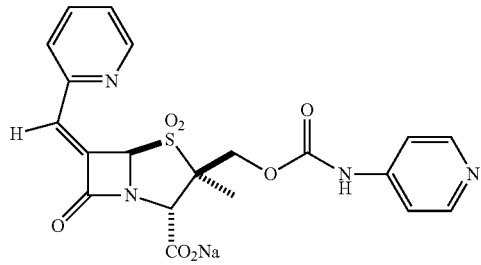

19c

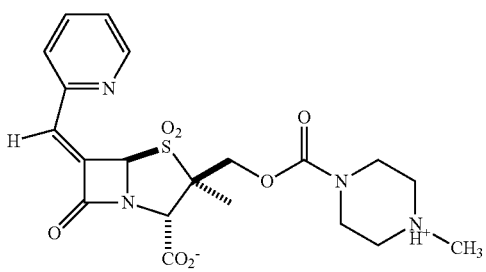

19g

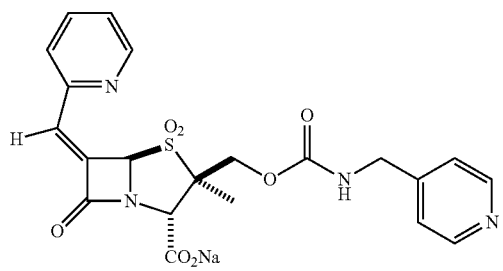

$^1$H NMR (400 MHz, D$_2$O): δ 1.59 (s, 3H), 4.32-4.41 (m, 2H), 4.54 (d, 1H, J=14.44 Hz) 6.06 (s, 1H), 7.32 (brs, 2H), 7.46 (m, 2H), 7.57 (d, 1H, J=7.4 Hz), 7.90 (t, 1H, J=7.52 Hz), 8.37 (brs, 2H), 8.66 (d, 1H, J=3.64 Hz).

¹H NMR (400 MHz, D₂O): δ 1.63 (s, 3H), 2.3 (s 3H), 2.52 (brs, 4H), 3.52 (brs, 4H), 4.46 (s, 1H), 4.60 (d, 1H, J=11.96 Hz), 4.76 (d, 1H, J=11.96 Hz), 6.04 (s, 1H), 7.44 (t, 1H, J=6.36 Hz), 7.5 (s, 1H), 7.57 (d, 1H, J=7.68 Hz), 7.86 (t, 1H, J=7.72 Hz), 8.63 (d, 1H, J=4.56 Hz).

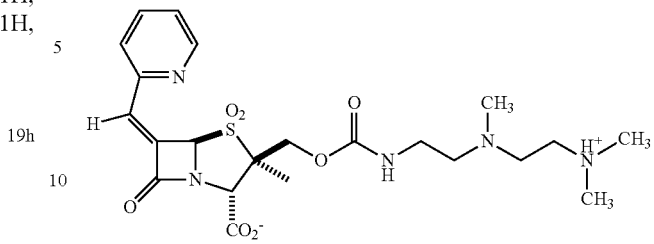

19l

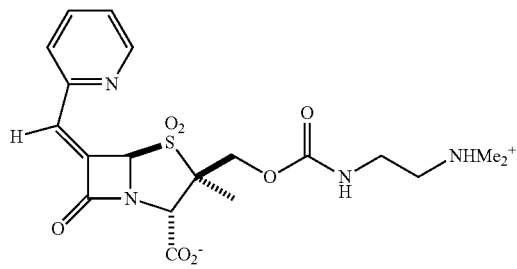

19h

¹H NMR (400 MHz, D₂O): δ 1.6 (s, 3H), 2.28 (s, 3H), 2.61-2.8 (m, 10H), 3.06 (t, 2H, J=6.54 Hz), 3.28 (t, 2H), 4.52 (m, 2H), 4.70 (d, 1H, J=12.11 Hz), 6.07 (s, 1H), 7.46 (t, 1H, J=5.96 Hz), 7.53 (s, 1H), 7.62 (d, 1H, J=7.65 Hz), 7.90 (t, 1H, J=7.6 Hz), 8.65 (d, 1H, J=4.29 Hz).

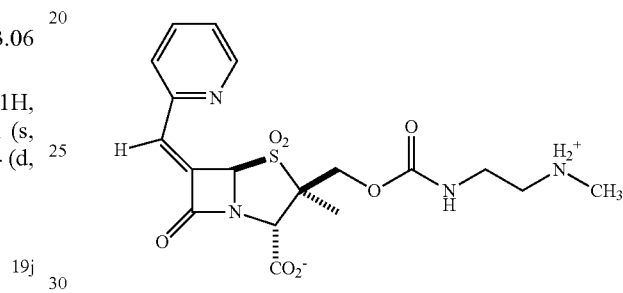

19m

¹H NMR (400 MHz, D₂O): δ 1.6 (s, 3H), 2.72 (s 6H), 3.06 (t, 2H, J=6 Hz), 3.46 (t, 2H, J=5.68

Hz), 4.51 (s, 1H), 4.55 (d, 1H, J=12.08 Hz), 4.73 (d, 1H, J=12.08 Hz), 6.06 (s, 1H), 7.46 (t, 1H, J=5.12 Hz), 7.51 (s, 1H), 7.60 (d, 1H, J=7.64 Hz), 7.90 (t, 1H, J=7.6 Hz), 8.64 (d, 1H, J=4.04 Hz).

¹H NMR (400 MHz, D₂O): δ 1.65 (s, 3H), 2.93-2.97 (d, 3H), 3.08 (m, 2H), 3.45-3.53 (m, 2H), 4.48-4.74 (m, 2H), 6.08 (s, 1H), 7.46 (t, 1H, J=5.08 Hz), 7.54 (s, 1H), 7.61 (d, 1H, J=7.36 Hz), 7.90 (t, 1H, J=7.52 Hz), 8.65 (d, 1H, J=3.36 Hz).

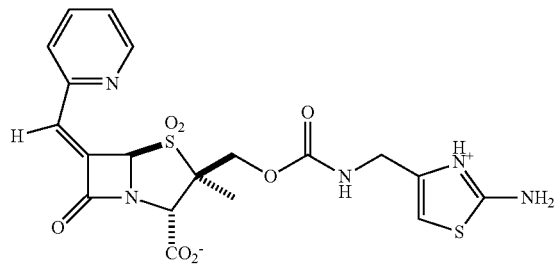

19j

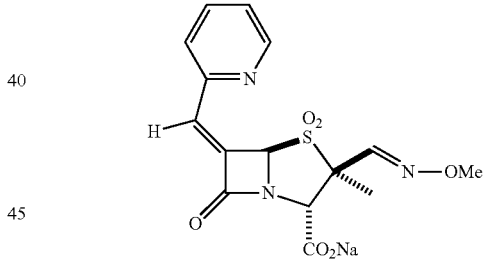

19n

¹H NMR (400 MHz, D₂O): δ 1.59 (s, 3H), 4.14 (s, 2H) 4.51-4.54 (m, 2H), 4.72 (d, 1H, J=12.08 Hz), 6.05 (s, 1H), 6.4 (s, 1H), 7.46 (m, 2H), 7.59 (d, 1H, J=7.68 Hz), 7.89 (t, 1H, J=7.72 Hz), 8.64 (d, 1H, J=4.04 Hz).

¹H NMR (400 MHz, D₂O): δ 1.73 (s, 3H), 3.96 (s, 3H), 4.94 (s, 1H), 6.17 (s, 1H), 7.46 (t, 1H, J=6.28 Hz), 7.55 (s, 1H), 7.62 (d, 1H, J=7.76 Hz), 7.69 (s, 1H), 7.90 (t, 1H, J=7.72 Hz), 8.66 (d, 1H, J=4.52 Hz).

19k

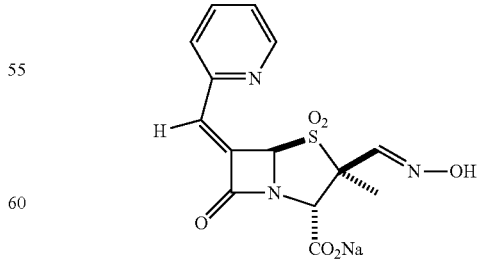

19o

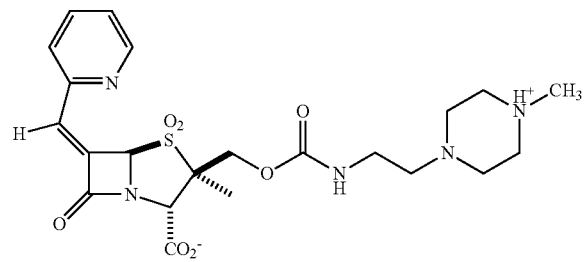

¹H NMR (400 MHz, D₂O): δ 1.59 (s, 3H), 2.5 (s, 3H), 2.60 (t, 2H, J=6.44 Hz), 2.72-2.86 (m, 8H), 3.30 (t, 2H, J=6.16 Hz), 4.49 (s, 1H), 4.52 (d, 1H, J=12.12 Hz), 4.70 (d, 1H, J=12.12 Hz), 6.04 (s, 1H), 7.45 (t, 1H, J=5.96 Hz), 7.5 (s, 1H), 7.59 (d, 1H, J=7.68 Hz), 7.88 (t, 1H, J=7.72 Hz), 8.64 (d, 1H, J=4.24 Hz).

¹H NMR (400 MHz, D₂O): δ 1.73 (s, 3H), 4.86 (s, 1H), 6.17 (s, 1H), 7.46 (t, 1H, J=4.8 Hz), 7.55 (s, 1H), 7.62 (d, 1H, J=7.6 Hz), 7.7 (s, 1H), 7.90 (t, 1H, J=7.64 Hz), 8.66 (d, 1H, J=4.24 Hz).

Example 14
TABLE 2
Preparation of compounds 19(p-s)
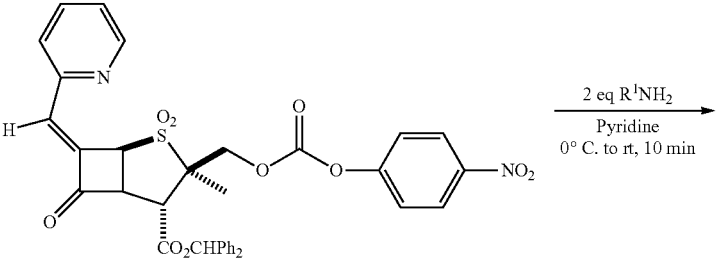
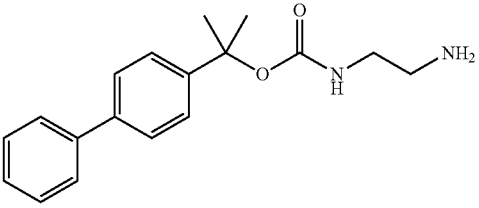 [SMILES: CC(C)(OC(=O)NCCN)c1ccc(-c2ccccc2)cc1]
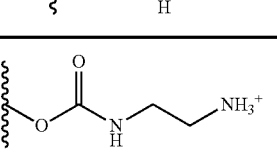
| $R^1$—$NH_2$ | Coupling yield | | Deprotection yield |
|---|---|---|---|
| 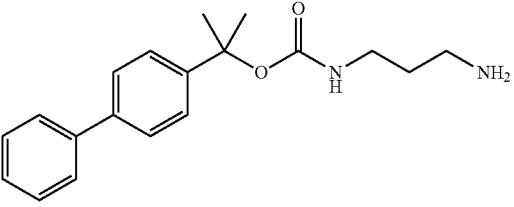 | 66 | | 37 |
| 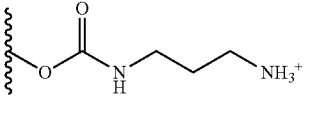 [SMILES: *OC(=O)NCCC[NH3+]] | 91 | | 45 |

TABLE 2-continued
| | | |
|---|---|---|
| 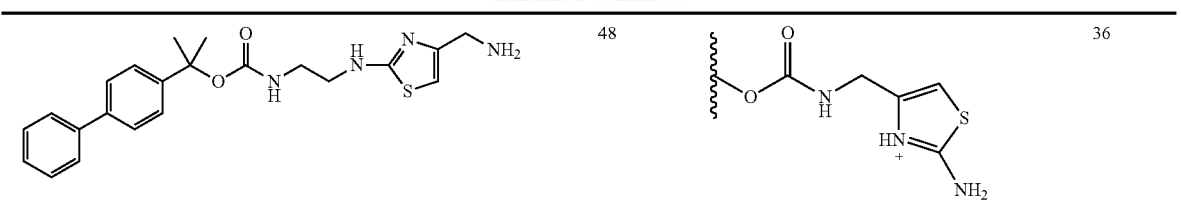 | 48 | 36 |
| 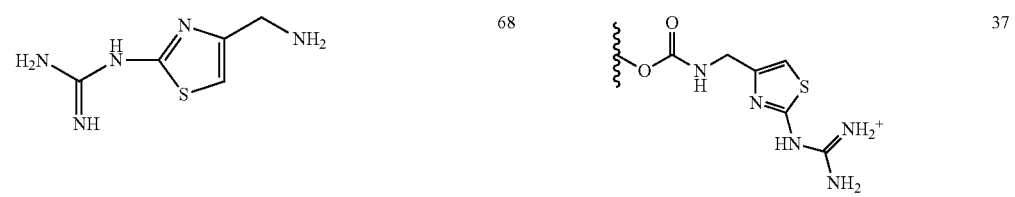 | 68 | 37 |
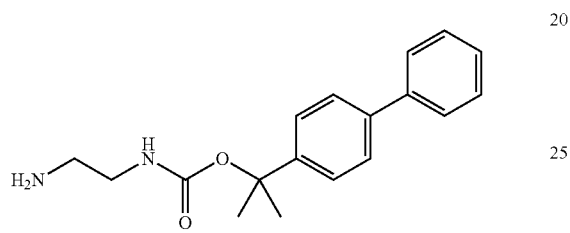
20
25
Reagent
$^1$H NMR (400 MHz, CDCl$_3$): δ 1.41 (brs, 4H), 1.8 (s, 6H), 2.78 (t, 2H), 3.15 (t, 2H), 5.09 (brs, 1H, Amide), 7.25-7.58 (m, 9H).
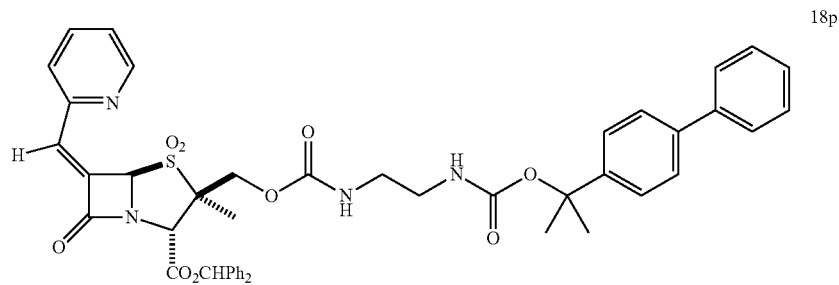
18p
$^1$H NMR (400 MHz, CDCl$_3$): δ 1.18 (s, 3H), 1.77 (s, 6H), 3.2 (m, 4H), 4.31 (d, 1H, J=11.92 Hz), 4.62 (d, 1H, J=11.92 Hz), 4.86 (s, 1H), 5.19 (brs, 1H, Amide), 5.34 (brs, 1H, Amide), 5.78 (s, 1H), 6.98 (s, 1H), 7.3-7.56 (m, 23H), 7.65 (t, 1H, J=7.14 Hz), 8.66 (d, 1H, J=3.8 Hz).
$^{13}$C NMR (100 MHz, CDCl$_3$): δ 15.6, 28.89, 28.99, 40.62, 40.97, 60.2, 64.86, 66.35, 74.06, 79.26, 80.66, 124.66, 124.85, 126.33, 126.92, 126.98, 127.04, 127.48, 128.34, 128.52, 128.61, 128.71, 129.53, 133.82, 136.86, 138.53, 138.68, 139.55, 140.73, 150.4, 150.76, 155.32, 166.15, 167.71.
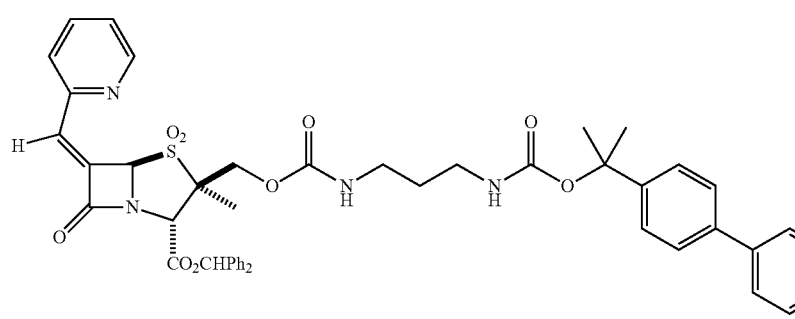
18q $^1$H NMR (400 MHz, CDCl$_3$): δ 1.09 (s, 3H), 1.51-1.54 (m, 2H), 1.7 (s, 3H), 1.71 (s, 3H), 3.02-3.1 (m, 4H), 4.21 (d, 1H, J=11.88 Hz), 4.52 (d, 1H, J=11.88 Hz), 4.77 (s, 1H), 5.08 (brs, 1H, Amide), 5.15 (brs, 1H, Amide), 5.7 (s, 1H), 6.9 (s, 1H), 7.21-7.48 (m, 23H), 8.57 (d, 1H, J=3.68 Hz).

$^{13}$C NMR (100 MHz, CDCl$_3$): δ 15.56, 28.97, 29.14, 30.21, 37.14, 37.74, 60.29, 64.92, 66.3, 74.14, 79.26, 80.41, 124.66, 124.84, 126.33, 126.91, 127.0, 127.05, 127.51, 128.34, 128.53, 128.62, 128.72, 129.51, 133.93, 136.87, 138.56, 138.7, 139.53, 140.78, 150.4, 150.81, 155.44, 166.17, 167.73.

IR (thin film): 1102.83, 1142.28, 1247.49, 1329.82, 1513.31, 1717.46, 1782.25, 3404.15 cm$^{-1}$.

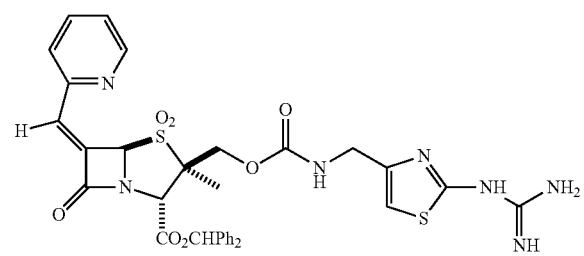

18s $^1$H NMR (400 MHz, CDCl$_3$): δ 1.07 (s, 3H), 4.03-4.18 (m, 3H), 4.57 (d, 1H, J=11.92 Hz), 4.85 (s, 1H), 5.7 (s, 1H), 5.81 (brs, 1H, amide), 6.23 (s, 1H), 6.88 (s, 1H), 7.02-7.30 (m, 13H), 7.53 (t, 1H, J=7.68 Hz), 8.52 (d, 1H, J=4.44 Hz).

General Deprotection Procedure (Procedure B):

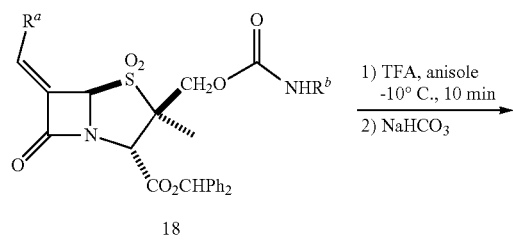

Benzhydryl ester (0.171 mmol) was dissolved in anisole (1.0 mL), cooled to –10° C. and trifluoroacetic acid (2.0 mL) was added. The mixture was stirred for 10 minutes at –10° C. Then the flask was hooked up to a vacuum line and the volatile components removed at 0.1 mm Hg. The residue was then dissolved in EtOAc (5.0 mL) and treated with aqueous NaHCO$_3$ solution (28 mg of NaHCO$_3$ was dissolved in 5.0 mL of deionized water). The separated aqueous layer was then purified on a column of CHP2OP (Mitsubishi Chemical Corporation) using deionized water and increasing concentrations of EtOH/water as eluent. After the fractions containing product were identified (UV spectroscopy), the EtOH was removed on the rotary evaporator, and replaced with deionized water. The resultant solution was lyophilized to give products 19(p-s).

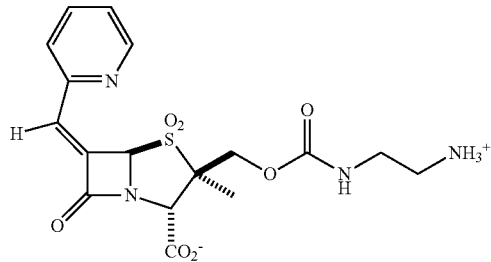

19t $^1$H NMR (400 MHz, D$_2$O): δ 1.6 (s, 3H), 3.09 (t, 2H, J=5.65 Hz), 3.44 (t, 2H, J=5.53 Hz), 4.52 (s, 1H), 4.56 (d, 1H, J=12.0 Hz), 4.72 (d, 1H, J=12.0 Hz), 6.07 (s, 1H), 7.46 (t, 1H, J=4.83 Hz), 7.52 (s, 1H), 7.61 (d, 1H), 7.90 (t, 1H, J=6.1 Hz), 8.65 (d, 1H, J=4.04 Hz).

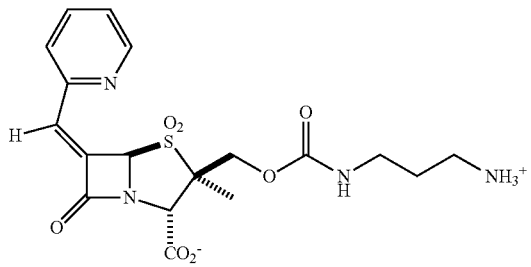

19u $^1$H NMR (400 MHz, D$_2$O): δ 1.59 (s, 3H), 1.82-1.92 (m, 2H), 3.00 (t, 2H, J=7.48 Hz), 3.22-3.25 (t, 2H, J=6.4 Hz), 4.5 (s, 1H), 4.51 (d, 1H, J=12.56 Hz), 4.71 (d, 1H, J=12.56 Hz), 6.05 (s, 1H), 7.45 (t, 1H, J=4.84 Hz), 7.51 (s, 1H), 7.60 (d, 1H, J=7.64 Hz), 7.89 (t, 1H, J=7.68 Hz), 8.65 (d, 1H, J=4.44 Hz).

$^{13}$C NMR (100 MHz, D$_2$O): δ 18.27, 29.98, 39.81, 40.17, 64.61, 66.89, 70.64, 75.87, 128.49, 129.67, 133.63, 134.12, 140.8, 153.19, 160.07, 173.22, 175.22.

Scheme 2

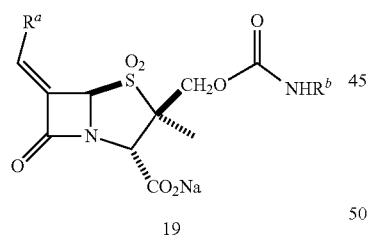

-continued
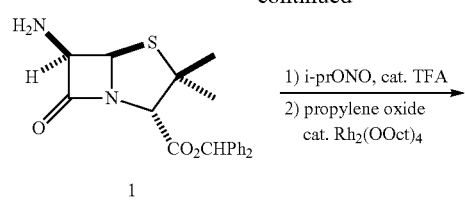
1
1) i-prONO, cat. TFA
2) propylene oxide
cat. Rh₂(OOct)₄
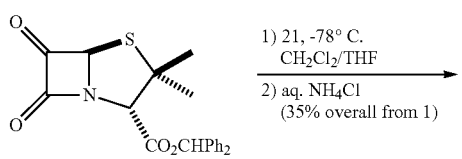
1) 21, -78° C. CH₂Cl₂/THF
2) aq. NH₄Cl
(35% overall from 1)
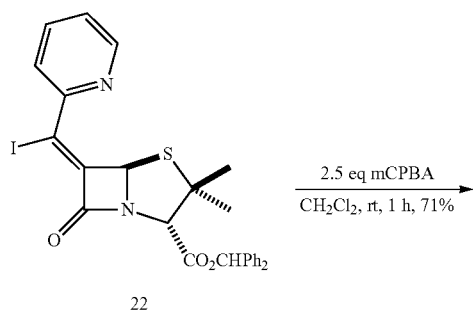
22
2.5 eq mCPBA
CH₂Cl₂, rt, 1 h, 71%
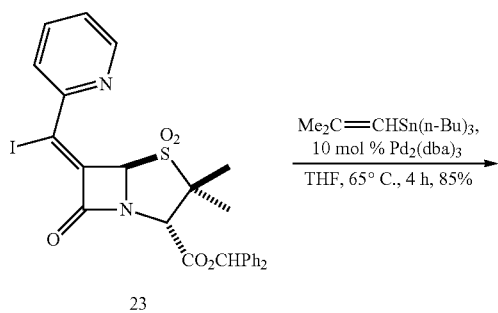
23
Me₂C=CHSn(n-Bu)₃,
10 mol % Pd₂(dba)₃
THF, 65° C., 4 h, 85%
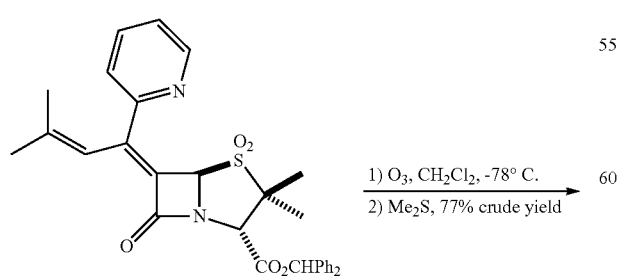
24
1) O₃, CH₂Cl₂, -78° C.
2) Me₂S, 77% crude yield
-continued
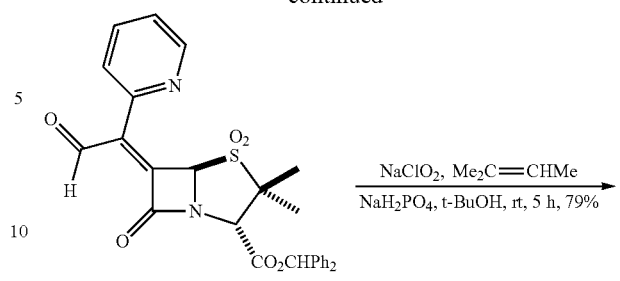
25
NaClO₂, Me₂C=CHMe
NaH₂PO₄, t-BuOH, rt, 5 h, 79%
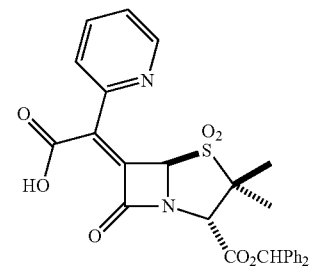
26
NaBH₄, CeCl₃, THF
0° C., 15 min, 60%
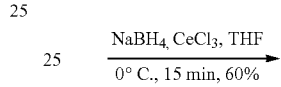
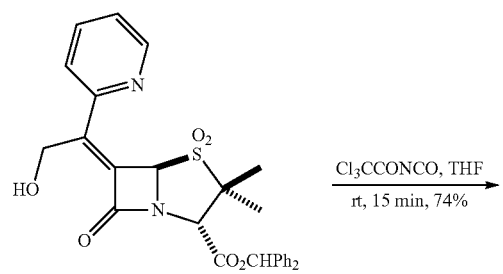
27
Cl₃CCONCO, THF
rt, 15 min, 74%
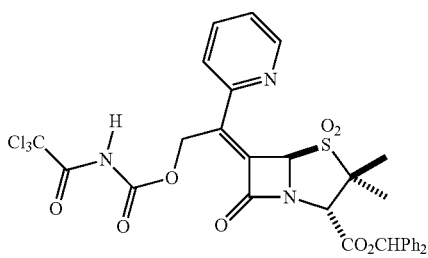
28
MeOH
2,6-lutidine
1 h, rt, 93%
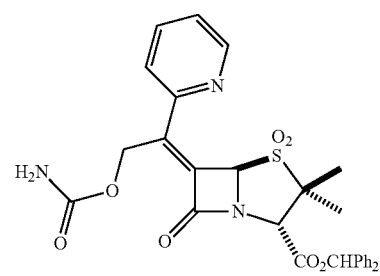
29

Scheme 3.
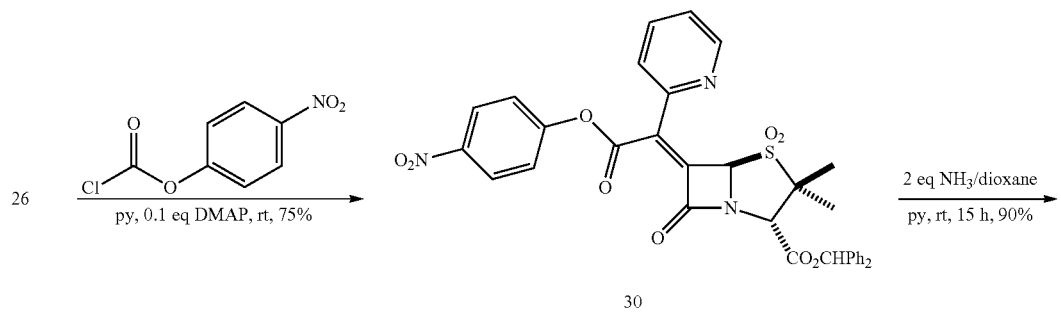
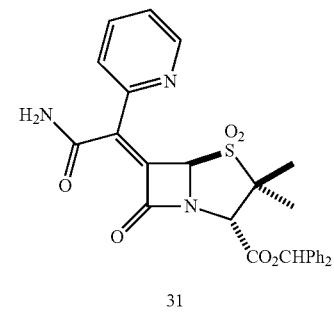
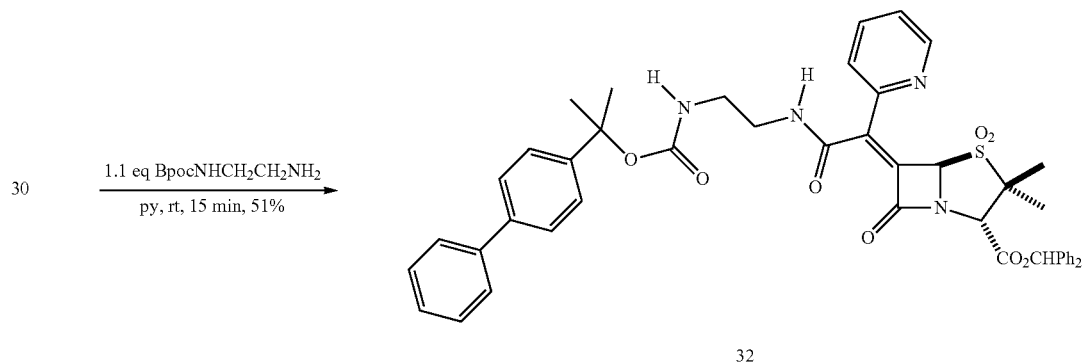
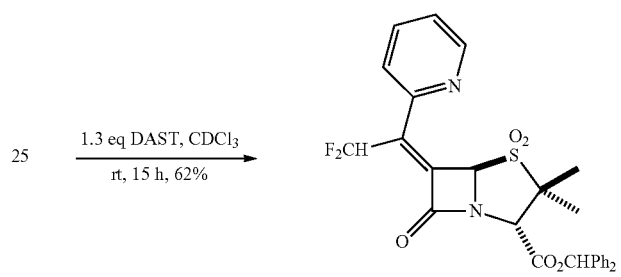

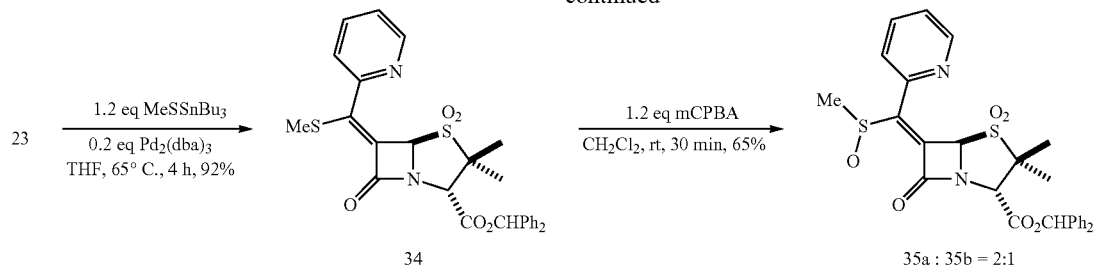
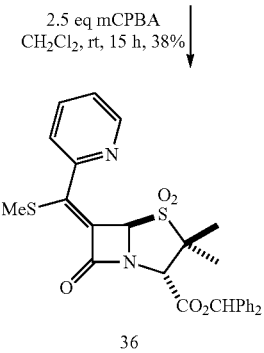
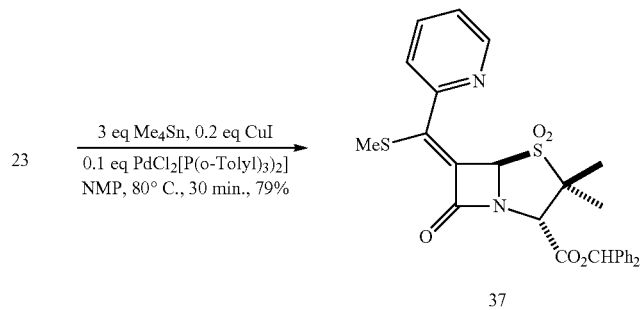
Scheme 4.
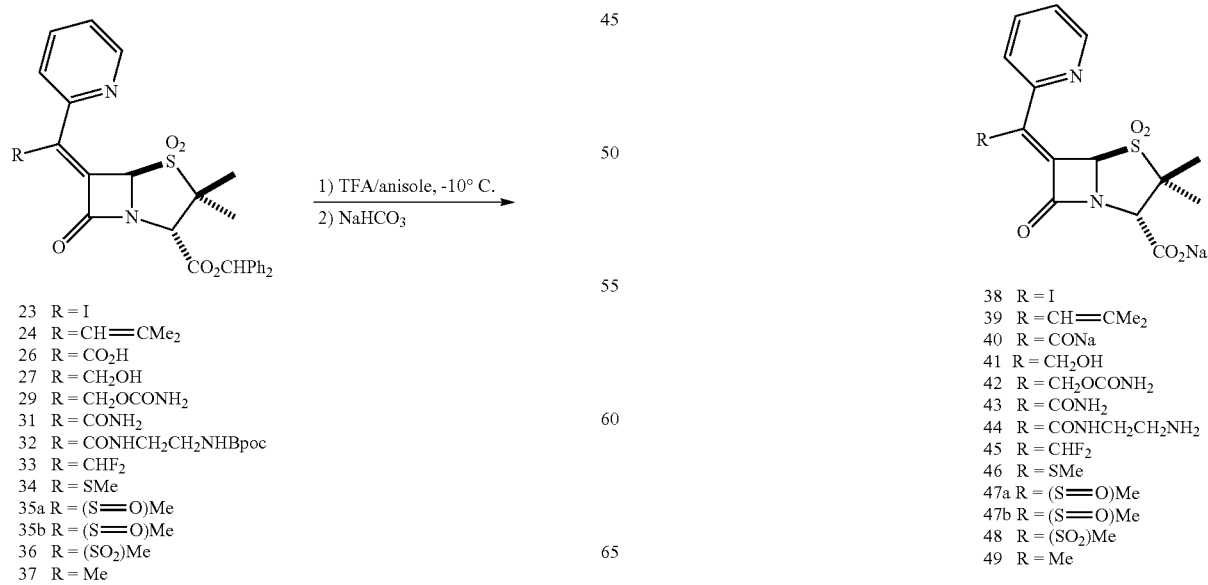

Example 15

Preparation of [Iodo(2'-pyridyl)methyl]triphenylphosphonium iodide (20)

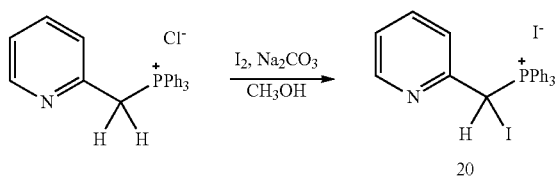

A solution of iodine (39 g, 153.92 mmol) in MeOH (150 mL) was added dropwise at 0-5° C. to a well-stirred two-phase system consisting of solid $K_2CO_3$ (21.27 g, 153.92 mmol) and 2-pyridylmethyltriphenylphosphonium chloride (60 g, 153.92 mmol) in MeOH (150 mL) solution. The temperature was then maintained between 0° C. and 5° C. during 4 h. The resultant precipitate was collected, washed once with cold MeOH, and dried under vacuum to produce 88 g of product (94% yield).

$^1$H-NMR (400 MHz, $d_6$-DMSO): 7.18-7.22 (m, 1H), 7.48 (d, 1H, J=6.8 Hz), 7.50-7.60 (m, 1H), 7.68-7.72 (m, 6H), 7.81-7.90 (m, 10H), 8.29 (d, 1H, J=4 Hz).

$^{31}$P-NMR (162 MHz, $d_6$-DMSO): 29.6.

Example 16

Preparation of Benzhydryl 6E-iodo-6Z-(α-Pyridylmethylidene)penicillinate (22)

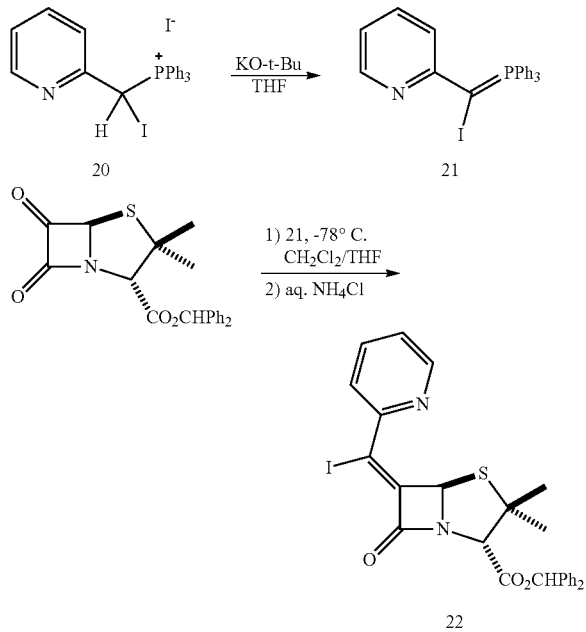

To a solution of [iodo(2'-pyridyl)methyl]triphenylphosphonium iodide (20) (88.0 g, 145 mmol), in dry THF (400 mL) was added KO$^t$Bu (17.7 g, 145 mmol) and the reaction mixture was then stirred at room temperature for 2 h, then chilled to −78° C. In a second flask, benzhydryl 6-oxopenicillinate (160 mmol, prepared as described in J. D. Buynak et al Tetrahedron Letters 39, 4945-4946 (1998)) was dissolved in dry $CH_2Cl_2$ (800 mL) and the resultant solution cooled to −78° C. Then the cooled (−78° C.) solution of the above Wittig reagent was slowly added to ketone at −78° C., via a cannula, and the resultant reaction mixture stirred at this temperature for 30 min. Then a saturated aqueous solution of $NH_4Cl$ was added and the reaction mixture slowly warmed to room temperature with stirring. The layers were separated and the aqueous layer extracted with an additional portion of $CH_2Cl_2$. The combined organic layers were washed with water (800 mL) and brine (800 mL). Then it was dried over $Na_2SO_4$, concentrated and purified by column chromatography using 2% EtOAc-$CH_2Cl_2$ as eluent to give 30.0 g (35.5% yield) of product.

$^1$H-NMR (400 MHz, CDCl$_3$): 1.25 (s, 3H), 1.57 (s, 3H), 4.73 (s, 1H), 6.35 (s, 1H), 6.96 (s, 1H), 7.29-7.39 (m, 11H), 7.73-7.77 (m, 1H), 7.93-7.95 (d, 1H, J=7.28 Hz), 8.54 (m, 1H).

$^{13}$C-NMR (100 MHz, CDCl$_3$): 25.54, 33.45, 62.45, 70.68, 74.72, 78.11, 94.65, 123.7, 126.98, 127.48, 127.56, 128.01, 128.19, 128.44, 128.49, 128.55, 137.33, 139.16, 139.23, 148.66, 148.9, 153.65, 167.15, 168.61.

Example 17

Preparation of Benzhydryl 6E-iodo-6Z-(α-Pyridylmethylidene)penicillinate-1,1-dioxide (23)

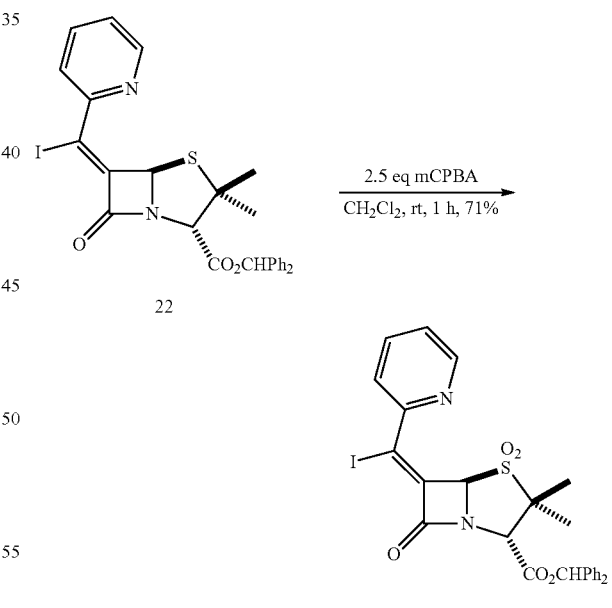

To a solution of sulfide 22 (20.0 g, 34.36 mmol), in $CH_2Cl_2$ (200 mL) was added mCPBA (19.2 g, 86 mmol) and reaction mixture was stirred at room temperature for 1 h. The reaction mixture was then diluted with $CH_2Cl_2$ (300 mL) and quenched with aqueous sodium metabisulfite solution (5 g, in 100 mL). The layers were separated and the organic layer was washed with aqueous $NaHCO_3$ (250 mL) followed by water and brine (250 mL each). Then it was dried over $Na_2SO_4$.

Concentration and purification by column chromatography using 5% EtOAc-CH$_2$Cl$_2$ as eluent produced 15 g (71% yield) of pure product.

$^1$H-NMR (400 MHz, CDCl$_3$): 1.19 (s, 3H), 1.59 (s, 3H), 4.55 (s, 1H), 5.68 (s, 1H), 7.0 (s, 1H), 7.29-7.40 (m, 11H), 7.80-7.84 (m, 1H), 7.93-7.95 (d, 1H, J=7.96 Hz), 8.59-8.60 (m, 1H).

$^{13}$C-NMR (100 MHz, CDCl$_3$): 18.16, 19.81, 62.75, 64.19, 75.59, 78.72, 100.78, 124.85, 126.68, 127.36, 128.11, 128.39, 128.47, 128.58, 136.21, 137.71, 138.63, 138.82, 149.14, 152.29, 166.29, 168.29.

Example 18

Preparation of Sodium 6E-iodo-6Z-(α-Pyridylmethylidene)penicillinate-1,1-dioxide (38)

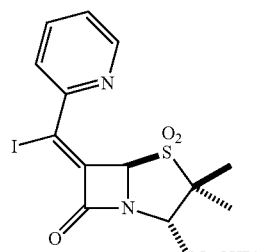

23

1) TFA/anisole, -10° C.
2) NaHCO$_3$, 35% overall

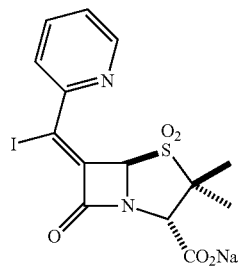

38

Ester 23 (150 mg, 0.244 mmol) was dissolved in anisole (1.5 mL), cooled to –10° C., and trifluoroacetic acid (3.0 mL) was added to reaction mixture under argon atmosphere. The reaction mixture was stirred for 10 minutes at –10° C. The volatile components were evaporated in vacuuo. The remaining residue was dissolved ethyl acetate (5.0 mL) and treated with aqueous NaHCO$_3$ solution (41 mg of NaHCO$_3$ was dissolved in 5.0 mL of deionized water). The two phase system was allowed to stir for 15 min. The separated aqueous layer was then purified on a column of CHP2OP (Mitsubishi chemical corporation) using deionized water as eluant and lyophilized to give 40 mg of pure sodium salt (35% yield).

$^1$H-NMR (400 MHz, D$_2$O): 1.48 (s, 3H), 1.61 (s, 3H), 4.29 (s, 1H), 5.97 (s, 1H), 7.47 (d of t, 1H, J=3.47 Hz, J=1.3 Hz), 7.99-8.03 (m, 2H), 8.60 (d, 1H, J=4.54 Hz).

Example 19

Preparation of Benzhydryl 6E-(2'-methylprop-'-enyl)-6Z-(α-pyridylmethylidene)penicillinate-1,1-dioxide (24)

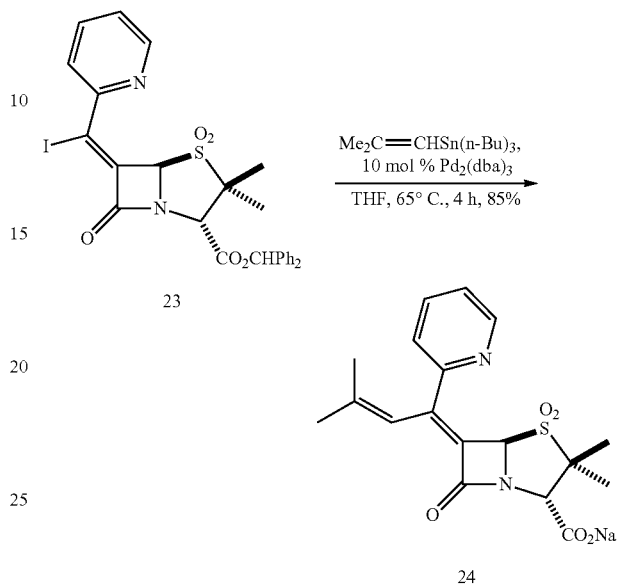

To a solution of iodide 23 (2.0 g, 3.25 mmol) in anhydrous THF (20.0 mL) were added tributyl(2-methylprop-1-enyl)stannane (1.34 g, 3.9 mmol), and Pd$_2$(dba)$_3$ (297 mg, 0.325 mmol) under an argon atmosphere. The reaction mixture was stirred at 65° C. for 4 h and was monitored by $^1$H NMR. After completion of the reaction, the solvent was removed under reduced pressure and the remaining residue dissolved in CH$_2$Cl$_2$. The solution was then washed with water (100 mL) and brine (100 mL). The organic layer was concentrated and purified by column chromatography using EtOAc/CH$_2$Cl$_2$ as eluent to obtain pure product 1.5 g (85% yield).

$^1$H-NMR (400 MHz, CDCl$_3$): 1.2 (s, 3H), 1.57 (s, 3H), 1.74 (s, 3H), 2.0 (s, 3H), 4.49 (s, 1H), 5.6 (s, 1H), 6.1 (s, 1H), 6.99 (s, 1H), 7.27-7.40 (m, 11H), 7.5-7.52 (d, 1H, J=7.84 Hz), 7.69-7.74 (d, 1H, J=6.0 Hz, J=1.82 Hz) 8.71-8.72 (d, 1H, J=3.82 Hz).

Example 20

Preparation of Sodium 6E-(2'-methylprop-'-enyl)-6Z-(α-pyridylmethylidene)penicillinate-1,1-dioxide (39)

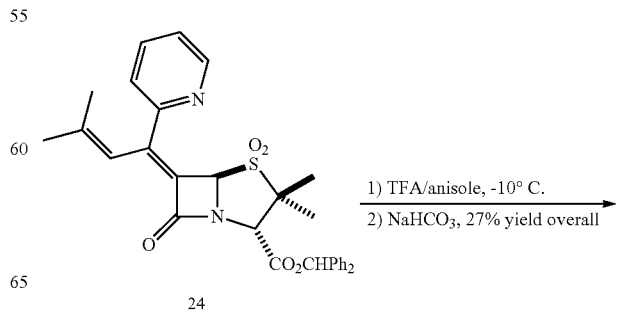

24

1) TFA/anisole, -10° C.
2) NaHCO$_3$, 27% yield overall

-continued

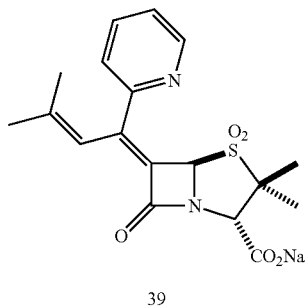

39

The general procedure used in Example 18 was followed with the isolation of 20 mg of pure product. (27% yield).

$^1$H-NMR (400 MHz, D$_2$O): 1.48 (s, 3H), 1.6 (s, 3H), 1.66 (s, 3H), 2.0 (s, 3H), 4.2 (s, 1H), 5.78 (s, 1H), 6.27 (s, 1H), 7.46-7.49 (t, 1H, J=5.88), 7.65-7.66 (d, 1H, J=7.86), 7.88-7.92 (t, 1H, J=7.74), 8.66-8.67 (d, 1H, J=4.59).

Example 21

Preparation of Benzhydryl 6E-Formyl-6Z-(α-pyridylmethylidene)penicillinate-1,1-dioxide (25)

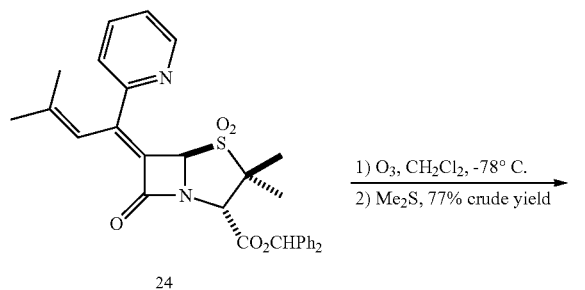

25

To a solution of diene 24 (1.5 g, 2.76 mmol) in CH$_2$Cl$_2$ (150 mL) was passed O$_3$ at −78° C. for 4.5 minutes. Dimethylsulfide (10.0 mL) was then added in one portion and the reaction allowed to warm to room temperature. The organic layer was concentrated to obtain 1.1 g (77% crude yield) crude product, which was used without further purification.

$^1$H-NMR (400 MHz, CDCl$_3$): 1.22 (s, 3H), 1.63 (s, 3H), 4.63 (s, 1H), 5.69 (s, 1H), 7.02 (s, 1H), 7.34-7.39 (m, 11H), 7.75-7.79 (d of t, 1H, J=5.94 Hz, J=1.82 Hz), 8.32-8.34 (d, 1H, J=7.98 Hz), 8.71-8.73 (q of d, 1H, J=2.12 Hz, J=0.83 Hz), 10.61 (s, 1H).

Example 22

Preparation of Benzhydryl 6E-(hydroxymethyl)-6Z-(α-pyridylmethylidene)penicillinate-1,1-dioxide (27)

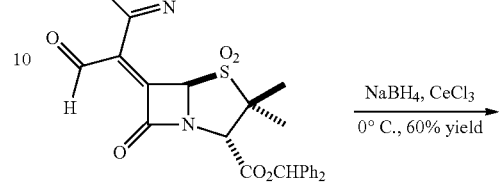

25

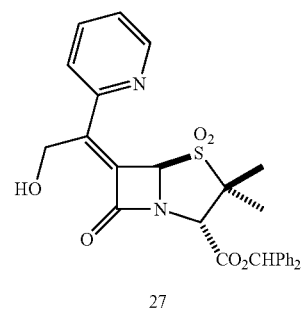

27

To a solution of aldehyde (950 mg, 1.84 mmol) in MeOH: THF (10:8 mL) was added CeCl$_3$.7H$_2$O (684 mg, 1.84 mmol). The mixture was then stirred for 10 minutes, chilled to 0° C., and was added NaBH$_4$ (139 mg, 3.68 mmol) portionwise. The reaction mixture was then stirred for 15 minutes and subsequently quenched with acetic acid. The solution was diluted with CH$_2$Cl$_2$ and the organic layer washed with aq NaHCO$_3$ (50 mL), water (50 mL), and brine (50 mL). The organic layer was dried over Na$_2$SO$_4$, concentrated, and purified by column chromatography using EtOAc/CH$_2$Cl$_2$ as eluent to obtain 570 mg (60% yield) of product.

$^1$H-NMR (400 MHz, CDCl$_3$): 1.18 (s, 3H), 1.56 (s, 3H), 4.52 (s, 1H), 4.85-4.96 (AB q, 1H, J=13.44, J=14.24), 5.58 (s, 1H), 6.97 (s, 1H), 7.21-7.38 (m, 10H), 7.67-7.68 (t, 1H, J=5.24), 8.65-8.66 (d, 1H, J=4.32).

$^{13}$C-NMR (100 MHz, CDCl$_3$): 18.18, 19.85, 58.99, 62.76, 64.34, 72.19, 78.74, 122.98, 124.63, 126.7, 127.48, 128.12, 128.44, 128.5, 128.61, 129.42, 136.96, 138.69, 138.89, 144.45, 149.75, 150.98, 166.44, 168.87.

Example 23

Preparation of Sodium 6E-Formyl-6Z-(α-pyridylmethylidene)penicillinate-1,1-dioxide (41)

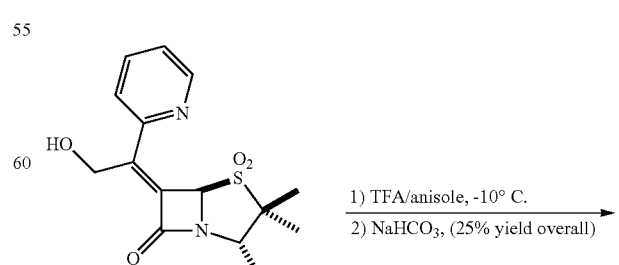

27

-continued

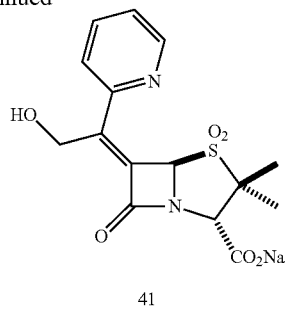

41

The general procedure described in Example 18 was utilized starting from ester 27 (100 mg, 0.193 mmol) to produce 19 mg sodium salt 41 (25% yield).

$^1$H-NMR (400 MHz, D$_2$O): 1.39 (s, 3H), 1.5 (s, 3H), 4.17 (s, 1H), 4.79-4.9 (AB q, 1H, J=17.31 Hz, J=13.28 Hz), 5.76 (s, 1H), 7.37-7.4 (d of t, 1H, J=4.9, J=2.63), 7.69-7.71 (d, 1H, J=7.88), 7.8-7.84 (d of t, 1H, J=6.2 Hz, J=1.3 Hz), 8.57-8.58 (d, 1H, J=4.15 Hz).

Example 24

Preparation of Benzhydryl 6E-(2,2,2-trichloroethanoylcarbamoyloxy)methyl)-6Z-(α-pyridylmethylidene)penicillinate-1,1-dioxide (28)

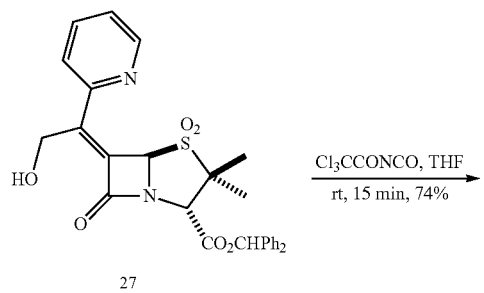

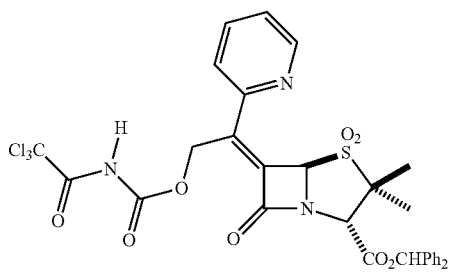

28

To a solution of alcohol 27 (140 mg, 0.27 mmol) in THF (1.0 mL) were added trichloroacetyl isocyanate (35 µL, 0.297 mmol) at room temperature. The resultant mixture was stirred at room temperature for 15 minutes, THF was removed under reduced pressure, and the crude product was diluted with EtOAc and washed successively with saturated aqueous solution of NaHCO$_3$ and brine. The organic layer was dried over Na$_2$SO$_4$, and concentrated under reduced pressure to obtain crude product (141 mg, 74% crude yield), which was used for next reaction without further purification.

$^1$H-NMR (400 MHz, CDCl$_3$): 1.09 (s, 3H), 1.39 (s, 3H), 4.46 (s, 1H), 5.21 (s, 2H), 5.48 (s, 1H), 6.9, (s, 1H), 7.22-7.29 (m, 11H), 7.54-7.56 (d, 1H, J=7.84), 7.66-7.70 (d of t, 1H, J=6.52 Hz, J=1.22 Hz), 8.63-8.64 (d, 1H, J=4.35).

Example 25

Preparation of Benzhydryl 6E-(carbamoyloxymethyl)-6Z-(α-pyridylmethylidene)penicillinate-1,1-dioxide (29)

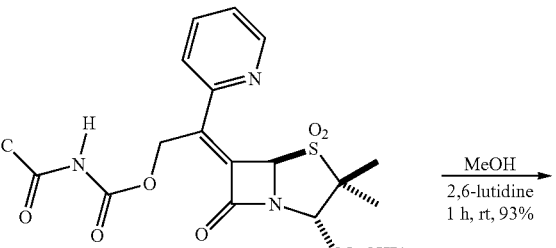

28

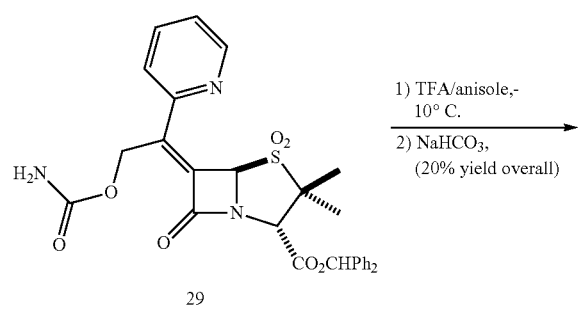

29

The crude (trichloroacetyl)imide 28 (141 mg, 0.2 mmol) was dissolved in MeOH (2.0 mL) containing 2,6-lutidine (23 µL, 0.2 mmol). After stirring 1.0 h at room temperature, the reaction mixture was diluted with CH$_2$Cl$_2$ (20.0 mL) and the solution was washed successively with 5% (w/v) citric acid solution (20.0 mL), saturated aqueous NaHCO$_3$ solution (20.0 mL) and brine (20.0 mL). The organic layer was dried over Na$_2$SO$_4$, evaporated, and then purified by silica gel column chromatography using EtOAc/CH$_2$Cl$_2$ as eluent to obtain 105 mg pure product (93% yield). SA-3-229

$^1$H-NMR (400 MHz, CDCl$_3$): 1.19 (s, 3H), 1.58 (s, 3H), 4.54 (s, 1H), 4.9 (brs, 2H), 5.33-5.47 (AB q, 1H, J=29.29 Hz, J=12.83 Hz), 5.59 (s, 1H), 7.0 (s, 1H), 7.27-7.39 (m, 11H), 7.57-7.59 (d, 1H, J=7.9 Hz), 7.72-7.76 (d of t, 1H, J=6.34 Hz, J=1.4 Hz) 8.69-8.7 (d of d, 1H, J=3.84 Hz, J=0.756 Hz).

$^{13}$C-NMR (100 MHz, CDCl$_3$): 18.35, 19.98, 59.15, 62.94, 64.33, 72.58, 78.85, 122.72, 124.8, 126.81, 127.57, 128.24, 128.54, 128.6, 128.7, 133.06, 137.18, 138.47, 138.75, 138.96, 150.07, 150.72, 155.96, 166.54, 167.74.

Example 26

Preparation of Sodium 6E-(carbamoyloxymethyl)-6Z-(α-pyridylmethylidene)penicillinate-1,1-dioxide (42)

-continued

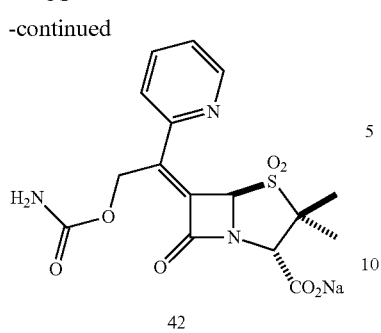

42

The general procedure described in Example 18 was utilized starting from ester 29 (100 mg, 0.178 mmol) to produce 15 mg sodium salt 42 (20% yield).

$^1$H-NMR (400 MHz, D$_2$O): 1.19 (s, 3H), 1.58 (s, 3H), 4.54 (s, 1H), 4.9 (brs, 2H), 5.33-5.47 (AB q, 1H, J=12.83, J=29.29), 5.59 (s, 1H), 7.0 (s, 1H), 7.27-7.39 (m, 10H), 7.57-7.59 (d, 1H, J=7.90), 7.74 (m, 1H) 8.69-8.7 (d, 1H, J=3.8 Hz).

$^{13}$C-NMR (100 MHz, D$_2$O): 18.35, 19.98, 59.15, 62.94, 64.33, 72.58, 78.85, 122.72, 124.8, 126.81, 127.57, 128.24, 128.54, 128.6, 128.7, 133.06, 137.18, 138.47, 138.75, 138.96, 150.07, 150.72, 155.96, 166.54, 167.74.

Example 27

Preparation of Benzhydryl 6E-carboxy-6Z-(α'-pyridylmethylidene)penicillinate-1,1-dioxide (26)

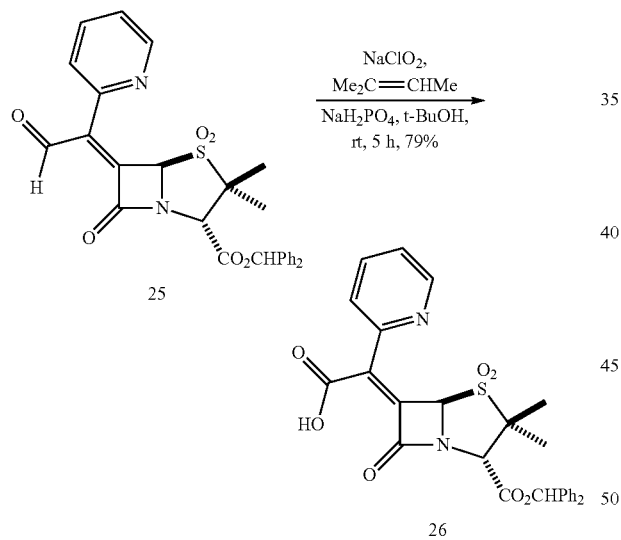

A solution of the crude aldehyde (1.47 g, 2.84 mmol) in 2-methyl-2-butene (6.0 mL, 56.8 mmol) and tert-butanol (30 mL) was prepared. In a second flask was prepared a solution of NaClO$_2$ (1.53 g, 17.04 mmol) and NaH$_2$PO$_4$.H$_2$O (808 mg, 5.85 mmol) in water (30 mL). This aqueous mixture was added to the first flask containing the aldehyde and the resultant reaction mixture was stirred at room temperature for 5 h. The layers were separated and the aqueous phase was extracted three times with EtOAc. The combined organic layers were washed once with brine, dried over Na$_2$SO$_4$, concentrated under reduced pressure and purified on column chromatography using 5% MeOH/DCM as eluent to give 1.2 g (79% yield) of product. SA-4-78

$^1$H-NMR (400 MHz, CDCl$_3$): 1.18 (s, 3H), 1.56 (s, 3H), 4.47 (s, 1H), 5.64 (s, 1H), 6.95 (s, 1H), 7.31-7.37 (m, 11H), 7.69-7.72 (d oft, 1H, J=4.72 Hz, J=1.45 Hz), 7.8-7.82 (d, 1H, J=7.34 Hz), 8.63 (d, 1H, J=3.64 Hz).

Example 28

Preparation of Disodium 6E-carboxy-6Z-(α'-pyridylmethylidene)penicillinate-1,1-dioxide (40)

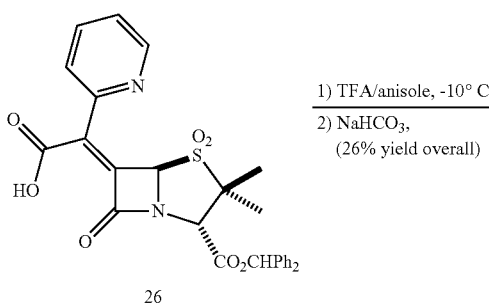

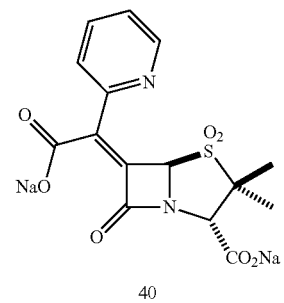

40

The general procedure described in Example 18 was utilized starting from ester 26 (150 mg, 0.281 mmol) to produce 30 mg sodium salt 40 (26% yield).

$^1$H-NMR (400 MHz, D$_2$O): 1.51 (s, 3H), 1.61 (s, 3H), 4.27 (s, 1H), 5.96 (s, 1H), 7.47-7.5 (m, 1H), 7.57-7.59 (m, 1H), 7.91-7.95 (m, 1H), 8.69-8.7 (d, 1H, J=3.4 Hz).

$^{13}$C-NMR (100 MHz, D$_2$O): 20.6, 22.56, 68.1, 68.5, 74.76, 127.27, 128.06, 128.41, 140.93, 146.14, 152.41, 153.16, 172.68, 173.55, 176.12.

Example 29

Preparation of Benzhydryl 6E-(p-nitrophenyloxy)carbonyl-6Z-(α'-pyridylmethylidene)penicillinate-1,1-dioxide (30)

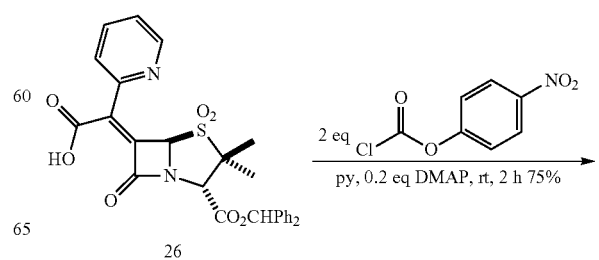

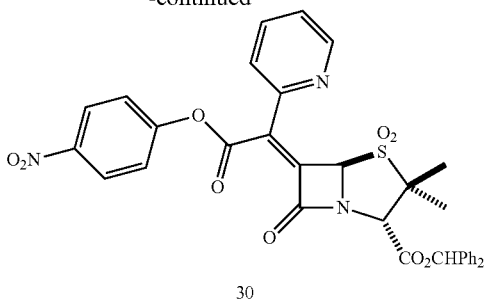

30

To a solution of acid 26 (500 mg, 0.939 mmol) in pyridine (5.0 mL) was added p-nitrophenyl chloroformate (377 mg, 1.878 mmol), and DMAP (22.8 mg, 0.187 mmol). The reaction mixture was stirred for 2 h at room temperature, then diluted with CH$_2$Cl$_2$ (50 mL) and washed with water (50.0 mL), and brine (50.0 mL). The organic layer was dried over Na$_2$SO$_4$, concentrated and purified by column chromatography using CH$_2$Cl$_2$ as eluent to obtain pure product 470 mg (75.5% yield).

$^1$H-NMR (400 MHz, CDCl$_3$): 1.23 (s, 3H), 1.63 (s, 3H), 4.65 (s, 1H), 5.71 (s, 1H), 7.02 (s, 1H), 7.31-7.38 (m, 11H), 7.52-7.54 (d, 1H, J=7.29 Hz), 7.73-7.80 (m, 2H), 8.24-8.27 (d, 1H, J=7.18 Hz), 8.70 (d, 1H, J=4.66 Hz).

Example 30

Preparation of Benzhydryl 6E-carboxamido-6Z-(α'-pyridylmethylidene)penicillinate-1,1-dioxide (31)

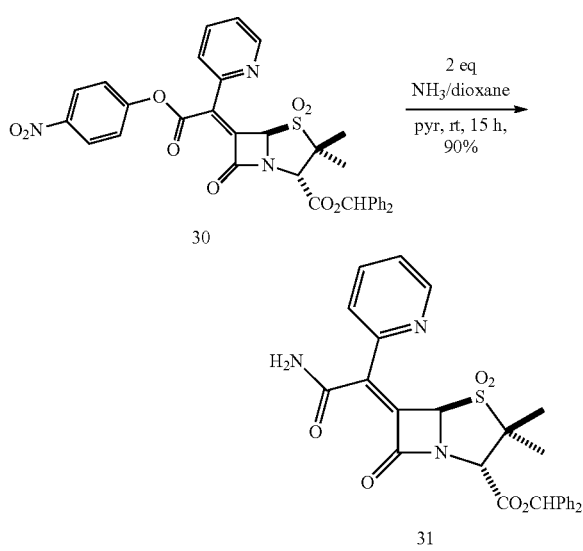

To a solution of p-nitrophenylester 30 (150 mg, 0.229 mmol) in pyridine (1.5 mL) was added a solution of ammonia in dioxane (Sigma-Aldrich, 0.5 M, 0.916 mL, 0.458 mmol) and the reaction mixture was stirred for 15 h at room temperature. The reaction mixture was then diluted with CH$_2$Cl$_2$ (25 mL) and washed with water (25 mL) and brine (25 mL). The organic layer was dried over Na$_2$SO$_4$, concentrated, and purified by column chromatography using 5% EtOAc in CH$_2$Cl$_2$ as eluent to obtain the product 110 mg (90% yield).

$^1$H-NMR (400 MHz, CDCl$_3$): 1.98 (s, 3H), 1.6 (s, 3H), 4.56 (s, 1H), 5.6 (s, 1H), 6.23 (brs, 2H), 6.99 (s, 1H), 7.29-7.37 (m, 11H), 7.7-7.74 (d of t, 1H, J=5.98 Hz, J=1.8 Hz), 8.03-8.05 (d, 1H, J=7.99 Hz), 8.68-8.69 (dd, 1H, J=3.86 Hz, J=0.8 Hz).

$^{13}$C-NMR (100 MHz, CDCl$_3$): 18.25, 19.98, 63.19, 64.35, 72.51, 78.99, 124.91, 125.52, 126.83, 127.47, 128.29, 128.57, 128.62, 128.72, 133.72, 136.71, 136.99, 138.67, 138.82, 149.67, 149.78, 164.19, 166.17, 167.61.

Example 31

Preparation of Sodium 6E-carboxamido-6Z-(α'-pyridylmethylidene)penicillinate-1,1-dioxide (43)

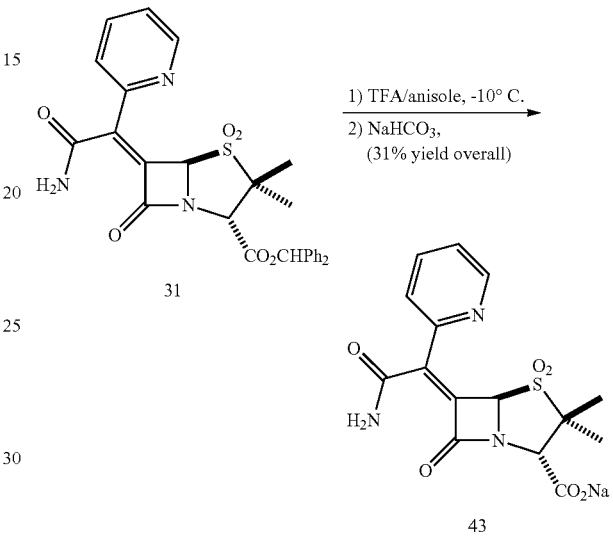

The general procedure described in Example 18 was utilized starting from ester 31 (110 mg, 0.207 mmol) to produce 25 mg sodium salt 43 (31% yield).

$^1$H-NMR (400 MHz, D$_2$O): 1.52 (s, 3H), 1.63 (s, 3H), 4.33 (s, 1H), 6.02 (s, 1H), 7.51-7.54 (d of t, 1H, J=4.81 Hz, J=2.76 Hz)), 7.57-7.59 (d, 1H, J=7.9 Hz), 7.91-7.95 (d of t, 1H, J=6.56 Hz, J=1.44 Hz), 8.69-8.70 (d, 1H, J=4.4 Hz).

$^{13}$C-NMR (100 MHz, D$_2$O): 18.06, 20.08, 65.86, 65.99, 72.1, 124.83, 126.34, 131.0, 138.14, 138.54, 149.02, 150.82, 168.1, 168.83, 173.24.

Example 32

Preparation of 2-(biphenyl-4-yl)propan-2-yl phenyl carbonate

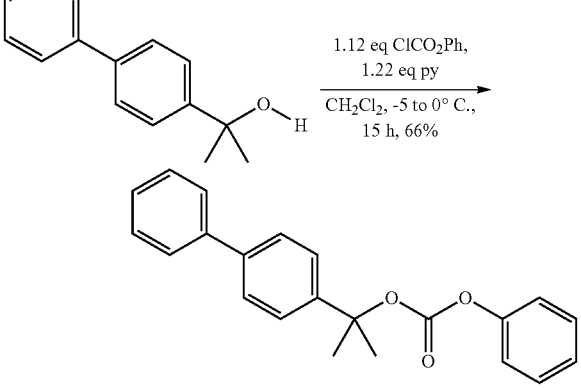

To a solution of 2-(4-biphenyl)-2-propanol (53 g, 250 mmol) in dry CH$_2$Cl$_2$ (250.0 mL) was added pyridine (24.6 mL, 305 mmol) and phenylchlorofomate (35.0 mL, 280 mmol) in CH$_2$Cl$_2$ (125.0 mL) at −5° C. After addition forms a thick precipitate, which, after the reaction mixture is allowed to stand overnight at 0° C. is mostly dissolved. The mixture is poured onto ice and diluted with CH$_2$Cl$_2$ (1000 mL). The organic phase is separated and washed three times with cold water. After drying over Na$_2$SO$_4$ the organic layer is evaporated at reduced pressure at a bath temp of <30° C. The crystalline residue is dissolved in diethyl ether (1000 mL) and the solution is then concentrated with a stream of nitrogen at atmospheric pressure at bath temperature of 60° C. to approximately 200 mL and then rapidly cooled to 0° C. to produce a pure crystalline product 55.0 g (66% yield).

$^1$H-NMR (400 MHz, CDCl$_3$): 1.9 (s, 6H), 7.1-7.59 (m, 14H).

Example 33

Preparation of 2-(biphenyl-4-yl)propan-2-yl 2-aminoethylcarbamate

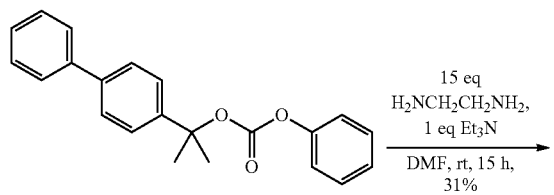

15 eq
H$_2$NCH$_2$CH$_2$NH$_2$,
1 eq Et$_3$N
DMF, rt, 15 h,
31%

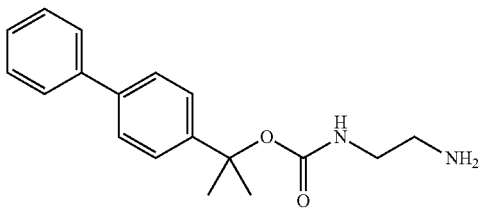

To a solution of ethylenediamine (10.83 mL, 162.45 mmol) in DMF (30 mL) was added Et$_3$N (1.509 ml, 10.83 mmol) and 2-(biphenyl-4-yl)propan-2-yl phenyl carbonate (3.6 g, 10.83 mmol) at room temperature. The resultant solution was stirred overnight. The reaction mixture was diluted with CH$_2$Cl$_2$ (200 mL) and washed 5 times with water (200 mL each time) and brine (200 mL). The organic layer was dried over Na$_2$SO$_4$, concentrated under reduced pressure, and purified by using column chromatography to give 1.0 g of mono protected ethylenediamine (31% yield).

$^1$H-NMR (400 MHz, CDCl$_3$): 1.41 (brs, 2H), 1.8 (s, 6H), 2.78 (m, 2H), 2.15-2.16 (m, 2H), 5.09 (brs, 1H)), 7.25-7.58 (m, 9H).

Example 34

Preparation of Benzhydryl 6E-[2-((biphenyl-4-yl) propanoxycarbonylamino)ethanaminocarbonyl]-6Z-(α'-pyridylmethylidene)penicillinate-1,1-dioxide (32)

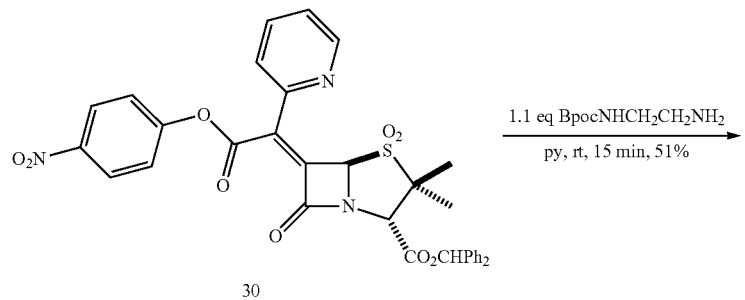

30

1.1 eq BpocNHCH$_2$CH$_2$NH$_2$
py, rt, 15 min, 51%

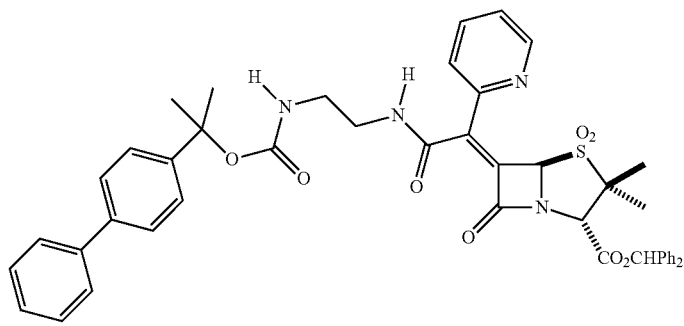

32

To a solution of p-nitrophenylester 30 (140 mg, 0.214 mmol) in pyridine (1.5 mL) was added the monoprotected ethylenediamine (70 mg, 0.235 mmol) and the resultant solution was stirred for 15 min at room temperature. The reaction mixture was diluted with $CH_2Cl_2$ (25 mL) and washed with water (25 mL), and brine (25 mL). The organic layer was dried over $Na_2SO_4$, concentrated and purified by column chromatography using 50% EtOAc in $CH_2Cl_2$ as eluent to obtain pure product 90 mg (51% yield).

$^1$H-NMR (400 MHz, $CDCl_3$): 1.2 (s, 3H), 1.59 (s, 3H), 1.77 (s, 6H), 3.28-3.37 (m, 3H), 3.66-3.69 (m, 1H), 4.55 (s, 1H), 5.64 (s, 1H), 5.85 (t, 1H, J=5.61 Hz), 6.99 (s, 1H), 7.28-7.55 (m, 20H), 7.68 (d of t, 1H, J=6.19 Hz, J=1.64 Hz), 7.84 (d, 1H, J=7.9 Hz), 8.68 (d, 1H, J=4.2 Hz).

$^{13}$C-NMR (100 MHz, $CDCl_3$): 18.26, 19.97, 28.94, 29.1, 40.17, 40.39, 63.22, 64.42, 72.29, 79.02, 80.59, 124.68, 124.89, 125.09, 126.85, 126.88, 127.01, 127.45, 128.3, 128.56, 128.58, 128.6, 128.72, 137.16, 138.66, 138.81, 139.44, 140.81, 145.67, 149.35, 150.04, 155.56, 162.84, 166.17, 167.79.

Example 35

Preparation of Sodium 6E-(2-aminoethanaminocarbonyl)-6Z-(α'-pyridylmethylidene)penicillinate-1,1-dioxide (44)

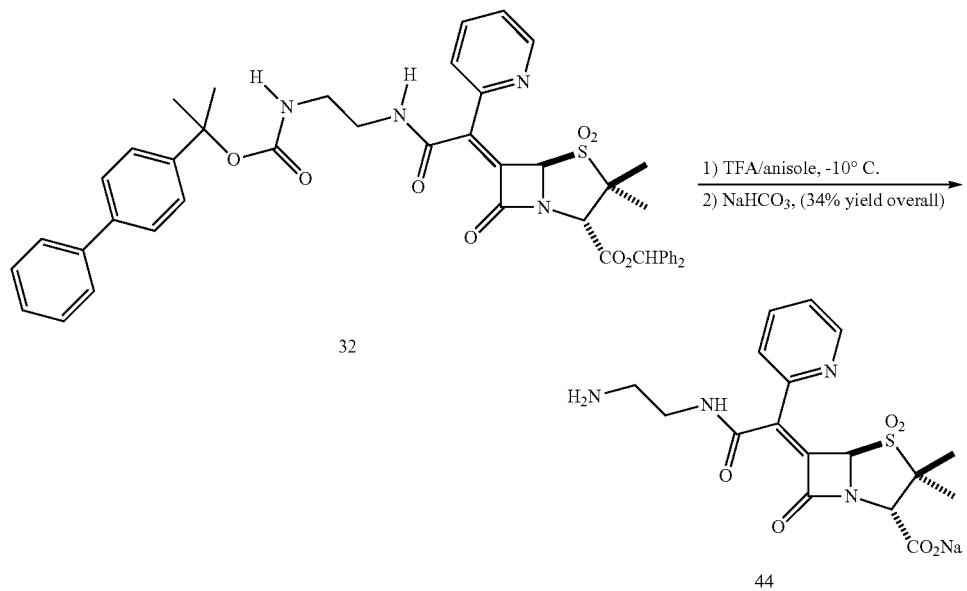

The general procedure described in Example 18 was utilized starting from ester 32 (90 mg, 0.11 mmol) to produce 16 mg sodium salt 44 (34% yield).

$^1$H-NMR (400 MHz, $D_2O$): 1.53 (s, 3H), 1.63 (s, 3H), 3.33-3.37 (m, 2H), 3.69-3.74 (m 1H), 3.85-3.9 (m, 1H), 4.36 (s, 1H), 6.07 (s, 1H), 7.51-7.55 (d of t, 1H, J=4.82 Hz, J=2.76 Hz)), 7.57-7.59 (d, 1H, J=7.86 Hz), 7.91-7.95 (d of t, 1H, J=6.42 Hz, J=1.43 Hz), 8.69-8.7 (d, 1H, J=4.42 Hz).

$^{13}$C-NMR (100 MHz, $D_2O$): 20.44, 22.52, 39.98, 41.66, 68.37, 68.58, 74.54, 127.45, 128.98, 134.12, 140.68, 140.99, 151.21, 153.37, 168.7, 171.85, 175.56.

Example 36

Preparation of Benzhydryl 6E-difluoromethyl-6Z-(α'-pyridylmethylidene)penicillinate-1,1-dioxide (33)

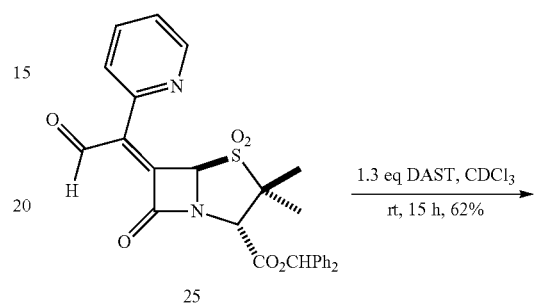

-continued

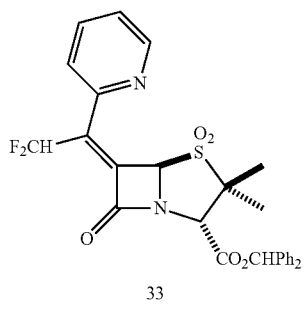

To a solution of aldehyde 25 (200 mg, 0.387 mmol) in CDCl$_3$ (2.0 mL) was slowly added (66.0 µl, 0.503 mmol) of diethylaminosulfur trifluoride (DAST) at room temperature. The reaction mixture was subsequently stirred at room temperature overnight and then quenched with 10% aq NaHCO$_3$ solution (4.0 mL). The aqueous layer was re-extracted with CH$_2$Cl$_2$ (2×20 mL), then the combined organic layers were dried with anhydrous Na$_2$SO4. The solvent was removed under reduced pressure and the residue purified by column chromatography using 2% EtOAc/DCM as eluent to give 130 mg product (62% yield).

$^1$H-NMR (400 MHz, CDCl$_3$): 1.2 (s, 3H), 1.6 (s, 3H), 4.57 (s, 1H), 5.63 (s, 1H), 7.01 (s, 1H), 7.31-7.38 (m, 11H), 7.74 (d of t, 1H, J=6.04 Hz, J=1.78 Hz), 7.84-7.86 (d, 1H, J=7.86 Hz), 8.70-8.71 (dd, 1H, J=3.97 Hz, J=0.59 Hz)

$^{13}$C-NMR (100 MHz, CDCl$_3$): 18.25, 19.94, 63.2.38, 64.4, 71.8, 79.01, 124.76, 125.28, 126.82, 127.54, 128.3, 128.6, 128.63, 128.73, 137.01, 138.65, 138.84, 147.13, 150.31, 166.15, 166.38.

Example 37

Preparation of Sodium 6E-difluoromethyl-6Z-(α'-pyridylmethylidene)penicillinate-1,1-dioxide (45)

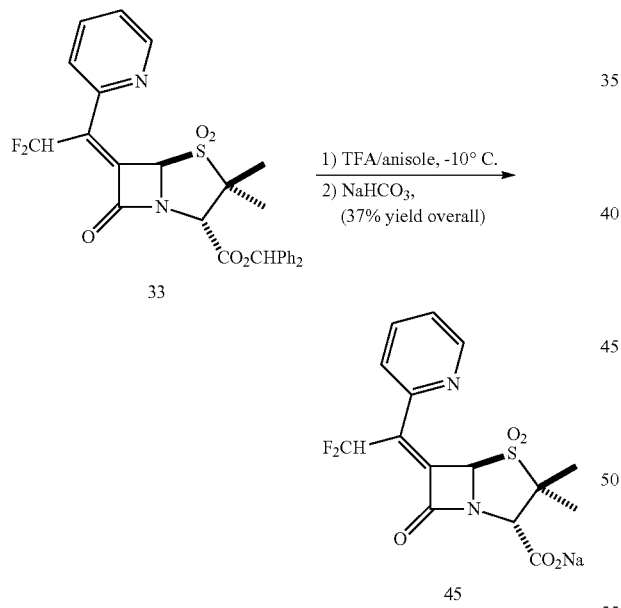

The general procedure described in Example 18 was utilized starting from ester 33 (130 mg, 0.241 mmol) to produce 35 mg sodium salt 45 (37% yield).

$^1$H-NMR (400 MHz, D$_2$O): 1.52 (s, 3H), 1.64 (s, 3H), 4.36 (s, 1H), 6.0 (s, 1H), 7.17-7.43 (m, 1H), 7.55 (d of t, 1H, J=5.8 Hz, J=2.44 Hz), 7.95-7.99 (m, 2H), 8.73 (d, 1H, J=4.23 Hz)

$^{13}$C-NMR (100 MHz, D$_2$O): 20.59, 22.61, 68.33, 68.53, 74.34, 111.37, 113.75, 116.12, 127.61, 128.84, 140.83, 150.03, 153.24, 170.81, 175.67.

Example 38

Preparation of Benzhydryl 6E-thiomethyl-6Z-(α'-pyridylmethylidene)penicillinate-1,1-dioxide (34)

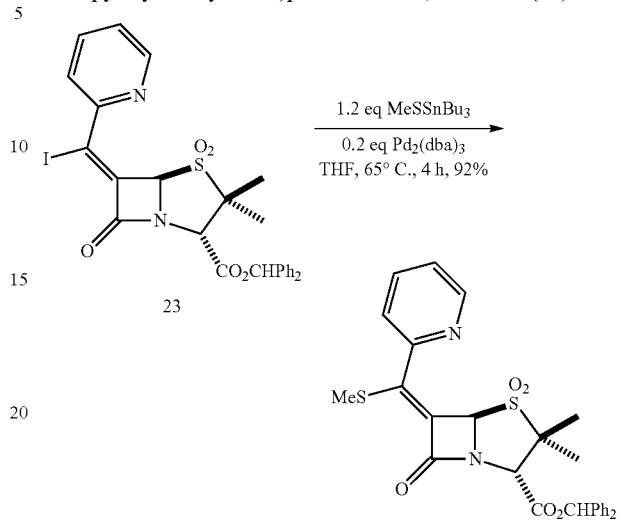

To a solution of iodide 23 (1.5 g, 2.44 mmol) in anhydrous THF (15 mL) were added thiomethyl tributylstannane (984 mg, 2.92 mmol) and Pd$_2$(dba)$_3$ (446 mg, 0.488 mmol) under an Ar atmosphere. The reaction mixture was stirred at 65° C. for 4 h and was monitored by $^1$H NMR. After completion of the reaction, the solvent was removed under reduced pressure and the residue dissolved in CH$_2$Cl$_2$. The solution was then washed with water (100 mL) and brine (100 mL). The organic layer was concentrated and purified by column chromatography using EtOAc/CH$_2$Cl$_2$ as eluent to obtain pure product 1.2 g (92% yield).

$^1$H-NMR (400 MHz, CDCl$_3$): 1.16 (s, 3H), 1.59 (s, 3H), 2.77 (s, 3H), 4.51 (s, 1H), 5.28 (s, 1H), 7.0 (s, 1H), 7.3-7.37 (m, 11H), 7.74 (d of t, 1H, J=6.46 Hz, J=1.06 Hz), 7.91-7.93 (dd, 1H, J=7.17 Hz, J=0.73 Hz), 8.72-8.74 (t of d, 1H, J=2.98 Hz, J=0.86 Hz).

$^{13}$C-NMR (100 MHz, CDCl$_3$): 13.56, 16.41, 18.08, 18.48, 20.15, 26.58, 29.11, 62.72, 64.13, 73.05, 78.75, 123.17, 124.73, 124.98, 126.77, 126.84, 127.61, 127.69, 128.19, 128.55, 128.61, 128.71, 137.22, 138.85, 139.08, 147.14, 149.65, 151.9, 167.0, 167.38.

Example 39

Preparation of Sodium 6E-thiomethyl-6Z-(α'-pyridylmethylidene)penicillinate-1,1-dioxide (46)

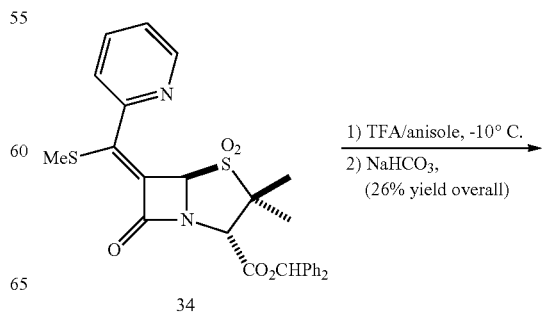

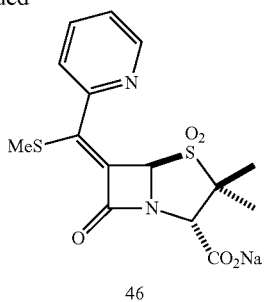

46

The general procedure described in Example 18 was utilized starting from ester 34 (100 mg, 0.187 mmol) to produce 19 mg sodium salt 46 (26% yield).

$^1$H-NMR (400 MHz, D$_2$O): 1.41 (s, 3H), 1.59 (s, 3H), 2.56 (s, 3H), 4.2 (s, 1H), 5.46 (s, 1H) 7.55 (d, 1H, J=4.87 Hz), 7.91 (d, 1H, J=6.87 Hz), 7.98 (d of t, 1H, J=6.31 Hz, J=1.54 Hz), 8.67 (d, 1H, J=4.25 Hz)

$^{13}$C-NMR (100 MHz, D$_2$O): 19.55, 20.58, 22.43, 67.94, 68.32, 74.25, 126.42, 127.24, 128.6, 141.32, 152.59, 152.66, 154.17, 172.65, 176.07.

Example 40

Preparation of Benzhydryl 6E-methylsulfinyl-6Z-(α'-pyridylmethylidene)penicillinate-1,1-dioxides (35a and 35b)

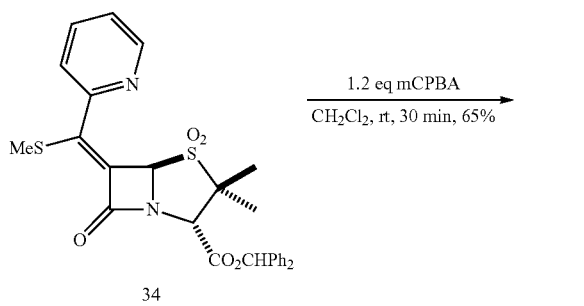

35a: 35b = 2:1

To a solution of sulfide 34 (300 mg, 0.561 mmol), in DCM (3.0 mL) were added mCPBA (150 mg of 77% mCPBA, 0.673 mmol) and the mixture was stirred at room temperature for 30 min. The reaction mixture was diluted with CH$_2$Cl$_2$ (50 mL), quenched with aqueous sodium metabisulfite solution (2.5 g, in 50 mL), and the layers were separated. The organic layer was washed with aqueous NaHCO$_3$ solution (50 mL) followed by water and brine (50 mL each), and subsequently dried over Na$_2$SO$_4$. The solution was concentrated at reduced pressure and the residue purified by column chromatography using 10% EtOAc-CH$_2$Cl$_2$ as eluent to give two sulfoxide diastereomers (35a, 130 mg; and 35b, 70 mg, 65% yield).

Sulfoxide-35a (Less Polar)

$^1$H-NMR (400 MHz, CDCl$_3$): 1.18 (s, 3H), 1.59 (s, 3H), 2.94 (s, 3H), 4.51 (s, 1H), 5.51 (s, 1H), 7.0 (s, 1H), 7.32-7.38 (m, 11H), 7.76-7.81 (d of t, 1H, J=6.04 Hz, J=1.8 Hz), 8.66-8.68 (d, 1H, J=7.98 Hz), 8.73-8.75 (t ofd, 1H, J=2.39 Hz, J=0.86 Hz).

$^{13}$C-NMR (100 MHz, CDCl$_3$): 18.17, 19.98, 41.15, 63.38, 64.22, 71.27, 79.0, 124.8, 125.92, 126.86, 127.45, 128.32, 128.58, 128.63, 128.73, 134.39, 137.14, 138.66, 138.82, 147.71, 147.9, 150.49, 165.25, 166.08.

Sulfoxide-35b (More Polar)

$^1$H-NMR (400 MHz, CDCl$_3$): 1.18 (s, 3H), 1.6 (s, 3H), 3.06 (s, 1H), 4.6 (s, 1H), 5.48 (s, 1H), 7.0 (s, 1H), 7.31-7.4 (m, 11H), 7.79-7.81 (t, 1H, J=6.04 Hz), 8.27-8.29 (d, 1H, J=7.92 Hz), 8.75-8.76 (d, 1H, J=3.96 Hz).

Example 41

Preparation of Sodium 6E-methylsulfinyl-6Z-(α'-pyridylmethylidene)penicillinate-1,1-dioxide (47a)

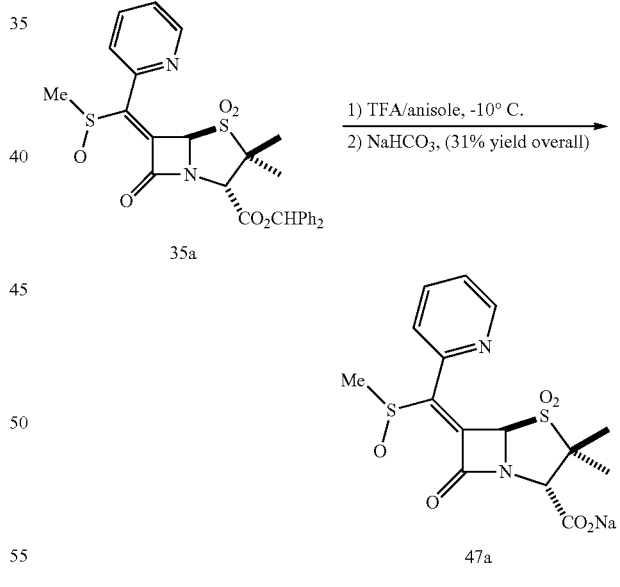

The general procedure described in Example 18 was utilized starting from ester 35a (130 mg, 0.236 mmol) to produce 30 mg sodium salt 47a (31% yield).

$^1$H-NMR (400 MHz, D$_2$O): 1.41 (s, 3H), 1.59 (s, 3H), 2.56 (s, 3H), 4.20 (s, 1H), 5.46 (s, 1H) 7.55 (m, 1H), 7.9-7.91 (m, 1H), 7.97-8.0 (m, 1H), 8.67 (d, 1H, J=3.3 Hz).

$^{13}$C-NMR (100 MHz, D$_2$O): 19.55, 20.58, 22.43, 67.94, 68.32, 74.25, 126.42, 127.24, 128.6, 141.32, 152.59, 152.66, 154.17, 172.65, 176.07.

Example 42

Preparation of Sodium 6E-methylsulfinyl-6Z-(α'-pyridylmethylidene)penicillinate-1,1-dioxide (47b)

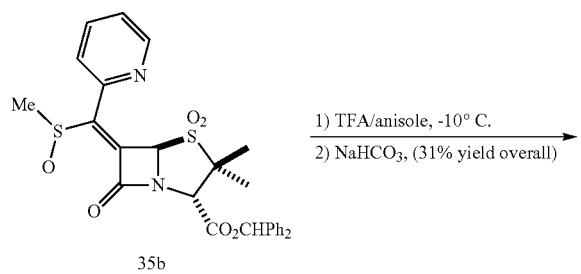

The general procedure described in Example 18 was utilized starting from ester 35b (70 mg, 0.127 mmol) to produce 16 mg sodium salt 47b (31% yield).

¹H-NMR (400 MHz, D$_2$O): 1.48 (s, 3H), 1.64 (s, 3H), 3.10 (s, 3H), 4.38 (s, 1H), 5.75 (s, 1H) 7.60-7.63 (m, 1H), 7.9-7.91 (m, 1H), 7.97-8.0 (m, 1H), 8.67 (d, 1H, J=3.3 Hz)

¹³C-NMR (100 MHz, D$_2$O): 20.53, 22.52, 42.29, 68.20, 68.89, 73.25, 127.47, 129.42, 137.35, 141.12, 149.15, 152.98, 153.69, 168.69, 175.50.

Example 43

Preparation of Benzhydryl 6E-methylsulfonyl-6Z-(α'-pyridylmethylidene)penicillinate-1,1-dioxide (36)

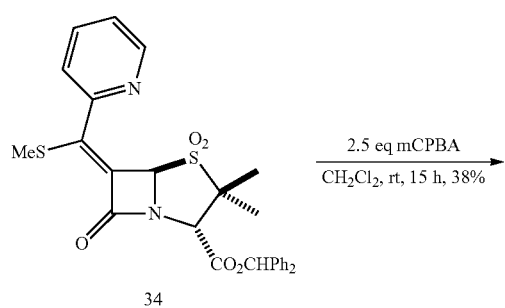

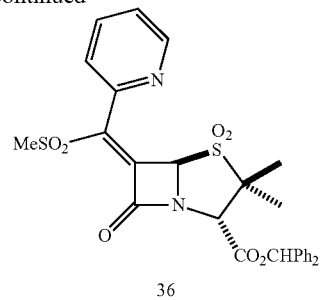

To a solution of sulfide 34 (300 mg, 0.561 mmol), in DCM (3.0 mL) were added mCPBA (312 mg of 77% mCPBA, 1.4 mmol) then the mixture was stirred at room temperature overnight. The reaction mixture was diluted with CH$_2$Cl$_2$ (50 mL) and quenched with aqueous sodium metabisulfite solution (2.5 g, in 50 mL). The layers were separated, and the organic layer was washed with aqueous NaHCO$_3$ solution (50 mL), followed by water and brine (50 mL each). Then it was dried over Na$_2$SO$_4$, concentrated, and the residue purified by column chromatography using 2% EtOAc-DCM as eluent to give sulfone (120 mg, 37.7% yield).

¹H-NMR (400 MHz, CDCl$_3$): 1.17 (s, 3H), 1.62 (s, 3H), 3.37 (s, 3H), 4.61 (s, 1H), 5.33 (s, 1H), 6.99 (s, 1H), 7.33-7.37 (m, 11H), 7.78-7.83 (d of t, 1H, J=6.08 Hz, J=1.77 Hz), 8.28-8.3 (d, 1H, J=8.07 Hz), 8.75-8.77 (q of d, 1H, J=2.15 Hz, J=0.74 Hz).

¹³C-NMR (100 MHz, CDCl$_3$): 18.28, 20.05, 44.38, 63.51, 64.0, 72.16, 79.08, 125.21, 125.49, 126.82, 126.86, 127.41, 128.32, 128.57, 128.62, 128.67, 128.73, 137.28, 138.57, 138.7, 141.77, 143.21, 147.18, 150.23, 163.59, 165.88.

Example 44

Preparation of Sodium 6E-methylsulfonyl-6Z-(α'-pyridylmethylidene)penicillinate-1,1-dioxide (48)

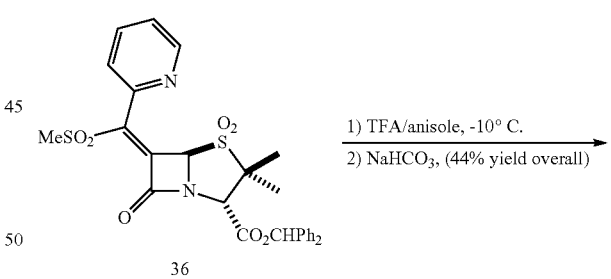

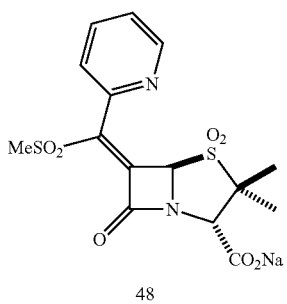

The general procedure described in Example 18 was utilized starting from ester 36 (120 mg, 0.212 mmol) to produce 40 mg sodium salt 48 (44% yield).

¹H-NMR (400 MHz, D₂O): 1.43 (s, 3H), 1.62 (s, 3H), 3.48 (s, 3H), 4.43 (s, 1H), 5.68 (s, 1H), 7.63 (d of t, 1H, J=4.89 Hz, J=1.65 Hz), 8.0-8.05 (m, 2H), 8.74 (d, 1H, J=3.99 Hz).

¹³C-NMR (100 MHz, D₂O): 20.5, 22.52, 46.08, 68.1, 69.3, 73.26, 128.19, 129.29, 141.43, 144.98, 146.29, 146.36, 149.72, 153.35, 167.21, 175.15.

Example 45

Preparation of Benzhydryl 6E-methyl-6Z-(α'-pyridylmethylidene)penicillinate-1,1-dioxide (37)

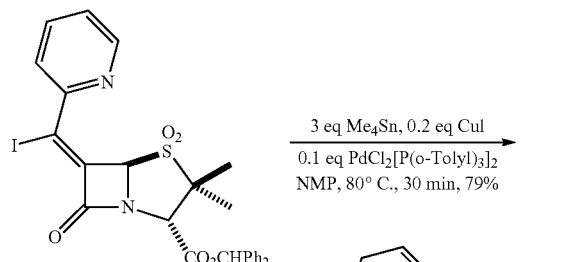

A solution of tetramethyltin (135 μl, 0.975 mmol), in dry NMP (1.0 mL) was added to degassed mixture of iodide (200 mg, 0.325 mmol), PdCl₂[P(o-Tolyl)₃]₂ (25 mg, 0.0325 mmol), and CuI (12 mg, 0.065 mmol) in dry NMP (2.0 mL) and the mixture was stirred under nitrogen at 80° C. for 30 min. It was then cooled to rt, poured into a saturated aqueous NH₄Cl solution (25 mL) and extracted with CH₂Cl₂ (6×25 mL). The organic extract was washed with brine (2×50 mL), dried over Na₂SO₄ and concentrated under reduced pressure. The resulting crude product was purified by silica gel column chromatography using a mixture 2% EtOAc in CH₂Cl₂ as eluent to give 130 mg of pure product (79% yield).

Example 46

Preparation of Sodium 6E-methyl-6Z-(α'-pyridylmethylidene)penicillinate-1,1-dioxide (49)

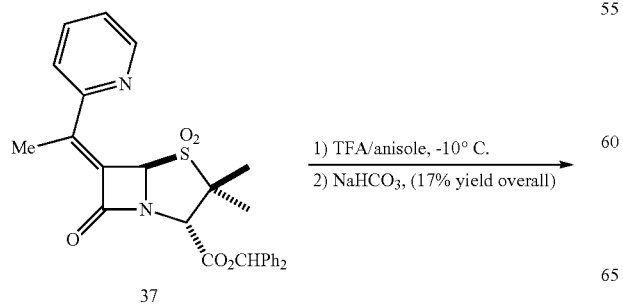

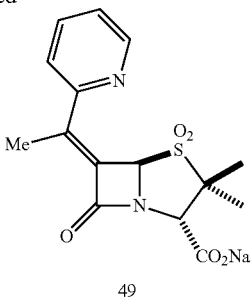

The general procedure described in Example 18 was utilized starting from ester 37 (120 mg, 0.239 mmol) to produce 15 mg sodium salt 49 (17% yield).

¹H-NMR (400 MHz, D₂O): 1.5 (s, 3H), 1.6 (s, 3H), 2.54 (s, 3H), 4.22 (s, 1H), 5.89 (s, 1H), 7.47 (d of t, 1H, J=5.78 Hz, J=1.81 Hz), 7.76 (d, 1H, J=7.93 Hz), 7.94 (d of t, J=6.13 Hz, J=1.67 Hz), 8.66 (d, 1H, J=4.64 Hz).

Scheme 5

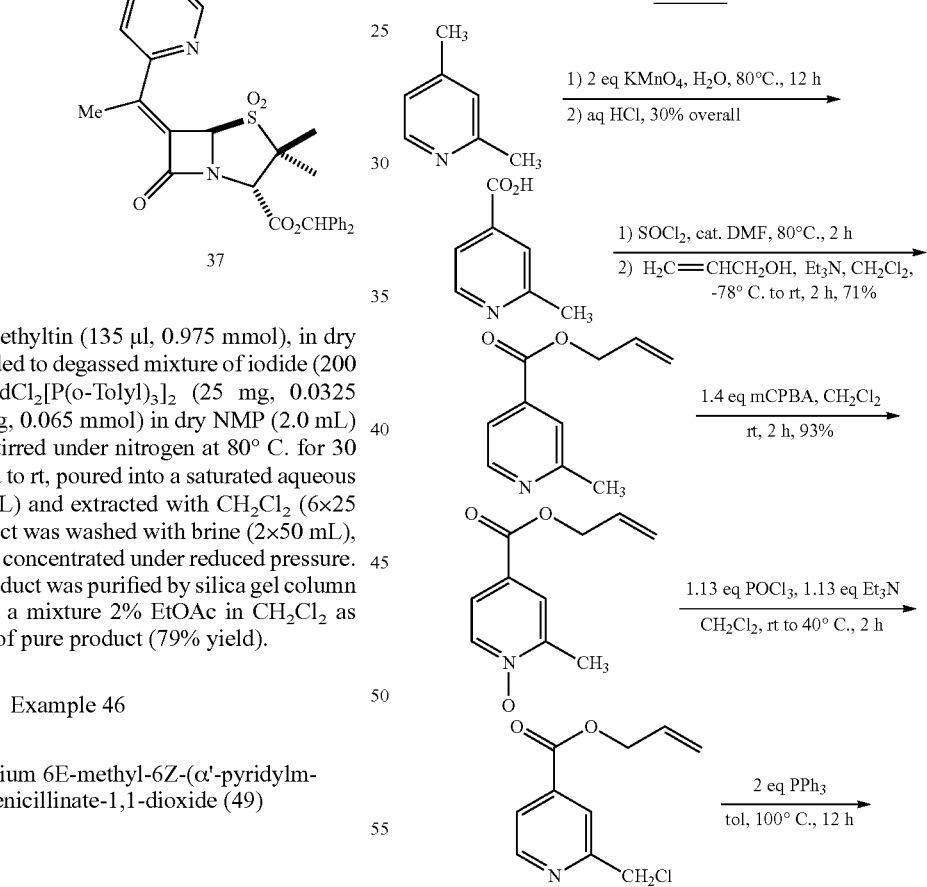

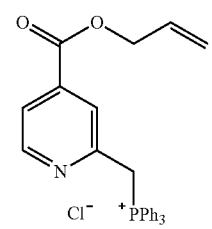

Scheme 6
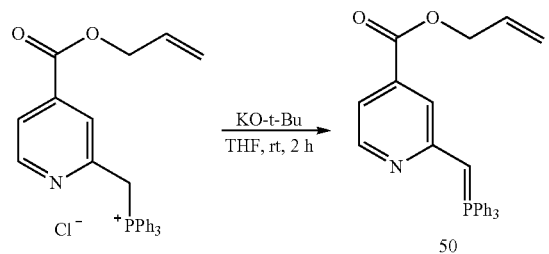
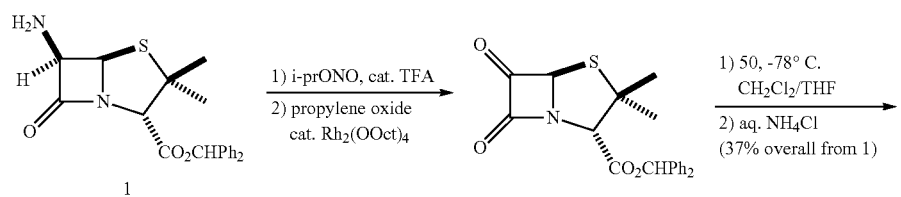
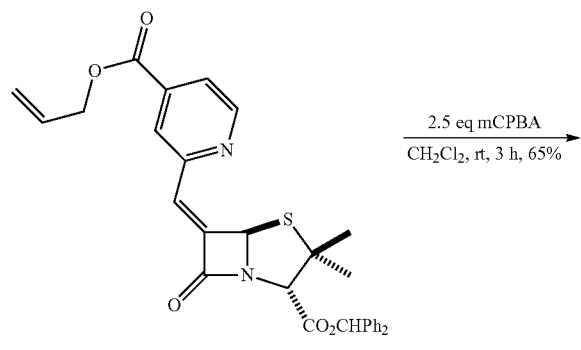
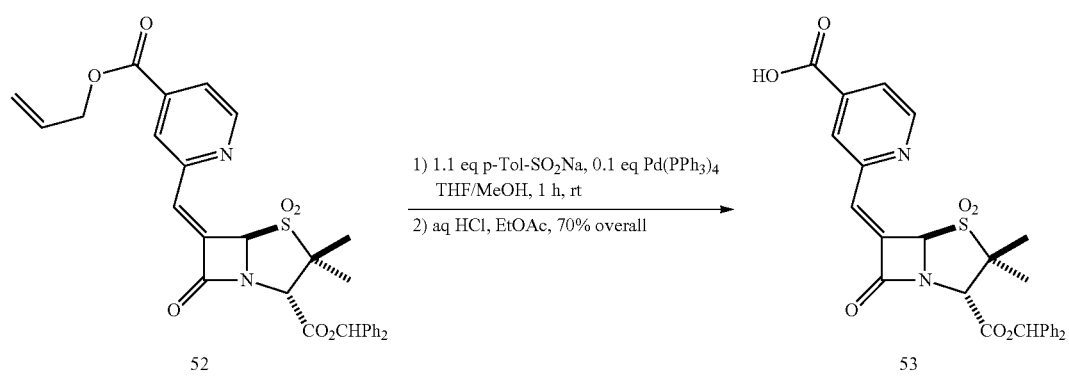

Scheme 7
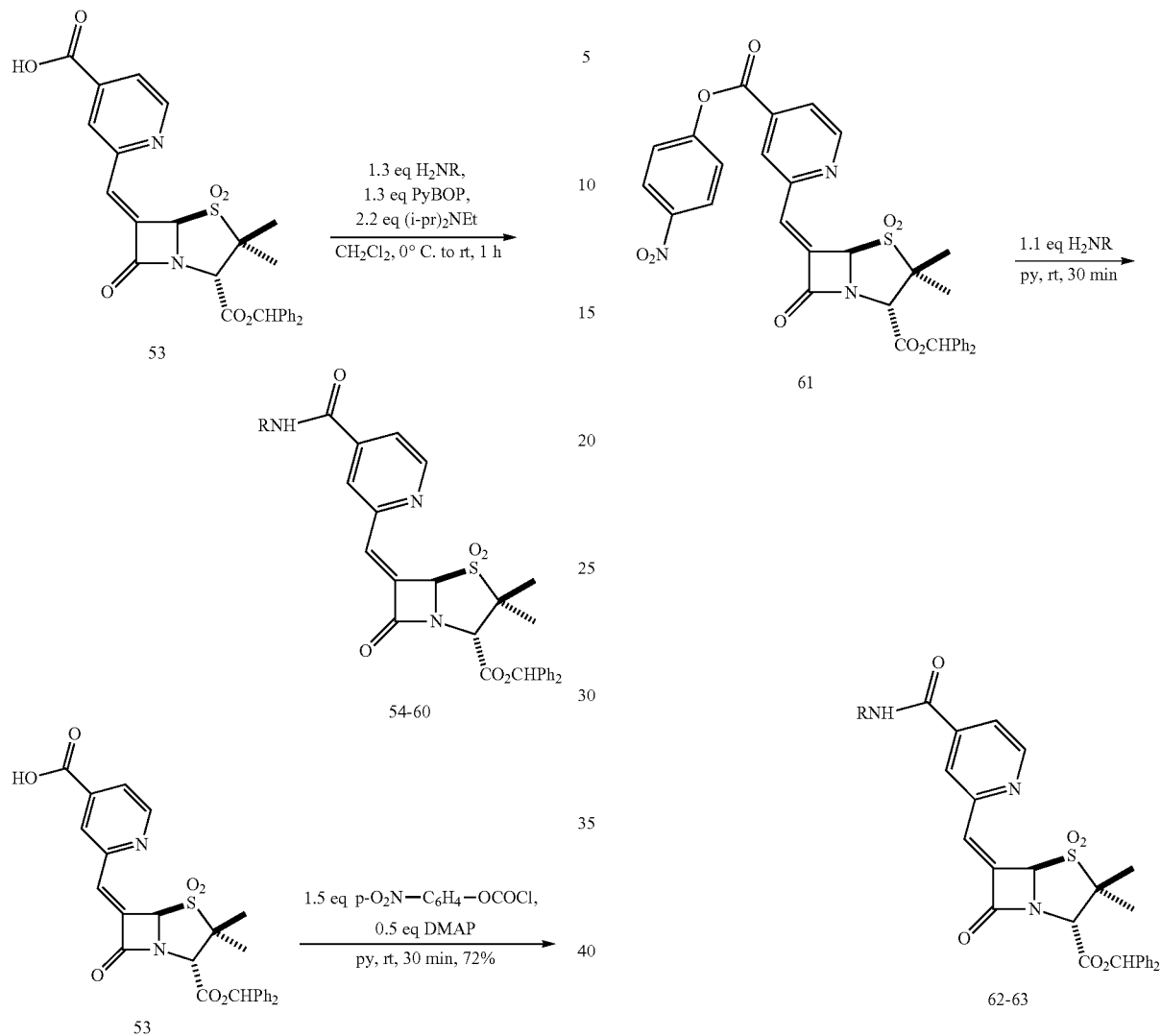
Scheme 8
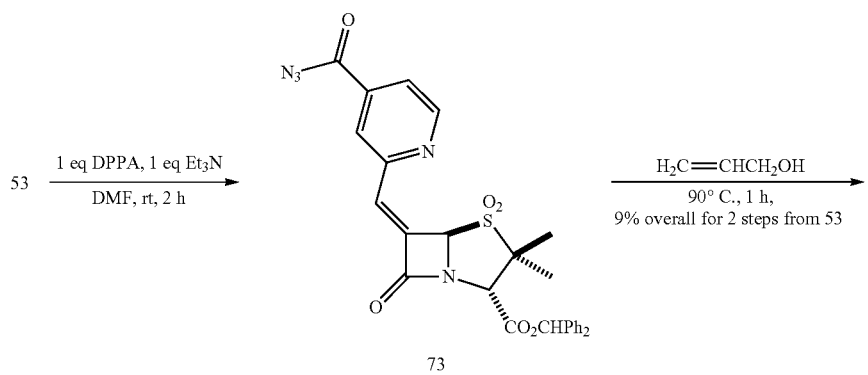

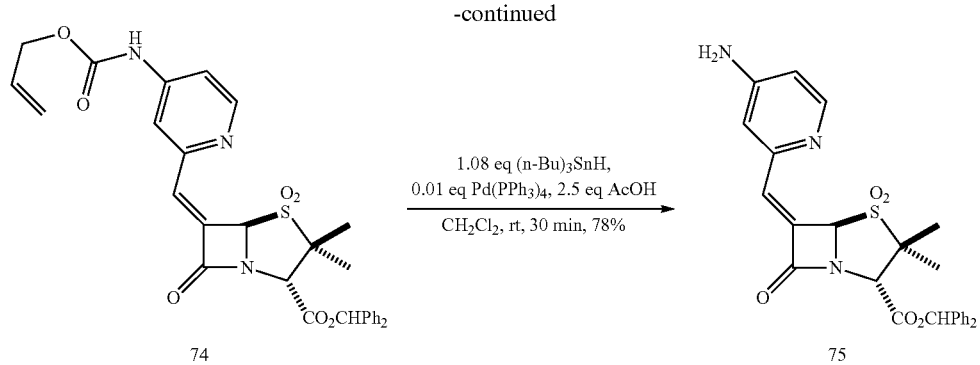
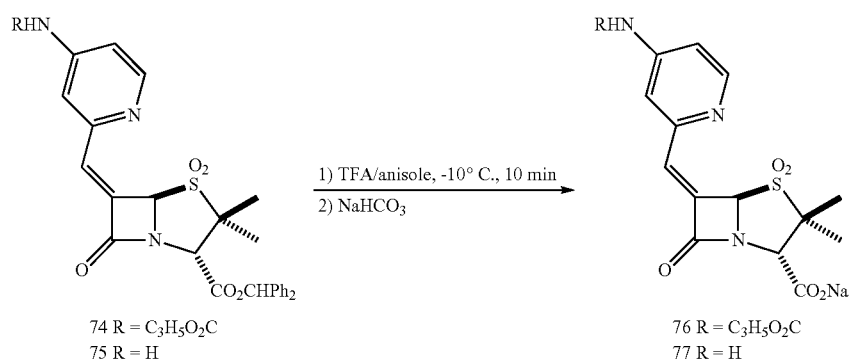
Scheme 9
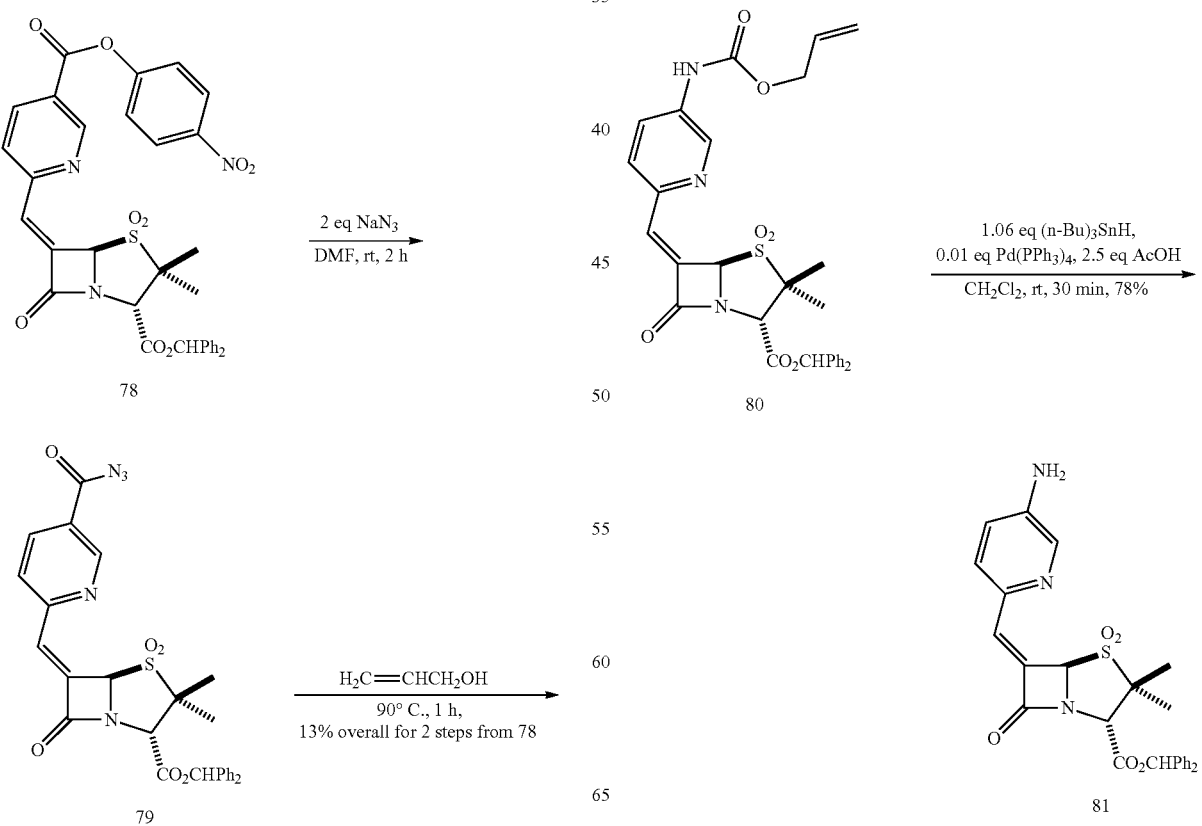

Scheme 10

-continued

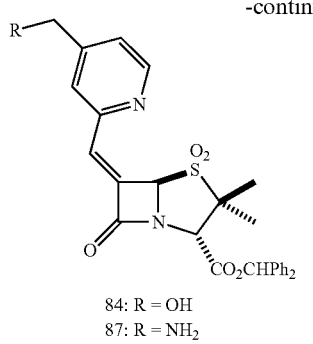

84: R = OH
87: R = NH$_2$

1) TFA/anisole, -10° C., 10 min
2) NaHCO$_3$

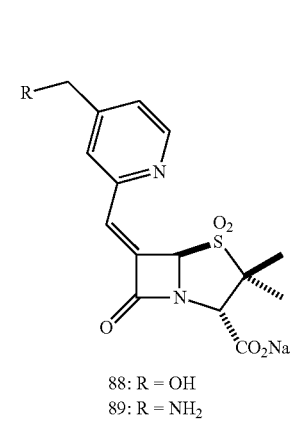

88: R = OH
89: R = NH$_2$

Example 47

Preparation of 2-methylpyridine-4-carboxylic acid

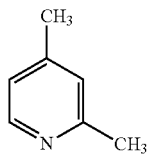

1) 2 eq KMnO$_4$, H$_2$O, 80° C., 12 h
2) aq HCl, 30% overall

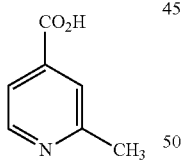

To a mechanically (overhead) stirred solution of 2,4-lutidine (140 g, 1.31 mol) in water (1500 mL) was added KMnO$_4$ (412 g, 2.61 mol) portion-wise at 80° C. over a period of 3 h, taking care to allow each portion to react before adding the next. The reaction mixture was then stirred at 80° C. for overnight. The solution was allowed to settle and the aqueous layer separated from the precipitated MnO$_2$. The water was then removed under reduced pressure to produce a volume of approximately 400 mL. Remaining water was chilled in an ice bath and acidified to pH 3.0 with dilute HCl. Solid was allowed to precipitate for an addition hour, then filtered and dried under high vacuum at 50° C. for 48 h to give white solid product (54.9 g, 30% yield).

Example 48

Preparation of allyl 2-methylpyridine-4-carboxylate

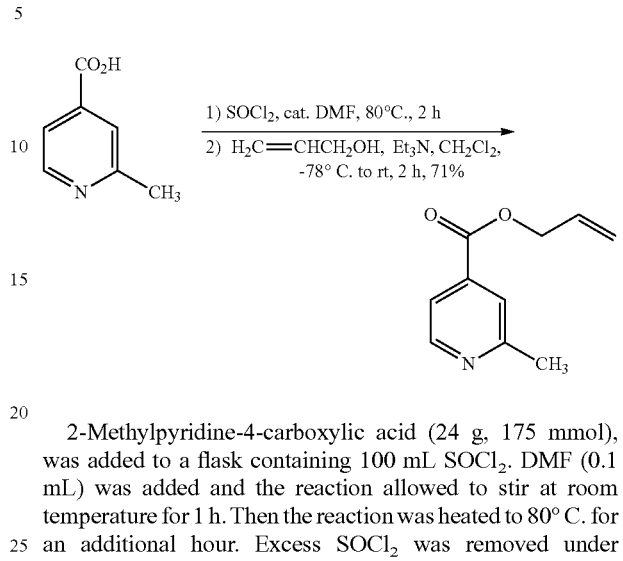

2-Methylpyridine-4-carboxylic acid (24 g, 175 mmol), was added to a flask containing 100 mL SOCl$_2$. DMF (0.1 mL) was added and the reaction allowed to stir at room temperature for 1 h. Then the reaction was heated to 80° C. for an additional hour. Excess SOCl$_2$ was removed under vacuum. To ensure complete removal of SOCl$_2$, dry toluene (ca 20 mL) was added (2×) and subsequently removed under high vacuum.

The resultant black solid was dissolved in dry CH$_2$Cl$_2$ (300 mL) and chilled to –78° C. Then allyl alcohol (30.5 g, 36 mL, 525 mmol) and Et$_3$N (53 g, 73 mL, 525 mmol) were added. The reaction was then allowed to warm to room temperature over a 2 h period. The reaction was worked up by pouring into aq Na$_2$CO$_3$, separating the layers, washing the organic layer with water. The organic layer was subsequently dried over Na$_2$SO$_4$, concentrated under reduced pressure, and the remaining product distilled under high vacuum (bp=95° C. at 0.2 mm) to produce 22 g product (71% yield).

$^1$H-NMR (400 MHz, CDCl$_3$): 2.64 (s, 3H), 4.84 (d, 2H, J=4.47 Hz), 5.31-5.45 (ABq, 2H, J=14.46 Hz, J=8.44 Hz), 6.0-6.07 (m, 1H), 7.66 (dd, 1H, J=4.0 Hz, J=0.5 Hz), 7.73 (s, 1H), 8.65 (d, 1H, J=5.11 Hz).

Example 49

Preparation of allyl 2-methylpyridine-4-carboxylate-N-oxide

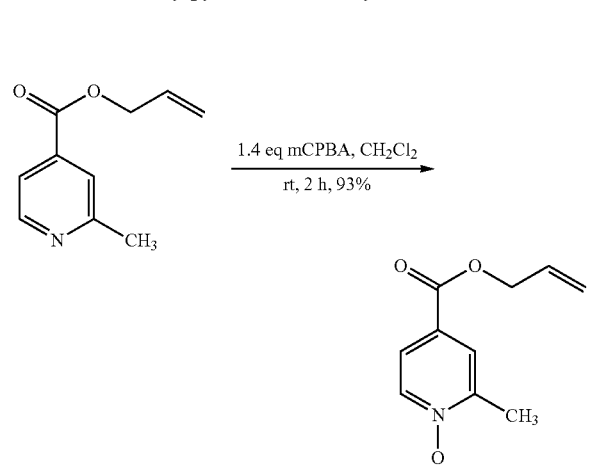

To a solution of allyl 2-methylpyridine-4-carboxylate (21.7 g, 122 mmol) in CH$_2$Cl$_2$ (250 mL) was added mCPBA (77%, 39.3 g, 159 mmol). The reaction was allowed to stir at room temperature for 2 h. The reaction mixture was then quenched with aqueous sodium metabisulfite solution (5 g, in 100 mL) and the layers were separated. The organic layer was washed with aqueous NaHCO$_3$ solution (200 mL) followed by water and brine (200 mL each). Then it was dried over Na$_2$SO$_4$, concentrated and purified by column chromatography using 50% EtOAc-CH$_2$Cl$_2$ as eluent to give 105 g of pure N-Oxide (93% yield).

$^1$H-NMR (400 MHz, CDCl$_3$): 2.53 (s, 3H), 4.82-4.84 (d, 2H, J=3.178 Hz), 5.32-5.44 (ABq, 2H, J=15.76 Hz, J=8.08 Hz), 5.44-6.05 (m, 1H), 7.75-7.77 (dd, 1H, J=4.34 Hz, J=2.44 Hz), 7.89-7.9 (d, 1H, J=2.47 Hz), 8.26-8.28 (d, 1H, J=6.76 Hz).

Example 50

Preparation of allyl 2-(chloromethyl)pyridine-4-carboxylate

To a stirred solution of N-Oxide (105 g, 544 mmol) in CH$_2$Cl$_2$ (600 mL) under nitrogen atmosphere, the addition of solution of phosphoryl chloride (57.3 mL, 615 mmol) in CH$_2$Cl$_2$ (500 mL) was begun. After one-tenth of the phosphoryl chloride solution had been added, simultaneously the addition of a solution of Et$_3$N (85.5 mL, 615 mmol) in CH$_2$Cl$_2$ (500 mL) was begun. The rate of addition of the phosphoryl chloride and the triethylamine solutions was the same and was set so that the heat of reaction caused the CH$_2$Cl$_2$ to reflux. After the addition of the phosphoryl chloride solution had been completed, the remaining one-tenth of the triethylamine solution was completed. Then the reaction mixture was stirred at rt for another hour. The reaction mixture was basified to pH 8 with saturated aqueous NaHCO$_3$, the layers were separated, and the organic layer was washed with water (500 mL) followed by brine (500 mL). Then the solution was dried over Na$_2$SO$_4$ and concentrated to give 103 g of crude chloride (90% crude yield).

$^1$H-NMR (400 MHz, CDCl$_3$): 4.78 (s, 2H), 4.87-4.88 (d, 2H, J=3.32 Hz), 5.33-5.46 (ABq, 2H, J=14.64 Hz, J=9.24 Hz), 6.0-6.07 (m, 1H), 7.88-7.89 (d, 1H, J=3.84 Hz), 8.1 (s, 1H), 8.76-8.77 (d, 1H, J=5.08 Hz).

Example 51

Preparation of allyl 2-[(triphenylphosphonium)methyl)]pyridine-4-carboxylate chloride

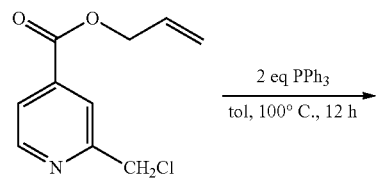

2 eq PPh$_3$
tol, 100° C., 12 h

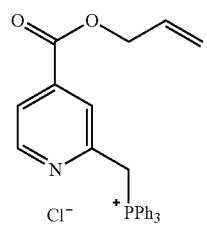

$^1$H-NMR (400 MHz, d$_6$-DMSO): 4.80 (d of t, 2H, J=3.86 and 1.04 Hz), 5.30 (d, 1H, J=7.55 Hz), 5.39 (d, 1H, J=12.43 Hz), 5.75 (d, 2H, J=11.3 Hz), 5.06-5.12 (m, 1H), 7.70-7.90 (m, 17H), 8.58 (d, 1H, J=5.08 Hz).

$^{31}$P-NMR (162 MHz, d$_6$-DMSO): 24.9

Example 52

Preparation of Benzhydryl 6Z-[4"-(Allyloxycarbonyl)-α-pyridylmethylidene]penicillinate (51)

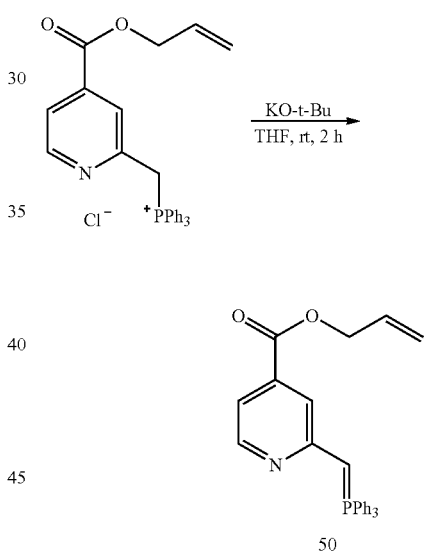

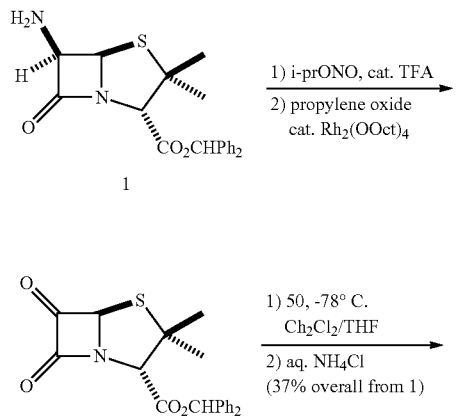

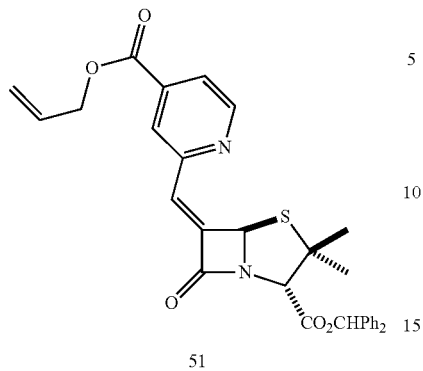

51

To a solution of triphenyl[2-pyridyl(4-allyloxycarbonyl)methyl]phosphonium chloride (32.0 g, 67.5 mmol), in dry THF (300 mL) was added KO$^t$Bu (6.5 g, 54.0 mmol) and reaction mixture was stirred at room temperature for 2 h to generate the Wittig ylide, then this solution was chilled to −78° C. In a second flask, benzhydryl 6-oxopenicillinate (67.5 mmol, 25.7 g, prepared as described in J. D. Buynak et al., *Tetrahedron Letters* 39, 4945-4946 (1998)) was dissolved in dry CH$_2$Cl$_2$ (800 mL) and the resultant solution cooled to −78° C. Then the cooled (−78° C.) solution of the above Wittig reagent was then slowly added to ketone at −78° C. (by cannula) and the resultant reaction mixture stirred at this temperature for 30 min. Then a saturated aqueous solution of NH$_4$Cl was added and the reaction mixture slowly warmed to room temperature with stirring. The layers were separated and the aqueous layers extracted with an additional portion of CH$_2$Cl$_2$ (200 mL). The combined organic layers were washed with water (500 mL), brine (500 mL). Then it was dried over Na$_2$SO$_4$. Concentrated and purified by column chromatography using 2% EtOAc-CH$_2$Cl$_2$ as eluent to give 13.5 g (37% yield) of product.

Example 53

Preparation of Benzhydryl 6Z-[4'-(Allyloxycarbonyl)-α-pyridylmethylidene]penicillinate-1,1-dioxide (52)

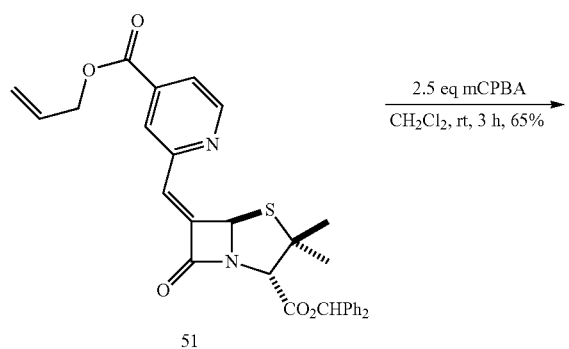

Sulfone 52 was prepared according to the general procedure described in Example 17 (yield=65%).

Example 54

Preparation of Benzhydryl 6Z-[4'-carboxy-α-pyridylmethylidene]penicillinate-1,1-dioxide (53)

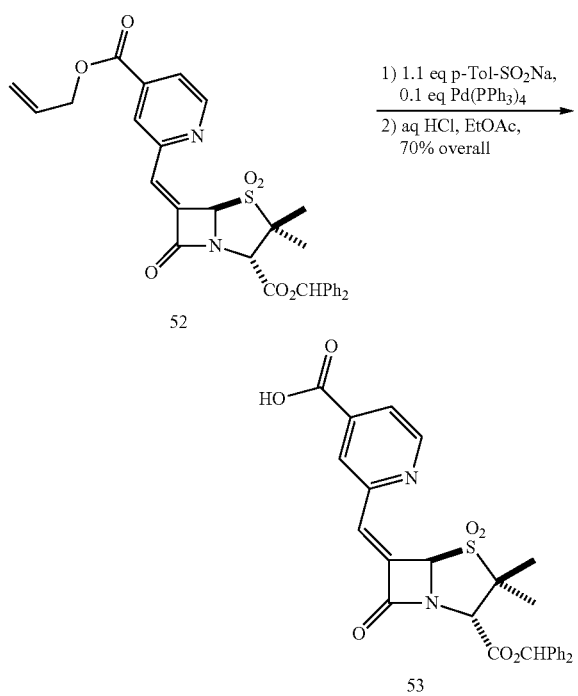

To a solution of allyl ester 52 (4.01 g, 7.0 mmol) in THF (40.0 mL) was added Pd(PPh$_3$)$_4$ (800 mg, 0.7 mmol). Then a solution of sodium p-toluene sulfinate (1.37 g, 7.7 mmol) in MeOH (25.0 mL) was added in one portion. The reaction mixture was allowed to stir at room temperature, while monitoring TLC (CH$_2$Cl$_2$ eluent). After 1 hour, the reddish black solution was concentrated and re-dissolved in EtOAc (100.0 mL) (partially soluble). While stirring this slurry a dilute aqueous solution of HCl (50.0 mL of 0.24 M) was added, the color immediately changed to light green and everything went into solution. The ethyl acetate layer was separated, concentrated and purified on column chromatography using CH$_2$Cl$_2$ containing 5% MeOH and 0.5% acetic acid in CH$_2$Cl$_2$ as eluent to give 2.6 g of pure product (70% yield).

¹H-NMR (400 MHz, CDCl₃): 1.21 (s, 3H), 1.59 (s, 3H), 4.56 (s, 1H), 5.71 (s, 1H), 7.01 (s, 1H), 7.32-7.38 (m, 11H), 7.88 (d, 1H, J=3.84 Hz), 7.94 (s, 1H), 8.86 (d, 1H, J=4.9 Hz).

TABLE 3

Preparation of compounds 54-60

[Structure 53: pyridine-carboxylic acid fused β-lactam sulfone with CO₂CHPh₂]

Reagents: 1.3 eq H₂NR, 1.3 eq PyBOP, 2.2 eq (i-pr)₂NEt, CH₂Cl₂, 0° C. to rt, 1 h

[Structure 54-60: amide product]

| Compound | H₂NR = | Yield |
|---|---|---|
| 54 | H₂N-CH₂CH₂-NMe₂ | 44% |
| 55 | H₂N-CH₂CH₂-NH-C(=O)-C(CH₃)₂-(4-biphenyl) | 37% |
| 56 | 4-(aminomethyl)-2-aminothiazole | 55% |
| 57 | H₂N-CH₂CH₂-NH-C(=NH)-NH₂ · HCl | 28% |
| 58 | H₂N-(CH₂)₃-NH-C(=O)-C(CH₃)₂-(4-biphenyl) | 21% |
| 59 | 3-aminopyrrolidine | 15% |
| 60 | H₂N-(CH₂)₃-NH-C(=O)-C(CH₃)₂-(4-biphenyl) | 25% |

54

¹H-NMR (400 MHz, CDCl₃): 1.19 (s, 3H), 1.56 (s, 3H), 2.34 (s, 6H), 2.65 (s, 2H), 3.52 (s, 2H), 4.54 (s, 1H), 5.69 (s, 1H), 6.99 (s, 1H), 7.3-7.37 (m, 11H), 7.57 (d, 1H, J=3.84 Hz), 7.7 (s, 1H), 8.69 (d, 1H, J=4.92 Hz).

¹³C-NMR (100 MHz, CDCl₃): 18.35, 19.88, 44.64, 63.13, 64.54, 71.9, 78.9, 121.97, 123.55, 126.81, 127.62, 128.25, 128.62, 128.72, 129.31, 133.85, 138.76, 138.98, 151.1, 151.74, 166.46.

55

¹H-NMR (400 MHz, CDCl₃): 1.2 (s, 3H), 1.57 (s, 3H), 1.75 (s, 3H), 1.77 (s, 3H), 3.34 (t, 2H, J=4.91), 3.46-3.47 (t, 2H, J=4.66 Hz), 4.54 (s, 1H), 5.35 (s, 1H), 6.29 (brs, 1H), 7.03 (s, 1H), 7.27-7.4 (m, 20H), 7.50 (d, 1H, J=4.52 Hz), 7.53 (s, 1H), 8.20 (brs, 1H), 8.61 (d, 1H, J=4.79 Hz)

¹³C-NMR (100 MHz, CDCl₃): 17.92, 19.55, 28.8, 29.07, 39.17, 41.85, 48.02, 48.24, 48.45, 48.66, 48.88, 49.09, 49.3, 62.86, 64.4, 71.51, 76.68, 77.0, 77.32, 78.88, 80.94, 121.9, 122.96, 124.22, 126.45, 126.51, 126.63, 126.96, 127.32, 128.11, 128.42, 128.46, 128.52, 129.48, 132.86, 138.53, 138.67, 139.07, 139.91, 145.22, 150.74, 151.26, 157.3, 165.15, 166.35, 168.25.

IR (thin film): 847.7, 1171.4, 1262.09, 1326.28, 1455.61, 1538.27, 1698.7, 1783.79

56
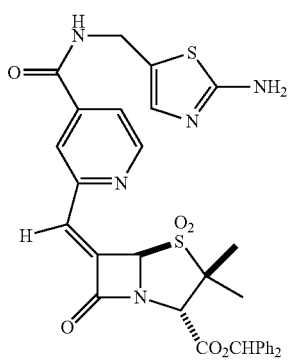
¹H-NMR (400 MHz, CDCl₃): 1.2 (s, 3H), 1.56, (s, 3H), 3.57-3.61 (m, 2H), 4.40 (d, 2H, J=5.46 Hz), 4.53 (s, 1H), 5.72 (s, 1H), 5.92 (brs, 2H, Amine), 6.29 (s, 1H), 7.0 (s, 1H), 7.28-7.4 (m, 11H), 7.71 (d of d, 1H, J=3.48 Hz, J=1.46 Hz), 7.83 (s, 1H), 8.21 (t, 1H), 8.68 (d, 1H, J=4.93 Hz).
57
¹H-NMR (400 MHz, CDCl₃): 1.14 (s, 3H), 1.5, (s, 3H), 3.57-3.61 (m, 2H), 4.40-4.41 (m, 2H), 4.45 (s, 1H), 5.65 (s, 1H), 6.93 (s, 1H), 7.25-7.31 (m, 11H), 7.73 (m, 1H), 7.87 (s, 1H), 8.68 (d, 1H, J=4.94 Hz).
58
¹H-NMR (400 MHz, CDCl₃): 1.21 (s, 3H), 1.58 (s, 3H), 1.62-1.67 (m, 2H), 1.79 (s, 6H), 3.21-3.25 (q, 2H, J=6.2 Hz), 3.41-3.45 (q, 2H, J=5.68 Hz), 4.56 (s, 1H), 5.1-5.13 (t, 1H, J=6.6 Hz), 5.62 (s, 1H), 7.01 (s, 1H), 7.18 (s, 1H), 7.32-7.48 (m, 21H), 8.6-8.61 (d, 1H, J=4.92 Hz).
¹³C-NMR (100 MHz, CDCl₃): 18.34, 19.89, 28.96, 29.01, 29.31, 35.5, 36.71, 63.12, 64.52, 71.89, 78.88, 81.21, 122.04, 123.38, 124.47, 126.79, 126.83, 127.18, 127.57, 128.25, 128.56, 128.61, 128.65, 128.71, 129.58, 133.4, 138.74, 138.95, 139.68, 142.41, 145.25, 150.87, 151.41, 156.54, 164.18, 166.49, 168.12.
IR (thin film): 911.25, 1119.09, 1169.17, 1261.01, 1326.96, 1528.91, 1664.32, 1701.29, 1785.29, 2249.92, 2979.45, 3385.96.
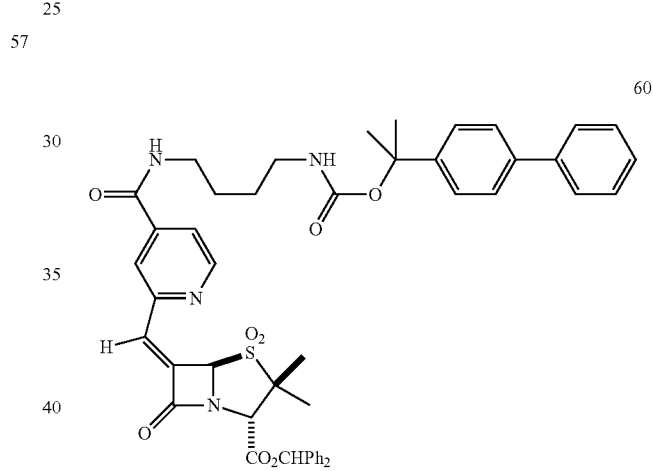
60
¹H-NMR (400 MHz, CDCl₃): 1.21 (s, 3H), 1.51-1.56 (m, 4H), 1.58 (s, 3H), 1.76 (s, 6H), 3.10 (d, 2H, J=5.9 Hz), 3.34-3.37 (q, 2H, J=5.74 Hz), 4.57 (s, 1H), 5.0-5.01 (t, 1H, Amide), 5.65 (s, 1H), 7.01 (s, 1H), 7.21-7.5 (m, 22H), 8.57-8.58 (d, 1H, J=4.87 Hz).
¹³C-NMR (400 MHz, D₂O): 18.27, 19.86, 25.47, 27.76, 29.02, 29.14, 39.67, 63.07, 64.59, 71.86, 78.91, 80.71, 122.14, 123.45, 124.54, 126.8, 126.87, 127.15, 127.55, 128.25, 128.56, 128.6, 128.65, 128.7, 129.62, 138.69, 138.9, 139.48, 140.42, 142.6, 145.34, 150.84, 151.41, 155.74, 164.48, 166.4, 168.04.
IR (thin film): 911.08, 1169.73, 1253.21, 1326.28, 1537.61, 1660.46, 1704.24, 1784.16, 2936.46, 3346.46.

Example 55

Preparation of P-Nitrophenyl Ester 61

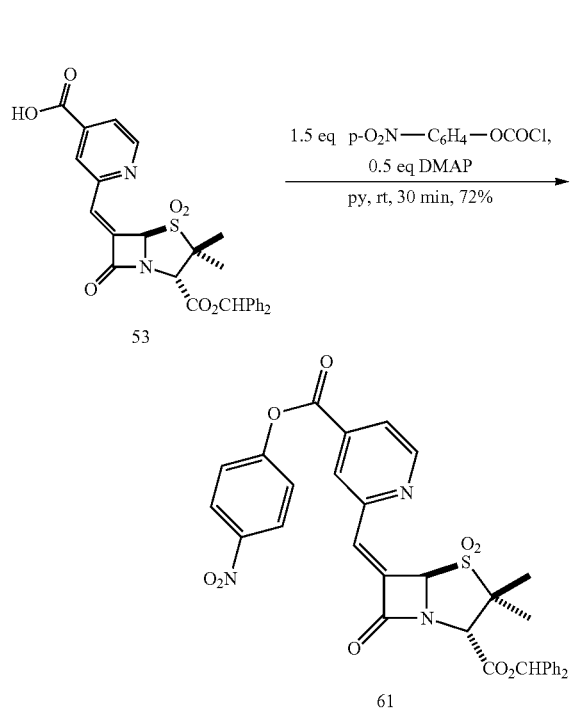

To a solution of acid 53 (1.0 g, 1.88 mmol) in pyridine (10.0 mL) was added p-nitrophenychloroformate (567 mg, 2.82 mmol), and DMAP (115 mg, 0.94 mmol) at room temperature. The reaction mixture was then stirred 30 min and subsequently diluted with $CH_2Cl_2$ (25.0 mL). The organic layer was washed with water (25 mL) and brine (25 mL). The organic layer was dried over $Na_2SO_4$, concentrated and purified by column chromatography using $CH_2Cl_2$ as eluent to obtain pure product 880 mg (72% yield).

$^1$H-NMR (400 MHz, $CDCl_3$): 1.23 (s, 3H), 1.61 (s, 3H), 4.6 (s, 1H), 5.75 (s, 1H), 7.02 (s, 1H), 7.35-7.39 (m, 12H), 7.44 (d, 2H, J=9.12 Hz), 7.98 (dd, 1H, J=3.41 Hz, J=1.49 Hz), 8.04 (s, 1H), 8.33-8.35 (d, 2H, J=9.12 Hz), 8.92 (d, 1H, J=4.89 Hz).

Example 56

Preparation of Compounds 61-63

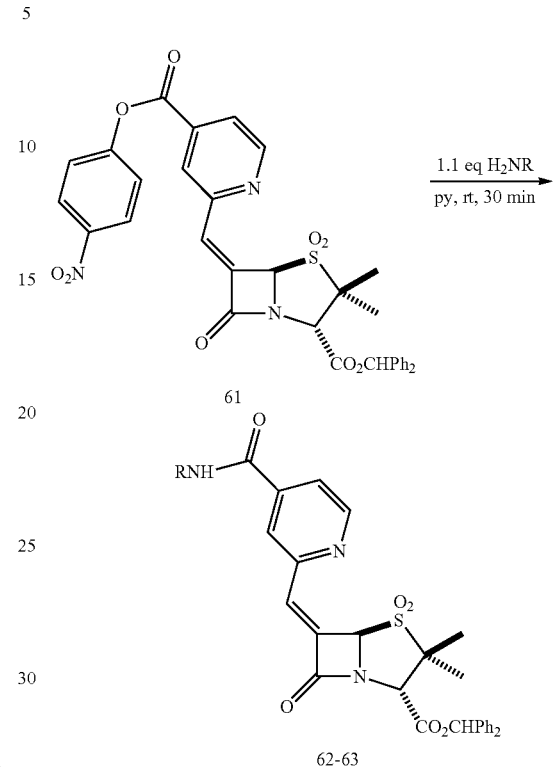

62: $H_2NR = H_3N$ (74% yield)
63: $H_2NR = H_2NMe$ (55% yield)

General Procedure:

To a solution of p-nitrophenylester (1.0 eq) in pyridine was added amine (1.1 eq) at room temperature and the reaction mixture was stirred for 10-30 min. The reaction mixture was then diluted with $CH_2Cl_2$ and washed with water and brine. The organic layer was dried over $Na_2SO_4$, concentrated and purified by column chromatography using appropriate EtOAc in DCM as eluent to obtain pure product.

For the removal of the benzhydryl ester, the general procedure described in Example 18 was followed.

TABLE 4

Preparation of compounds 64-72

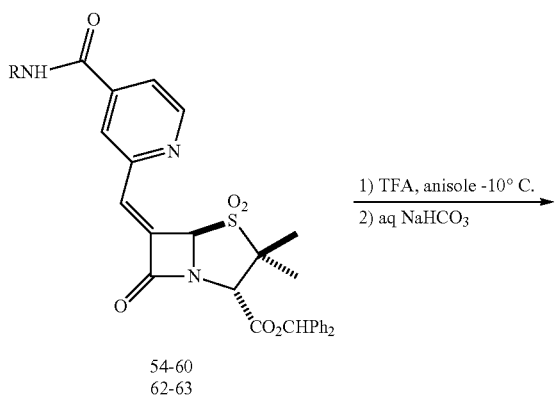

TABLE 4-continued

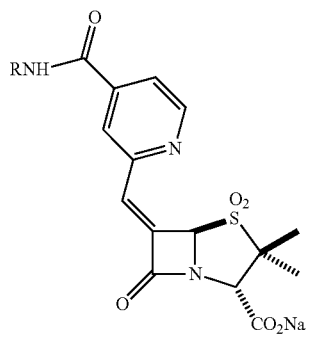

64-72

| | | | | Yield |
|---|---|---|---|---|
| 54: HNR = | (HN-CH₂CH₂-NMe₂) | 64: HNR = | (HN-CH₂CH₂-NMe₂) | 21% |
| 55: HNR = | (HN-CH₂CH₂-NHC(O)C(CH₃)₂-biphenyl) | 65: HNR = | (HN-CH₂CH₂-NH₂) | 33% |
| 56: HNR = | (HN-CH₂-2-aminothiazol-4-yl) | 66: HNR = | (HN-CH₂-2-aminothiazol-4-yl) | 19% |
| 57: HNR = | (HN-CH₂CH₂-NH-C(=NH)NH₂ · HCl) | 67: HNR = | (HN-CH₂CH₂-NH-C(=NH)NH₂⁺) | 30% |
| 58: HNR = | (HN-CH₂CH₂CH₂-NHC(O)C(CH₃)₂-biphenyl) | 68: HNR = | (HN-CH₂CH₂CH₂-NH₂) | 43% |
| 59: HNR = | (HN-3-pyrrolidinyl) | 69: HNR = | (HN-3-pyrrolidinyl) | 25% |
| 60: HNR = | (HN-(CH₂)₄-NHC(O)C(CH₃)₂-biphenyl) | 70: HNR = | (HN-(CH₂)₄-NH₂) | 43% |
| 61: HNR = | H₂N | 71: HNR = | H₂N | 27% |
| 62: HNR = | HNCH₃ | 72: HNR = | HNCH₃ | 33% |

64
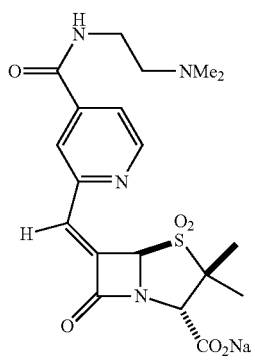
¹H-NMR (400 MHz, D₂O): 1.53 (s, 3H), 1.61 (s, 3H), 2.69 (s, 6H), 3.11 (t, 2H, J=5.88 Hz), 3.72 (t, 2H, J=6.16 Hz), 4.3 (s, 1H), 6.04 (s, 1H), 7.55 (s, 1H), 7.73 (d, 1H, J=4.4 Hz), 7.87 (s, 1H)), 8.80 (d, 1H, J=4.84 Hz).
¹³C-NMR (100 MHz, D₂O): 20.58, 22.51, 46.03, 46.15, 59.39, 68.36, 68.63, 74.49, 125.46, 126.61, 133.12, 134.74, 154.06, 154.46, 171.25, 173.41, 175.79.
65
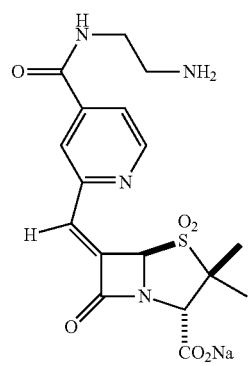
¹H-NMR (400 MHz, D₂O): 1.52 (s, 3H), 1.61 (s, 3H), 3.25 (t, 2H, J=6.0 Hz), 3.73 (t, 2H, J=5.89 Hz), 4.3 (s, 1H), 5.97 (s, 1H), 7.5 (s, 1H), 7.72-7.73 (dd, 1H, J=3.64 Hz, J=1.26 Hz), 7.84 (s, 1H), 8.77 (d, 1H, J=4.96 Hz).
¹³C-NMR (100 MHz, D₂O): 18.08, 20.01, 38.27, 39.54, 65.87, 66.12, 71.95, 122.96, 124.17, 130.55, 132.25, 142.47, 151.56, 151.94, 168.83, 170.87, 173.28.
66
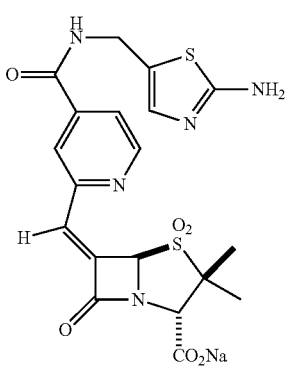
¹H-NMR (400 MHz, D₂O): 1.53 (s, 3H), 1.61 (s, 3H), 4.3 (s, 1H), 4.44 (s, 1H) 6.06 (s, 1H), 6.53 (s, 1H), 7.57 (s, 1H), 7.73 (d, 1H, J=4.88 Hz), 7.87 (s, 1H), 8.80 (d, 1H, J=4.9 Hz).
¹³C-NMR (100 MHz, D₂O): 18.09, 20.03, 40.24, 65.88, 66.15, 72.02, 105.34, 123.02, 124.17, 130.74, 132.26, 142.98, 146.96, 151.57, 151.98, 168.26, 170.97, 171.28, 173.35.
67
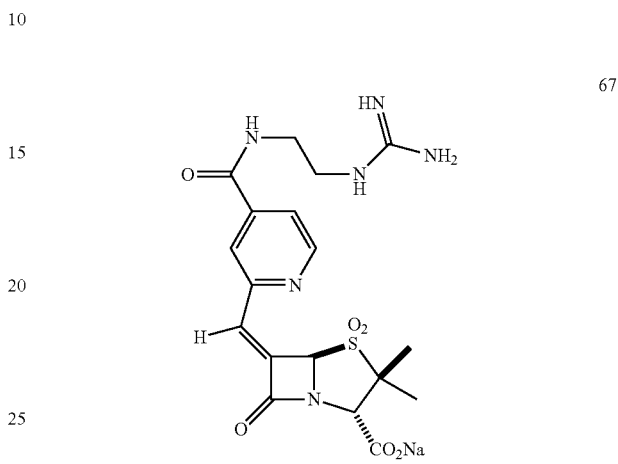
¹H-NMR (400 MHz, D₂O): 1.53 (s, 3H), 1.61 (s, 3H), 3.43 (t, 2H, J=5.09 Hz), 3.55 (t, 2H, J=5.3 Hz), 4.31 (s, 1H), 6.07 (s, 1H) 7.58 (s, 1H), 7.68 (d, 1H, J=4.97 Hz), 7.83 (s, 1H), 8.80 (d, 1H, J=4.96 Hz).
¹³C-NMR (100 MHz, D₂O): 18.09, 20.03, 22.27, 38.95, 39.84, 65.87, 66.15, 72.04, 122.92, 124.11, 130.77, 132.27, 143.24, 151.58, 152.01, 160.65, 168.1, 168.74, 170.99, 173.35, 174.91.
68
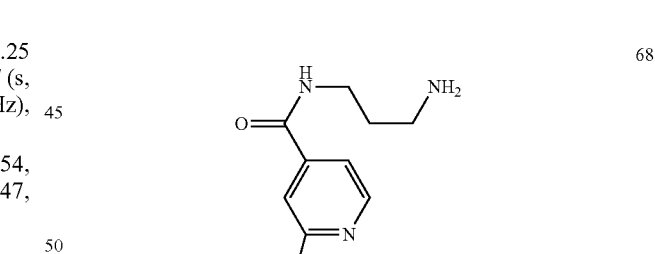
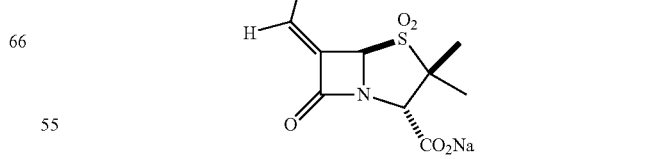
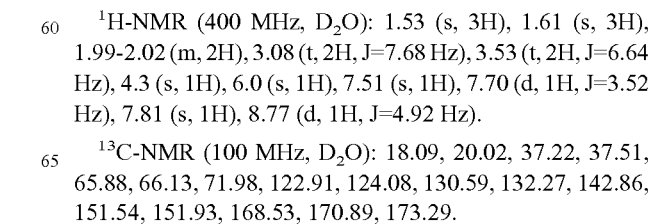
¹H-NMR (400 MHz, D₂O): 1.53 (s, 3H), 1.61 (s, 3H), 1.99-2.02 (m, 2H), 3.08 (t, 2H, J=7.68 Hz), 3.53 (t, 2H, J=6.64 Hz), 4.3 (s, 1H), 6.0 (s, 1H), 7.51 (s, 1H), 7.70 (d, 1H, J=3.52 Hz), 7.81 (s, 1H), 8.77 (d, 1H, J=4.92 Hz).
¹³C-NMR (100 MHz, D₂O): 18.09, 20.02, 37.22, 37.51, 65.88, 66.13, 71.98, 122.91, 124.08, 130.59, 132.27, 142.86, 151.54, 151.93, 168.53, 170.89, 173.29.

105

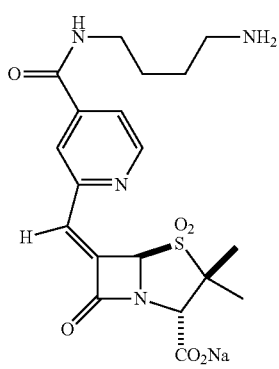
70

¹H-NMR (400 MHz, D₂O): 1.53 (s, 3H), 1.61 (s, 3H), 1.72 (m, 4H), 3.03 (d, 2H, J=6.72 Hz), 3.45 (t, 2H, J=6.11 Hz), 4.46 (s, 1H), 6.02 (s, 1H), 7.51 (s, 1H), 7.66 (d, 1H, J=4.77 Hz), 7.79 (s, 1H), 8.74 (d, 1H, J=4.84 Hz).

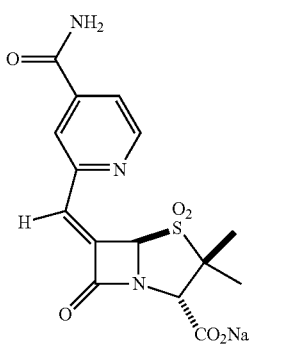
71

¹H-NMR (400 MHz, D₂O): 1.53 (s, 3H), 1.61 (s, 3H), 4.31 (s, 1H), 6.06 (s, 1H), 7.58 (s, 1H), 7.74-7.76 (dd, 1H, J=3.38 Hz, J=1.62 Hz), 7.89 (s, 1H), 8.80 (d, 1H, J=5.0 Hz).

¹³C-NMR (100 MHz, D₂O): 20.57, 22.51, 68.34, 68.62, 74.52, 125.66, 126.86, 133.2, 134.73, 144.97, 154.07, 154.48, 173.07, 173.47, 175.82.

Example 57

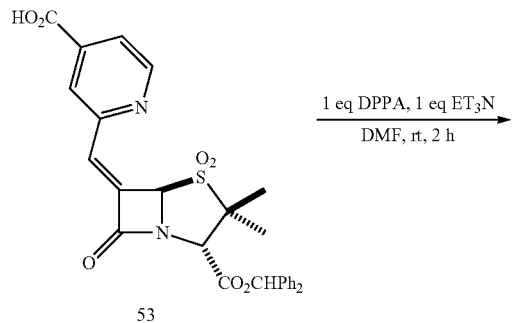

106

73

To a solution of acid 53 (532 mg, 1.0 mmol) in DMF (3.0 mL) at 35° C., was added diphenylphosphorylazide (DPPA) (275 mg, 215 μL, 1.0 mmol) followed by Et₃N (139 μl, 1.0 mmol). The reaction mixture was stirred for 2 h at 35° C. The reaction was then cooled to room temperature and diluted with ether (100 mL), washed with water (100 mL), and brine (100 mL) and the organic layer dried over Na₂SO₄ to give acyl azide, which was used without further purification.

Example 57(a)

Alternative Procedure

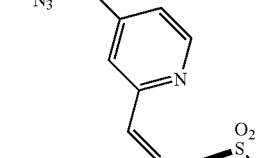
61

73

To a solution of p-nitrophenyl ester (500 mg, 0.765 mmol) in DMF (5 mL) was added sodium azide (74 mg, 1.14 mmol) in one portion and the reaction mixture was stirred at room temperature for 3 h. The solution was then diluted with CH₂Cl₂ (50 mL), washed 5 times with water (50 mL each), dried over Na₂SO₄, and concentrated under reduced pressure to give 400 mg of crude acyl azide, which was used for the next reaction without further purification.

$^1$H-NMR (400 MHz, CDCl$_3$): 1.21 (s, 3H), 1.58 (s, 3H), 4.56 (s, 1H), 5.71 (s, 1H), 7.01 (s, 1H), 7.26-7.38 (m, 11H), 7.82-7.83 (dd, 1H, J=3.46 Hz, J=1.47 Hz), 7.89 (s, 1H) 8.86-8.87 (d, 1H, J=4.76 Hz).

Example 58

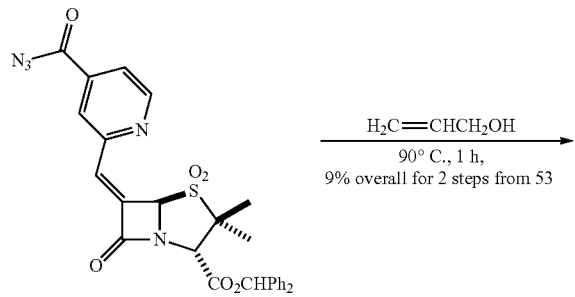

400 mg (0.718 mmol) of acyl azide was dissolved in allyl alcohol (20 mL) and heated at 90-95° C. for 1 h. The reaction reaction mixture was then diluted with CH$_2$Cl$_2$ (50 mL), washed with water (50 mL), dried over Na$_2$SO$_4$, concentrated at reduced pressure, and purified by column chromatography by using 10% EtOAc in CH$_2$Cl$_2$ to give 55 mg (9% yield for two steps from 53) of allyl carbamate and 150 mg of acid.

$^1$H-NMR (400 MHz, CDCl$_3$): 1.14 (s, 3H), 1.53 (s, 3H), 4.5 (s, 1H), 4.59 (d, 2H, J=5.6 Hz), 5.18-5.30 (ABq, 2H, J=36.96 Hz, J=9.44 Hz), 5.67 (s, 1H), 5.82-5.89 (m, 1H), 6.92 (s, 1H), 7.06 (s, 1H), 7.11 (d, 1H, J=0.47 Hz), 7.18 (s, 1H), 7.24-7.30 (m, 10H), 7.39 (d, 1H, J=1.61 Hz), 8.32 (d, 1H, J=5.47 Hz).

Example 59

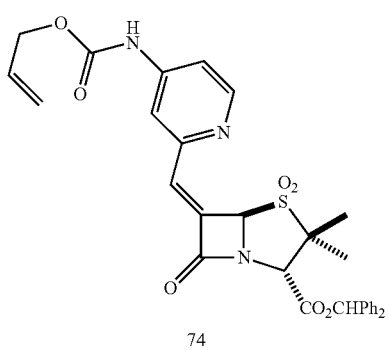

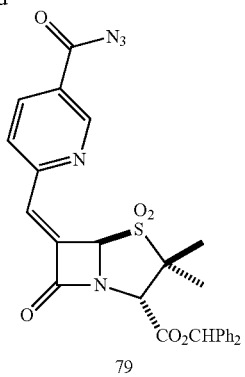

To a solution of p-nitrophenyl ester 78 (1.0 g, 1.53 mmol) in DMF (10 mL) was added sodium azide (200 mg, 3.06 mmol) at one portion and reaction mixture was then stirred at room temperature for 3 h. The solution was diluted with CH$_2$Cl$_2$ (100 mL), washed 5 times with water (50 mL each), dried over Na$_2$SO$_4$, and concentrated under reduced pressure to give 800 mg of crude acyl azide, which was used for next reaction without further purification.

Example 60

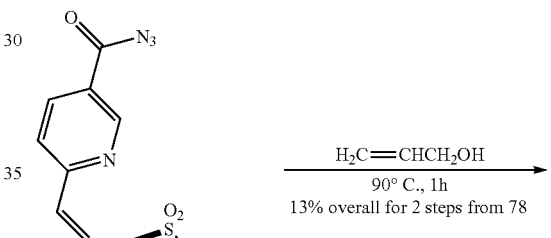

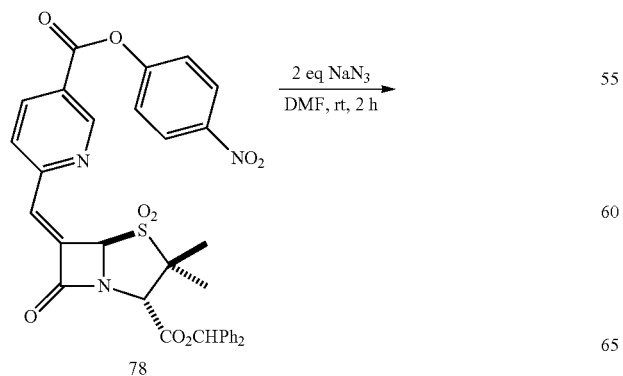

800 mg (1.436 mmol) of acyl azide 79 was dissolved in allyl alcohol (40 mL) and heated to 90-95° C. for 1 h. The reaction mixture was then diluted with CH$_2$Cl$_2$ (100 mL), washed with water (50 mL), and dried over Na$_2$SO$_4$. Concentration at reduced pressure and purification by column chromatography by using 10% EtOAc in CH$_2$Cl$_2$ produced 120 mg (0.204 mmol, 14% overall yield from 78) of allyl carbamate as well as 350 mg of acid.

Example 61

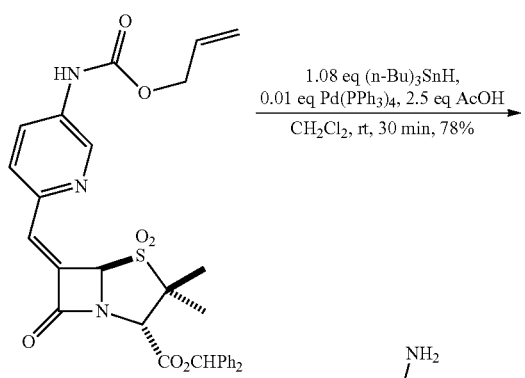

To a solution of allyl carbamate 80 (120.0 mg, 0.204 mmol), in $CH_2Cl_2$ (6 mL) were added acetic acid (28 μL, 0.5 mmol), tributyltin hydride (63 μL, 0.22 mmol) and tetrakis(triphenylphosphine)palladium (0) 2.3 mg, 0.002 mmol). The reaction was observed to evolve gas. After completion of such gas evolution it was stirred for an additional 15 min. Then was added saturated $NaHCO_3$ solution (5 mL), followed by brine (5 mL). The organic layer was dried over $Na_2SO_4$, concentrated and purified on silica gel using 20% EtOAc in $CH_2Cl_2$ as an eluent to give 80.0 mg (78% yield) product.

$^1$H-NMR (400 MHz, $CDCl_3$): 1.2 (s, 3H), 1.56 (s, 3H), 4.14 (brs, 2H), 4.49 (s, 1H), 5.65 (s, 1H), 6.78 (dd, 1H, J=5.52 Hz, J=2.76 Hz), 7.0 (s, 1H), 7.06 (d, 1H, J=8.28 Hz), 7.11 (s, 1H), 7.30-7.39 (m, 1H, 10H), 8.08 (d, 1H, J=2.56 Hz).

$^{13}$C-NMR (100 MHz, $CDCl_3$): 18.4, 19.88, 62.86, 64.52, 72.07, 78.78, 119.62, 126.77, 127.1, 127.62, 128.19, 128.52, 128.58, 128.69, 130.51, 138.66, 138.79, 139.03, 140.44, 144.21, 166.87, 169.37.

IR (thin film): 1117.8, 1170.42, 1320.47, 1580.6, 1770.11, 3373.02.

Example 62

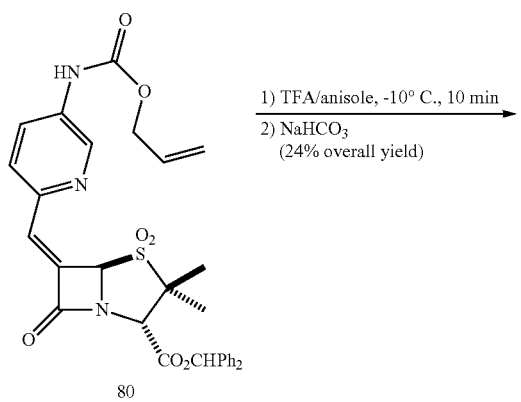

This reaction was performed according to the general procedure described in Example 18, with an overall yield (after purification) of 24%.

$^1$H-NMR (400 MHz, $D_2O$): 1.52 (s, 3H), 1.6 (s, 3H), 4.26 (s, 1H), 4.7-4.71 (d, 2H, J=5.2 Hz), 5.29-5.42 (ABq, 2H, J=15.96 Hz, J=9.4 Hz), 6.0 (s, 1H), 6.02-6.03 (m, 1H), 7.44 (s, 1H), 7.55 (d, 1H, J=8.52 Hz), 7.95 (dd, 1H, J=6.56 Hz, J=2.08 Hz), 8.60 (d, 1H, J=2.28 Hz).

Example 63

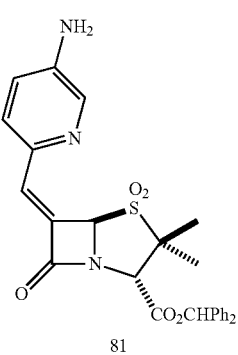

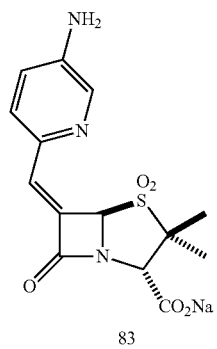

This reaction was performed according to the general procedure described in Example 18, with an overall yield (after purification) of 43%.

$^1$H-NMR (400 MHz, $D_2O$): 1.51 (s, 3H), 1.59 (s, 3H), 4.22 (s, 1H), 5.97 (s, 1H), 7.14-7.17 (dd, 1H, J=5.64 Hz, J=2.76 Hz), 7.38 (s, 1H), 7.41 (d, 1H, J=8.44 Hz) 8.17 (d, 1H, J=2.48 Hz).

Example 64

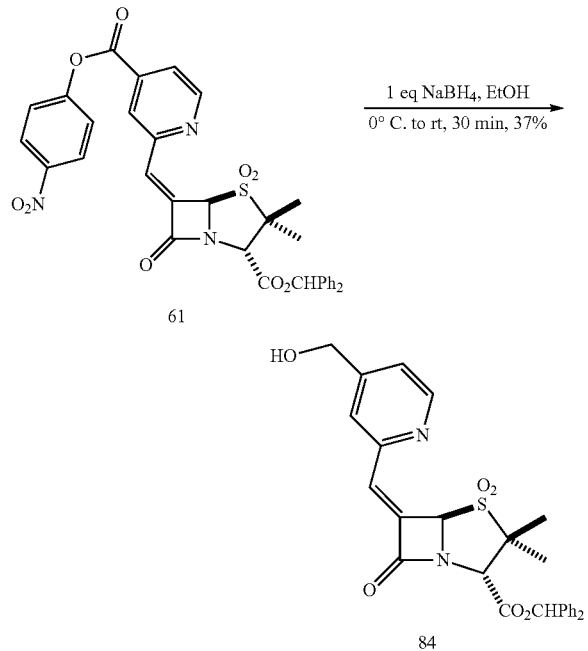

To a solution of p-nitrophenylester 61 (10 g, 15.3 mmol) in a mixture of EtOH (50 mL) and THF (50 mL) was added NaBH$_4$ (566 mg, 15.3 mmol) at 0° C. The reaction mixture was then warmed to room temperature, stirred for 30 min, and quenched with saturated aq NH$_4$Cl. The organic layer was separated and concentrated at reduced pressure. The remaining residue was diluted with CH$_2$Cl$_2$, washed with water, dried over Na$_2$SO$_4$ concentrated at reduced pressure, and purified on silica gel column chromatography using 30% EtOAc in CH$_2$Cl$_2$ to give 3.0 g of pure alcohol (37% yield).

$^1$H-NMR (400 MHz, CDCl$_3$): 1.1 (s, 3H), 1.47 (s, 3H), 2.93 (brs, 1H), 4.44 (s, 1H), 4.5 (s, 2H), 5.59 (s, 1H), 6.91 (s, 1H), 7.06-7.07 (m, 2H), 7.16-7.3 (m, 10H), 8.42 (d, 1H, J=4.88 Hz).

$^{13}$C-NMR (100 MHz, CDCl$_3$): 18.22, 19.78, 62.57, 62.94, 64.47, 71.88, 78.89, 122.07, 123.62, 126.69, 127.53, 128.19, 128.55, 128.66, 130.25, 132.4, 138.61, 138.83, 150.2, 150.68, 151.61, 166.54, 168.51.

Example 65

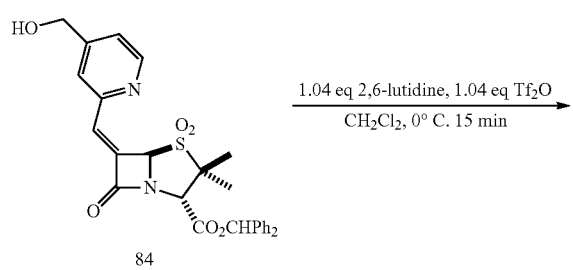

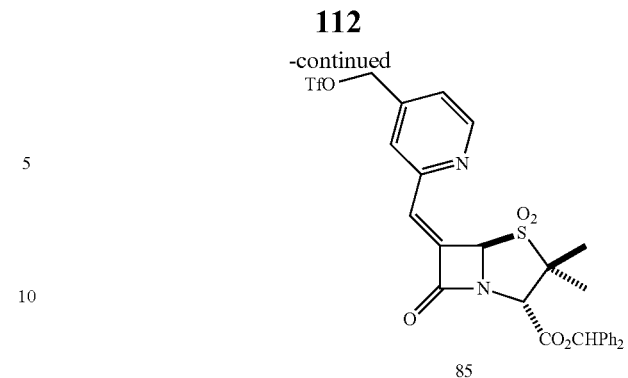

To a chilled (0° C.) solution of alcohol 84 (500 mg, 0.96 mmol) in CH$_2$Cl$_2$ (5 mL) was added 2,6 lutidine (120 µL, 1 mmol) followed by triflic anhydride (170 µL, 1 mmol). The reaction mixture was stirred at 0° C. for 15 min. Diluted with CH$_2$Cl$_2$ (50 mL) washed with aq NaHCO$_3$ (50 mL), water and brine (50 mL each), dried over Na$_2$SO$_4$, concentrated under reduced pressure and used for the next reaction without further purification.

$^1$H-NMR (400 MHz, CDCl$_3$): 1.21 (s, 3H), 1.58 (s, 3H), 4.56 (s, 1H), 5.54-5.55 (d, 1H, J=3.52 Hz), 5.74 (s, 1H), 7.0 (s, 1H), 7.26-7.39 (m, 13H), 8.78 (d, 1H, J=5.16 Hz).

Example 66

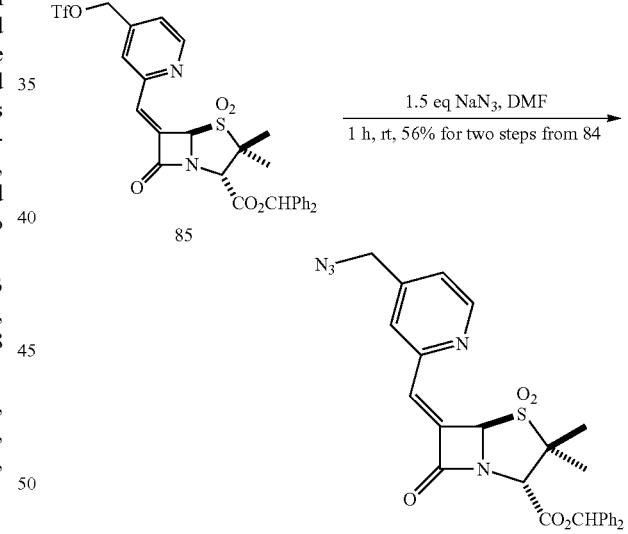

To a solution of triflate 85 (0.96 mmol) in DMF (5 mL) was added sodium azide (93 mg, 1.44 mmol) in one portion and the reaction mixture was stirred at room temperature for 1 h, diluted with CH$_2$Cl$_2$ (50 mL), washed 5 times with water (50 mL each), dried over Na$_2$SO$_4$ concentrated and purified on silica gel column chromatography by using 2% EtOAc in CH$_2$Cl$_2$ to give 290 mg of pure azide (56% yield).

$^1$H-NMR (400 MHz, CDCl$_3$): 1.21 (s, 3H), 1.58 (s, 3H), 4.44 (s, 2H), 4.55 (s, 1H), 5.71 (s, 1H), 7.01 (s, 1H), 7.26-7.40 (m, 13H), 8.68-8.69 (d, 1H, J=4.88 Hz).

IR (thin film): 1119.84, 1170.19, 1325.9, 1783.24, 2106.24.

Example 67

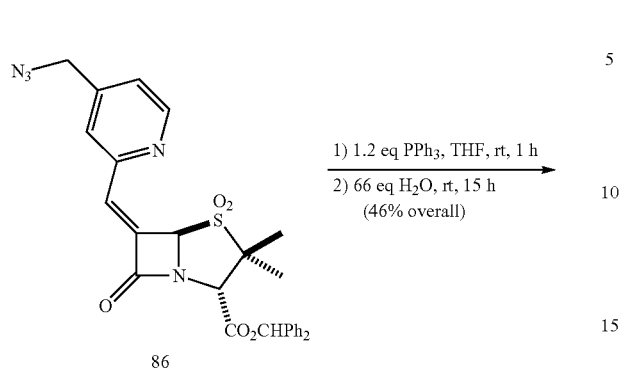

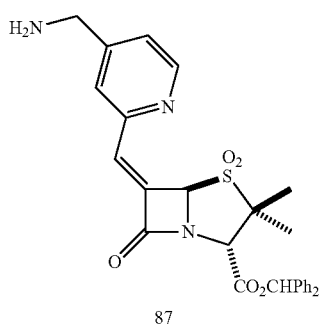

To a solution of azide 86 (230 mg, 0.423 mmol), in THF (5 mL) was added triphenylphosphine (133 mg, 507 mmol) and the reaction mixture was stirred at rt for 1 h. Then was added water (500 µL) and the resultant mixture stirred at room temperature overnight. The reaction was then diluted with $CH_2Cl_2$ (50 mL), the organic layer was separated and dried over $Na_2SO_4$, concentrated under reduced pressure, and purified by silica gel column chromatograpy using 10% MeOH in $CH_2Cl_2$ to give 100 mg of amine (46% yield).

$^1$H-NMR (400 MHz, $CDCl_3$): 1.2 (s, 3H), 1.57 (s, 3H), 3.89 (s, 2H), 4.54 (s, 1H), 5.72 (s, 1H), 7.0 (s, 1H), 7.24-7.4 (m, 13H), 8.58 (d, 1H, J=4.9 Hz).

$^{13}$C-NMR (100 MHz, $CDCl_3$): 18.34, 19.88, 63.06, 64.45, 71.98, 78.82, 123.15, 124.7, 126.79, 127.57, 128.21, 128.53, 128.58, 128.68, 130.12, 132.82, 138.74, 138.96, 150.46, 151.0, 166.55, 168.43.

Example 68

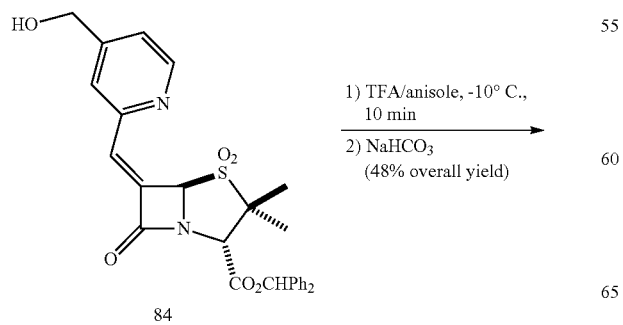

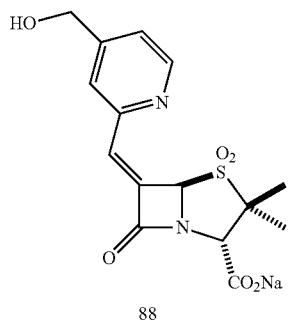

Ester 84 (100 mg, 0.193 mmol) was deprotected to give 35 mg of pure sodium salt 88 (48% yield) according to the procedure shown in Example 18.

$^1$H-NMR (400 MHz, $D_2O$): 1.53 (s, 3H), 1.61 (s, 3H), 4.29 (s, 1H), 6.06 (s, 1H), 7.44 (d, 1H, J=4.84 Hz), 7.54 (s, 1H), 7.6 (s, 1H), 8.63 (d, 1H, J=4.96 Hz).

Example 69

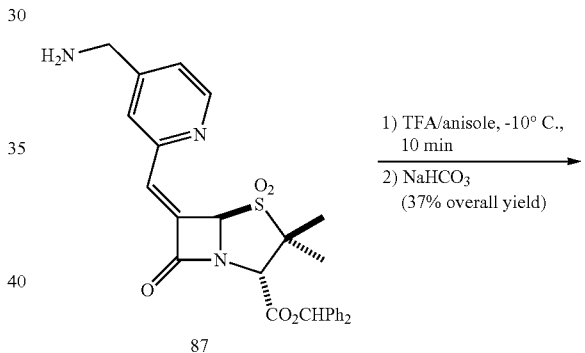

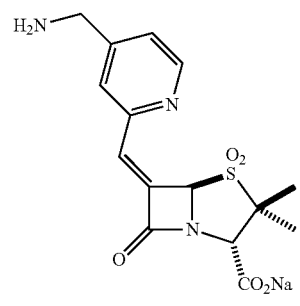

Ester 87 (100 mg, 0.193 mmol) was deprotected to give 27 mg of pure sodium salt 89 (37% yield) according to the procedure shown in Example 18.

$^1$H-NMR (400 MHz, $D_2O$): 1.53 (s, 3H), 1.61 (s, 3H), 4.3 (s, 1H), 6.07 (s, 1H), 7.5 (d, 1H), 7.55 (s, 1H), 7.65 (d, 1H), 8.72 (d, 1H, J=3.56 Hz).

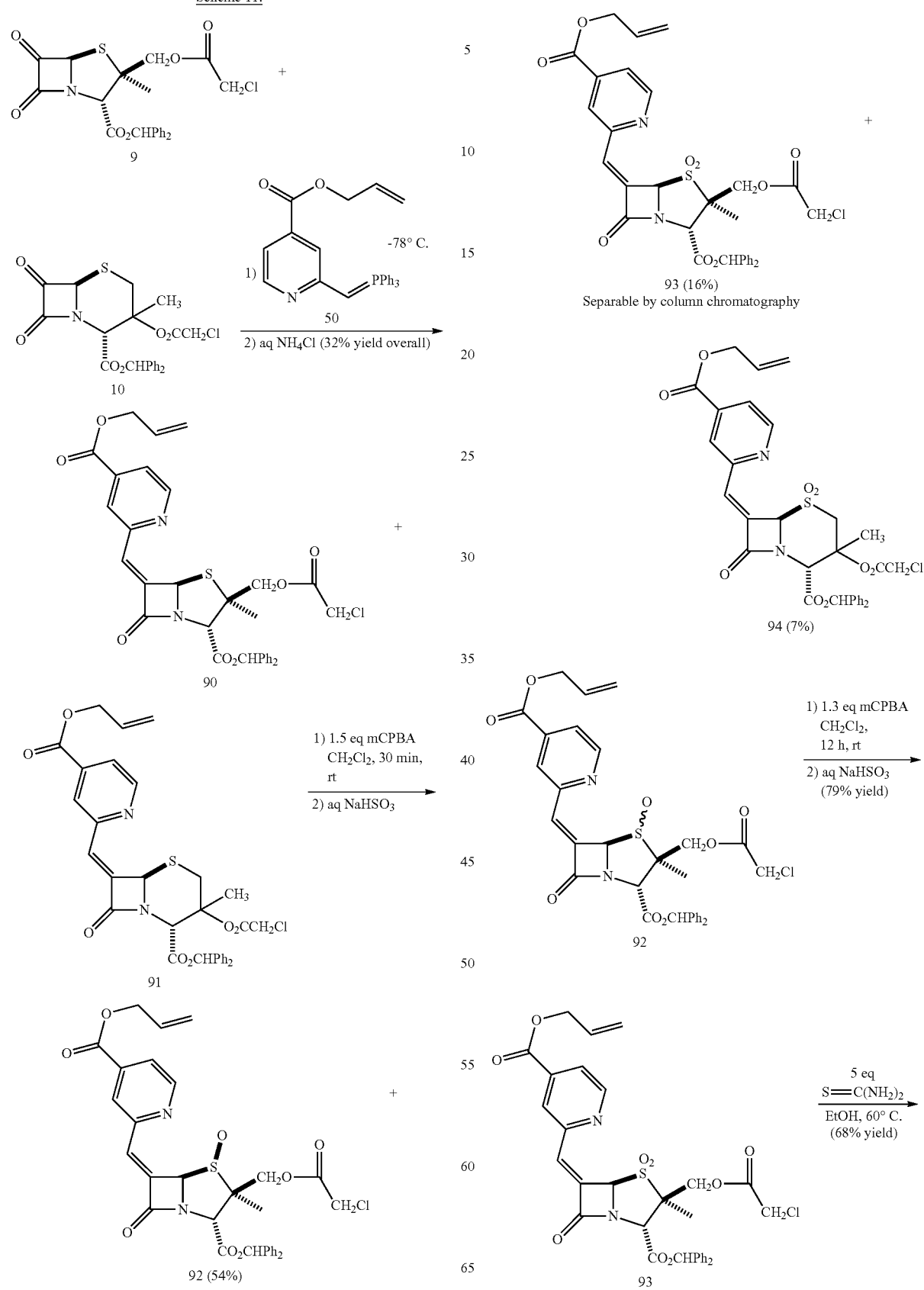

117
-continued

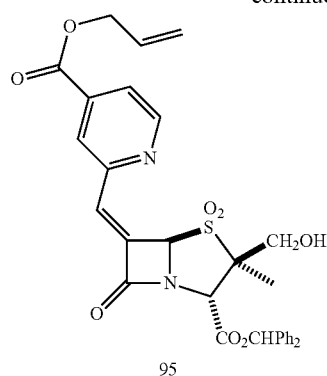
95

1) 1.5 eq p-NO$_2$C$_6$H$_4$O$_2$CCl,
0.5 eq DMAP, py, rt, 2 h
2) NH$_3$, dioxane, rt, 30 min
(63% overall)

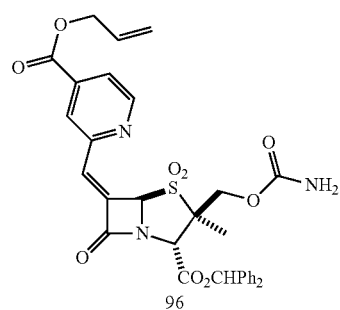
96

1) 1.1 eq p-TolSO$_2$Na,
0.1 eq Pd(PPh$_3$)$_4$
THF-MeOH, rt, 1 h
2) aq HCl
(84% overall yield)

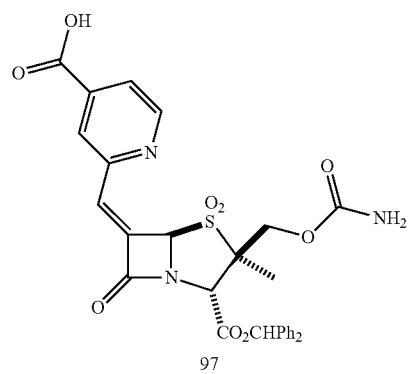
97

1.5 eq
p-NO$_2$C$_6$H$_4$O$_2$CCl,
0.5 eq DMAP,
py, rt, 30 min
(74% yield)

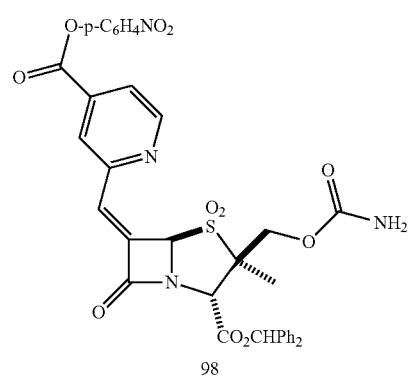
98

1) 1.0 eq NaBH$_4$,
THF, EtOH,
0° C., 30 min
2) aq NH$_4$Cl
(62% yield)

118
-continued

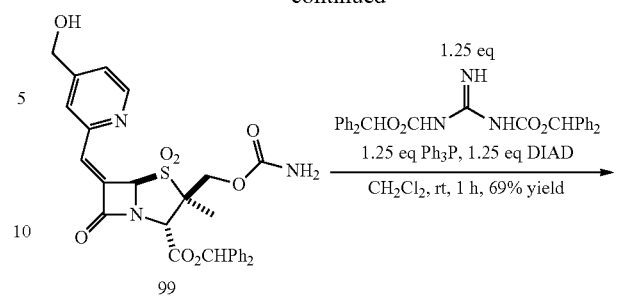
99

1.25 eq
Ph$_2$CHO$_2$CHN⎯C(=NH)⎯NHCO$_2$CHPh$_2$
1.25 eq Ph$_3$P, 1.25 eq DIAD
CH$_2$Cl$_2$, rt, 1 h, 69% yield

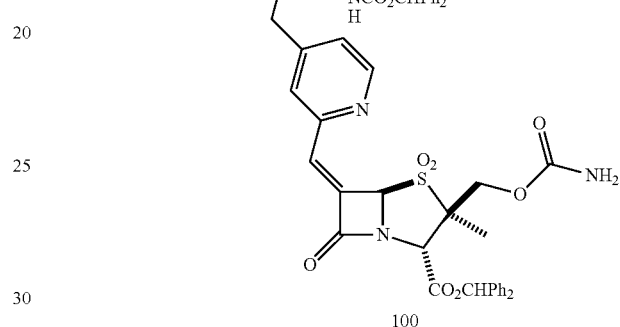
100

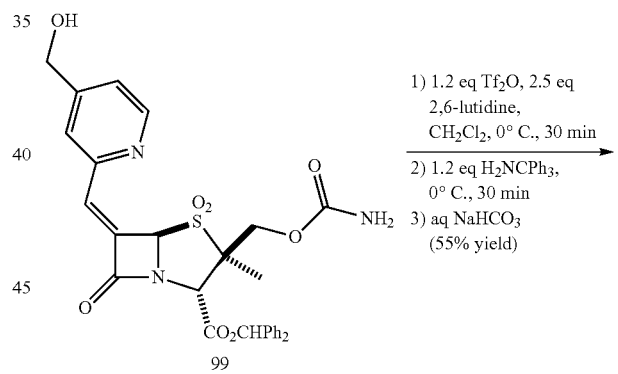
99

1) 1.2 eq Tf$_2$O, 2.5 eq
2,6-lutidine,
CH$_2$Cl$_2$, 0° C., 30 min
2) 1.2 eq H$_2$NCPh$_3$,
0° C., 30 min
3) aq NaHCO$_3$
(55% yield)

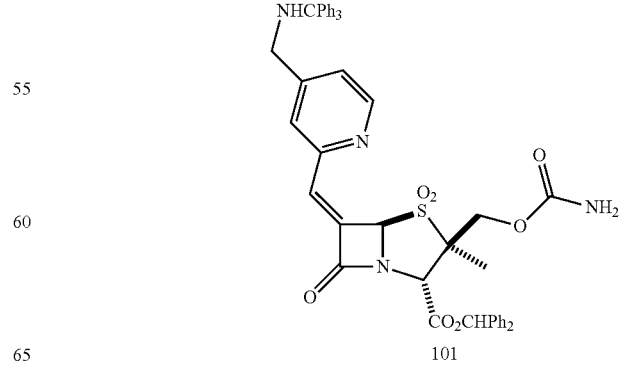
101

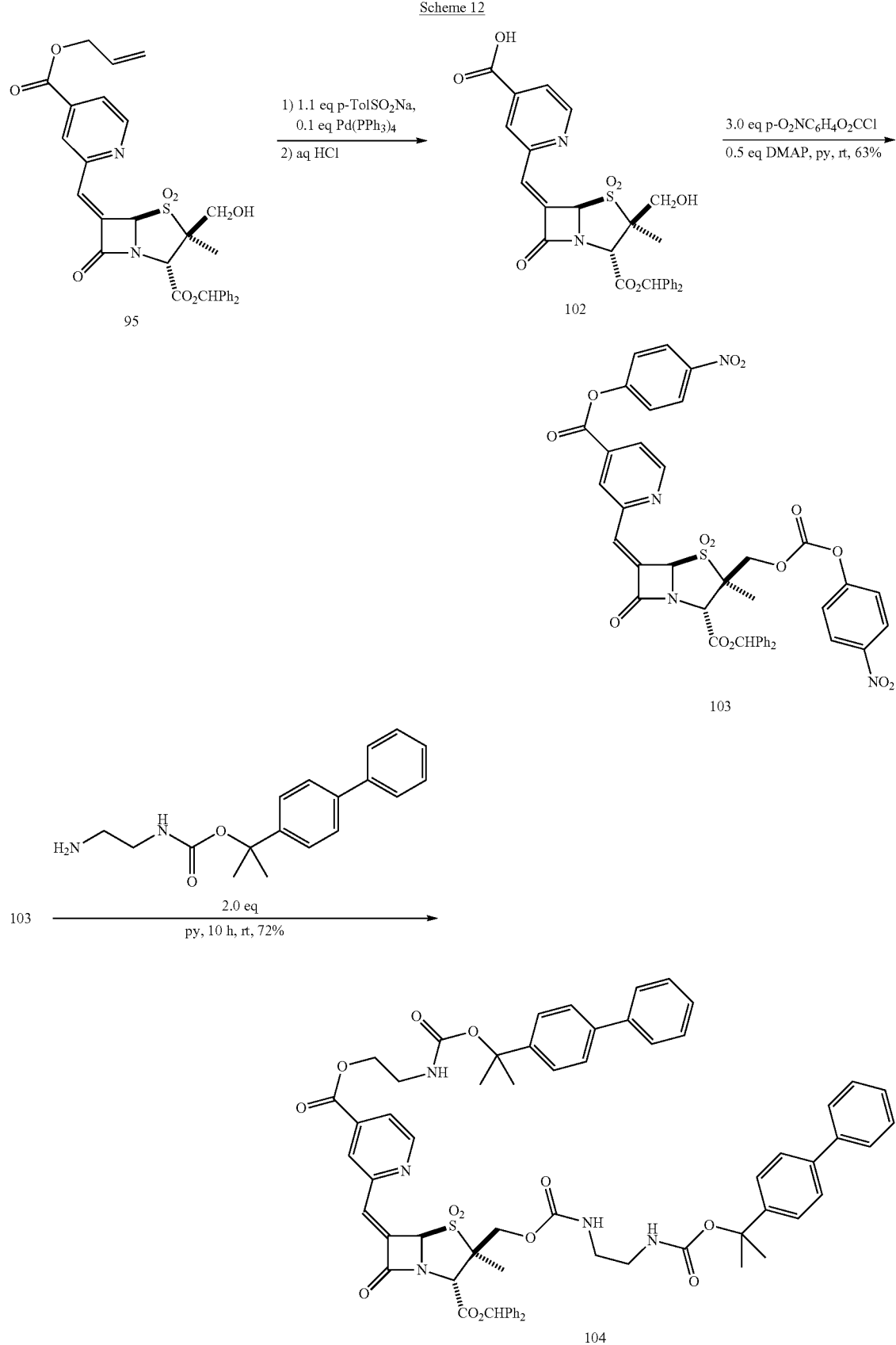

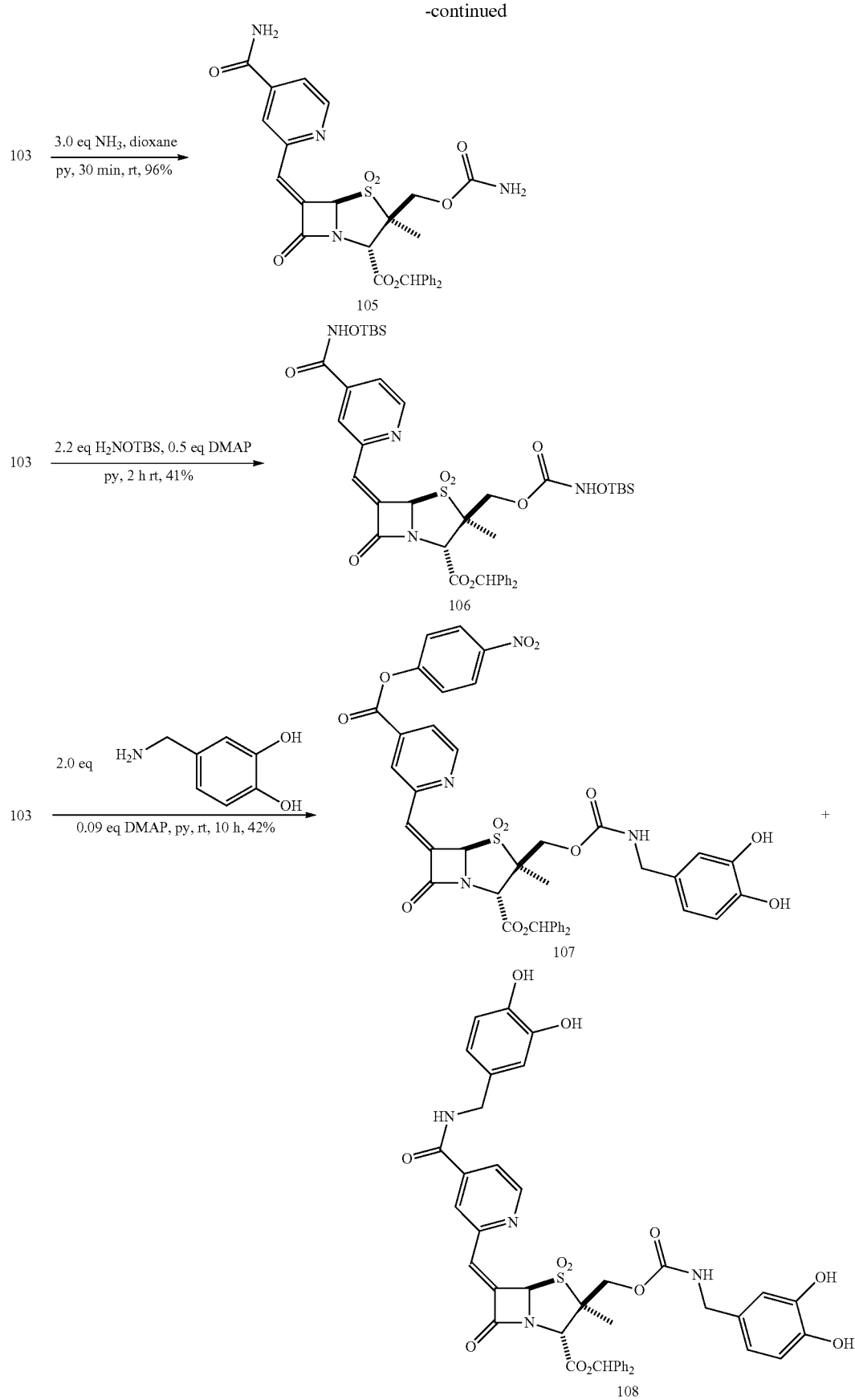

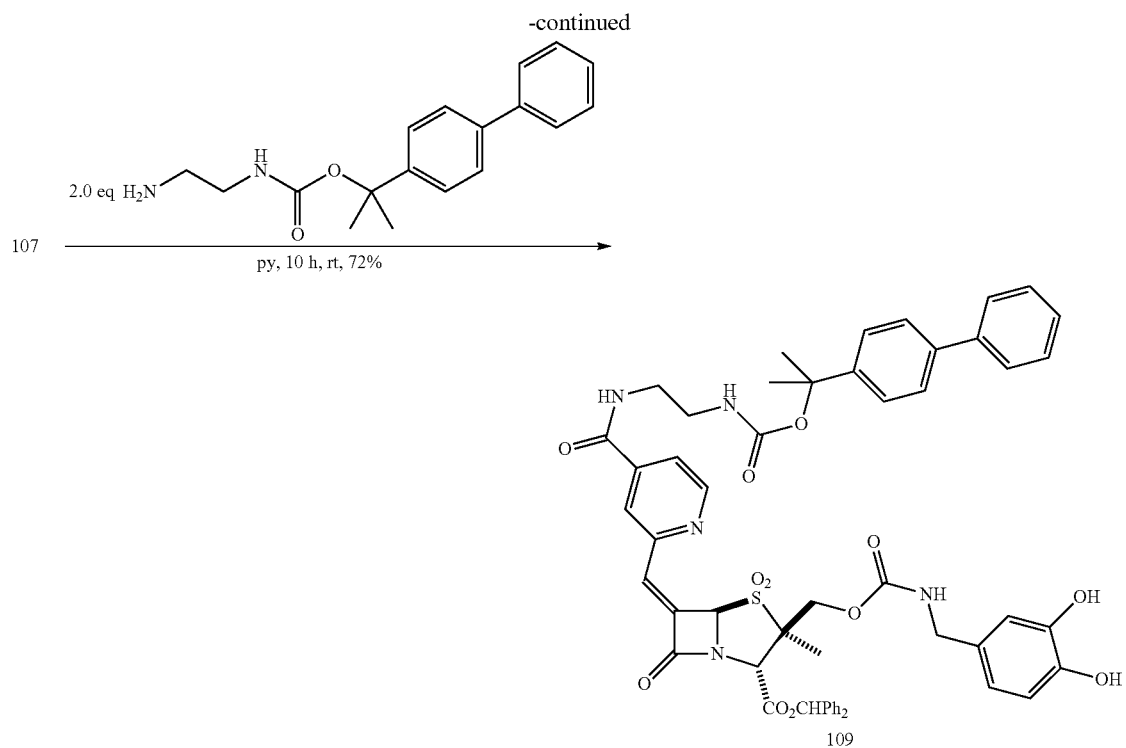
Scheme 13.
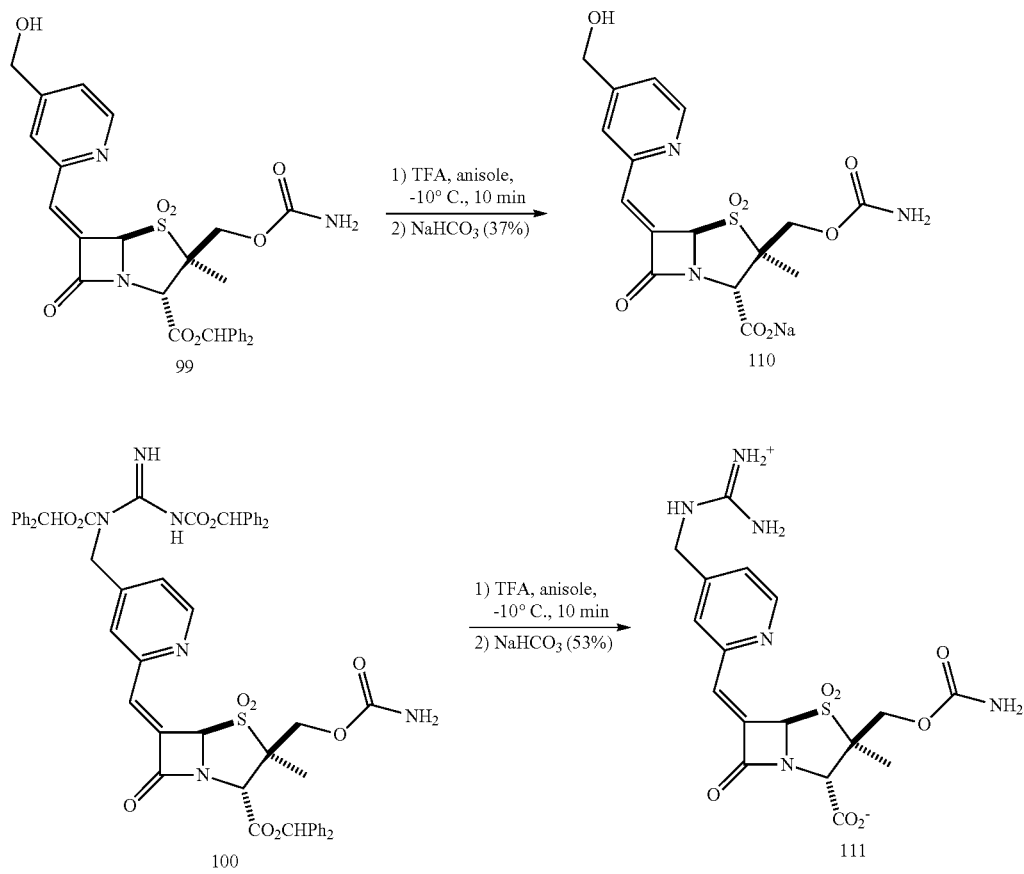

-continued
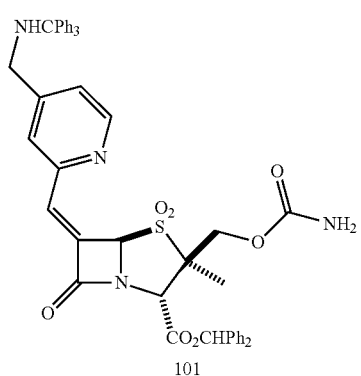 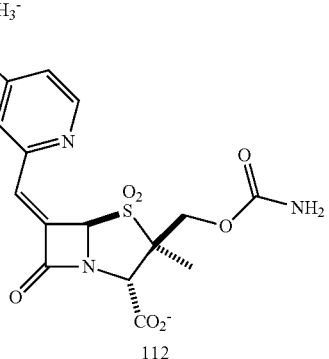
101 → 112
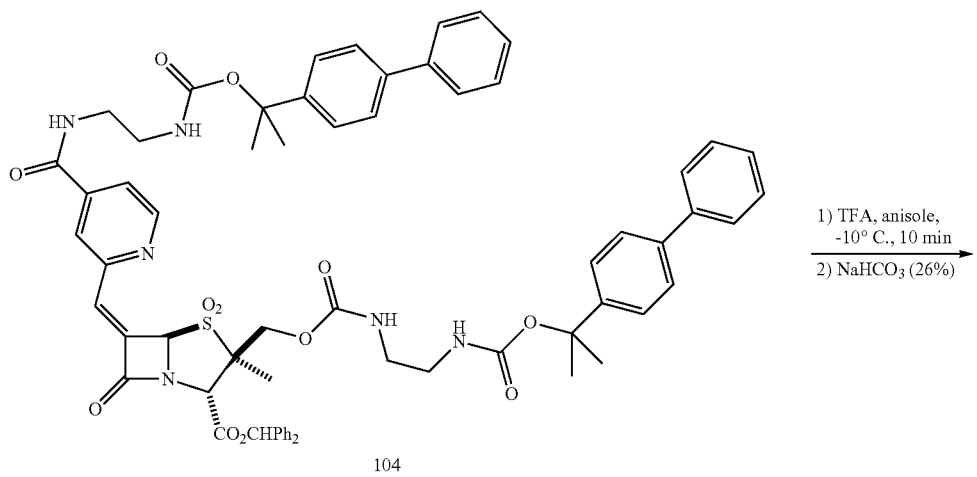
104 →
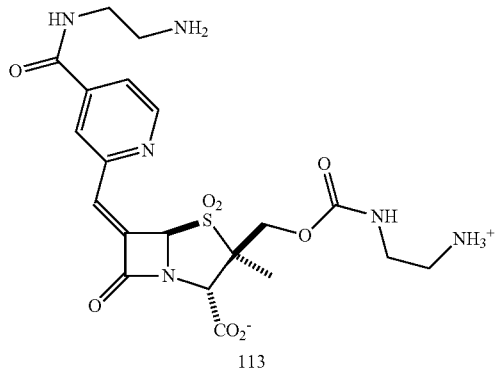
113
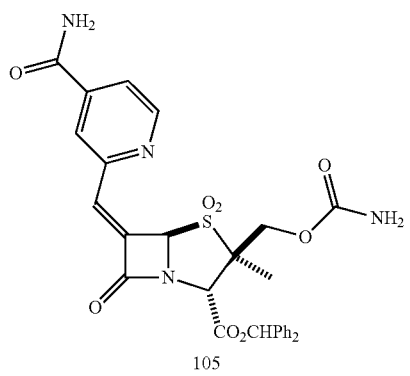 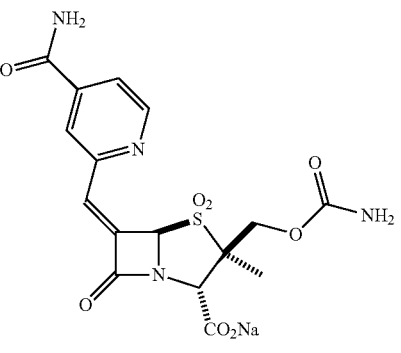
105 → 114

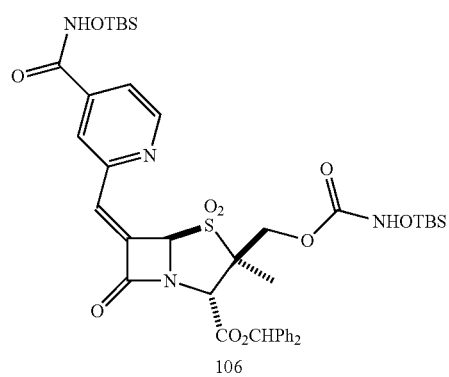
106
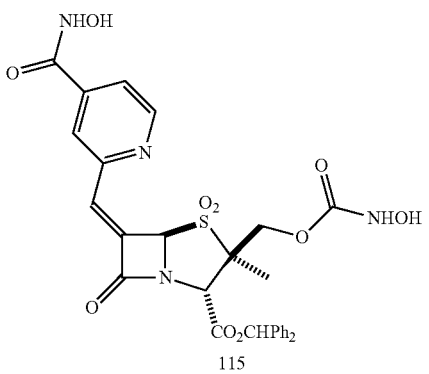
115
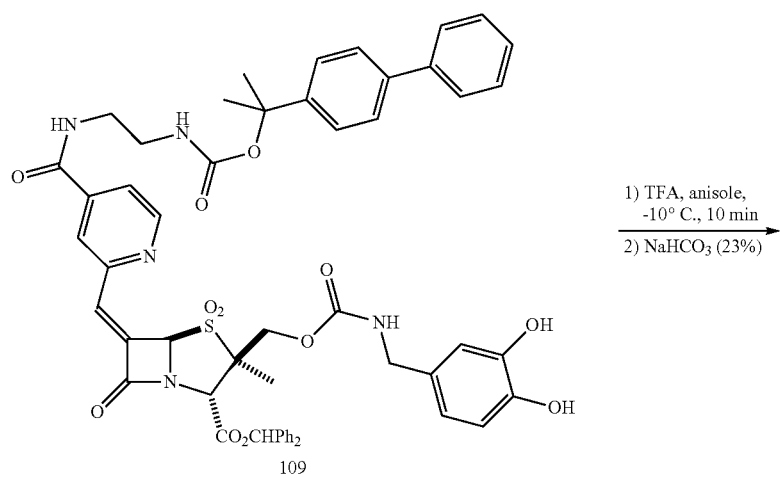
109
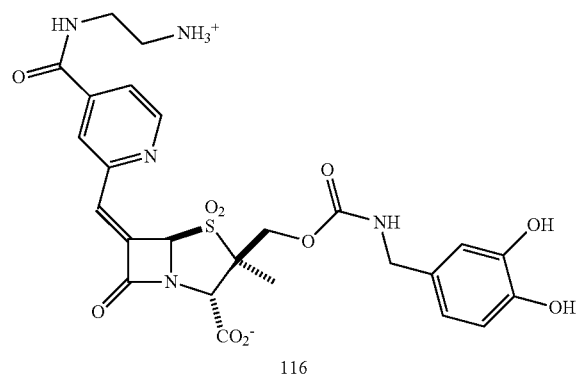
116
Example 70
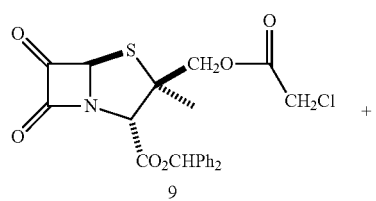
9
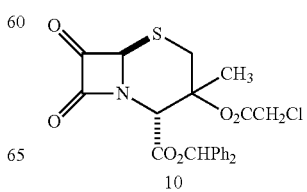
10
-continued
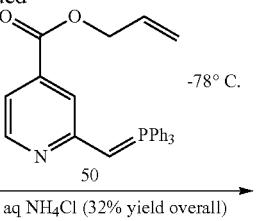

Example 71

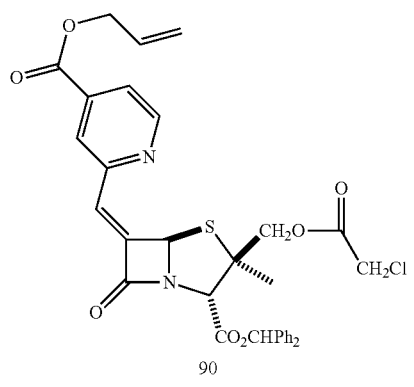
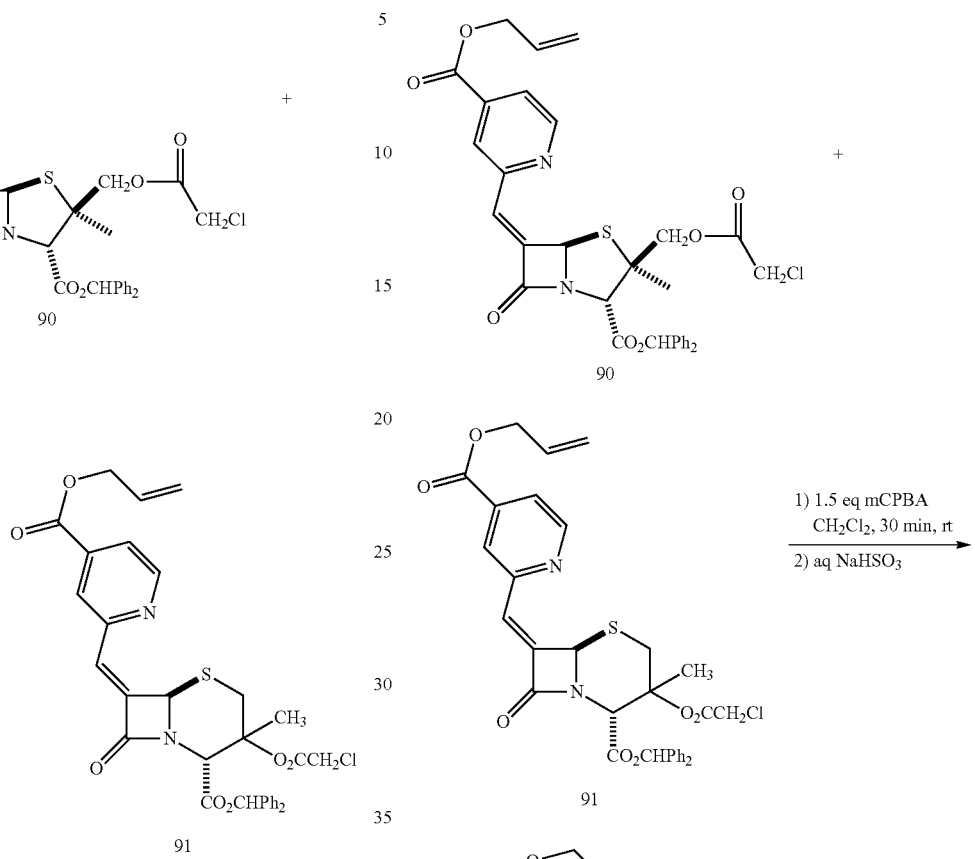

To a solution of (4-allyloxycarbonyl)-2-(triphenylphosphoniummethyl)pyridine chloride (32.0 g, 67.5 mmol), in dry THF (300 mL) was added KO-t-Bu (6.5 g, 54.0 mmol) and the reaction mixture was stirred at room temperature for 2 h to generate the ylide 50. In a separate flask, the ketone 9 (67.5 mmol) was dissolved in dry $CH_2Cl_2$ (600 mL) and cooled to −78° C. The solution of 50 was then chilled to −78° C. and slowly added to the cold solution of ketone 9 (also at −78° C.) by cannula and the resultant reaction mixture stirred at this temperature for 30 min. Then a saturated aqueous solution of $NH_4Cl$ was added and the reaction mixture slowly warmed to room temperature with stirring. The layers were separated and the aqueous layers extracted with an additional portion of $CH_2Cl_2$ (200 mL). The combined organic layers were washed with water (500 mL), brine (500 mL). Then the solution was dried over $Na_2SO_4$. Concentration and purification by column chromatography using 2% EtOAc/$CH_2Cl_2$ as eluent produced 13.5 g (31.5% yield) of product. This penam contaminated with 25-30% of cepham.

$^1$H-NMR of 90 (400 MHz, $CDCl_3$): 1.23 (s, 3H), 1.57 (s, 3H), 3.90 (d, 1H, J=11.64 Hz), 4.11 (s, 1H, J=10.5 Hz), 4.22 (s, 1H, J=11.66 Hz), 4.87 (d, 2H, J=3.41 Hz) 4.99 (s, 1H), 5.29-5.45 (m, 2H), 5.98-6.06 (m, 1H), 6.3 (d, 1H), 6.98 (s, 1H), 7.3-7.41 (m, 11H), 7.81 (dd, 1H, J=3.44 Hz, J=1.46 Hz), 7.92 (s, 1H), 8.78 (d, 1H, J=4.89 Hz).

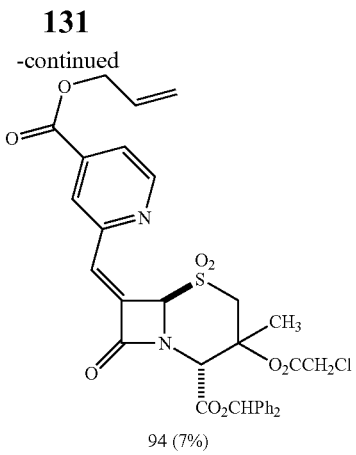

94 (7%)

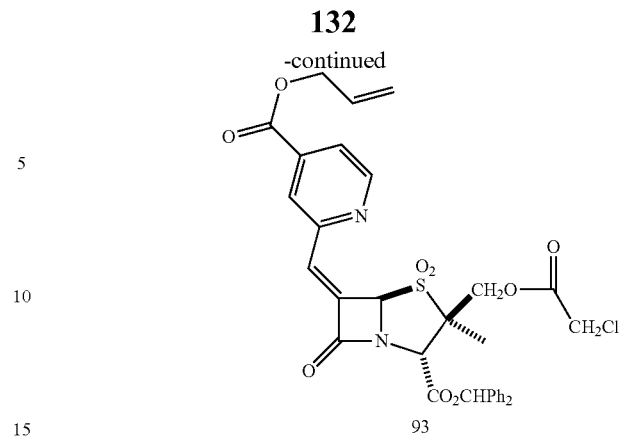

93

To a solution of sulfide 90 (10.5 g, 16.58 mmol), in CH₂Cl₂ (100 mL) was added mCPBA (5.57 g of 77% mCPBA, 24.87 mmol) and the mixture was subsequently stirred at room temperature for 30 min. The reaction mixture was quenched with aqueous sodium metabisulfite solution (5 g, in 100 mL) and the layers were separated. The organic layer was washed with aqueous NaHCO₃ solution (100 mL) followed by water and brine (100 mL each). Then the solution was dried over Na₂SO₄, concentrated, and purified by column chromatography using 10% EtOAc/CH₂Cl₂ as eluent to give two stereoisomers of penam sulfoxides (5.85 g, 9.01 mmol, 54%), penam sulfone (1.75 g, 2.63 mmol, 16%) and cephem sulfone (0.75 g, 7%), (at this stage cephem was separated from penam).

Sulfoxide 1:

$^1$H-NMR (400 MHz, CDCl₃): 1.05 (s, 3H), 4.12 (d, 1H, J=12.3 Hz), 4.27 (d, 1H, J=12.02 Hz), 4.43 (d, 1H, J=12.03 Hz), 4.59 (d, 1H, J=11.91 Hz), 4.79 (s, 1H), 4.86 (s, 2H), 5.33-5.46 (m, 2H), 5.84 (s, 1H), 5.99-6.06 (m, 1H), 7.01 (s, 1H), 7.31-7.43 (m, 11H), 7.85 (dd, J=3.45 Hz, J=1.49 Hz), 7.95 (s, 1H), 8.81 (d, 1H, J=4.86 Hz).

Sulfoxide 2:

$^1$H-NMR (400 MHz, CDCl₃): 1.05 (s, 3H), 4.06 (s, 2H), 4.09-4.14 (AB, q, 2H, J=7.14 Hz, 7.13 Hz), 4.59 (d, 1H, J=11.89 Hz), 4.79 (s, 1H), 4.87 (d, 1H, J=11.26 Hz), 5.33-5.45 (m, 2H), 5.89 (s, 1H), 5.99-6.06 (m, 1H), 7.01 (s, 1H), 7.31-7.43 (m, 11H), 7.85 (dd, 1H, J=3.58 Hz, J=1.29 Hz), 7.95 (s, 1H), 8.81 (d, 1H, J=4.89 Hz).

Example 72

To a solution of sulfoxides 92 (5.85 g, 9.01 mmol), in CH₂Cl₂ (100 mL) was added mCPBA (2.62 mg, 11.71 mmol) and the reaction mixture was subsequently stirred at room temperature overnight. The reaction mixture was then quenched with aqueous sodium metabisulfite solution (5 g, in 100 mL water), the layers were separated, the organic layer was washed with aqueous NaHCO₃ solution (100 mL) followed by water and brine (100 mL each). Then the solution was dried over Na₂SO₄, concentrated and purified by column chromatography using 5% EtOAc/CH₂Cl₂ as eluent to give 4.75 g (79% yield) of product.

$^1$H-NMR (400 MHz, CDCl₃): 1.23 (s, 3H), 4.03-4.12 (m, 4H) 4.50 (d, 1H, J=12.2 Hz) 4.68 (d, 1H, J=12.2 Hz), 4.79 (s, 1H), 4.86 (d, 2H, J=5.76 Hz), 5.33-5.45 (dd, 2H, J=17.17 Hz, J=10.4 Hz), 5.75 (s, 1H), 6.02-6.03 (m, 1H), 7.0 (s, 1H), 7.25-7.38 (m, 11H), 7.87 (d, 1H, J=4.88 Hz), 7.94 (s, 1H), 8.83 (d, 1H, J=4.92 Hz).

Example 73

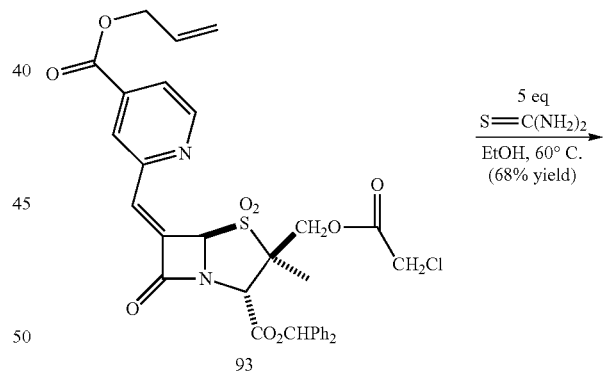

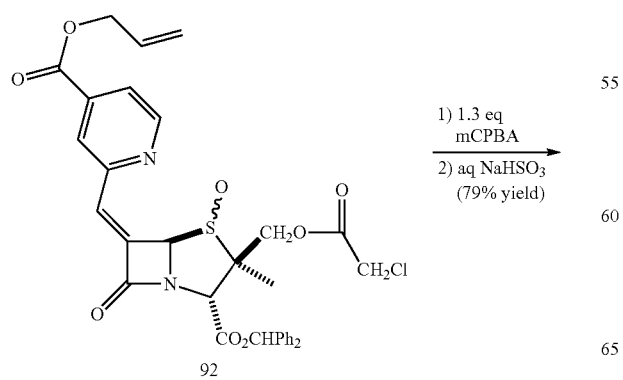

92

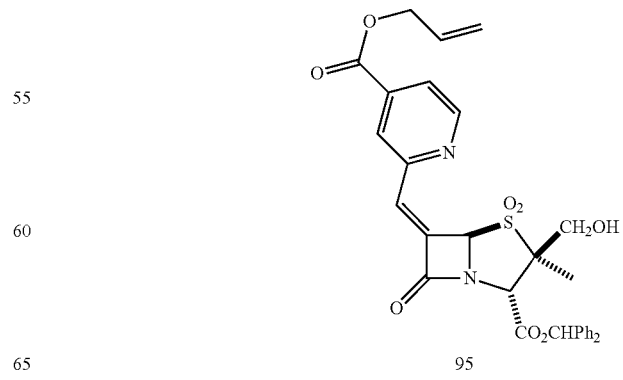

95

To a solution of sulfone 93 (2.0 g, 3.0 mmol), in ethanol (40 mL) was added thiourea (1.14 g, 15.0 mmol) and reaction mixture was heated to 60° C. for 20 min. After completion of reaction ethanol was removed under reduced pressure and the residue was dissolved in CH$_2$Cl$_2$ (100 mL) and washed with water (100 mL). The layers were separated, and the organic layer was washed with water (100 mL) followed by brine (100 mL). Then the solution was dried over Na$_2$SO$_4$, concentrated and purified by column chromatography using 20% EtOAc/CH$_2$Cl$_2$ as eluent to give 1.2 g (68% yield) of product.

$^1$H-NMR (400 MHz, CDCl$_3$): 1.09 (s, 3H), 3.80 (d, 1H, J=10.36 Hz), 4.05 (d, 1H, J=10.36 Hz), 4.86 (d, 2H, J=5.72 Hz), 5.25 (s, 1H), 5.33-5.45 (dd, 2H, J=15.92 Hz, J=10.4 Hz), 5.71 (s, 1H), 6.02-6.03 (m, 1H), 7.01 (s, 1H), 7.26-7.37 (m, 11H), 7.87-7.89 (d, 1H, J=3.6 Hz), 7.94 (s, 1H), 8.83-8.85 (d, 1H, J=4.72 Hz).

dried over Na$_2$SO$_4$, concentrated and purified by column chromatography using 5% EtOAc/CH$_2$Cl$_2$ as eluent to obtain 2.3 g (63% yield) product.

$^1$H-NMR (400 MHz, CDCl$_3$): 1.19 (s, 3H), 4.28 (d, 1H, J=11.95 Hz), 4.62 (d, 1H, J=11.95 Hz), 4.83 (d, 2H, J=5.78 Hz), 4.89 (s, 1H), 5.3 (brs, 2H), 5.3-5.43 (dd, 2H, J=15.91 Hz, J=9.65 Hz), 5.77 (s, 1H), 5.97-6.04 (m, 1H), 6.98 (s, 1H), 7.29-7.4 (m, 11H), 7.82-7.83 (dd, 1H, J=3.45 Hz, J=1.33 Hz), 7.9 (s, 1H), 8.81 (d, 1H, J=4.89 Hz).

$^{13}$C-NMR (100 MHz, CDCl$_3$): 15.41, 60.16, 64.7, 66.24, 66.43, 73.86, 79.24, 119.22, 123.9, 125.15, 126.94, 127.42, 128.26, 128.46, 128.54, 128.64, 131.16, 134.94, 138.45, 138.58, 151.1, 151.77, 155.31, 163.89, 165.98, 167.22.

IR (thin film): 912.17, 1279.72, 1331.68, 1411.86, 1596.93, 1731.68, 1785.27, 3379.95, 3483.29 cm$^{-1}$.

Example 74

Example 75

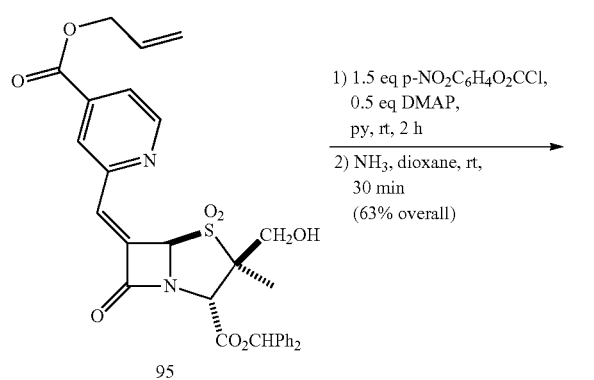

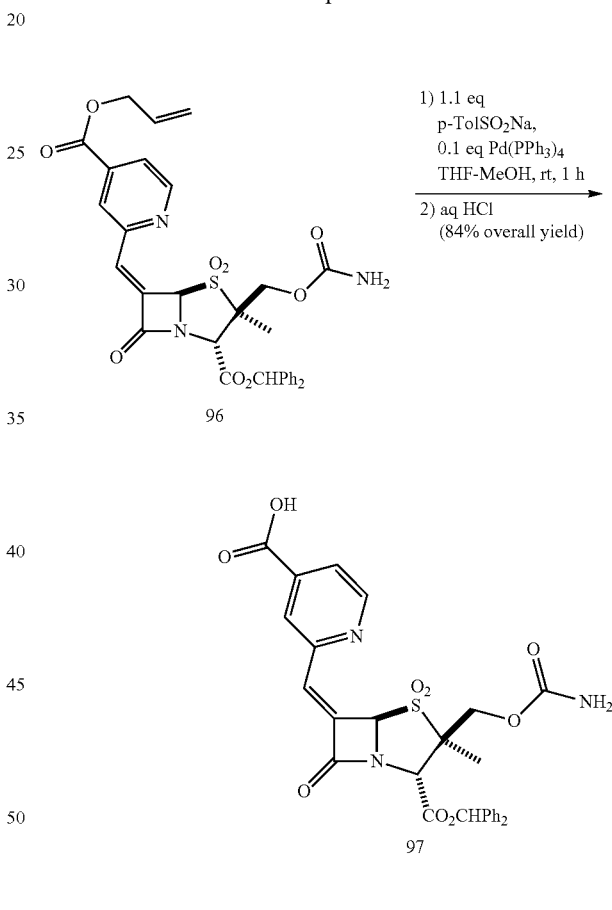

To a solution of alcohol 95 (3.41 g, 5.79 mmol) in dry pyridine (20.0 mL) was added p-nitrophenyl chloroformate (1.74 g, 8.68 mmol), and DMAP (352 mg, 2.89 mmol) at room temperature. The reaction was then allowed to stir at room temperature while monitoring by NMR for 2.0 h. After formation of p-nitrophenyl carbonate, a solution of ammonia in dioxane (52.0 mL of 0.5 M) and the reaction was subsequently stirred at room temperature for 30 min. The reaction mixture was diluted with CH$_2$Cl$_2$ (100 mL) and washed with water (75 mL), and brine (75 mL). The organic layer was To a solution of allyl ester 96 (2.3 g, 3.64 mmol) in THF (24.0 mL) was added Pd(PPh$_3$)$_4$ (420 mg, 0.364 mmol). Then a solution of sodium p-toluenesulfinate (712 mg, 4.0 mmol) in MeOH (14.0 mL) was added in one portion. The reaction mixture was allowed to stir at room temperature, while monitoring TLC (CH$_2$Cl$_2$ eluent). The reaction was judged to be complete in approximately 1 hour and the reddish black solution was concentrated and re-dissolved in EtOAc (100 mL) (sparingly soluble). This two phase mixture was stirred while adding a dilute aqueous solution of HCl (50.0 mL of 0.24 M). The color immediately changed to light yellow and everything went into solution. The ethyl acetate later was then separated, dried over Na$_2$SO$_4$, concentrated, and purified on column chromatography using CH$_2$Cl$_2$ containing 5% MeOH and 0.5% acetic acid as eluent to give 1.8 g of product (84% yield).

$^1$H-NMR (400 MHz, CDCl$_3$): 1.19 (s, 3H), 4.28 (d, 1H, J=11.88 Hz), 4.63 (d, 1H, J=11.88 Hz), 4.88 (s, 1H), 5.78 (s, 1H), 7.00 (s, 1H), 7.26-7.40 (m, 11H), 7.87-7.88 (d, 1H, J=5.23 Hz), 7.94 (s, 1H), 8.86 (d, 1H, J=4.45 Hz).

Example 76

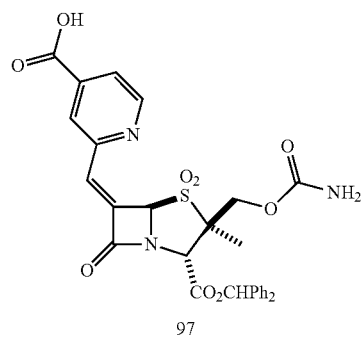

To a solution of acid 97 (1.8 g, 3.04 mmol) in pyridine (15.0 mL) was added p-nitrophenyl chloroformate (916 mg, 4.56 mmol), and DMAP (185 mg, 1.52 mmol) and the reaction mixture was stirred for 30 min at room temperature. The reaction mixture was diluted with CH$_2$Cl$_2$ (75.0 mL) and washed with water (50 mL) and brine (50 mL). The organic layer was dried over Na$_2$SO$_4$, concentrated and purified by column chromatography using 5% EtOAc in CH$_2$Cl$_2$ as eluent to obtain product 1.6 g (74% yield).

$^1$H-NMR (400 MHz, CDCl$_3$): 1.2 (s, 3H), 4.28 (d, 1H, J=11.96 Hz), 4.63 (d, 1H, J=11.96 Hz), 4.9 (s, 1H), 5.8 (s, 1H), 7.0 (s, 1H), 7.33-7.45 (m, 13H), 8.0-8.02. (dd, 1H, J=3.36 Hz, J=1.51 Hz), 8.06 (s, 1H), 8.35 (d, 2H, J=9.12 Hz), 8.95-8.96 (d, 1H, J=4.86 Hz).

Example 77

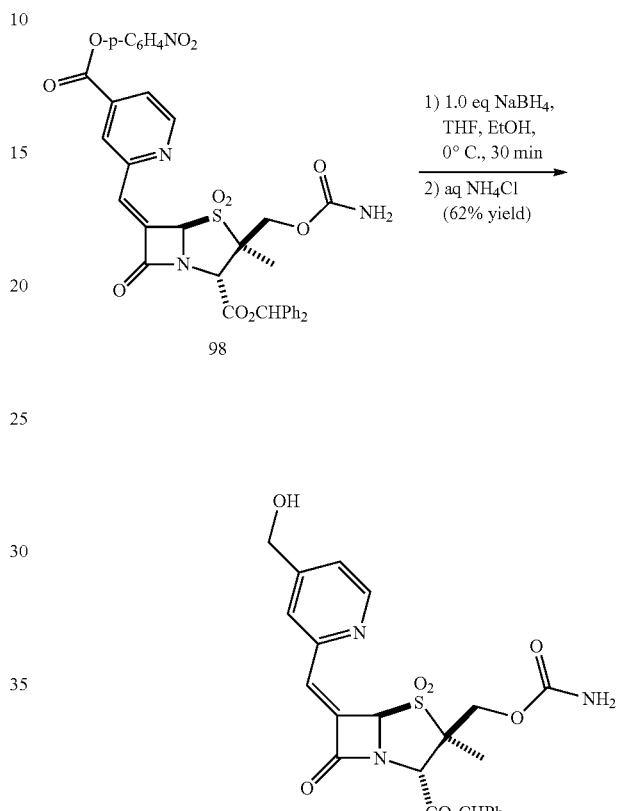

To a solution of p-nitrophenyl ester 98 (1.6 g, 2.247 mmol) in THF (8.0 mL) and EtOH (8.0 mL) was added NaBH$_4$ (83 mg, 2.247 mmol) at 0° C. The reaction was subsequently stirred for 30 min at 0° C., quenched with aqueous ammonium chloride, diluted with CH$_2$Cl$_2$ (75 mL) and washed with water (50 mL), and brine (50 mL). The organic layer was dried over Na$_2$SO$_4$, concentrated and purified by column chromatography using 20% EtOAc in CH$_2$Cl$_2$ as eluent to obtain 800 mg product (62% yield).

$^1$H-NMR (400 MHz, CDCl$_3$): 1.19 (s, 3H), 4.29 (d, 1H, J=11.89 Hz), 4.62 (d, 1H, J=11.89 Hz), 4.74 (d, 2H, J=5.88 Hz), 4.84 (s, 1H), 5.79 (s, 1H), 6.99 (s, 1H), 7.22-7.41 (m, 13H), 8.61-8.63 (d, 1H, J=4.91 Hz).

$^{13}$C-NMR (100 MHz, CDCl$_3$): 15.42, 59.85, 62.46, 64.43, 66.38, 73.81, 79.29, 122.13, 123.84, 126.91, 127.44, 128.29, 128.51, 128.58, 128.68, 130.09, 133.05, 138.47, 138.57, 150.01, 150.56, 151.65, 155.53, 166.1, 167.89.

IR (thin film): 911.27, 1166.66, 1328.27, 1601.58, 1736.06, 1781.88, 3385.7, 3489.19 cm$^{-1}$.

Example 78

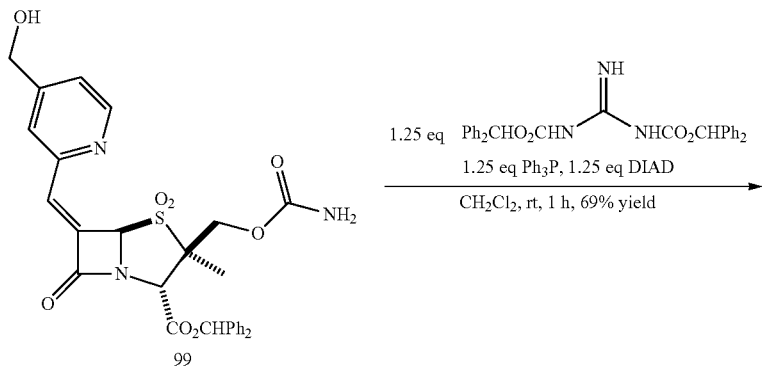

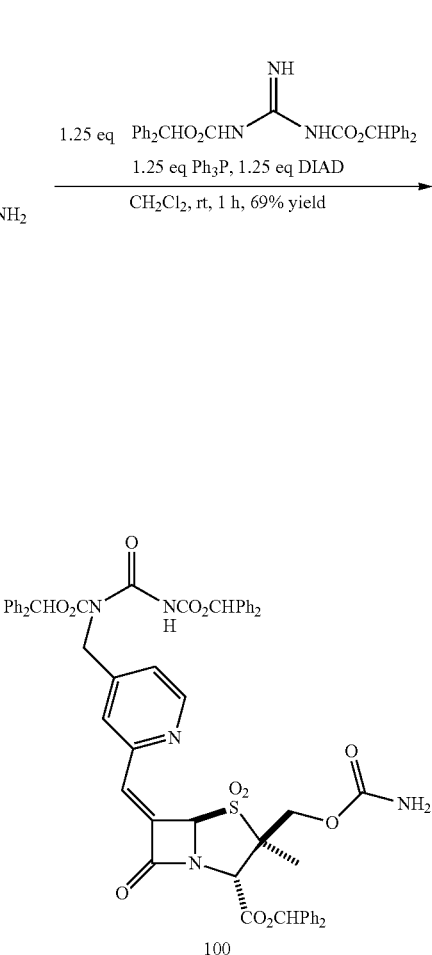

To a stirred solution of alcohol 99 (200 mg, 0.346 mmol), PPh₃ (113 mg, 0.432 mmol), and bis(benzhydrylcarbonyloxy)guanidine (207 mg, 0.432 mmol) in CH$_2$Cl$_2$ (5.0 mL) was added diisopropyl azodicarboxylate (DIAD) (85.0 µL, 0.432 mmol) at room temperature. After stirring for 1 h at same temperature, the reaction mixture was concentrated in vacuo and directly purified by flash column chromatography using 5% EtOAc in DCM as eluent to obtain 250 mg product (69% yield).

¹H-NMR (400 MHz, CDCl₃): 1.22 (s, 3H), 4.30 (d, 1H, J=11.93 Hz), 4.65 (d, 1H, J=11.93 Hz), 4.86 (s, 1H), 5.01-5.04 (m, 1H), 5.27-5.33 (m, 1H), 5.76 (s, 1H), 6.69 (s, 1H), 6.75 (s, 1H), 6.97-7.39 (m, 34H), 8.51 (d, 1H, J=5.56 Hz), 9.18 (brs, 1H), 9.43 (brs, 1H).

¹³C-NMR (100 MHz, CDCl₃): 16.03, 22.4, 47.13, 60.69, 65.31, 66.81, 70.41, 74.48, 77.26, 77.58, 77.9, 78.78, 79.84, 81.42, 123.76, 127.38, 127.4, 127.55, 128.05, 128.16, 128.89, 129.07, 129.1, 129.16, 129.2, 129.22, 129.25, 134.42, 138.51, 139.08, 139.21, 141.23, 151.48, 155.06, 155.88, 160.68, 163.34, 166.7.

IR (thin film): 911.73, 1082.52, 1220.94, 1329.0, 1495.76, 1613.74, 1727.63, 1783.03, 3389.85 cm⁻¹.

Example 79

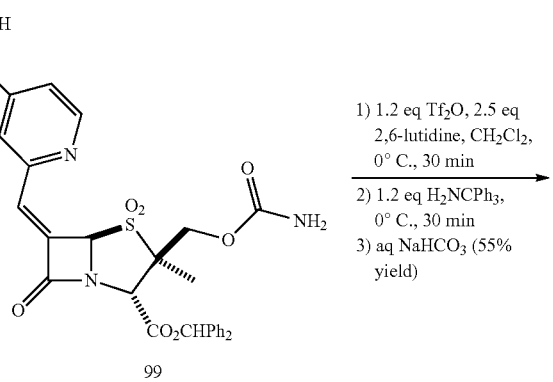

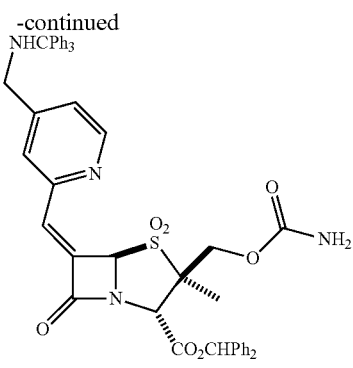

101

To a solution of alcohol 99 (180 mg, 0.311 mmol) in anhydrous CH$_2$Cl$_2$ (8.0 mL) cooled to 0° C. was added 2,6-lutidine (90.0 μL, 0.777 mmol) followed by trifluoromethanesulfonic anhydride (TFAA) (62 μL, 0.373 mmol). After stirring for 30 min at 0° C., tritylamine (96 mg, 0.373 mmol) was added and the reaction was stirred for an additional 30 min at 0° C. The reaction mixture was subsequently diluted with CH$_2$Cl$_2$ (50 mL) and washed with saturated aqueous NaHCO$_3$ (50 mL), water (50 mL) and brine (50 mL). The organic layer was dried over Na$_2$SO$_4$, concentrated and purified by column chromatography using 5% EtOAc in CH$_2$Cl$_2$ as eluent to obtain 140 mg product (55% yield).

$^1$H-NMR (400 MHz, CDCl$_3$): 1.32 (s, 3H), 3.41 (s, 2H), 4.42 (d, 1H, J=12.07 Hz), 4.75 (d, 1H, J=12.07 Hz), 4.89 (s, 1H), 5.96 (s, 1H), 7.02 (s, 1H), 7.2-7.59 (m, 27H), 7.8 (s, 1H), 8.57 (d, 1H, J=5.32 Hz).

Example 80

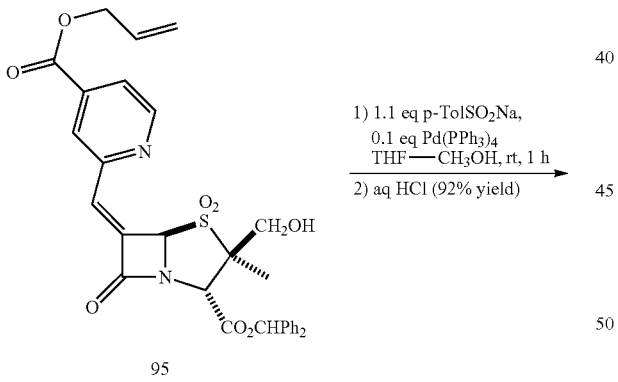

To a solution of allyl ester 95 (1.1 g, 1.87 mmol) in THF (12.0 mL) was added Pd(PPh$_3$)$_4$ (213 mg, 0.185 mmol). Then a solution of sodium p-toluenesulfinate (397 mg, 2.05 mmol) in MeOH (7.0 mL) was added in one portion. The reaction mixture was allowed to stir at room temperature, while monitoring TLC (CH$_2$Cl$_2$ eluent). After 1 hour, the reddish black solution was concentrated and EtOAc (50 mL) was added (sparingly soluble). While stirring this slurry a dilute aqueous solution of HCl (25.0 mL of 0.24 M) was added. The color immediately changed to light yellow and everything went into solution. The EtOAc layer was separated, concentrated and purified on column chromatography using CH$_2$Cl$_2$ containing 5% MeOH and 0.5% acetic acid as eluent to give 940 mg product (92% yield).

$^1$H-NMR (400 MHz, CDCl$_3$): 1.09 (s, 3H), 3.77 (d. 1H, J=13.12 Hz), 4.06 (d, 1H, J=13.12 Hz), 5.22 (s, 1H), 5.71 (s, 1H), 7.01 (s, 1H), 7.25 (s, 1H), 7.31-7.38 (m, 10H), 7.89 (d, 1H, J=4.62 Hz), 7.95 (s, 1H), 8.85 (d, 1H, J=4.8 Hz).

Example 81

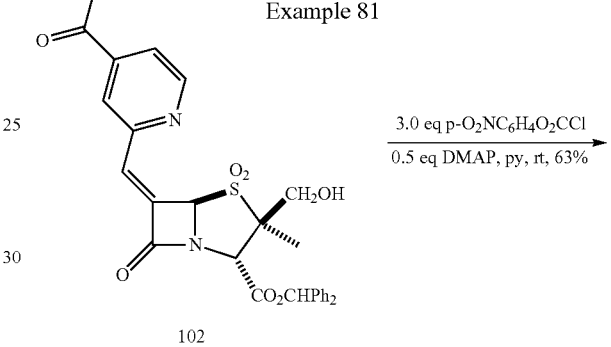

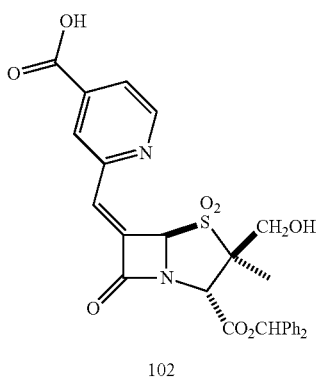

103

To a solution of acid 102 (840 mg, 1.532 mmol) in dry pyridine (8.0 mL) was added p-nitrophenyl chloroformate (923 mg, 4.596 mmol), and DMAP (93 mg, 0.766 mmol) at room temperature and the reaction mixture was stirred for 2.5 h. The reaction mixture was then diluted with CH$_2$Cl$_2$ (25 mL) and washed with water (25 mL) and brine (25 mL). The organic layer was dried over Na$_2$SO$_4$, concentrated and purified by column chromatography using CH$_2$Cl$_2$ as eluent to obtain 800 mg product (63% yield).

$^1$H-NMR (400 MHz, CDCl$_3$): 1.34 (s, 3H), 4.66 (d, 1H, J=12.08 Hz), 4.78 (d, 1H, J=12.08 Hz), 4.88 (s, 1H), 5.81 (s, 1H), 7.02 (s, 1H), 7.33-7.45 (m, 15H), 8.0-8.02 (dd, 1H, J=3.45 Hz, J=1.46 Hz), 8.07 (s, 1H), 8.23 (d, 2H, J=9.16 Hz), 8.32 (d, 2H, J=9.12 Hz), 8.93 (d, 1H, J=4.85 Hz).

Example 82

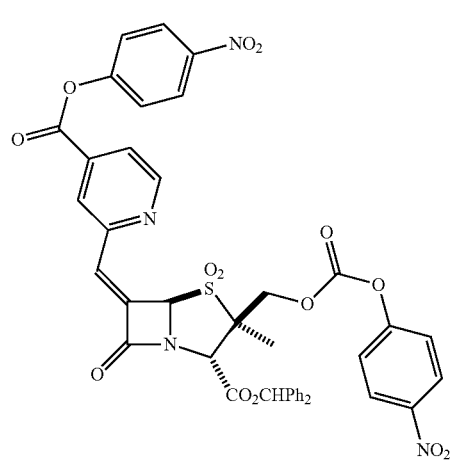
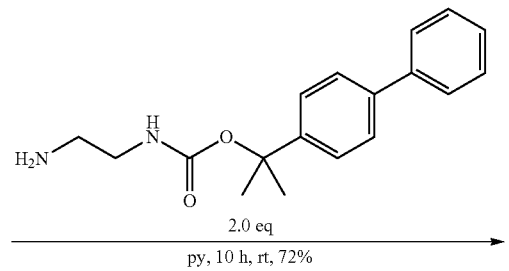
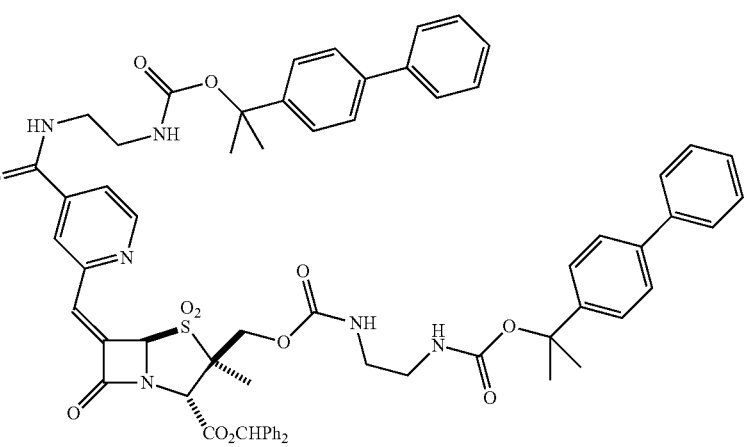

To a solution of p-nitrophenyl ester 103 (200 mg, 0.239 mmol) in dry pyridine (2.0 mL) was added 2-(biphenyl-4-yl)propan-2-yl 2-aminoethylcarbamate (142 mg, 0.478 mmol) at room temperature and reaction mixture was stirred for 10 h. The reaction mixture was then diluted with $CH_2Cl_2$ (25 mL) and washed with water (25 mL), and brine (25 mL). The organic layer was dried over $Na_2SO_4$, concentrated and purified by column chromatography using 50% EtOAc in $CH_2Cl_2$ as eluent to obtain 200 mg product (72% yield).

$^1$H-NMR (400 MHz, $CDCl_3$): 1.11 (s, 3H), 1.64 (s, 6H), 1.67 (s, 6H), 3.09 (m, 4H), 3.21 (m, 2H), 3.35 (m, 2H), 4.26 (d, 1H, J=11.92 Hz) 4.57 (d, 1H, J=11.92 Hz), 4.71 (s, 1H), 5.22 (s, 1H), 5.44 (brs, 1H), 5.67 (brs, 1H), 5.77 (brs, 1H), 6.92 (s, 1H), 7.18-7.47 (m, 30H), 7.79 (s, 1H), 8.46 (d, 1H, J=4.42 Hz).

Example 83

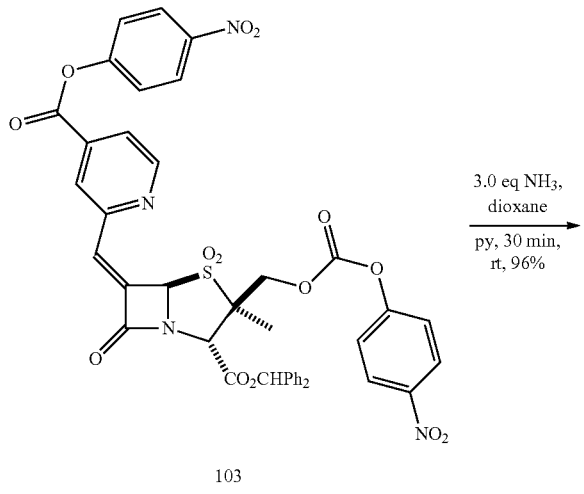

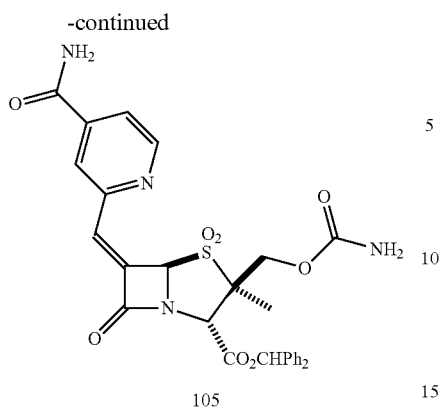

105

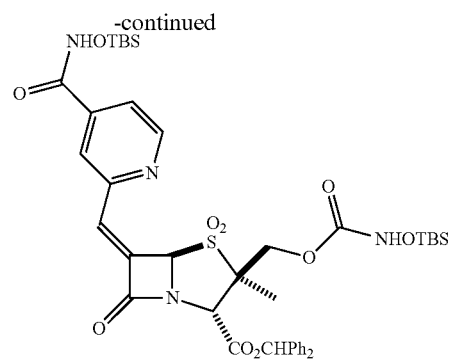

106

To a solution of p-nitrophenyl ester 103 (170 mg, 0.203 mmol) in pyridine (1.5 mL) was added a solution of ammonia in dioxane (1.2 mL, 0.6 mmol) at room temperature and the reaction mixture was stirred for 30 min. The reaction mixture was then diluted with $CH_2Cl_2$ (25 mL) and washed with water (25 mL), and brine (25 mL). The organic layer was dried over $Na_2SO_4$, concentrated and purified by column chromatography using 5% EtOAc in $CH_2Cl_2$ as eluent to obtain 115 mg product (96% yield).

$^1$H-NMR (400 MHz, $CDCl_3$): 1.17 (s, 3H), 4.27 (d, 1H, J=11.92 Hz), 4.66 (d, 1H, J=11.92 Hz), 4.96 (s, 1H), 5.44 (brs, 2H), 5.75 (s, 1H), 6.63 (brs, 1H), 6.94 (brs, 1H), 6.97 (s, 1H), 7.17 (s, 1H), 7.25-7.38 (m, 11H), 7.47 (s, 1H), 8.49 (d, 1H, J=4.12 Hz).

$^{13}$C-NMR (100 MHz, $CDCl_3$): 15.47, 60.36, 64.91, 66.91, 74.19, 79.43, 122.59, 123.86, 127.05, 127.52, 128.41, 128.62, 128.68, 128.78, 129.21, 134.43, 138.52, 138.66, 141.4, 150.91, 151.41, 155.51, 166.08, 166.72, 167.58

IR (thin film): 1328.0, 1594.9, 1682.4, 1732.0, 1783.4, 3365.0 $cm^{-1}$.

Example 84

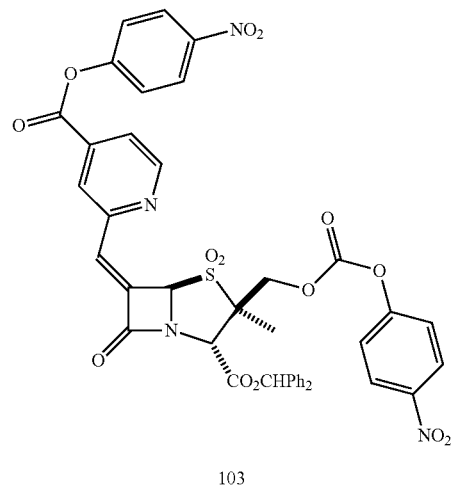

103

To a solution of p-nitrophenyl ester (120 mg, 0.143 mmol) in dry pyridine (1.5 mL) was added O-t-butyldimethylsilyl hydroxylamine (46 mg, 0.314 mmol) and DMAP (8.7 mg, 0.071 mmol) and the reaction mixture was stirred for 2 h at room temperature. The reaction mixture was then diluted with $CH_2Cl_2$ (25 mL) and washed with water (25 mL), and brine (25 mL). The organic layer was dried over $Na_2SO_4$, concentrated and purified by column chromatography using 5% EtOAc in $CH_2Cl_2$ as eluent to obtain 50 mg product (41% yield).

$^1$H-NMR (400 MHz, $CDCl_3$): 0.09 (s, 6H), 0.18 (s, 6H), 0.88 (s, 9H), 0.91 (s, 9H), 1.11 (s, 3H), 4.29 (d, 1H, J=11.9 Hz), 4.60 (d, 1H, J=11.9 Hz), 4.72 (s, 1H), 5.7 (s, 1H), 6.92 (s, 1H), 7.17-7.33 (m, 11H), 7.61 (d, 1H, J=3.96 Hz), 7.68 (s, 1H), 8.64 (d, 1H, J=4.96 Hz).

Example 85

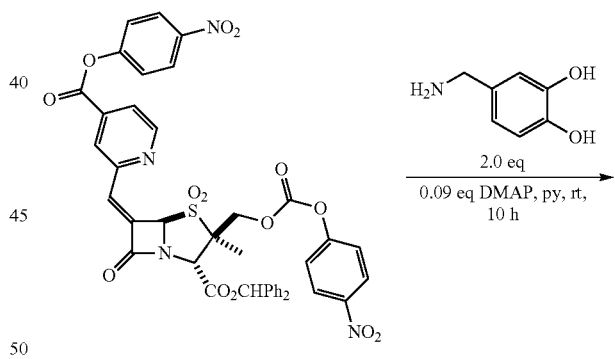

103

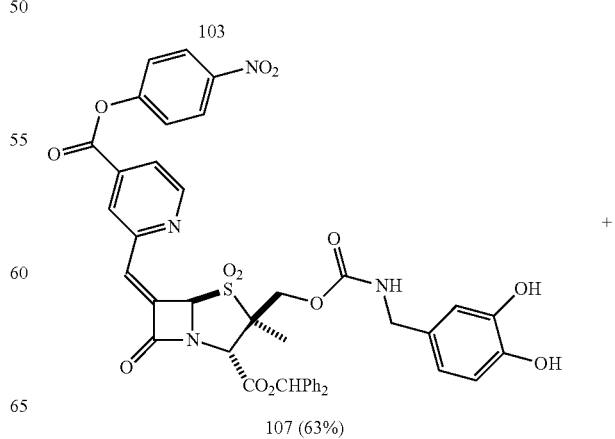

107 (63%)

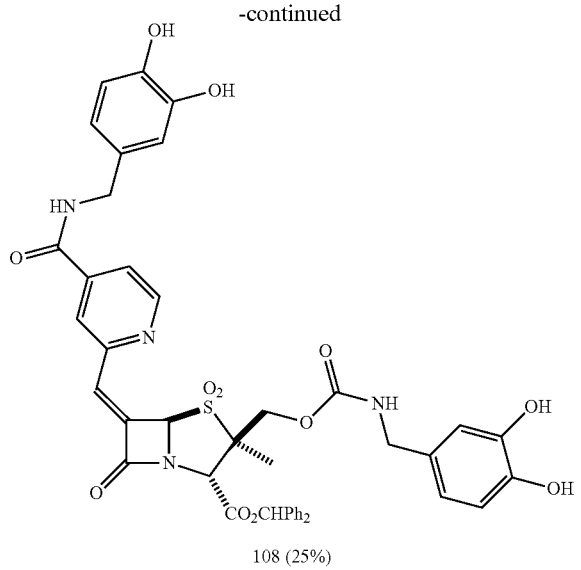

108 (25%)

To a solution of p-nitrophenylester 103 (200 mg, 0.238 mmol) in dry pyridine (2.0 mL) was added 3,4-dihydroxybenzylamine (106 mg, 0.48 mmol) and DMAP (2.5 mg) and the reaction mixture was stirred for 30 min at room temperature. The reaction mixture was then diluted with $CH_2Cl_2$ (25 mL) and washed with water (25 mL) and with brine (25 mL). The organic layer was dried over $Na_2SO_4$, concentrated and purified by column chromatography using 50% EtOAc in $CH_2Cl_2$ as eluent to obtain two products, mono substituted at 2'-position (107) 125.0 mg (63% yield) and disubstituted (108) 50.0 mg (25% yield).

$^1$H-NMR of 107 (400 MHz, $CDCl_3$): 1.17 (s, 3H), 4.03-4.08 (dd, 1H, J=9.76 Hz, J=5.0 Hz), 4.21-4.28 (m, 2H), 4.71 (d, 1H, J=11.96 Hz), 4.99 (s, 1H), 5.8 (s, 1H), 6.99 (s, 1H), 7.3-7.45 (m, 13H), 7.8-7.85 (m, 3H), 7.94-7.96 (m, 2H), 8.31 (d, 1H, J=9.05 Hz), 8.87 (d, 1H, J=4.84 Hz).

Example 86

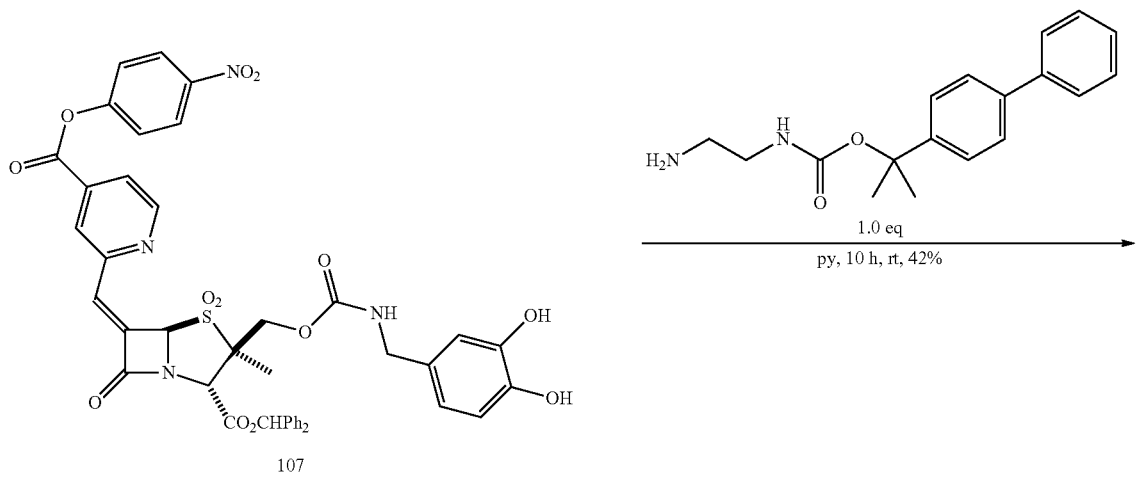

107

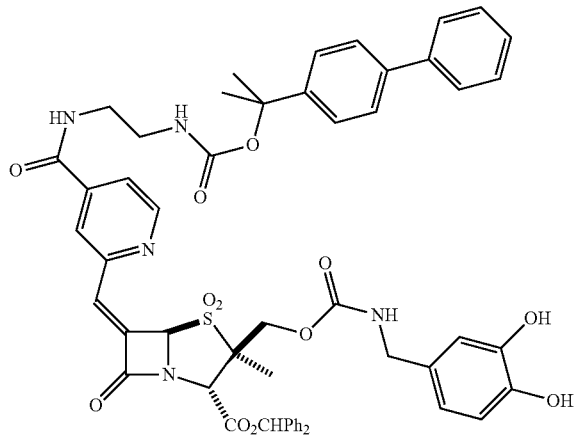

109

To a solution of p-nitrophenylester 107 (125 mg, 0.149 mmol) in dry pyridine (2.0 mL) was added 2-(biphenyl-4-yl) propan-2-yl2-aminoethylcarbamate (44 mg, 0.149 mmol) and the reaction mixture was stirred for 10 h at room temperature. The reaction mixture was diluted with CH$_2$Cl$_2$ (25 mL) and washed with water (25 mL) and with brine (25 mL). The organic layer was dried over Na$_2$SO$_4$, concentrated and purified by column chromatography using 50% EtOAc in CH$_2$Cl$_2$ as eluent to obtain 60 mg product (40% yield).

Example 87

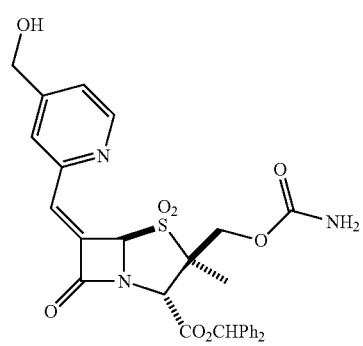

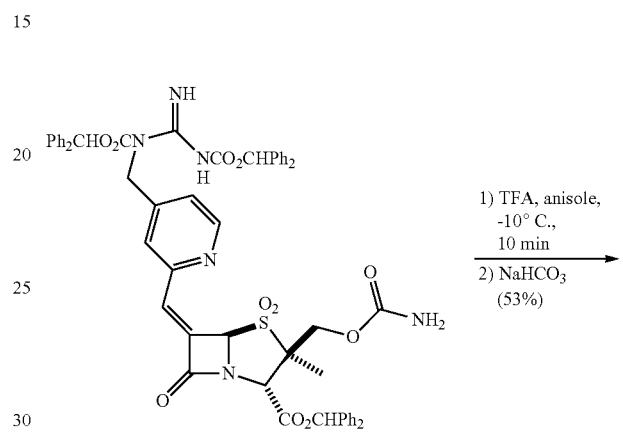

Ester 99 (125 mg, 0.216 mmol) was dissolved in anisole (1.0 mL) and cooled to −10° C. and trifluoroacetic acid (2.0 mL) was added to reaction mixture under argon atmosphere. The resultant mixture was stirred for 10 minutes at −10° C. The volatile components were evaporated in vacuo. The residue was dissolved ethyl acetate (5.0 mL) and treated with aqueous NaHCO$_3$ solution (36 mg of NaHCO$_3$ was dissolved in 5.0 mL of deionized water) The separated aqueous layer was then purified on a column of CHP2OP (Mitsubishi Chemical Corporation) using deionized water as eluent and lyophilized to give 35 mg of sodium salt (37% yield).

$^1$H-NMR (400 MHz, D$_2$O): 1.6 (s, 3H), 4.49-4.52 (m, 3H), 6.06 (s, 1H), 7.43 (d, 1H, J=4.8 Hz), 7.52 (s, 1H), 7.58 (s, 1H), 8.62 (d, 1H, J=5.01 Hz).

$^{13}$C-NMR (100 MHz, D$_2$O): 18.22, 64.78, 64.84, 67.07, 70.62, 75.95, 125.85, 127.11, 133.99, 134.1, 153.3, 153.54, 154.65, 160.78, 173.17, 175.27.

Example 88

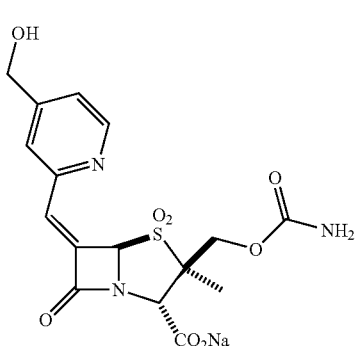

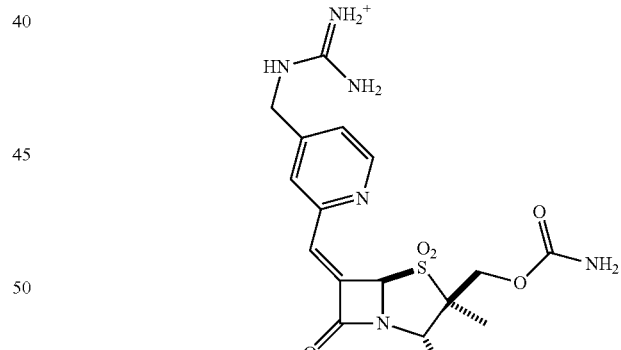

Ester 100 (250 mg, 0.24 mmol) was dissolved in anisole (1.5 mL) and cooled to −10° C. and trifluoroacetic acid (3.0 mL) was added to reaction mixture under argon atmosphere. The mixture was stirred for 10 minutes at −10° C. The volatile components were evaporated in vacuo. The residue was dissolved ethyl acetate (5.0 mL) and treated with aqueous NaHCO$_3$ solution (80 mg of NaHCO$_3$ was dissolved in 5.0 mL of deionized water). The separated aqueous layer was then purified on a column of CHP2OP (Mitsubishi Chemical Corporation) using deionized water as eluent and lyophilized to give 60 mg of product (53% yield).

$^1$H-NMR (400 MHz, D$_2$O): 1.59 (s, 3H), 4.49 (d, 1H, J=12.06 Hz), 4.55 (s, 2H), 4.66 (d, 1H, J=12.06 Hz), 6.01 (s, 1H), 7.39 (d, 1H, J=4.8 Hz), 7.47 (s, 1H), 7.52 (s, 1H), 8.63 (d, 1H, J=4.94 Hz).

$^{13}$C-NMR (100 MHz, D$_2$O): 15.72, 43.58, 62.42, 64.59, 68.1, 73.46, 123.52, 124.44, 131.16, 131.97, 148.04, 151.0, 151.39, 157.58, 158.24, 170.46, 172.7.

Example 89

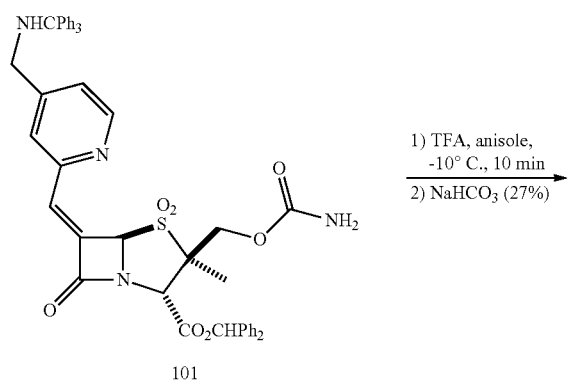

101

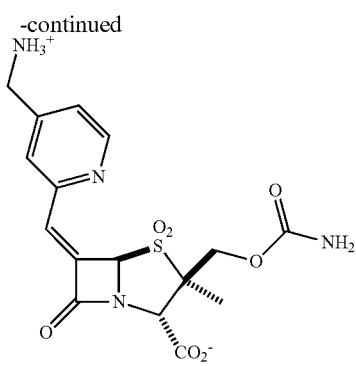

112

Ester 101 (140 mg, 0.171 mmol) was dissolved in anisole (1.0 mL) and cooled to −10° C. and trifluoroacetic acid (2.0 mL) was added to reaction mixture under argon atmosphere. The mixture was stirred for 10 minutes at −10° C. The volatile components were evaporated in vacuo. The residue was dissolved ethyl acetate (5.0 mL) and treated with aqueous NaHCO$_3$ solution (28 mg of NaHCO$_3$ was dissolved in 5.0 mL of deionized water) The separated aqueous layer was then purified on a column of CHP2OP (Mitsubishi Chemical Corporation) using deionized water as eluent and lyophilized to give 20 mg of pure salt (27% yield).

$^1$H-NMR (400 MHz, D$_2$O): 1.59 (s, 3H), 4.25 (brs, 2H), 4.50 (d, 2H, J=12.55 Hz), 4.52 (s, 1H), 4.67 (d, 1H, J=12.25 Hz), 6.05 (s, 1H), 7.48 (d, 1H, J=4.33 Hz), 7.52 (s, 1H), 7.62 (s, 1H), 8.70 (d, 1H, J=4.54 Hz).

Example 90

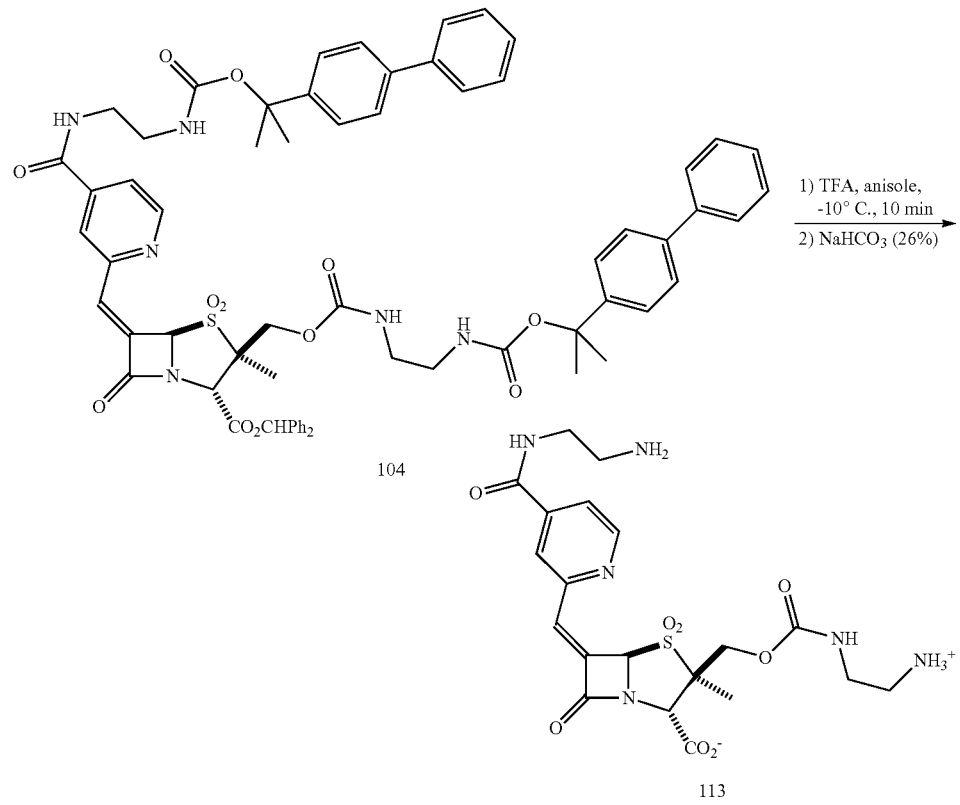

104

113

Ester 104 (200 mg, 0.173 mmol) was dissolved in anisole (1.0 mL), cooled to −10° C. and trifluoroacetic acid (2.0 mL) was added to the reaction mixture under argon atmosphere. The resultant mixture was stirred for 10 minutes at −10° C. The volatile components were evaporated in vacuo. The residue was dissolved ethyl acetate (5.0 mL) and treated with aqueous $NaHCO_3$ solution (58 mg of $NaHCO_3$ was dissolved in 5.0 mL of deionized water) The separated aqueous layer was then purified on a column of CHP2OP (Mitsubishi Chemical Corporation) using deionized water as eluent and lyophilized to give 25 mg of pure salt (27% yield).

$^1$H-NMR (400 MHz, $D_2O$): 1.58 (s, 3H), 3.03-3.12 (m, 4H), 3.39 (m, 2H), 3.63 (t, 2H, J=5.48 Hz), 4.53 (s, 1H), 6.04 (s, 1H) 7.52 (s, 1H), 7.71 (d, 1H, J=3.6 Hz), 7.83 (s, 1H), 8.77 (d, 1H, J=4.68 Hz).

Example 91

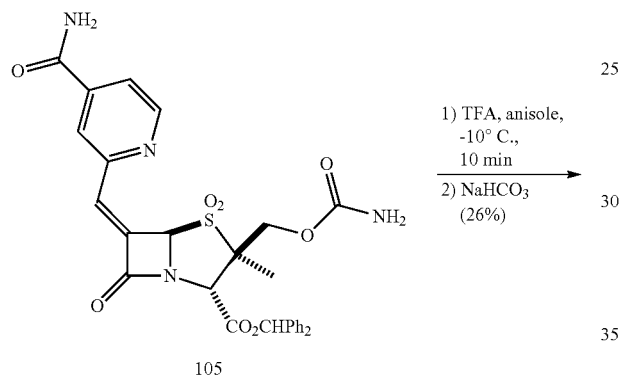

105

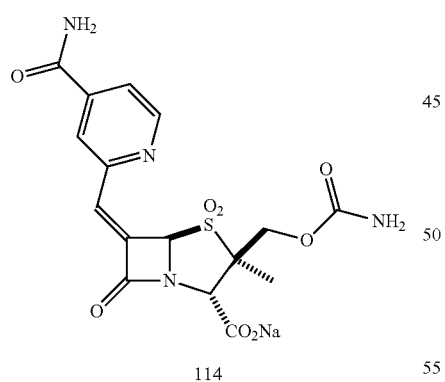

114

Ester 105 (115 mg, 0.195 mmol) was dissolved in anisole (1.0 mL), cooled to −10° C. and then trifluoroacetic acid (2.0 mL) was added to the reaction mixture under argon atmosphere. The resultant mixture was stirred for 10 minutes at −10° C. The volatile components were evaporated in vacuo. The residue was dissolved ethyl acetate (5.0 mL) and treated with aqueous $NaHCO_3$ solution (50 mg of $NaHCO_3$ was dissolved in 5.0 mL of deionized water). The separated aqueous layer was then purified on a column of CHP2OP (Mitsubishi Chemical Corporation) using deionized water as eluent and lyophilized to give 30 mg of pure salt (33% yield).

$^1$H-NMR (400 MHz, $D_2O$): 1.61 (s, 3H), 4.49 (d, 1H, J=12.1 Hz), 4.70 (d, 1H, J=12.1 Hz), 6.06 (s, 1H), 7.57 (s, 1H), 7.73-7.75 (dd, 1H, J=3.41 Hz, J=1.57 Hz), 7.88 (s, 1H), 8.80 (d, 1H, J=5.0 Hz).

$^{13}$C-NMR (100 MHz, $D_2O$): 15.77, 62.44, 64.63, 68.15, 73.55, 123.22, 124.42, 130.64, 132.59, 142.47, 151.55, 151.94, 158.3, 170.36, 170.56, 172.75.

Example 92

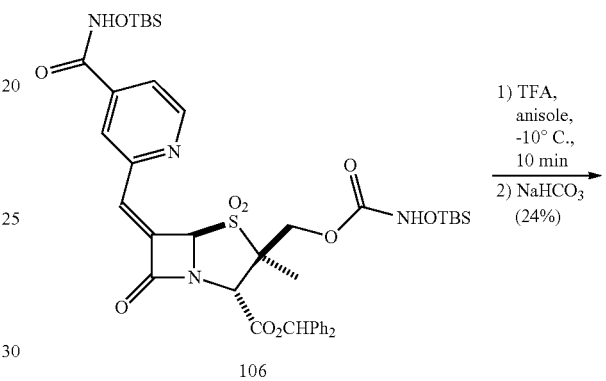

106

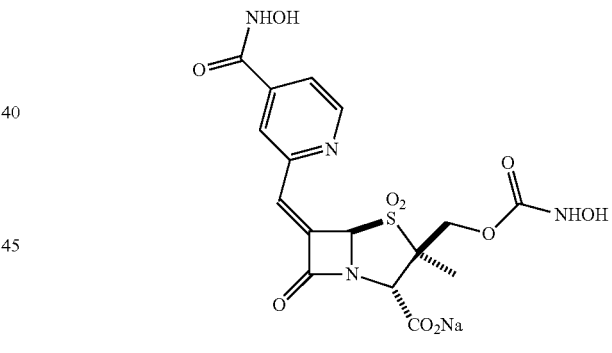

115

Ester 106 (50 mg, 0.058 mmol) was dissolved in anisole (1.0 mL) and cooled to −10° C. and trifluoroacetic acid (2.0 mL) was added to reaction mixture under argon atmosphere. The mixture was stirred for 10 minutes at −10° C. The volatile components were then evaporated in vacuo. The residue was dissolved ethyl acetate (5.0 mL) and treated with aqueous $NaHCO_3$ solution (15 mg of $NaHCO_3$ was dissolved in 5.0 mL of deionized water) The separated aqueous layer was then purified on a column of CHP2OP (Mitsubishi Chemical Corporation) using deionized water as eluent and lyophilized to give 7 mg of pure salt (24% yield).

$^1$H-NMR (400 MHz, $D_2O$): 1.61 (s, 3H), 2.23 (s, 1H), 4.5 (s, 1H), 6.08 (s, 1H), 7.59 (s, 1H), 7.66 (d, 1H, J=4.6 Hz), 7.82 (s, 1H), 8.71 (d, 1H, J=4.99 Hz).

Example 93

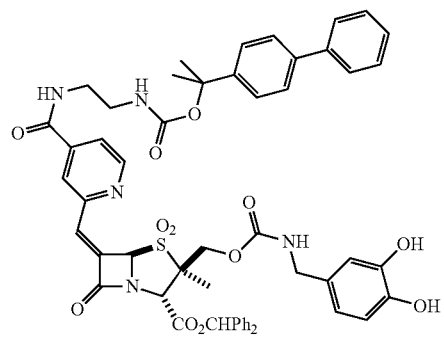

1) TFA, anisole, −10° C., 10 min
2) NaHCO₃
(23%)

109

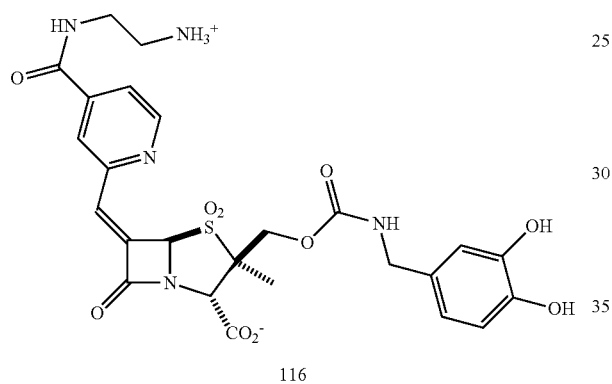

116

Ester 109 (60 mg, 0.06 mmol) was dissolved in anisole (1.0 mL) and cooled to −10° C. and trifluoroacetic acid (2.0 mL) was added to reaction mixture under argon atmosphere. The mixture was stirred for 10 minutes at −10° C. The volatile components were evaporated in vacuo. The residue was dissolved ethyl acetate (5.0 mL) and treated with aqueous NaHCO₃ solution (10 mg of NaHCO₃ was dissolved in 5.0 mL of deionized water) The separated aqueous layer was then purified on a column of CHP2OP (Mitsubishi Chemical Corporation) using deionized water as eluent and lyophilized to give 9 mg of pure salt (23% yield).

$^1$H-NMR (400 MHz, D$_2$O): 1.54 (s, 3H), 3.26-3.27 (m, 2H), 3.73 (m, 2H), 4.61 (s, 1H), 5.96 (s, 1H), 6.67-6.82 (m, 3H), 7.27 (s, 1H), 7.7 (s, 1H), 8.75 (s, 1H).

Exemplary Compounds

The following compounds have been prepared and characterized. The compounds are depicted in their un-ionized forms, although some have been isolated as various salts, such as sodium salts, or as zwitterionic forms.

Some of the compounds listed below have been evaluated for bioactivity as inhibitors of beta-lactamase enzymes, and some of these have been found to have potent bioactivity in this regard.

Compounds:

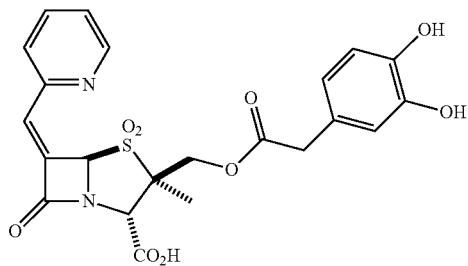

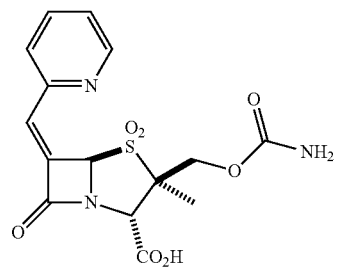

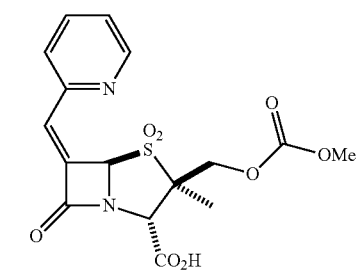

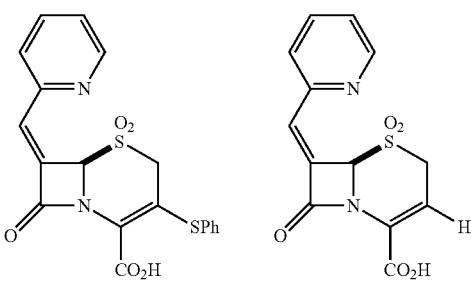

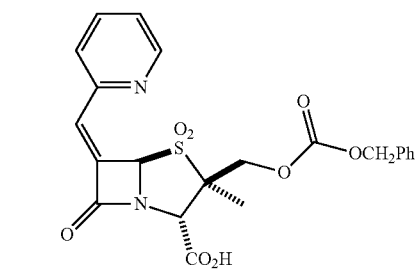

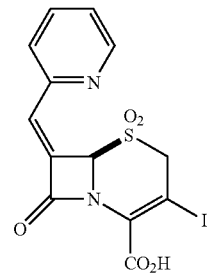

155
-continued
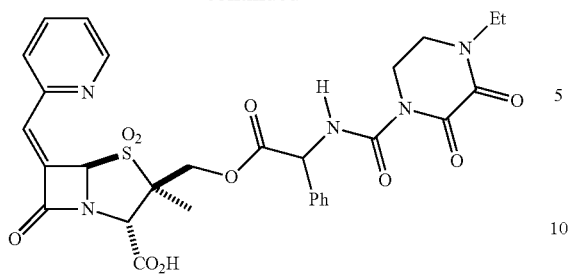
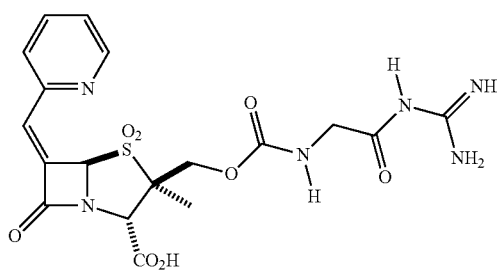
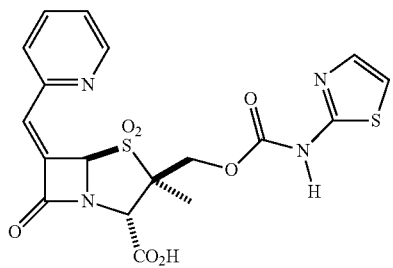
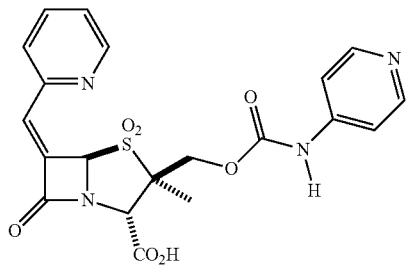
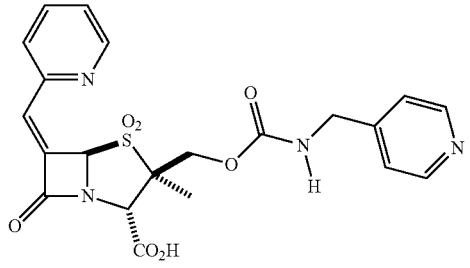
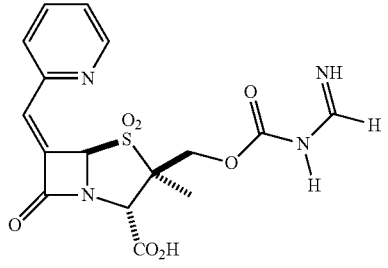
156
-continued
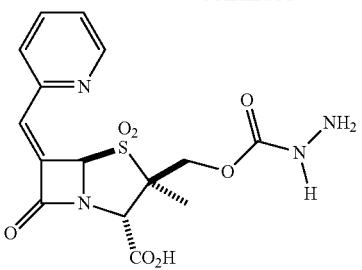
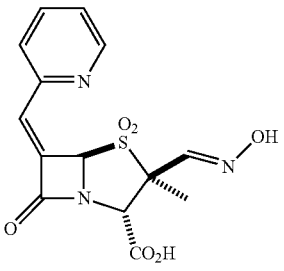
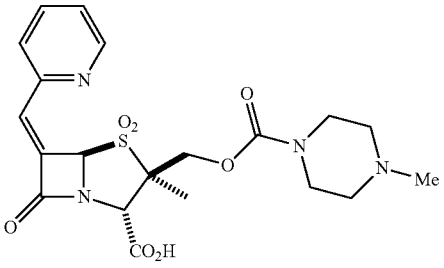
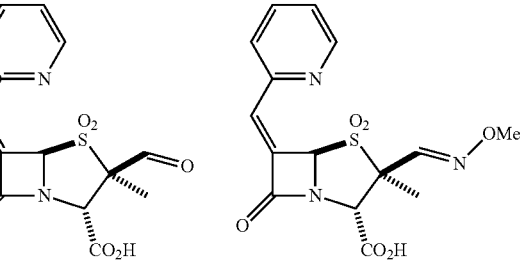
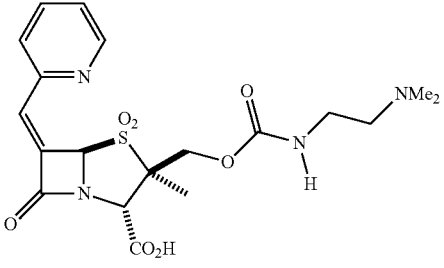
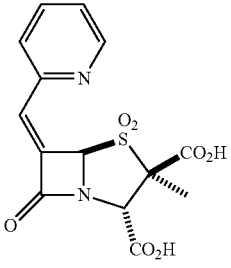

157
-continued
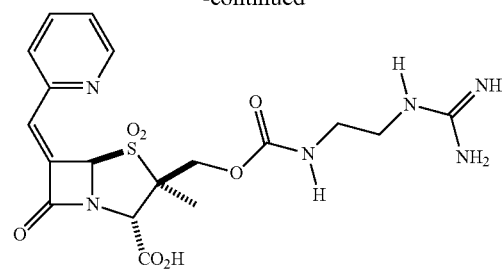
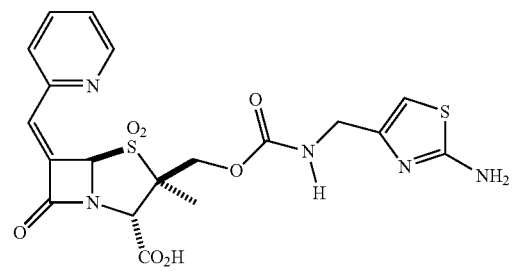
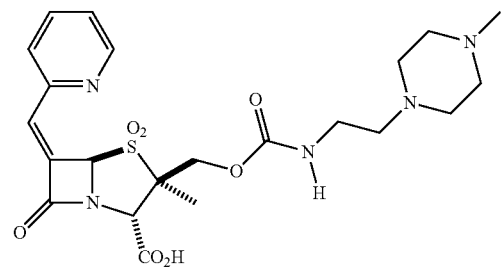
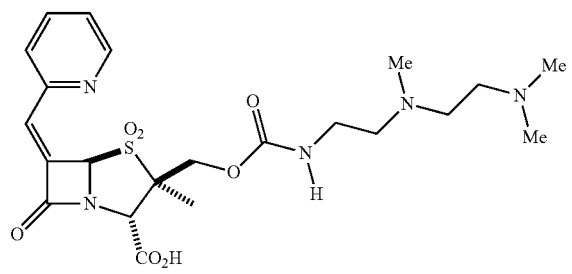
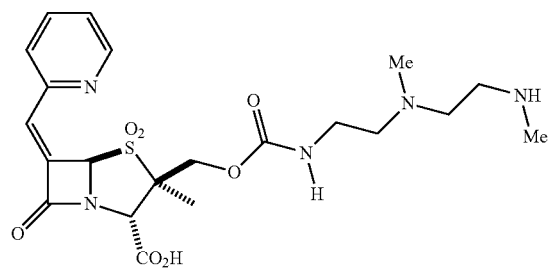
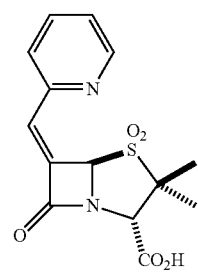
158
-continued
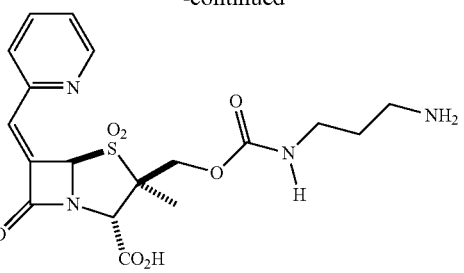
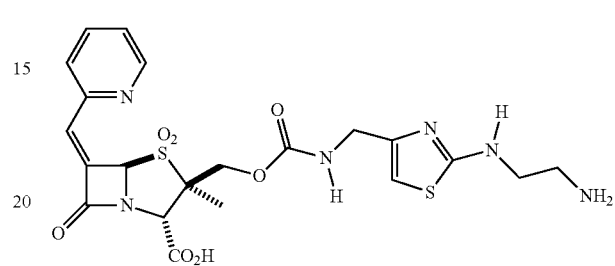
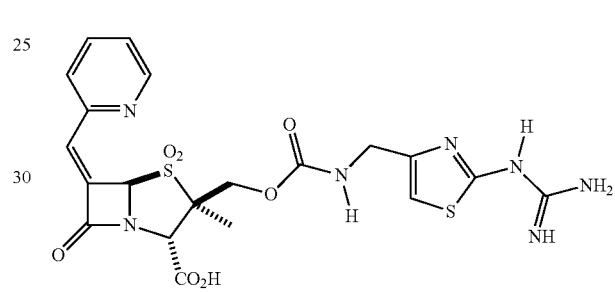
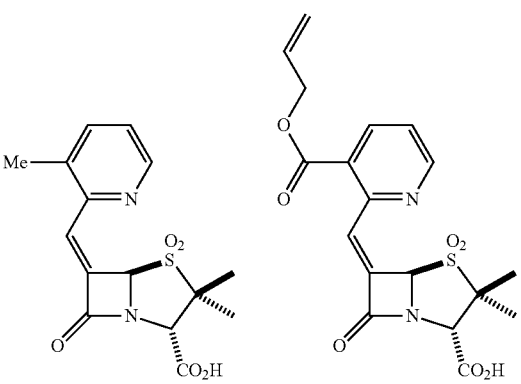
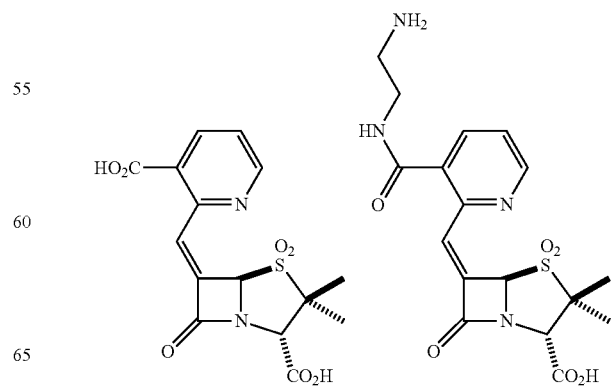

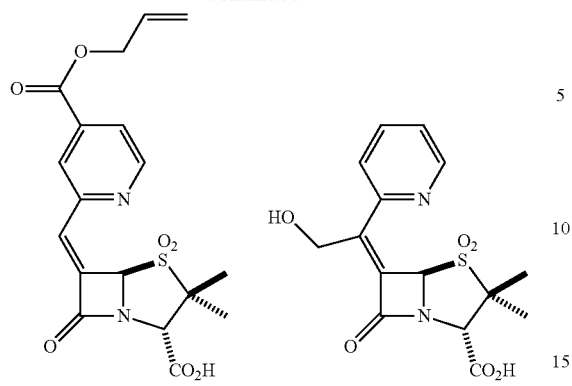
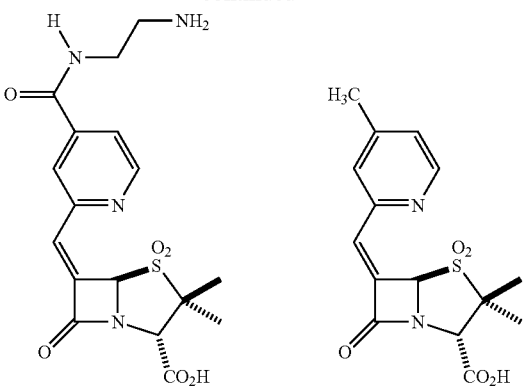
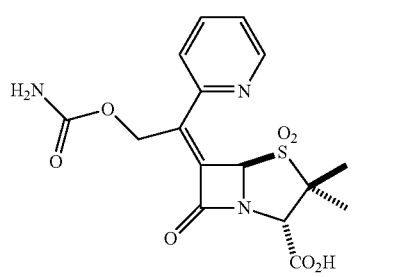
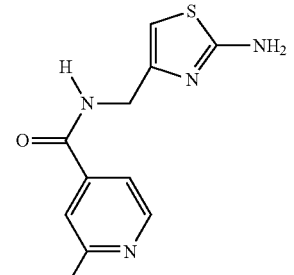
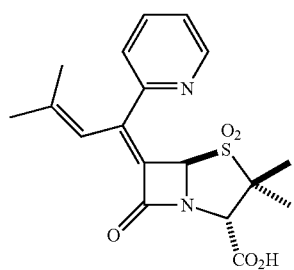
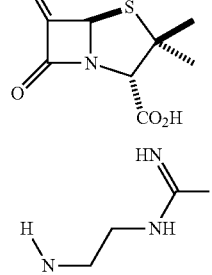
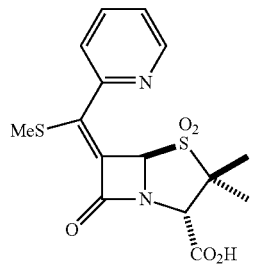
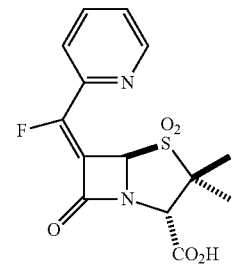
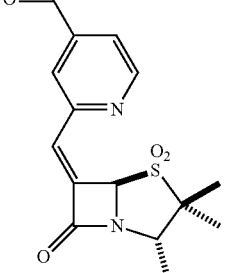
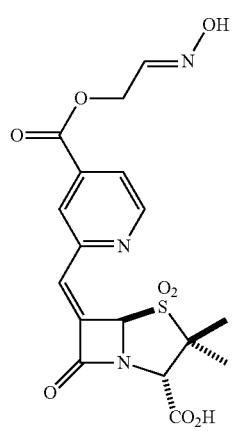
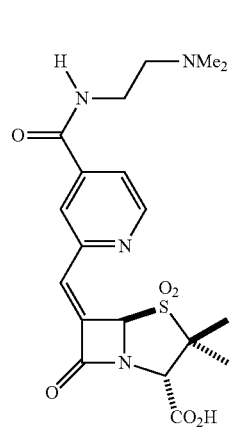
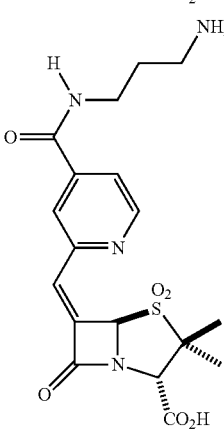
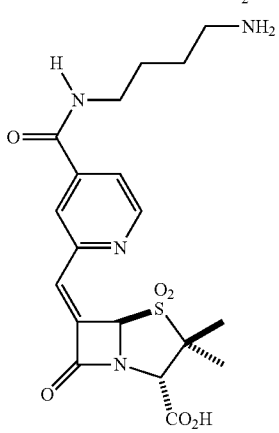

161
-continued
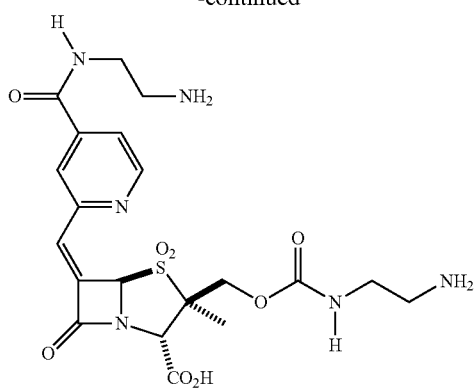
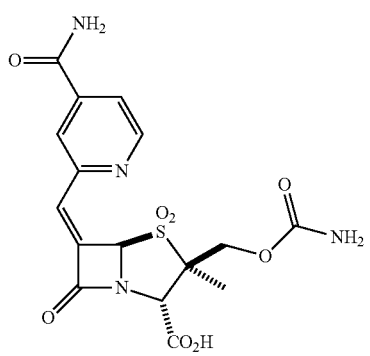
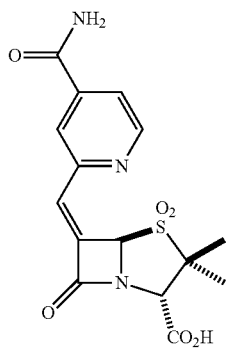
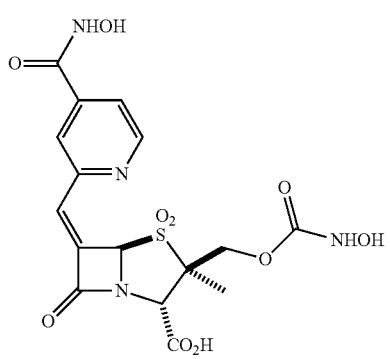
162
-continued
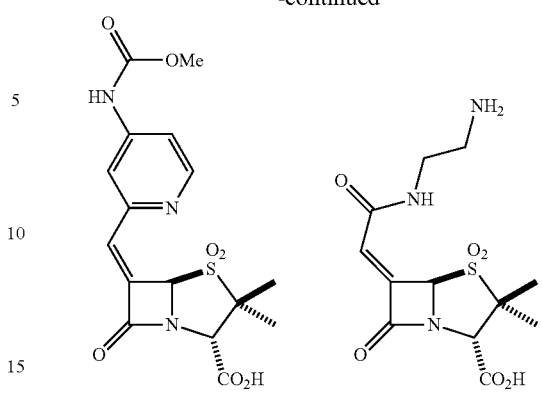
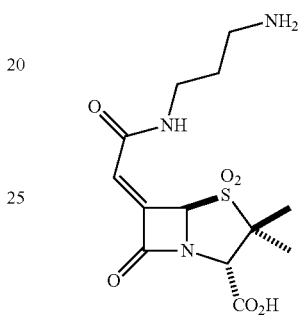
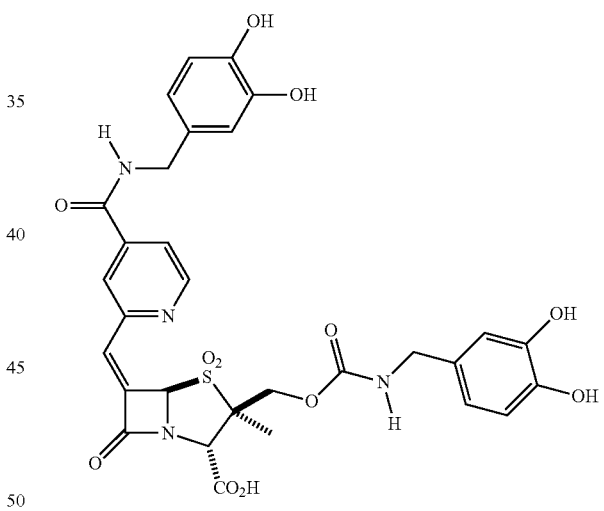
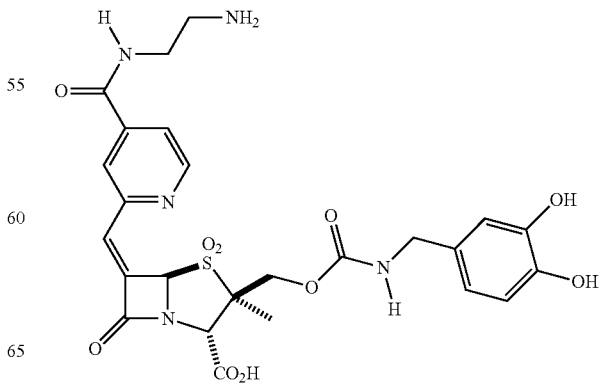

163
-continued
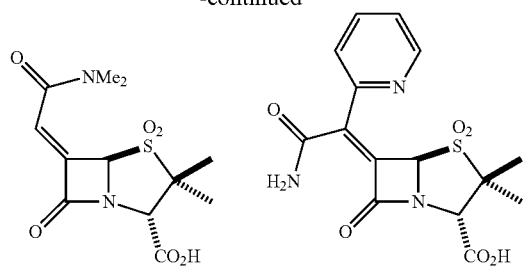
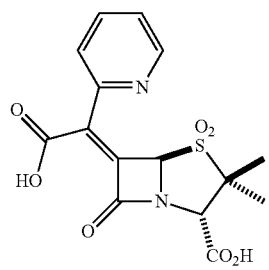
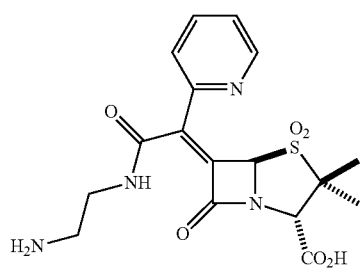
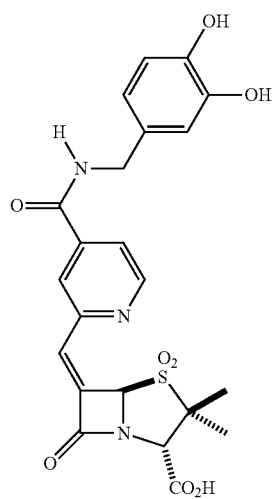
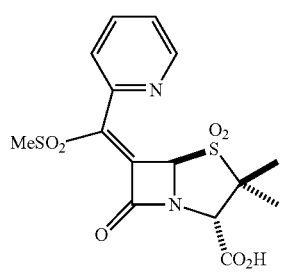
164
-continued
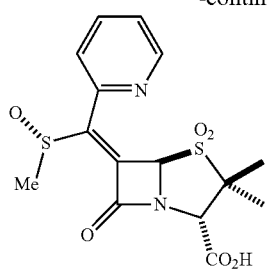
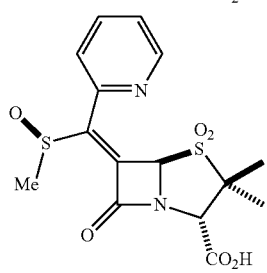
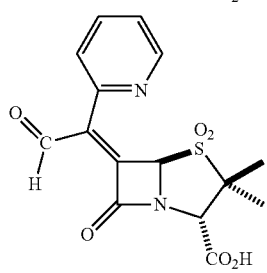
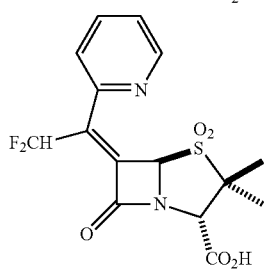
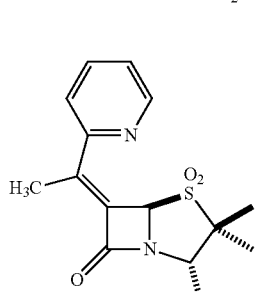
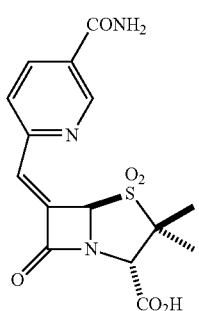
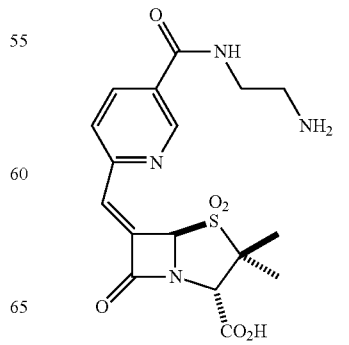

165
-continued
166
-continued
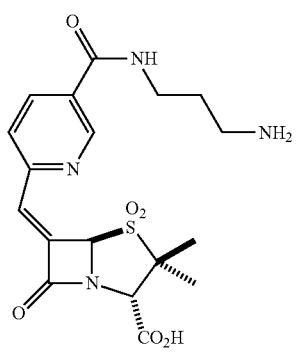
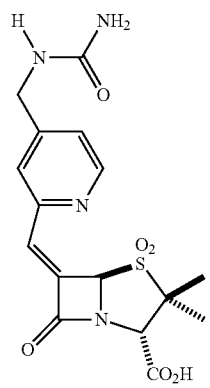
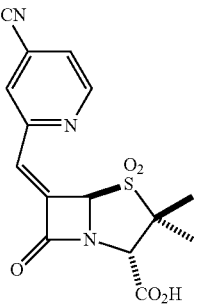
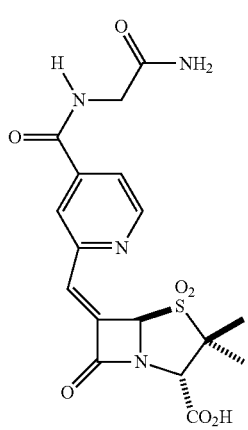
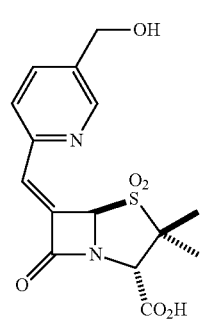
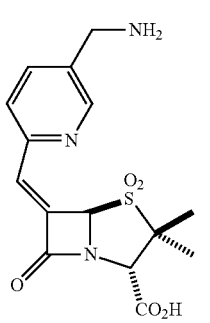
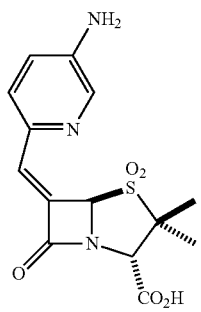
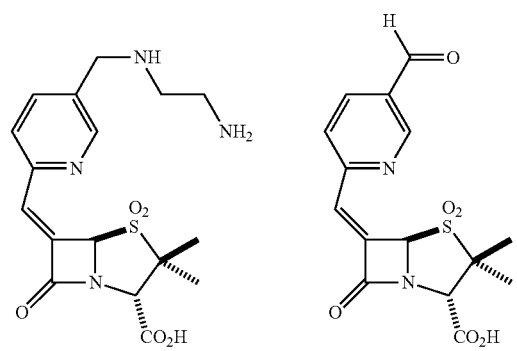
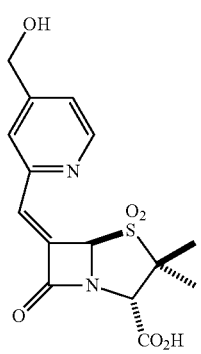
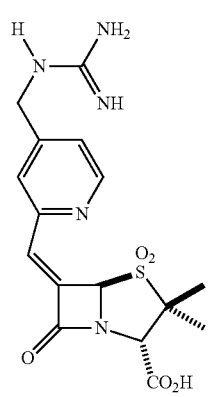
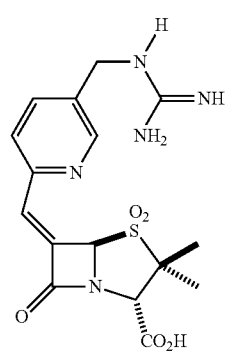

167
-continued
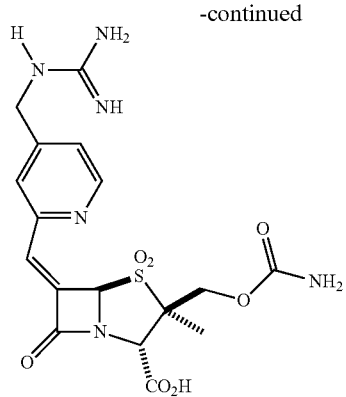
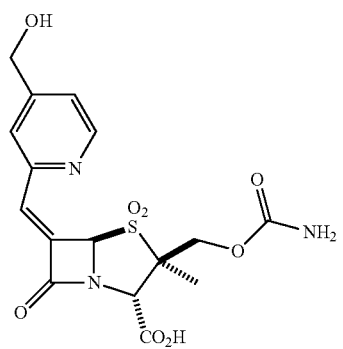
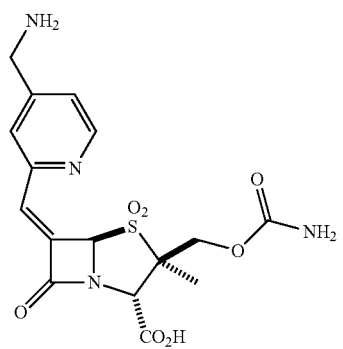
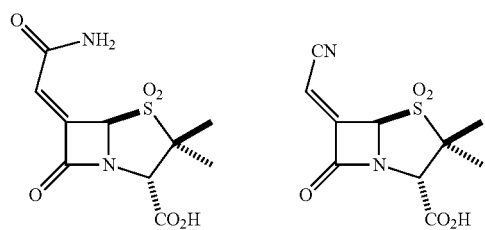
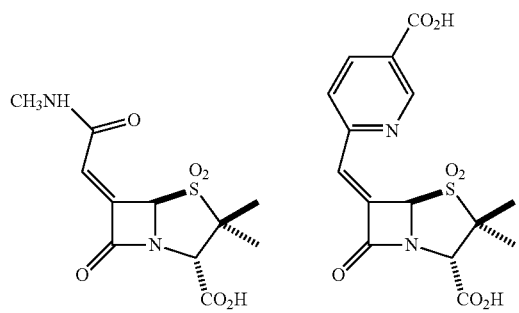
168
-continued
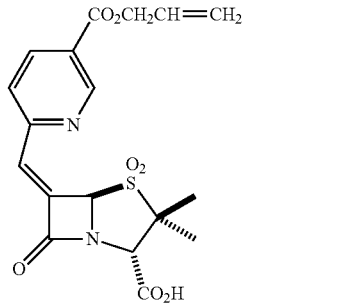
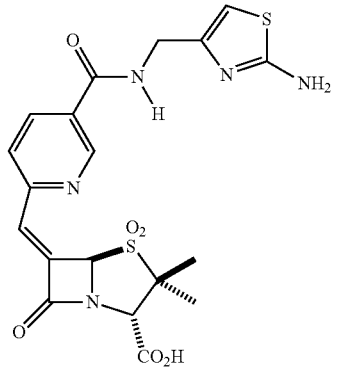
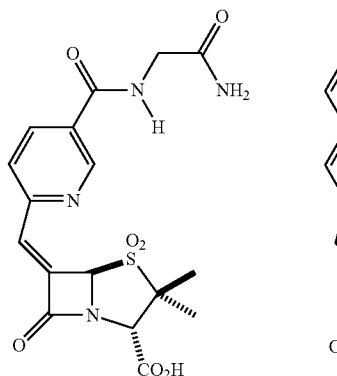
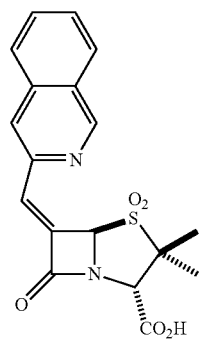
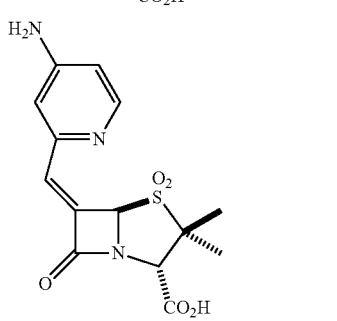
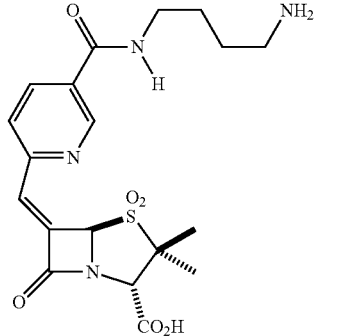

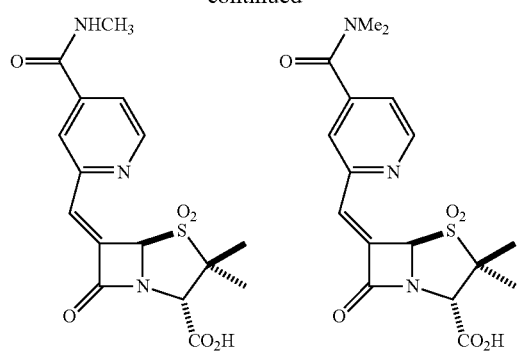
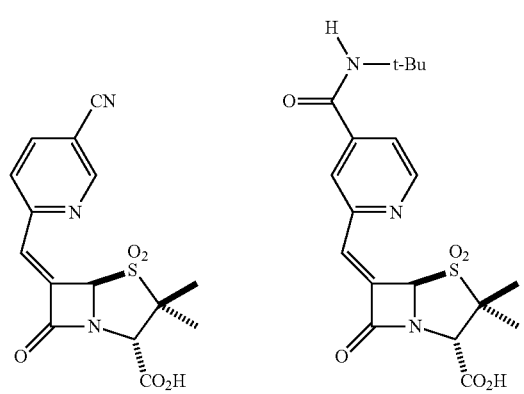
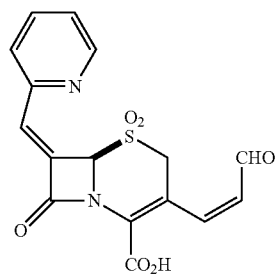
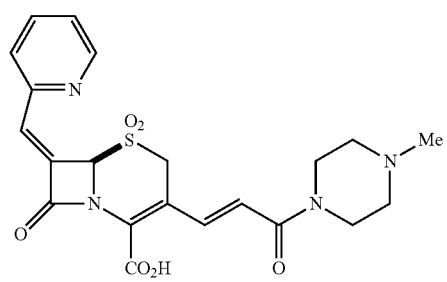
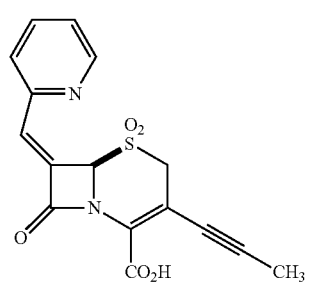
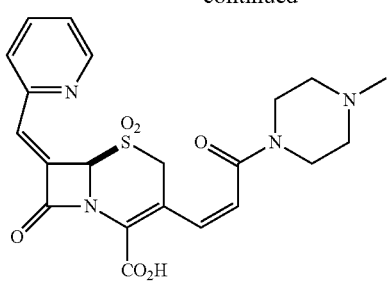
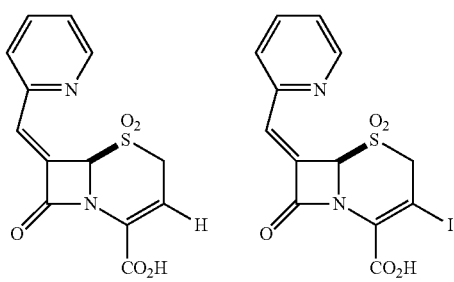
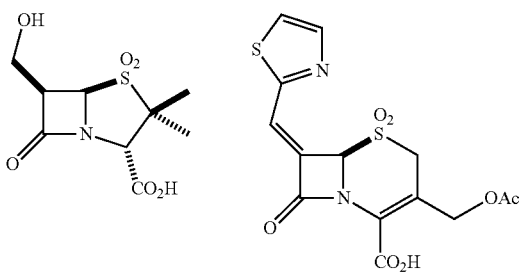
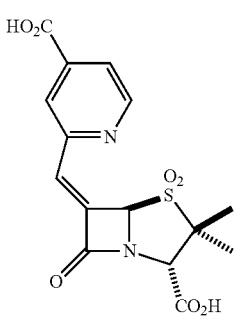
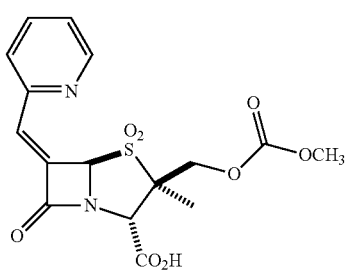
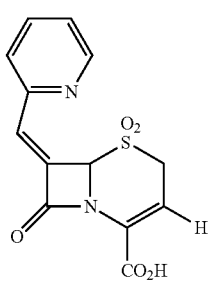

171
-continued
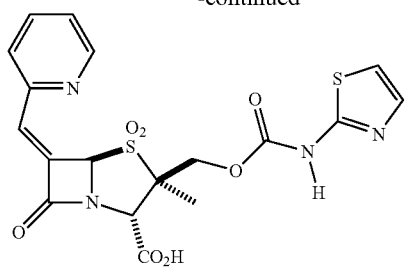
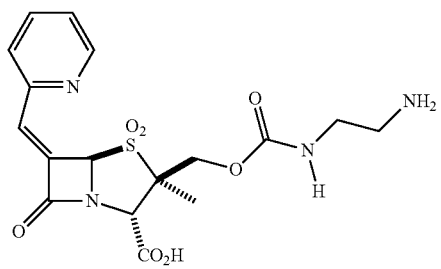
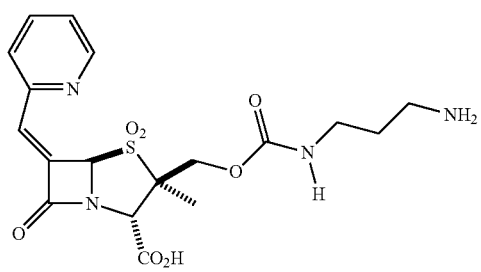
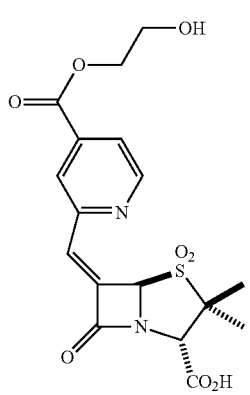
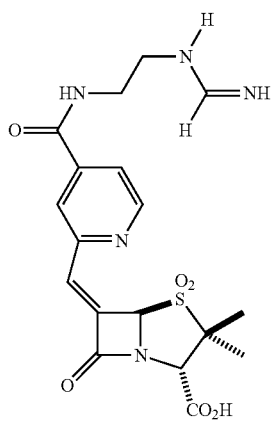
172
-continued
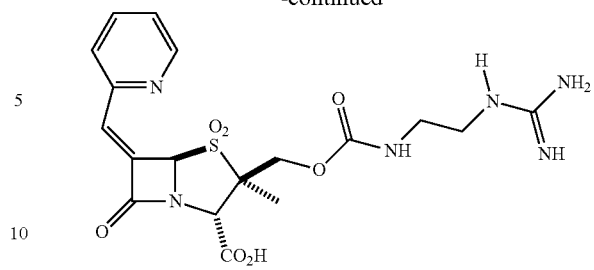
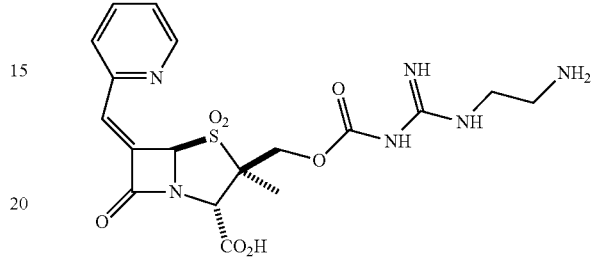
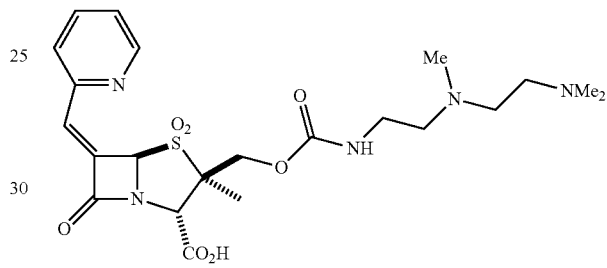
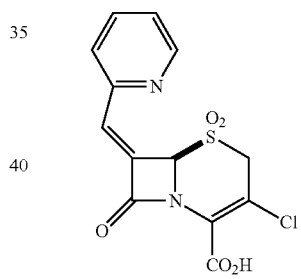
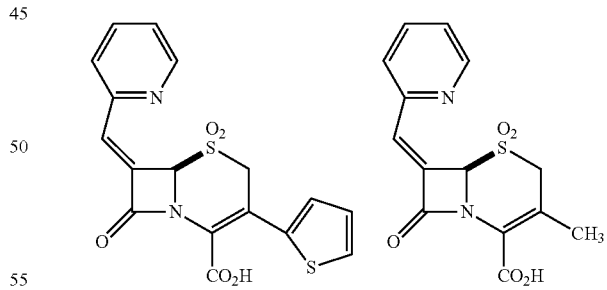
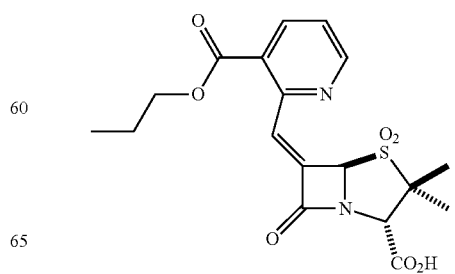

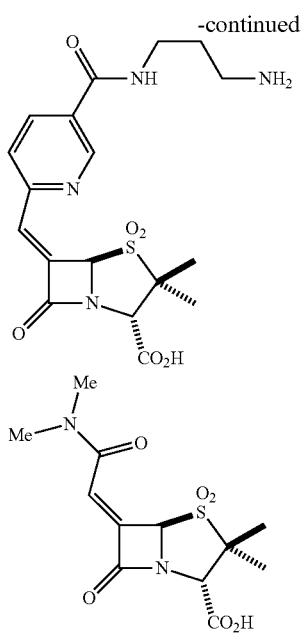

Biological Evaluation of Selected Compounds

Methods for testing the β-lactamase inhibitory bioactivity of compounds are well known in the art. For example, see T. Viswanantha, et al. (2008), "Assays for β-lactamase Activity and Inhibition,", *Methods in Molecular Medicine*, 142: *New Antibiotic Targets*, Chapter 19, pp. 239-260, and references cited therein.

Table 1 shows the $IC_{50}$ as a concentration (μmolar) of a series of inhibitory compounds of the invention against the β-lactamases produced by various bacterial strains. As can be seen, the inhibitor concentration causing a 50% loss of enzymatic activity in these β-lactamases is in the nanomolar to sub-nanomolar range.

TABLE 1

Inhibition of Representative β-lactamases ($IC_{50}$, μM)

| Inhibitor | TEM-1 E. Coli | AmpC P. aeruginosa | AmpC A. baumannii | OXA-40 A. baumannii | In serum AmpC P. aeruginosa |
|---|---|---|---|---|---|
| JDB/SA-3-18 | 0.0004 | 0.008 | 0.017 | 0.0060 | 0.012 |
| JDB/SA-4-11 | 0.00010 | 0.185 | 0.191 | 0.191 | 0.028 |
| JDB/SA-4-17 | 0.00003 | 0.012 | 0.020 | 0.007 | 0.014 |
| JDB/SA-4-141 | 0.0002 | 0.065 | 0.071 | 0.583 | 0.029 |
| JDB/SA-4-157 | 0.0006 | 0.201 | 0.515 | 0.888 | 0.080 |
| JDB/SA-4-196 | 0.0001 | 0.006 | 0.015 | 0.046 | 0.003 |
| JDB/SA-4-198 | 0.0001 | 0.039 | 0.052 | 0.079 | 0.015 |
| JDB/LN-1-255 | 0.00003 | 0.006 | 0.004 | 0.011 | 0.082 |

Tables 2 and 3 show the effectiveness of inhibitory compounds of the invention in killing resistant bacterial strains with imipenem, a β-lactam antibiotic.

TABLE 2

Synergy of Inhibitors with Imipenem Against Resistant *P. aeruginosa*

| | Imipenem (mg/L) | JDB/SA-3-18 (mg/L) | JDB/SA-4-11 (mg/L) | JDB/SA-4-17 (mg/L) | JDB/SA-4-141 (mg/L) | JDB/SA-4-157 (mg/L) | JDB/SA-4-196 (mg/L) | JDB/SA-4-198 (mg/L) | JDB/LN-1-255 (mg/L) |
|---|---|---|---|---|---|---|---|---|---|
| MIC | 20 | 0 | 0 | 0 | 0 | 0 | 0 | 0 | 0 |
| 0.5 MIC | 10 | 12.5 | 25 | 25 | 12.5 | 3.125 | 6.25 | 12.5 | 6.25 |
| 0.25 MIC | 5 | 100 | 50 | 50 | 25 | 12.5 | 12.5 | 25 | 25 |
| 0.125 MIC | 2.5 | 100 | 100 | 100 | 25 | 25 | 12.5 | 50 | 50 |
| 0.0625 MIC | 1.25 | >100 | >100 | >100 | 50 | 50 | 25 | 100 | 100 |
| 0.0313 MIC | 0.625 | >100 | >100 | >100 | >100 | >100 | >100 | >100 | >100 |

TABLE 3

Synergy of Inhibitors with Imipenem Against Resistant *A. baumannii*

| | Imipenem (mg/L) | JDB/SA-3-18 (mg/L) | JDB/SA-4-11 (mg/L) | JDB/SA-4-17 (mg/L) | JDB/SA-4-141 (mg/L) | JDB/SA-4-157 (mg/L) | JDB/SA-4-196 (mg/L) | JDB/SA-4-198 (mg/L) | JDB/LN-1-255 (mg/L) |
|---|---|---|---|---|---|---|---|---|---|
| MIC | 256 | 0 | 0 | 0 | 0 | 0 | 0 | 0 | 0 |
| 0.5 MIC | 128 | 12.5 | 25 | 25 | 0.782 | 0.196 | 3.125 | 12.5 | 6.25 |
| 0.25 MIC | 64 | 100 | 50 | 50 | >100 | 50 | 12.5 | 50 | 25 |
| 0.125 MIC | 32 | 100 | 100 | 100 | >100 | >100 | 50 | 100 | 50 |
| 0.0625 MIC | 16 | >100 | >100 | >100 | >100 | >100 | 100 | >100 | 100 |
| 0.0313 MIC | 8 | >100 | >100 | >100 | >100 | >100 | >100 | >100 | >100 |

Using the synthetic procedures provided herein, it is within ordinary skill to prepare any compounds of the invention. Using the knowledge of the person of ordinary skill combined with the above cited references and methods for evaluation of β-lactamase inhibitory bioactivity, the person of ordinary skill in the art can evaluate any compound so prepared for its effectiveness in inhibiting the β-lactamase enzyme, and for effectiveness in combination with a β-lactam antibiotic in killing bacterial strains genetically resistant to the antibiotic due to the effect of β-lactamase enzymes produced by the infective bacterial strain. Accordingly, the full scope of the claims provided below are enabled by the disclosure herein.

What is claimed is:

1. A beta-lactamase-inhibitory compound of Formula (II):

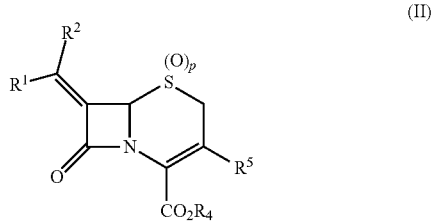

(II)

wherein p is 0, 1, or 2;
$R^1$ and $R^2$ each independently is H or pyridyl, wherein any pyridyl can be independently substituted with 0-3 J;
J is haloalkyl, $(CH_2)_n$—OR', $(CH_2)_n$—OC(O)N(R')$_2$, $(CH_2)_n$—CN, $CF_3$, $OCF_3$, O, S, C(O), S(O), methylenedioxy, ethylenedioxy, $(CH_2)_n$—N(R')$_2$, $(CH_2)_n$—SR', $(CH_2)_n$—S(O)R', $(CH_2)_n$—S(O)$_2$R', $(CH_2)_n$—S(O)$_2$N(R')$_2$, $(CH_2)_n$—SO$_3$R', $(CH_2)_n$—C(O)R', $(CH_2)_n$—C(O)C(O)R', $(CH_2)_n$—C(O)CH$_2$C(O)R', $(CH_2)_n$—C(S)R', $(CH_2)_n$—C(O)OR', $(CH_2)_n$—OC(O)R', $(CH_2)_n$—C(O)N(R')$_2$, $(CH_2)_n$—OC(O)N(R')$_2$, $(CH_2)_n$—C(S)N(R')$_2$, $(CH_2)_n$—NHC(O)R', $(CH_2)_n$—N(R')N(R')C(O)R', $(CH_2)_n$—N(R')N(R')C(O)OR', $(CH_2)_n$—N(R')N(R')CON(R')$_2$, $(CH_2)_n$—N(R')SO$_2$R', $(CH_2)_n$—N(R')SO$_2$N(R')$_2$, $(CH_2)_n$—N(R')C(O)OR', $(CH_2)_n$—N(R')C(O)R', $(CH_2)$, —N(R')C(S)R', $(CH_2)_n$—N(R')C(O)N(R')$_2$, $(CH_2)_n$—N(R')C(S)N(R')$_2$, $(CH_2)_n$—N(R')C(=NR)N(R')$_2$, $(CH_2)_n$—C(=NR)N(R')$_2$, $(CH_2)_n$—N(COR')COR', $(CH_2)_n$—N(OR')R', $(CH_2)_n$—C(=NH)N(R')$_2$, $(CH_2)_n$—C(O)N(OR')R', $(CH_2)_nN(R')C(=NR')N(R')_2$ or $(CH_2)_n$—C(=NOR')R', wherein n is 0 to 4, and wherein;

each R' is independently at each occurrence hydrogen, $(C_1-C_{12})$-alkyl, $(C_3-C_{10})$-cycloalkyl or $(C_3-C_{10})$-cycloalkenyl, $[(C_3-C_{10})$cycloalkyl or $(C_3-C_{10})$-cycloalkenyl$]$-$(C_1-C_{12})$-alkyl, $(C_6-C_{10})$-aryl, $(C_6-C_{10})$-aryl-$(C_1-C_{12})$-alkyl, $(C_3-C_{10})$-heterocyclyl, $(C_3-C_{10})$-heterocyclyl-$(C_1-C_{12})$-alkyl, $(C_5-C_{10})$-heteroaryl, or $(C_5-C_{10})$-heteroaryl-$(C_1-C_{12})$-alkyl, or, two R' groups together with a nitrogen atom to which both R' groups are attached or with two adjacent nitrogen atoms to which each R' group is respectively attached form a mono- or bicyclic ring system;

$R^4$ is H, a $(C_1-C_6)$alkyl or aryl group, or a pharmaceutically acceptable cation;

$R^5$ is a group of formula

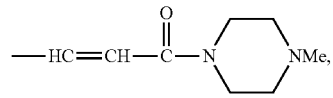

or a salt, pharmaceutically acceptable salt, tautomer, or stereoisomer thereof.

2. A beta-lactamase-inhibitory compound of claim 1, wherein the compound is any of the following compounds:

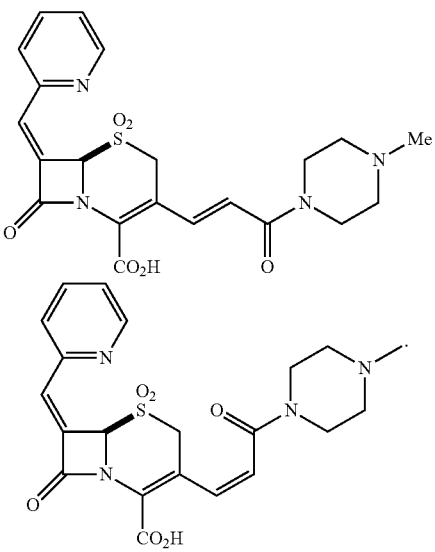

3. A pharmaceutical composition comprising a compound of claim 1 or 2 and a suitable excipient.

4. A pharmaceutical combination comprising a compound of claim 1 or 2 and a second medicament.

5. The combination of claim 4 wherein the second medicament is a beta-lactam antibiotic.

6. A pharmaceutical composition comprising the combination of claim 4 and a suitable excipient.

7. A method of inhibition of a beta-lactamase enzyme in vivo, comprising contacting the enzyme with an effective amount of any of the compounds of claim 1 or 2.

8. The method of claim 7 wherein the beta-lactamase enzyme is produced by a beta-lactam resistant bacterial population within the body of a patient.

9. A method of treatment of an infection caused by a beta-lactam resistant bacterial strain in a patient, comprising administering the compound of claim 1 or 2, in a dosage, at a frequency, and for a duration of time sufficient to provide a beneficial effect to the patient.

10. The method of claim 9 further comprising administering an effective amount of a beta-lactam antibiotic to the patient.

* * * * *

UNITED STATES PATENT AND TRADEMARK OFFICE
CERTIFICATE OF CORRECTION

| | | |
|---|---|---|
| PATENT NO. | : 8,575,144 B2 | Page 1 of 6 |
| APPLICATION NO. | : 13/629007 | |
| DATED | : November 5, 2013 | |
| INVENTOR(S) | : Buynak et al. | |

It is certified that error appears in the above-identified patent and that said Letters Patent is hereby corrected as shown below:

On the title page, Item (56), in column 2, under "Other Publications", line 6, delete "B-lactamases" and insert --B lactamases--, therefor On the title page, Item (56), in column 2, under "Other Publications", line 8, before "filed", insert --Application--, therefor On the title page, Item (57), in "Abstract", in column 2, equation (II), delete "$CO_2R_4$" and insert --$CO_2R^4$--, therefor In the Specifications In column 2, equation (II), delete "$CO_2R_4$" and insert --$CO_2R^4$--, therefor In column 2, line 52, delete "R'" and insert --$R^5$--, therefor In column 9, line 11, delete "R3N" and insert --$R_3N$--, therefor In column 9, line 31, delete "C(O)NR$_2$" and insert -- -C(O)NR$_2$--, therefor In column 10, line 54, delete "stoichiometic" and insert --stoichiometric--, therefor In column 10, line 58, delete "stoichiometic" and insert --stoichiometric--, therefor In column 14, equation (II), delete "$CO_2R_4$" and insert --$CO_2R^4$--, therefor In column 14, line 44, delete "R'" and insert --$R^5$--, therefor In column 15, line 10, delete "R4" and insert --$R^4$--, therefor Signed and Sealed this
Sixth Day of May, 2014

Michelle K. Lee
*Deputy Director of the United States Patent and Trademark Office*

In column 16, line 64 (approx.), after "rt", insert --,-- therefor

In column 20, line 27, delete "benzyhydryl" and insert --benzhydryl--, therefor

In column 20, line 38, delete "br s" and insert --brs--, therefor

In column 20, line 39, after "(s, 1H)", insert --,-- therefor

In column 21, line 17, after "(s, 1H)", insert --,-- therefor

In column 23, line 28, delete "chloroaceticacid" and insert --chloroacetic acid--, therefor In column 24, line 47, delete "(d, 1H, J=3.4 Hz) 4.79 (s, 1H)" and insert --(d, 1H, J=3.4 Hz), 4.79 (s, 1H),--, therefor In column 25, line 64, delete "□" and insert --δ--, therefor In column 28, line 48, delete "AB q" and insert --ABq--, therefor In column 29, line 41, after "2H)", insert --,-- therefor In column 30, line 25, delete "bs" and insert --brs--, therefor In column 30, line 26, delete "AB q," and insert --ABq,--, therefor In column 32, line 1-2, after "(d, 1H, J=12.0 Hz)", insert --,-- therefor In column 35, line 5, delete "aminocarbonyloxy)" and insert --(aminocarbonyloxy)--, therefor In column 36, line 41, after "Hz)", insert --,-- therefor In column 37, line 32, after "d", insert --,-- therefor In column 40, line 37, delete "aminocarbonyloxy)" and insert --(aminocarbonyloxy)--, therefor In column 42, line 15, after "Hz)", insert --,-- therefor In column 43, line 1, delete "(s 3H)" and insert --(s, 3H)--, therefor In column 43, line 21, delete "(s 6H)" and insert --(s, 6H)--, therefor In column 43, line 43, after "(s, 2H)", insert --,-- therefor

CERTIFICATE OF CORRECTION (continued)

In column 47, equation 18p, delete " 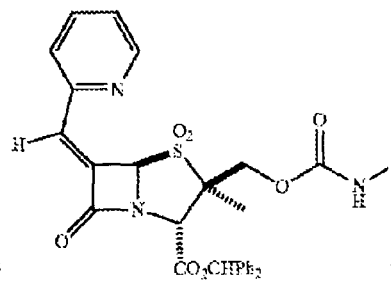 " and insert

-- 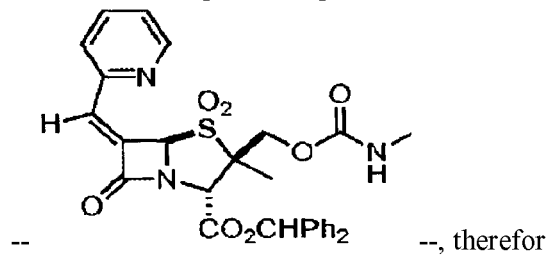 --, therefor

In column 56, reference Numeral 40, delete "CONa" and insert --$CO_2Na$--, therefor In column 60, line 44, after "Hz)", insert --,--, therefor In column 61, line 17, delete "product." and insert --product--, therefor In column 62, line 29, delete "$CeCl_3.7H_2O$" and insert --$CeCl_3 \cdot 7H_2O$--, therefor In column 62, line 40, delete "AB q" and insert --ABq--, therefor In column 63, line 19, delete "AB q" and insert --ABq--, therefor In column 63, line 65, delete "6.9," and insert --6.9--, therefor In column 64, line 41, delete "AB q" and insert --ABq--, therefor In column 64, line 44, after "Hz)", insert --,--, therefor In column 65, line 19, delete "AB q" and insert --ABq--, therefor In column 65, line 21, after "1H)", insert --,--, therefor In column 65, line 56, delete "$NaH_2PO_4.H_2O$" and insert --$NaH_2PO_4 \cdot H_2O$--, therefor In column 67, line 57, delete "p-nitrophenylester" and insert --p-nitrophenyl ester--, therefor In column 68, line 40, delete "Hz))," and insert --Hz),--, therefor In column 70, line 26, delete "(brs, 1H))" and insert --(brs, 1H)--, therefor In column 71, line 1, delete "p-nitrophenylester" and insert --p-nitrophenyl ester--, therefor In column 71, line 59, delete "(m 1H)" and insert --(m, 1H)--, therefor In column 71, line 61, delete "Hz))," and insert --Hz),--, therefor In column 73, line 17, after "Hz)", insert --.--, therefor In column 73, line 63, after "Hz)", insert --.--, therefor In column 75, line 20, after "1H)", insert --,--, therefor In column 75, line 22, after "Hz)", insert --.--, therefor In column 76, line 62, after "(s, 1H)", insert --,--, therefor In column 77, line 39, after "1H)", insert --,--, therefor In column 77, line 40, after "Hz)", insert --.--, therefor In column 88, equation 84, line 2, after "0° C.", insert --,--, therefor In column 92, line 17, after "24.9", insert --.--, therefor In column 96, line 58, after "Hz)", insert --.--, therefor In column 96, line 67, after "1783.79", insert --.--, therefor In column 97, line 44, delete "1.5, (s, 3H)" and insert --1.5 (s, 3H)--, therefor In column 99, line 35, delete "p-nitrophenychloroformate" and insert --p-nitrophenylchloroformate--, therefor In column 100, line 38, delete "p-nitrophenylester" and insert --p-nitrophenyl ester--, therefor In column 100, table 4, line 1, after "anisole", insert --,--, therefor In column 103, line 21, delete "(s, 1H))" and insert --(s, 1H)--, therefor In column 104, line 2, after "(s, 1H)", insert --,--, therefor In column 104, line 32, after "(s, 1H)", insert --,--, therefor In column 107, line 3, after "(s, 1H)", insert --,-- therefor In column 109, line 32, before "2.3", insert --(-- therefor In column 110, line 66, after "Hz)", insert --,-- therefor In column 111, line 32, delete "p-nitrophenylester" and insert --p-nitrophenyl ester--, therefor In column 111, line 61 (approx.), after "0° C.", insert --,-- therefor In column 129, line 63, after "Hz)", insert --,-- therefor In column 131, line 42, delete "AB, q" and insert --ABq--, therefor In column 132, line 29, after "4H)", insert --,-- therefor In column 132, line 29, after "Hz)", insert --,-- therefor In column 136, line 1, delete "8.0-8.02." and insert --8.0-8.02--, therefor In column 141, line 63, after "Hz)", insert --,-- therefor In column 143, line 38, after "167.58", insert --.-- therefor In column 143, line 57 (approx.), after "2 h", insert --,-- therefor In column 146, line 1, delete "p-nitrophenylester" and insert --p-nitrophenyl ester--, therefor In column 147, line 1, delete "p-nitrophenylester" and insert --p-nitrophenyl ester--, therefor In column 147, line 65, after "water)", insert --.-- therefor In column 150, line 24, after "water)", insert --.-- therefor In column 151, line 8, after "water)", insert --.-- therefor In column 151, line 15, after "(s, 1H)", insert --,-- therefor In column 152, line 60, after "water)", insert --.-- therefor In column 153, line 48, after "water)", insert --.-- therefor In the Claims In column 175, equation (II), in Claim 1, delete "$CO_2R_4$" and insert --$CO_2R^4$--, therefor In column 175, line 34, in Claim 1, delete "$SO_3R'$," and insert --$S(O)_3R'$,--, therefor In column 175, line 42, in Claim 1, delete "$(CH_2)$, -$N(R')C(S)R'$," and insert --$(CH_2)_n$-$N(R')C(S)R'$,--, therefor In column 175, line 46, in Claim 1, delete "$(CH_2)_nN(R')$" and insert --$(CH_2)_n$-$N(R')$--, therefor